United States Patent
Hwang et al.

(10) Patent No.: US 10,400,003 B2
(45) Date of Patent: Sep. 3, 2019

(54) ORGANOMETALLIC COMPOUND, ORGANIC LIGHT-EMITTING DEVICE INCLUDING THE SAME, AND DIAGNOSTIC COMPOSITION INCLUDING THE ORGANOMETALLIC COMPOUND

(71) Applicant: SAMSUNG ELECTRONICS CO., LTD., Suwon-si, Gyeonggi-do (KR)

(72) Inventors: Kyuyoung Hwang, Anyang-si (KR); Seungyeon Kwak, Suwon-si (KR); Seongjun Yoon, Yongin-si (KR); Jungin Lee, Hwaseong-si (KR); Jiyoun Lee, Anyang-si (KR); Chul Baik, Suwon-si (KR); Yongsuk Cho, Hwaseong-si (KR); Ohyun Kwon, Seoul (KR); Yoonhyun Kwak, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/788,129

(22) Filed: Oct. 19, 2017

(65) Prior Publication Data
US 2018/0141969 A1    May 24, 2018

(30) Foreign Application Priority Data
Nov. 18, 2016 (KR) .................... 10-2016-0154449

(51) Int. Cl.
| | |
|---|---|
| *H01L 51/54* | (2006.01) |
| *C09K 11/06* | (2006.01) |
| *C07F 15/00* | (2006.01) |
| *G01N 33/58* | (2006.01) |
| *H01L 51/00* | (2006.01) |
| *H01L 51/52* | (2006.01) |
| *H01L 51/50* | (2006.01) |

(52) U.S. Cl.
CPC .......... *C07F 15/0086* (2013.01); *C09K 11/06* (2013.01); *G01N 33/58* (2013.01); *G01N 33/582* (2013.01); *H01L 51/0087* (2013.01); *H01L 51/5218* (2013.01); *H01L 51/5221* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 8,877,353 B2 | 11/2014 | Che et al. | |
| 2007/0103060 A1* | 5/2007 | Itoh et al. ............ | C07D 213/06 313/504 |
| 2009/0261721 A1* | 10/2009 | Murakanni et al. ... | C09K 11/06 313/504 |
| 2009/0267500 A1* | 10/2009 | Kinoshita et al. ..... | C09K 11/06 313/504 |
| 2012/0018711 A1 | 1/2012 | Che et al. | |
| 2012/0061654 A1* | 3/2012 | Rayabarapu et al. ...................... | C07F 15/0033 257/40 |
| 2013/0274473 A1 | 10/2013 | Che et al. | |
| 2013/0324721 A1* | 12/2013 | Inoue et al. ........ | H01L 51/0071 544/225 |
| 2015/0236276 A1* | 8/2015 | Boudreault et al. ......................... | H01L 51/0085 257/40 |

FOREIGN PATENT DOCUMENTS

| | | |
|---|---|---|
| JP | 9-176629 A | 7/1997 |
| JP | 10-308277 A | 11/1998 |
| WO | 2012-009957 A1 | 1/2012 |

* cited by examiner

*Primary Examiner* — Marie R. Yamnitzky
(74) *Attorney, Agent, or Firm* — Cantor Colburn LLP

(57) ABSTRACT

An organometallic compound represented by Formula 1:

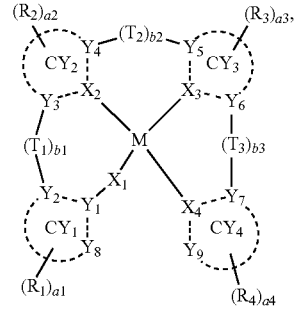

Formula 1 wherein in Formula 1, groups and variables are the same as described in the specification.

15 Claims, 1 Drawing Sheet

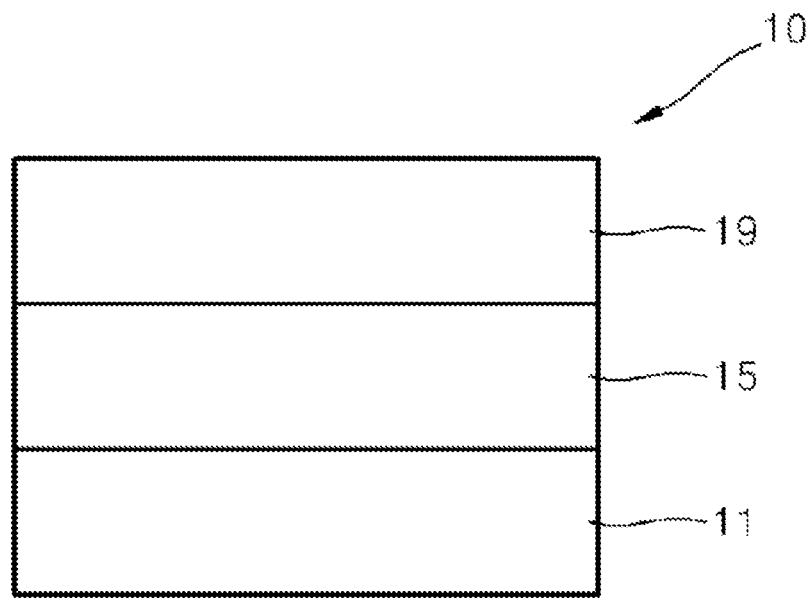

ORGANOMETALLIC COMPOUND, ORGANIC LIGHT-EMITTING DEVICE INCLUDING THE SAME, AND DIAGNOSTIC COMPOSITION INCLUDING THE ORGANOMETALLIC COMPOUND

CROSS-REFERENCE TO RELATED APPLICATION

This application claims priority to Korean Patent Application No. 10-2016-0154449, filed on Nov. 18, 2016, in the Korean Intellectual Property Office, and all the benefits accruing therefrom under 35 U.S.C. § 119, the content of which is incorporated herein in its entirety by reference.

BACKGROUND

1. Field

The present disclosure relates to an organometallic compound, an organic light-emitting device including the organometallic compound, and a diagnostic composition including the organometallic compound.

2. Description of the Related Art

Organic light-emitting devices (OLEDs) are self-emission devices that have excellent characteristics including wide viewing angles, high contrast ratios, short response times, excellent luminance, driving voltage, and response speed. In addition, OLEDs produce full-color images.

As an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. The excitons may transit from an excited state to a ground state, thereby generating light.

Meanwhile, luminescent compounds may be used to monitor, sense, or detect a biological material such as a cell or a protein, and an example of such luminescent compounds includes a phosphorescent luminescent compound.

Various types of organic light emitting devices are known. However, there still remains a need in OLEDs having low driving voltage, high efficiency, high brightness, and long lifespan.

SUMMARY

Provided are an organometallic compound, an organic light-emitting device including the organometallic compound, and a diagnostic composition including the organometallic compound.

Additional aspects will be set forth in part in the description which follows and, in part, will be apparent from the description, or may be learned by practice of the presented embodiments.

According to an aspect of an embodiment, an organometallic compound is represented by Formula 1:

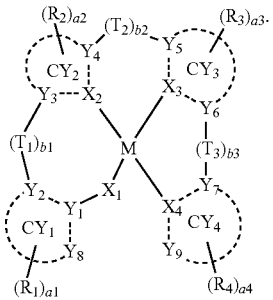

Formula 1

In Formula 1,

M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), $X_1$ is O or S, wherein a bond between $X_1$ and M is a covalent bond, $X_2$ is N, wherein a bond between $X_2$ and M is a coordinate bond, $X_3$ and $X_4$ are each independently C or N, one of a bond between $X_3$ and M and a bond between $X_4$ and M is a covalent bond, and the other thereof is a coordinate bond, $Y_1$ to $Y_7$ are each independently C or N, $Y_8$ and $Y_9$ are each independently C, N, O, or S, a bond or an atomic group between $Y_1$ and $Y_8$ and a bond or an atomic group between $Y_1$ and $Y_2$ form $CY_1$, a bond or an atomic group between $X_2$ and $Y_3$ and a bond or an atomic group between $X_2$ and $Y_4$ form $CY_2$, a bond or an atomic group between $X_3$ and $Y_5$ and a bond or an atomic group between $X_3$ and $Y_6$ form $CY_3$, and a bond or an atomic group between $X_4$ and $Y_7$ and a bond or an atomic group between $X_4$ and $Y_9$ form $CY_4$, $CY_1$, $CY_3$, and $CY_4$ are each independently selected from a $C_5$-$C_{30}$ carbocyclic group and a $C_1$-$C_{30}$ heterocyclic group, $CY_2$ is selected from an azacarbazole group, an azadibenzoborol group, an azadibenzophosphol group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, and an azadibenzothiophene 5,5-dioxide group, wherein each of these groups includes at least one N as a ring-forming atom, $T_1$ to $T_3$ are each independently selected from *—N[(L$_5$)$_{a5}$-(R$_5$)]—*', *—B(R$_5$)—*', *—P(R$_5$)—*', *—C(R$_5$)(R$_6$)—*', *—Si(R$_5$)(R$_6$)—*', *—Ge(R$_5$)(R$_6$)—*', *—S—*', *—Se—*', *—O—*', *—C(=O)—*', *—S(=O)—*', *—S(=O)$_2$—*', *—C(R$_5$)=*', *=C(R$_5$)—*', *—C(R$_5$)=C(R$_6$)—*', *—O(=S)—*', and *—C≡C—*'.

$L_5$ is selected from a single bond, a substituted or unsubstituted $C_5$-$C_{30}$ carbocyclic group, and a substituted or unsubstituted $C_1$-$C_{30}$ heterocyclic group, a5 is selected from 1 to 3, wherein, when a5 is two or more, two or more of groups $L_5$ are identical to or different from each other, $R_5$ and $R_6$ are optionally linked via a first linking group to form a substituted or unsubstituted $C_5$-$C_{30}$ carbocyclic group or a substituted or unsubstituted $C_1$-$C_{30}$ heterocyclic group, b1 to b3 are each independently 0, 1, 2, or 3, wherein, when b1 is 0, *-$(T_1)_{b1}$-*' is a single bond, when b2 is 0, *-$(T_2)_{b2}$-*' is a single bond, and when b3 is 0, *-$(T_3)_{b3}$-*' is a single bond, $R_1$ to $R_6$ are each independently selected from hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$, a1 to a4 are each independently 0, 1, 2, 3, 4, or 5, two groups $R_1$ selected from a1 number of groups $R_1$ are optionally linked to form a substituted or unsubstituted $C_5$-$C_{30}$ carbocyclic group or a substituted or unsubstituted $C_1$-$C_{30}$ heterocyclic group, two groups $R_2$ selected from a2 number of groups $R_1$ are optionally linked to form a substituted or unsubstituted $C_5$-$C_{30}$ carbocyclic group or a substituted or unsubstituted $C_1$-$C_{30}$ heterocyclic group, two groups $R_3$ selected from a3 number of groups $R_3$ are optionally linked to form a substituted or unsubstituted $C_5$-$C_{30}$ carbocyclic group or a substituted or unsubstituted $C_1$-$C_{30}$ heterocyclic group, two groups $R_4$ selected from a4 number of groups $R_4$ are optionally linked to form a substituted or unsubstituted $C_5$-$C_{30}$ carbocyclic group or a substituted or unsubstituted $C_1$-$C_{30}$ heterocyclic group, two or more neighboring groups selected from $R_1$ to $R_4$ are optionally linked to form a substituted or unsubstituted $C_5$-$C_{30}$ carbocyclic group or a substituted or unsubstituted $C_1$-$C_{30}$ heterocyclic group, one of $R_5$ and $R_6$ is optionally linked with $R_1$, $R_2$, $R_3$, or $R_4$ to form a substituted or unsubstituted $C_5$-$C_{30}$ carbocyclic group or a substituted or unsubstituted $C_1$-$C_{30}$ heterocyclic group, at least one substituent of the substituted $C_6$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_2$-$C_{60}$ heteroaryloxy group, the substituted $C_2$-$C_{60}$ heteroarylthio group, the substituted $C_3$-$C_{60}$ heteroarylalkyl group, the substituted monovalent non-aromatic condensed polycyclic group, and the substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, and $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group and a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group.

According to another aspect of an embodiment, an organic light-emitting device includes:

a first electrode;

a second electrode; and an organic layer disposed between the first electrode and the second electrode, wherein the organic layer includes an emission layer, and wherein the organic layer includes at least one organometallic compound.

Here, the at least one organometallic compound in the organic layer may serve as a dopant.

According to another aspect of an embodiment, there is provided a diagnostic composition including the at least one organometallic compound represented by Formula 1.

BRIEF DESCRIPTION OF THE DRAWING

These and/or other aspects will become apparent and more readily appreciated from the following description of the embodiments, taken in conjunction with the accompanying drawings in which:

The FIGURE is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound may be represented by Formula 1:

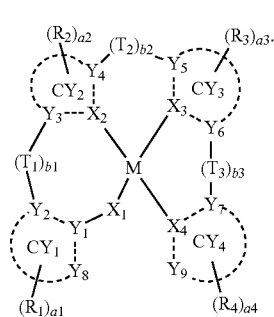

Formula 1

In Formula 1, M may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au).

For example, in Formula 1, M may be Pt, but embodiments of the present disclosure are not limited thereto.

The organometallic compound represented by Formula 1 may be a neutral compound that does not consist of ion pairs of cations and anions.

In Formula 1, $X_1$ may be O or S, wherein a bond between $X_1$ and M may be covalent bond.

In Formula 1, $X_2$ may be N, wherein a bond between $X_2$ and M may be a coordinate bond.

In Formula 1, $X_3$ and $X_4$ may each independently be C or N, one of a bond between $X_3$ and M and a bond between $X_4$ and M may be a covalent bond, and the other thereof may be a coordinate bond.

For example, in Formula 1, i) $X_3$ may be N, wherein a bond between $X_3$ and M may be a coordinate bond, and $X_4$ may be C, wherein a bond between $X_4$ and M may be a covalent bond; or ii) $X_3$ may be C, wherein a bond between $X_3$ and M may be a covalent bond, and $X_4$ may be N, wherein a bond between $X_4$ and M may be a coordinate bond.

In Formula 1, $Y_1$ to $Y_7$ may each independently be C or N.

In Formula 1, $Y_8$ and $Y_9$ may each independently be C, N, O, or S.

In an embodiment, in Formula 1, $X_3$ may be C, wherein a bond between $X_3$ and M may be a covalent bond, $X_4$ may be N, wherein a bond between $X_4$ and M may be a coordinate bond, and $Y_1$ to $Y_7$ may each independently be C. However, embodiments of the present disclosure are not limited thereto.

In an embodiment, in Formula 1, a bond or an atomic group between $Y_1$ and $Y_8$ and a bond or an atomic group between $Y_1$ and $Y_2$ may form $CY_1$, a bond or an atomic group between $X_2$ and $Y_3$ and a bond or an atomic group between $X_2$ and $Y_4$ may form $CY_2$, a bond or an atomic group between $X_3$ and $Y_5$ and a bond or an atomic group between $X_3$ and $Y_6$ may form $CY_3$, and a bond or an atomic group between $X_4$ and $Y_7$ and a bond or an atomic group between $X_4$ and $Y_9$ may form $CY_4$.

In Formula 1, $CY_1$, $CY_3$, and $CY_4$ may each independently be selected from a $C_5$-$C_{30}$ carbocyclic group and a $C_1$-$C_{30}$ heterocyclic group.

For example, in Formula 1, $CY_1$, $CY_3$, and $CY_4$ may each independently be selected from 6-membered rings.

In an embodiment, in Formula 1, $CY_1$, $CY_3$, and $CY_4$ may each independently be selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a pyrrole group, a thiophene group, a furan group, an indole group, a benzoborol group, a benzophosphol group, an indene group, a benzosilole group, a benzogermole group, a benzothiophene group, a benzoselenophene group, a benzofuran group, a carbazole group, a dibenzoborol group, a dibenzophosphol group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azacarbazole group, an azadibenzoborol group, an azadibenzophosphol group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, a tetrazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group, but embodiments of the present disclosure are not limited thereto.

In an embodiment, in Formula 1, $CY_1$, $CY_3$, and $CY_4$ may each independently be selected from a benzene group, a naphthalene group, a fluorene group, a carbazole group, a dibenzofuran group, a dibenzothiophene group, a dibenzosilole group, a dibenzoselenophene group, an azafluorene group, an azacarbazole group, an azadibenzofuran group, an azadibenzothiophene group, an azadibenzosilole group, an azadibenzoselenophene group, a 1,2,3,4-tetrahydronaphthalene group, a pyridine group, a pyrimidine group, a quinoline group, an isoquinoline group, a quinoxaline group, a quinazoline group, a 5,6,7,8-tetrahydroisoquinoline group, and a 5,6,7,8-tetrahydroquinoline group, but embodiments of the present disclosure are not limited thereto.

In Formula 1, $CY_2$ may be selected from an azacarbazole group, an azadibenzoborol group, an azadibenzophosphol group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, and an azadibenzothiophene 5,5-dioxide group, wherein each of these groups includes at least one N as a ring-forming atom.

The terms "an azacarbazole group, an azadibenzoborol group, an azadibenzophosphol group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, and an azadibenzothiophene 5,5-dioxide group" used herein mean heterocyclic rings which have the same backbone as "a carbazole group, a dibenzoborol group, a dibenzophosphol group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, and a dibenzothiophene 5,5-dioxide group", respectively, wherein at least one carbon atom among ring-forming carbon atoms may be substituted with a nitrogen atom.

For example, in Formula 1, $CY_2$ may be selected from an azacarbazole group, an azafluorene group, an azadibenzosilole group, an azadibenzothiophene group, an azadibenzoselenophene group, an azadibenzofuran group, and an azadibenzothiophene group, wherein each of these groups may include 1, 2, or 3 nitrogen atoms as ring-forming atoms. However, embodiments of the present disclosure are not limited thereto.

In Formula 1, $T_1$ to $T_3$ may each independently be selected from *—N[$(L_5)_{a5}$-$(R_5)$]—*', *—B$(R_5)$—*', *—P$(R_5)$—*', *—C$(R_5)(R_6)$—*', *—Si$(R_5)(R_6)$—*', *—Ge$(R_5)(R_6)$—*', *—S—*', *—Se—*', *—O—*', *—C(=O)—*', *—S (=O)—*', *—S(=O)$_2$—*', *—C(R$_5$)=*', *=C(R$_5$)—*', *—C(R$_5$)=C(R$_6$)—*', *—C(=S)—*', and *—C≡C—*', wherein R$_5$ and R$_6$ may be the same as those described later.

L$_5$ may be selected from a single bond, a substituted or unsubstituted C$_5$-C$_{30}$ carbocyclic group, and a substituted or unsubstituted C$_1$-C$_{30}$ heterocyclic group, and a5 may be selected from 1 to 3 (for example, a5 may be 1), wherein, when a5 is two or more, two or more of groups L$_5$ may be identical to or different from each other.

In an embodiment, L$_5$ may be selected from:

a single bond, a phenylene group, a naphthylene group, a fluorenylene group, a pyridinylene group, a pyrimidinylene group, and a carbazolylene group; and a phenylene group, a naphthylene group, a fluorenylene group, a pyridinylene group, a pyrimidinylene group, and a carbazolylene group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a biphenyl group, and a terphenyl group, but embodiments of the present disclosure are not limited thereto.

In an embodiment, in Formula 1, T$_1$ to T$_3$ may each independently be selected from *—N[(L$_5$)$_{a5}$-(R$_5$)]—*', *—C(R$_5$)(R$_6$)—*', *—Si(R$_5$)(R$_6$)—*', *—S—*', and *—O—*', but embodiments of the present disclosure are not limited thereto.

R$_5$ and R$_6$ may be optionally linked via a first linking group to form a substituted or unsubstituted C$_5$-C$_{30}$ carbocyclic group or a substituted or unsubstituted C$_1$-C$_{30}$ heterocyclic group (for example, a 5- to 7-membered cyclic group consisting of 5 or 6 carbon atoms, each substituted or unsubstituted with at least one selected from deuterium, a cyano group, —F, a C$_1$-C$_{10}$ alkyl group, and a C$_6$-C$_{14}$ aryl group).

In an embodiment, in Formula 1, T$_1$ to T$_3$ may each independently be selected from *—C(R$_5$)(R$_6$)—*', *—Si(R$_5$)(R$_6$)—*', and *—Ge(R$_5$)(R$_6$)—*', R$_5$ and R$_6$ may be linked via the first linking group, wherein the first linking group may be selected from a single bond, *—N[(L$_9$)$_{a6}$-(R$_9$)]—*', *—B(R$_9$)—*', *—P(R$_9$)—*', *—C(R$_9$)(R$_{10}$)—*', *—Si(R$_9$)(R$_{10}$)—*', *—Ge(R$_9$)(R$_{10}$)—*', *—S—*', *—Se—*', *—O—*', *—C(=O)—*', *—S(=O)—*', *—S(=O)$_2$—*', *—C(R$_9$)=*', *=C(R$_9$)—*', *—C(R$_9$)=C(R$_{10}$)—*', *—C(=S)—*', and *—C≡C—*', R$_9$ and R$_{10}$ may be the same as described herein in connection with R$_5$, L$_9$ may be the same as described herein in connection with L$_5$, a9 may be the same as described herein in connection with a5, and

* and *' may each independently be a binding site to a neighboring atom, but embodiments of the present disclosure are not limited thereto.

In Formula 1, b1 to b3 respectively indicate numbers of T$_1$ to T$_3$, and may each independently be 0, 1, 2, or 3. When b1 is 0, *-(T$_1$)$_{b1}$-*' may be a single bond, when b2 is 0, *-(T$_2$)$_{b2}$-*' may be a single bond, and when b3 is 0, *-(T$_3$)$_{b3}$-*' may be a single bond.

In an embodiment, in Formula 1, b1, b2, and b3 may each be 0, b1 may be 1, and b2 and b3 may each be 0;

b2 may be 1, and b1 and b3 may each be 0; or b3 may be 1, and b1 and b2 may each be 0, but embodiments of the present disclosure are not limited thereto.

In Formula 1, R$_1$ to R$_6$ may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted heterocycloalkyl group, a substituted or unsubstituted C$_3$-C$_{10}$ cycloalkenyl group, a substituted or unsubstituted heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_2$-C$_{60}$ heteroaryloxy group, a substituted or unsubstituted C$_2$-C$_{60}$ heteroarylthio group, a substituted or unsubstituted C$_3$-C$_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$).

For example, R$_1$ to R$_6$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and
—$N(Q_1)(Q_2)$, —$Si(Q_3)(Q_4)(Q_5)$, —$B(Q_6)(Q_7)$, and —$P(=O)(Q_5)(Q_9)$, and $Q_1$ to $Q_9$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$, an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In an embodiment, $R_1$ to $R_6$ may each independently be selected from:
hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group; and
—$N(Q_1)(Q_2)$, —$Si(Q_3)(Q_4)(Q_5)$, —$B(Q_6)(Q_7)$, and —$P(=O)(Q_9)(Q_9)$, and $Q_1$ to $Q_9$ may be the same as those described herein.

In an embodiment, $R_1$ to $R_6$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-142, and —$Si(Q_3)(Q_4)(Q_5)$ (wherein $Q_3$ to $Q_5$ may be the same as those described herein):

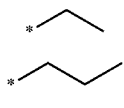
Formula 9-1

Formula 9-2

Formula 9-3

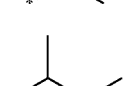
Formula 9-4

Formula 9-5

Formula 9-6

Formula 9-7

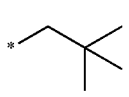
Formula 9-8

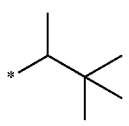
Formula 9-9

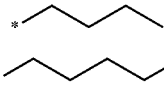
Formula 9-10

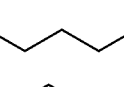
Formula 9-11

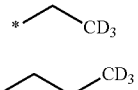
Formula 9-12

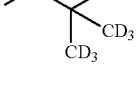
Formula 9-13

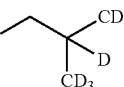
Formula 9-14

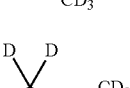
Formula 9-15

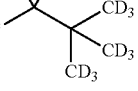
Formula 9-16

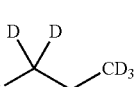
Formula 9-17

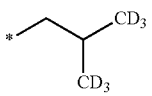
Formula 9-18

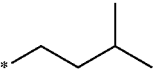
Formula 9-19

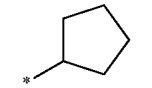
Formula 10-1

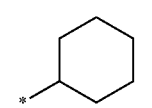
Formula 10-2

Formula 10-3

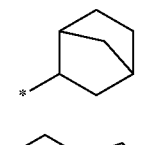
Formula 10-4

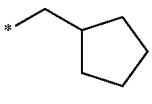
Formula 10-5

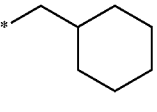
Formula 10-6

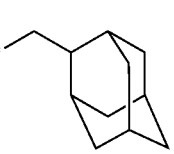
Formula 10-7

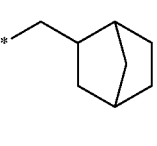
Formula 10-8

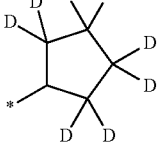
Formula 10-9

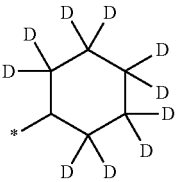
Formula 10-10

-continued
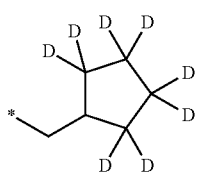
Formula 10-11
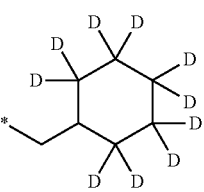
Formula 10-12
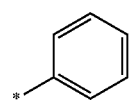
Formula 10-13
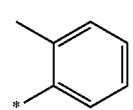
Formula 10-14
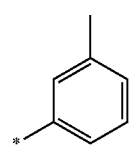
Formula 10-15
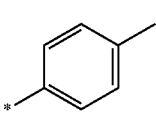
Formula 10-16
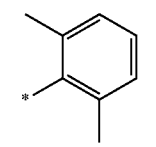
Formula 10-17
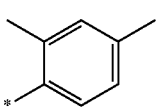
Formula 10-18
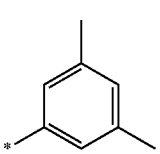
Formula 10-19
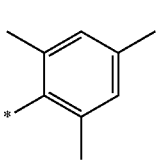
Formula 10-20
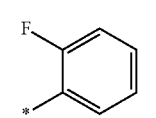
Formula 10-21
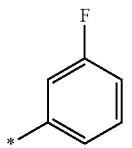
Formula 10-22
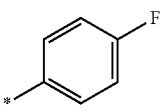
Formula 10-23
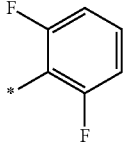
Formula 10-24
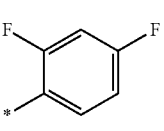
Formula 10-25
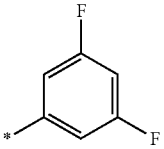
Formula 10-26
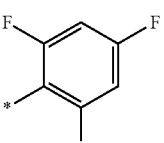
Formula 10-27
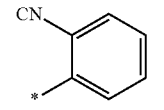
Formula 10-28
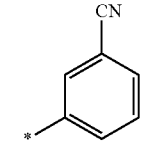
Formula 10-29
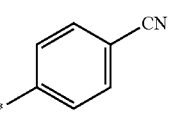
Formula 10-30
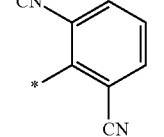
Formula 10-31
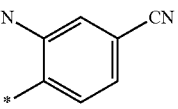
Formula 10-32

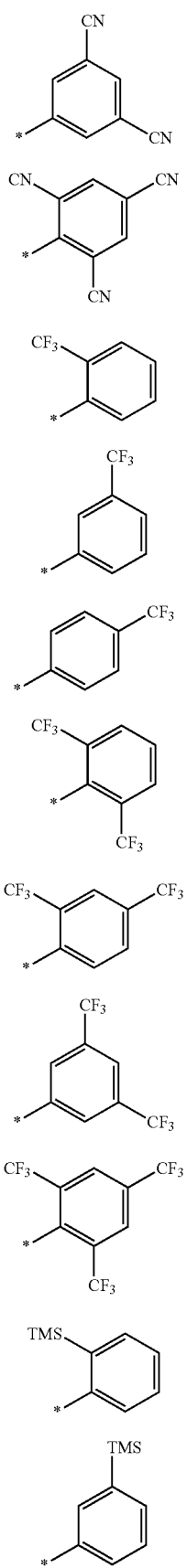
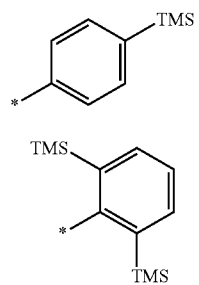
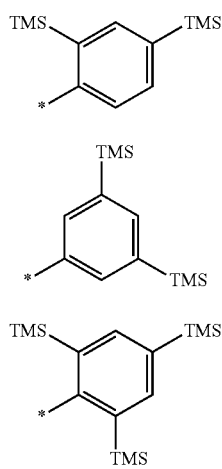
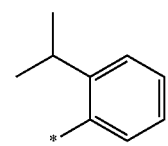
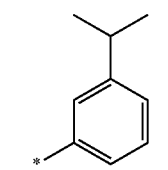
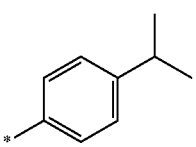
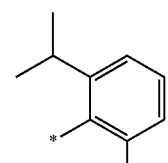
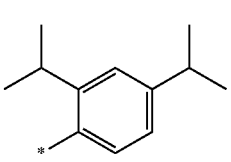

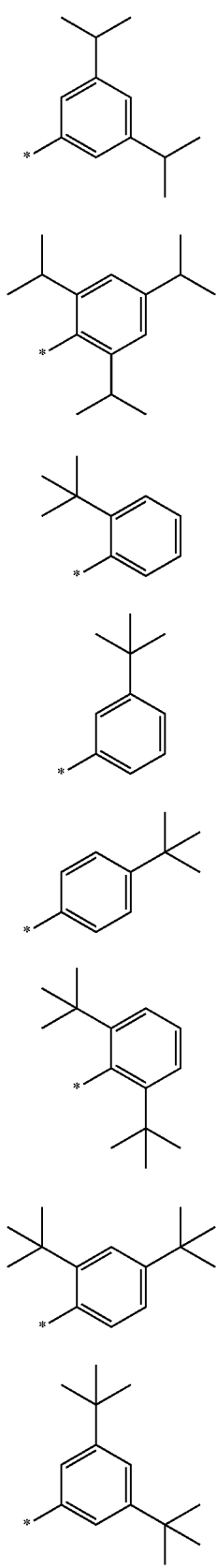
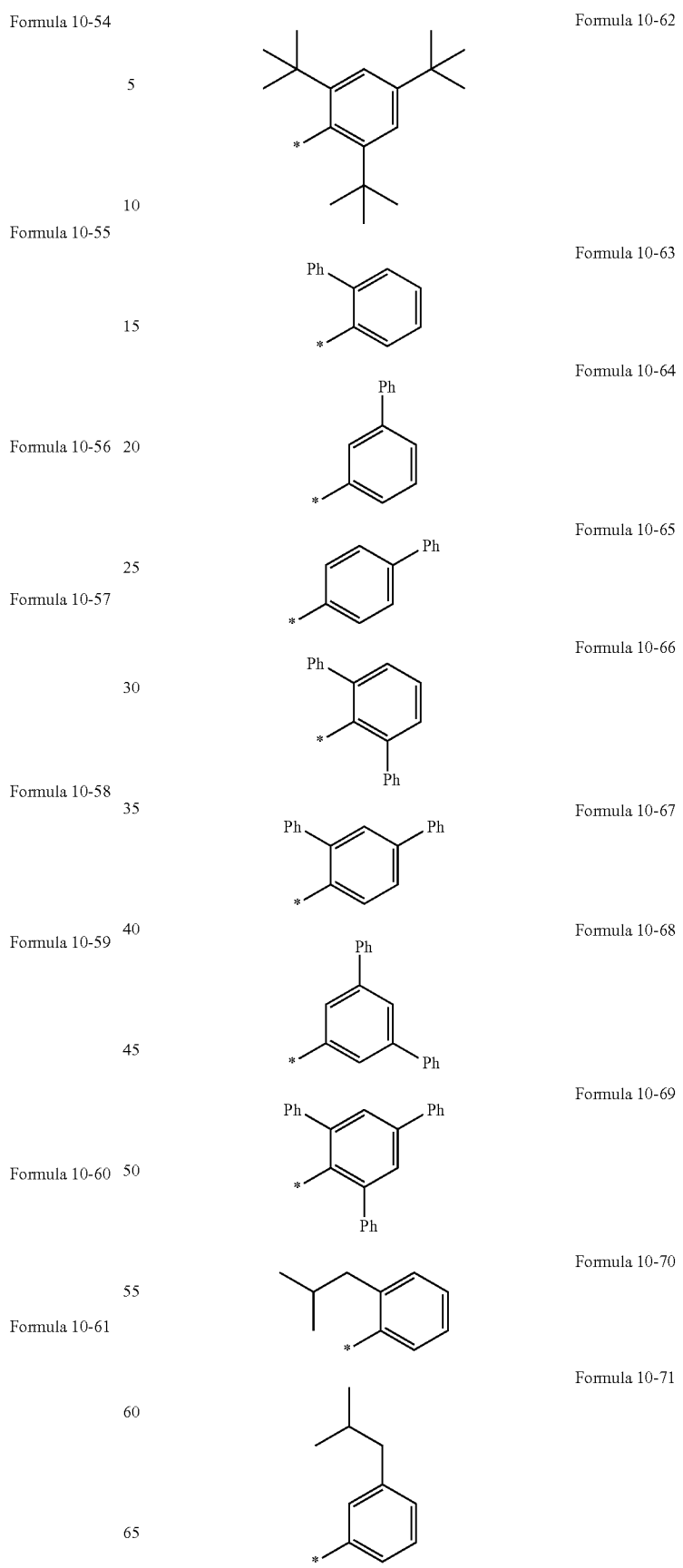

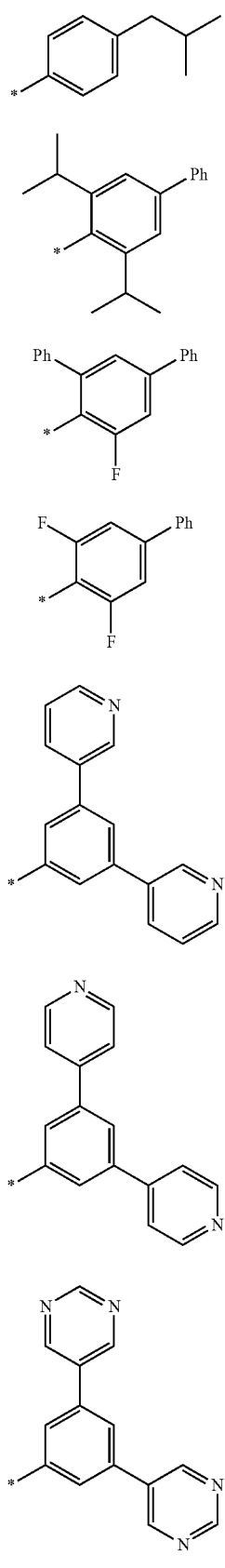
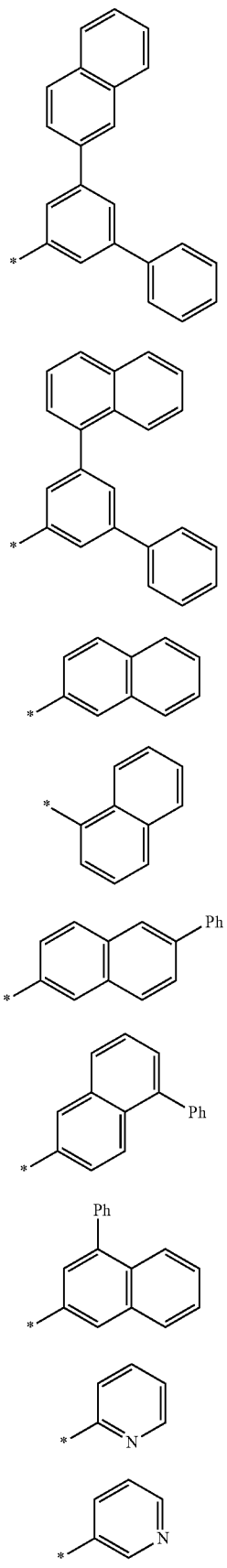

-continued
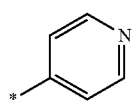
Formula 10-88
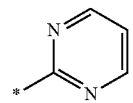
Formula 10-89
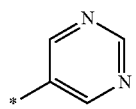
Formula 10-90
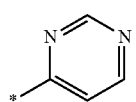
Formula 10-91
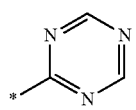
Formula 10-92
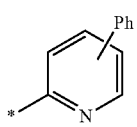
Formula 10-93
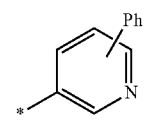
Formula 10-94
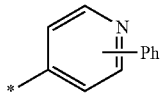
Formula 10-95
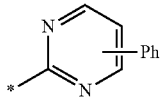
Formula 10-96
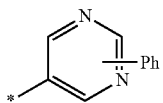
Formula 10-97
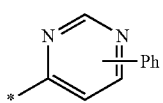
Formula 10-98
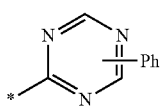
Formula 10-99
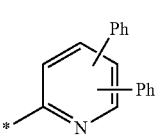
Formula 10-100
-continued
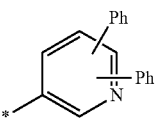
Formula 10-101
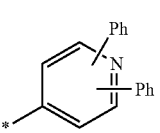
Formula 10-102
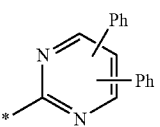
Formula 10-103
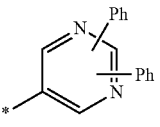
Formula 10-104
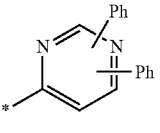
Formula 10-105
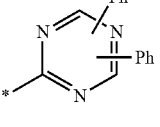
Formula 10-106
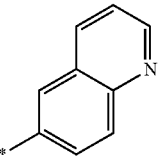
Formula 10-107
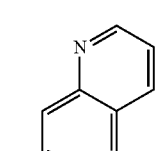
Formula 10-108
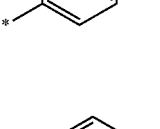
Formula 10-109
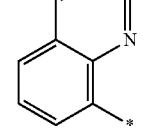
Formula 10-110
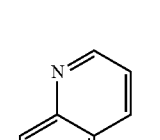

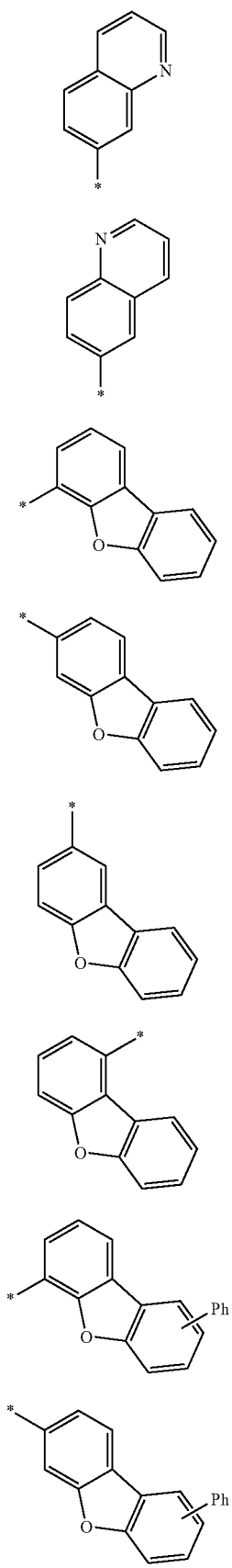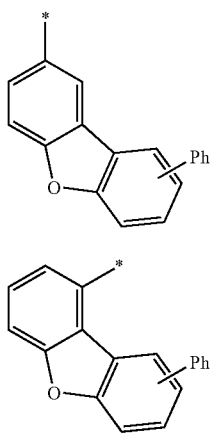
Formula 10-111
Formula 10-112
Formula 10-113
Formula 10-114
Formula 10-115
Formula 10-116
Formula 10-117
Formula 10-118
Formula 10-119
Formula 10-120
Formula 10-121
Formula 10-122
Formula 10-123
Formula 10-124
Formula 10-125
Formula 10-126

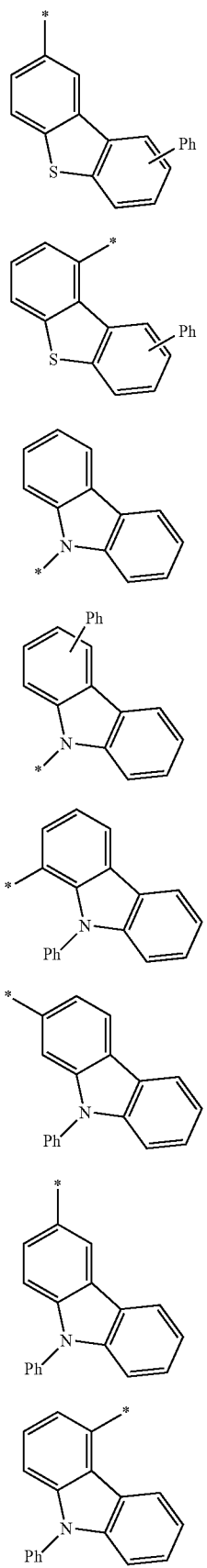
Formula 10-127
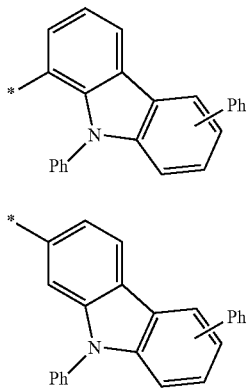
Formula 10-135
Formula 10-128
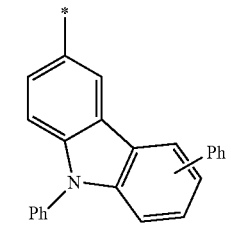
Formula 10-136
Formula 10-129
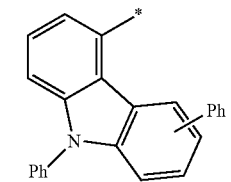
Formula 10-137
Formula 10-130
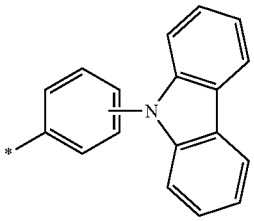
Formula 10-138
Formula 10-131
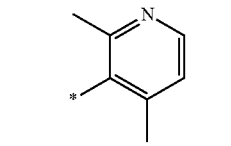
Formula 10-139
Formula 10-132

Formula 10-140
Formula 10-133
Formula 10-141
Formula 10-134
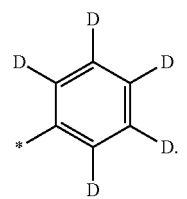
Formula 10-142

In Formulae 9-1 to 9-19 and 10-1 to 10-142, * indicates a binding site to a neighboring atom, the expression "Ph" indicates a phenyl group, and the expression "TMS" indicates a trimethylsilyl group.

In Formula 1, a1 to a4 respectively indicate numbers of $R_1$ to $R_4$, and may each independently be 0, 1, 2, 3, 4, or 5. When a1 is two or more, two or more groups $R_1$ may be identical to or different from each other. When a2 is two or more, two or more groups $R_2$ may be identical to or different from each other. When a3 is two or more, two or more groups $R_3$ may be identical to or different from each other. When a4 is two or more, two or more groups $R_4$ may be identical to or different from each other. However, embodiments of the present disclosure are not limited thereto.

In Formula 1, two selected from a1 number of groups $R_1$ may be optionally linked to form a substituted or unsubstituted $C_5$-$C_{30}$ carbocyclic group or a substituted or unsubstituted $C_1$-$C_{30}$ heterocyclic group, two selected from a2 number of groups $R_2$ may be optionally linked to form a substituted or unsubstituted $C_5$-$C_{30}$ carbocyclic group or a substituted or unsubstituted $C_1$-$C_{30}$ heterocyclic group, two selected from a3 number of groups $R_3$ may be optionally linked to form a substituted or unsubstituted $C_5$-$C_{30}$ carbocyclic group or a substituted or unsubstituted $C_1$-$C_{30}$ heterocyclic group, and two selected from a4 number of groups $R_4$ may be optionally linked to form a substituted or unsubstituted $C_5$-$C_{30}$ carbocyclic group or a substituted or unsubstituted $C_1$-$C_{30}$ heterocyclic group. In Formula 1, two or more selected from $R_1$ to $R_4$ may be optionally linked to form a substituted or unsubstituted $C_5$-$C_{30}$ carbocyclic group or a substituted or unsubstituted $C_1$-$C_{30}$ heterocyclic group, $R_3$ and at least one of $R_5$ and $R_6$ may be optionally linked to form a substituted or unsubstituted $C_5$-$C_{30}$ carbocyclic group or a substituted or unsubstituted $C_1$-$C_{30}$ heterocyclic group, and $R_1$, $R_2$, $R_3$ or $R_4$ and at least one of $R_5$ and $R_6$ may be optionally linked to form a substituted or unsubstituted $C_5$-$C_{30}$ carbocyclic group or a substituted or unsubstituted $C_1$-$C_{30}$ heterocyclic group.

For example, in Formula 1, i) a substituted or unsubstituted $C_5$-$C_{30}$ carbocyclic group or a substituted or unsubstituted $C_1$-$C_{30}$ heterocyclic group formed by optionally linking two selected from a1 number of groups $R_1$, ii) a substituted or unsubstituted $C_5$-$C_{30}$ carbocyclic group or a substituted or unsubstituted $C_1$-$C_{30}$ heterocyclic group formed by optionally linking two selected from a2 number of groups $R_2$, iii) a substituted or unsubstituted $C_5$-$C_{32}$ carbocyclic group or a substituted or unsubstituted $C_1$-$C_{30}$ heterocyclic group formed by optionally linking two selected from a3 number of groups $R_3$, iv) a substituted or unsubstituted $C_5$-$C_{30}$ carbocyclic group or a substituted or unsubstituted $C_1$-$C_{30}$ heterocyclic group formed by optionally linking two selected from a4 number of groups $R_4$, v) a substituted or unsubstituted $C_5$-$C_{30}$ carbocyclic group or a substituted or unsubstituted $C_1$-$C_{30}$ heterocyclic group formed by optionally linking two or more selected from $R_1$ to $R_4$, and vi) a substituted or unsubstituted $C_5$-$C_{30}$ carbocyclic group or a substituted or unsubstituted $C_1$-$C_{30}$ heterocyclic group formed by optionally linking at least one of $R_5$ and $R_6$ with $R_1$, $R_2$, $R_3$ or $R_4$ may each independently be selected from:

a pentadiene group, a cyclohexane group, a cycloheptane group, an adamantane group, a bicyclo-heptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group;

a pentadiene group, a cyclohexane group, a cycloheptane group, an adamantane group, a bicyclo-heptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group, each substituted with at least one $R_{1a}$, but embodiments of the present disclosure are not limited thereto.

$R_{1a}$ may be the same as the description provided herein in connection with $R_1$.

In an embodiment, in Formula 1, a moiety represented by

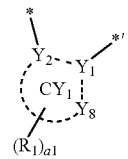

may be selected from groups represented by Formulae CY1-1 to CY1-16:

Formula CY1-1

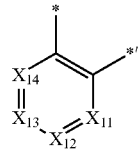

Formula CY1-2

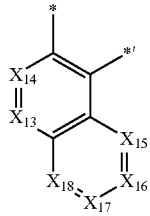

Formula CY1-3

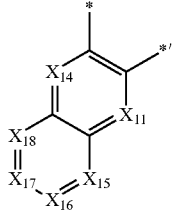

Formula CY1-4

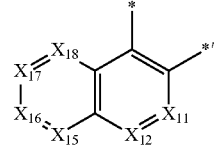

-continued

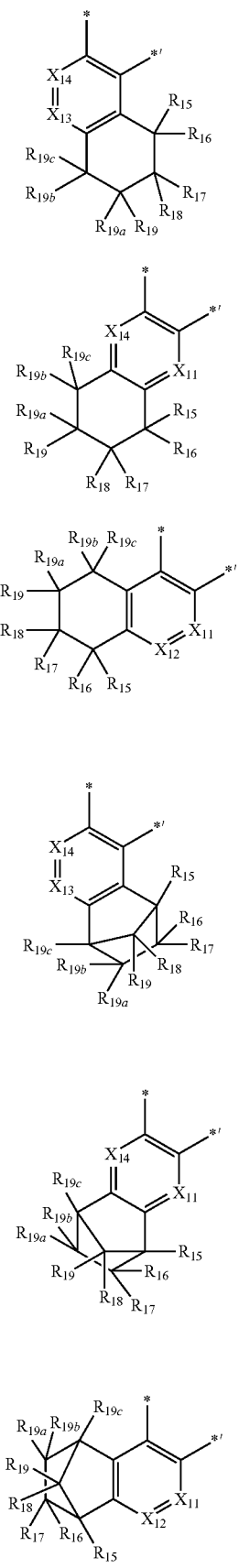

Formula CY1-5

Formula CY1-6

Formula CY1-7

Formula CY1-8

Formula CY1-9

Formula CY1-10

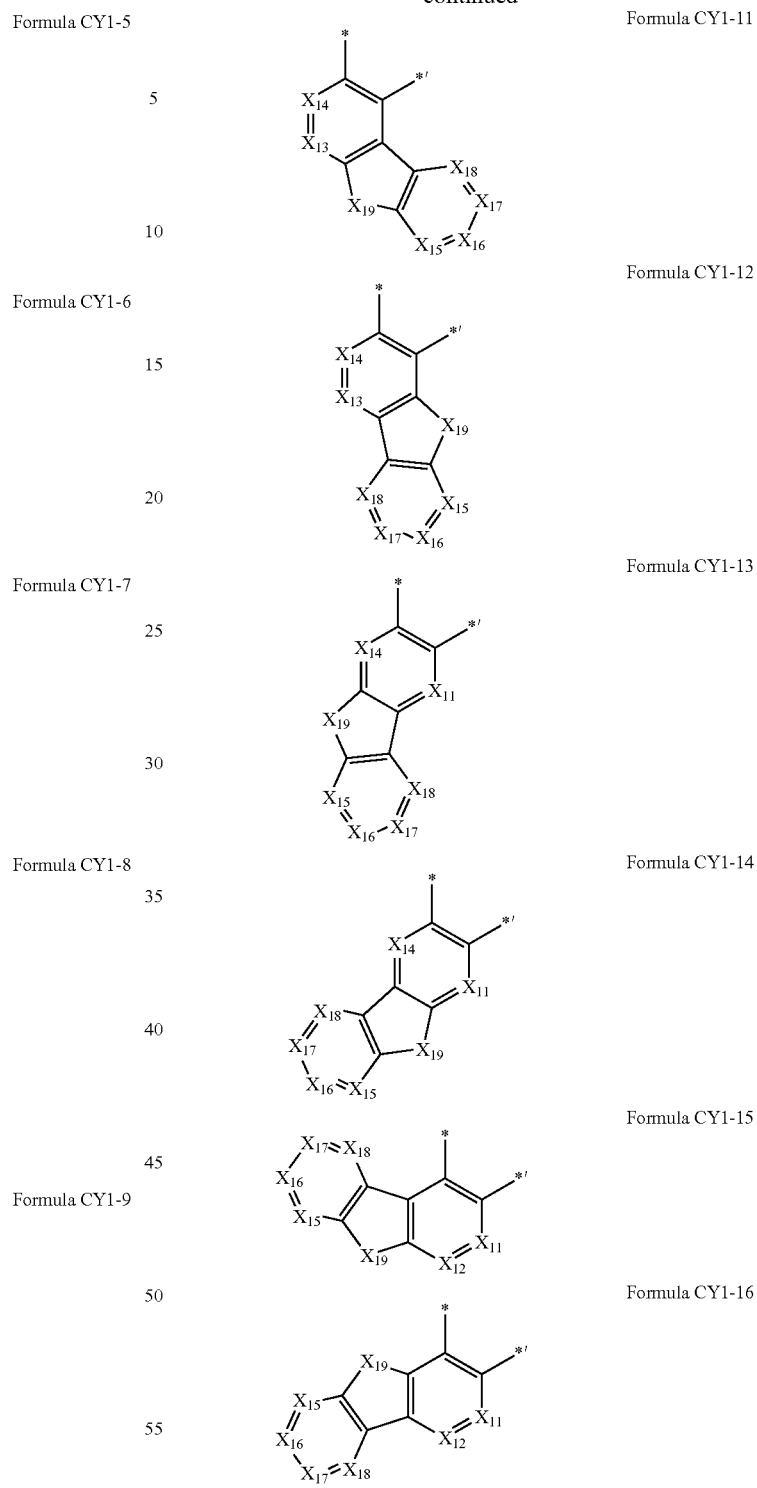

Formula CY1-11

Formula CY1-12

Formula CY1-13

Formula CY1-14

Formula CY1-15

Formula CY1-16

In Formulae CY1-1 to CY1-16, $X_{11}$ may be N or $C(R_{11})$, $X_{12}$ may be N or $C(R_{12})$, $X_{13}$ may be N or $CF(R_{13})$, $X_{14}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{18}$ may be N or $C(R_{16})$, $X_{17}$ may be N or $C(R_{17})$, and $X_{18}$ may be N or $C(R_{18})$, $X_{19}$ may be $C(R_{19a})(R_{19b})$, $N(R_{19})$, O, S, or $Si(R_{19a})(R_{19b})$, $R_{11}$ to $R_{19}$ and $R_{19a}$ to $R_{19c}$ may each independently be the same as described herein in connection with $R_1$, and

* and *' each independently indicate a binding site to a neighboring atom.

For example, in Formulae CY1-1 to CY1-16, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments of the present disclosure are not limited thereto.

In various embodiments, in Formula 1, a moiety represented by

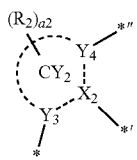

may be selected from groups represented by Formulae CY2-1 to CY2-4:

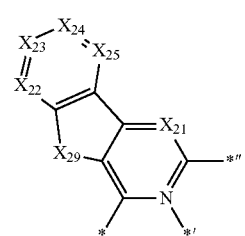

Formula CY2-1

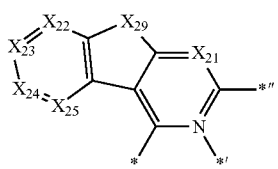

Formula CY2-2

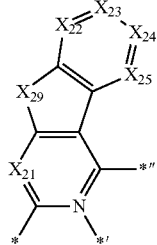

Formula CY2-3

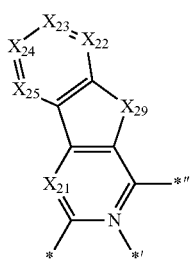

Formula CY2-4

In Formulae CY2-1 to CY2-4, $X_{21}$ may be N or $C(R_{21})$, $X_{22}$ may be N or $C(R_{22})$, $X_{23}$ may be N or $C(R_{23})$, $X_{24}$ may be N or $C(R_{24})$, and $X_{25}$ may be N or $C(R_{25})$, $X_{29}$ may be $C(R_{29a})(R_{29b})$, $N(R_{29})$, O, S, or $Si(R_{29a})(R_{29b})$, $R_{21}$ to $R_{25}$, $R_{29}$, and $R_{29a}$ to $R_{29c}$ may each independently be the same as described herein in connection with $R_2$, and

*, *', and *'' each independently indicate a binding site to a neighboring atom.

For example, in Formulae CY2-1 to CY2-4, $X_{21}$ may be N or $C(R_{21})$, $X_{22}$ may be N or $C(R_{22})$, $X_{23}$ may be $C(R_{23})$, $X_{24}$ may be $C(R_{24})$, and $X_{25}$ may be $C(R_{25})$, but embodiments of the present disclosure are not limited thereto.

In various embodiments, in Formula 1, a moiety represented by

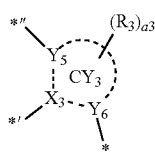

may be selected from groups represented by Formulae CY3-1 to CY3-22:

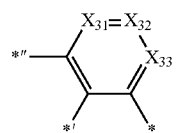

Formula CY3-1

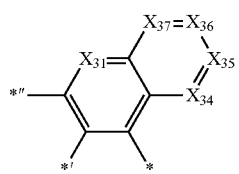

Formula CY3-2

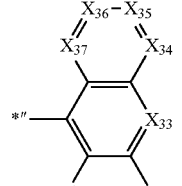

Formula CY3-3

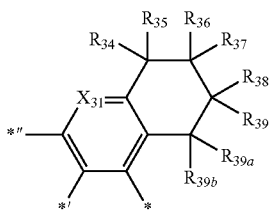

Formula CY3-4

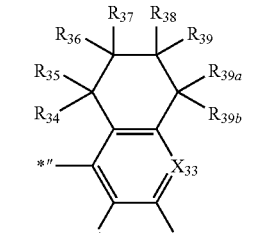

Formula CY3-5

Formula CY3-6
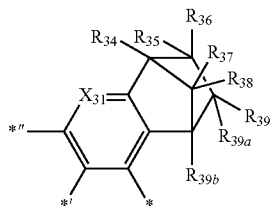
Formula CY3-7
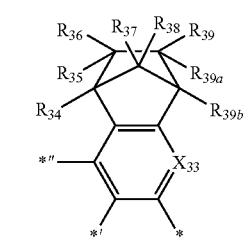
Formula CY3-8
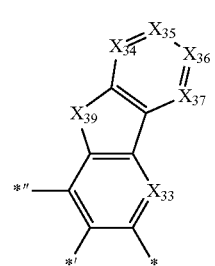
Formula CY3-9
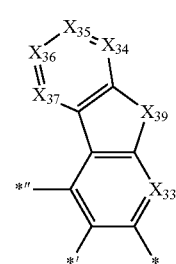
Formula CY3-10
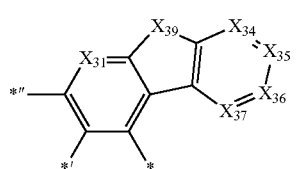
Formula CY3-11
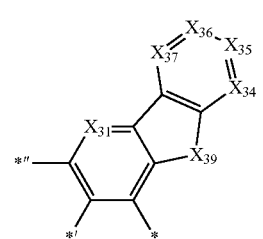
Formula CY3-12
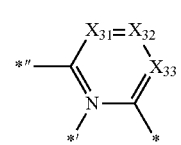
Formula CY3-13
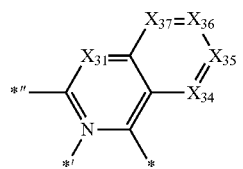
Formula CY3-14
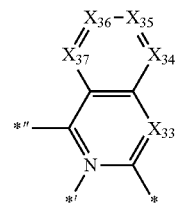
Formula CY3-15
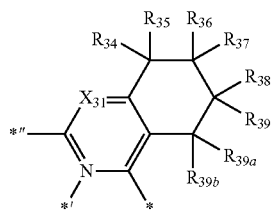
Formula CY3-16
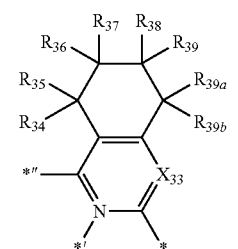
Formula CY3-17
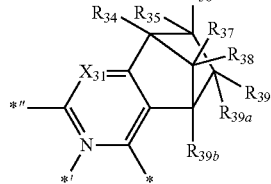
Formula CY3-18
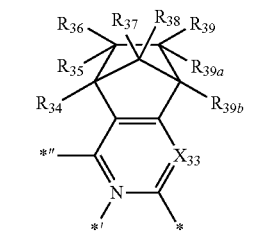
Formula CY3-19
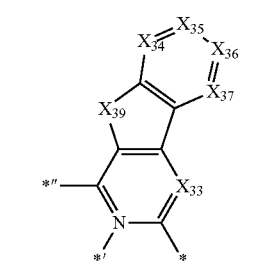

-continued

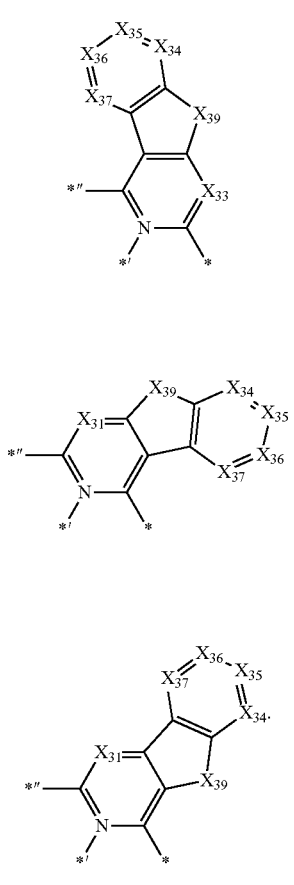

Formula CY3-20

Formula CY3-21

Formula CY3-22

In Formulae CY3-1 to CY3-22, $X_{31}$ may be N or $C(R_{31})$, $X_{32}$ may be N or $C(R_{32})$, $X_{33}$ may be N or $C(R_{33})$, $X_{34}$ may be N or $C(R_{34})$, $X_{35}$ may be N or $C(R_{35})$, $X_{36}$ may be N or $C(R_{36})$, and $X_{37}$ may be N or $C(R_{37})$, $X_{39}$ may be $C(R_{39a})(R_{39b})$, $N(R_{39})$, O, S, or $Si(R_{39a})(R_{39b})$, $R_{31}$ to $R_{39}$ and $R_{39a}$ to $R_{39b}$ may each independently be the same as described herein in connection with $R_3$, and

*, *', and *" each independently indicate a binding site to a neighboring atom.

For example, in Formulae CY3-1 to CY3-22, $X_{31}$ may be $C(R_{31})$, $X_{32}$ may be $C(R_{32})$, $X_{33}$ may be $C(R_{33})$, $X_{34}$ may be $C(R_{34})$, $X_{35}$ may be $C(R_{35})$, $X_{36}$ may be $C(R_{36})$, and $X_{37}$ may be $C(R_{37})$, but embodiments of the present disclosure are not limited thereto.

In various embodiments, in Formula 1, a moiety represented by

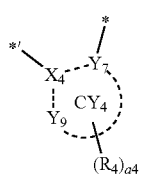

may be selected from groups represented by Formulae CY4-1 to CY4-8:

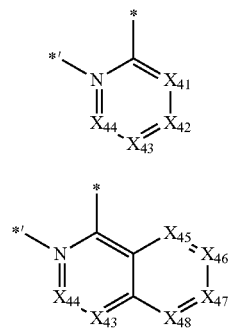

Formula CY4-1

Formula CY4-2

Formula CY4-3

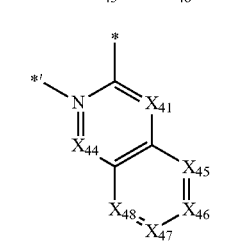

Formula CY4-4

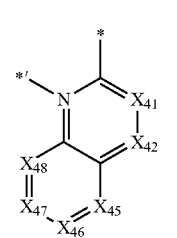

Formula CY4-5

Formula CY4-6

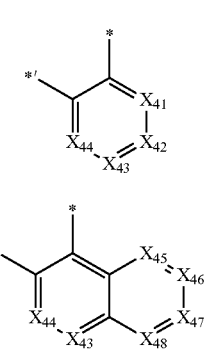

Formula CY4-7

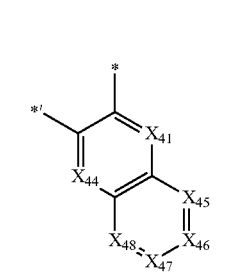

Formula CY4-8

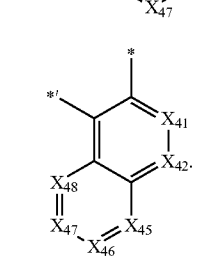

In Formulae CY4-1 to CY4-8, $X_{41}$ may be N or $C(R_{41})$, $X_{42}$ may be N or $C(R_{42})$, $X_{43}$ may be N or $C(R_{43})$, $X_{44}$ may be N or $C(R_{44})$, $X_{45}$ may be N or $C(R_{45})$, $X_{46}$ may be N or $C(R_{46})$, $X_{47}$ may be N or $C(R_{47})$, and $X_{48}$ may be N or $C(R_{48})$, $R_{41}$ to $R_{48}$ may each independently be the same as described herein in connection with $R_4$, and

* and *' each independently indicate a binding site to a neighboring atom.

For example, in Formulae CY4-1 to CY4-8, $X_{41}$ may be $C(R_{41})$, $X_{42}$ may be $C(R_{42})$, $X_{43}$ may be $C(R_{43})$, $X_{44}$ may be $C(R_{44})$, $X_{45}$ may be $C(R_{45})$, $X_{46}$ may be $C(R_{46})$, $X_{47}$ may be $C(R_{47})$, and $X_{48}$ may be $C(R_{48})$, but embodiments of the present disclosure are not limited thereto.

In various embodiments, in Formula 1, a moiety represented by

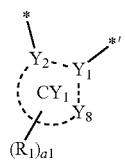

may be selected from groups represented by Formulae CY1-1 and CY1-5 to CY1-10, a moiety represented by

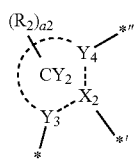

may be selected from groups represented by Formulae CY2-1 to CY2-4, a moiety represented by

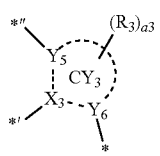

may be selected from groups represented by Formulae CY3-1 and CY3-4 to CY3-11, and a moiety represented by

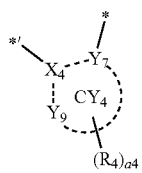

may be a group represented by Formula CY4-1, but embodiments of the present disclosure are not limited thereto.

In various embodiments, in Formula 1, $CY_1$ may be selected from groups represented by Formulae CY1(1) to CY1(9), $CY_2$ may be selected from groups represented by Formulae CY2-1 to CY2-4, $CY_3$ may be selected from groups represented by Formulae CY3(1) to CY3(14), and $CY_4$ may be selected from groups represented by Formulae CY4(1) to CY4(9), but embodiments of the present disclosure are not limited thereto:

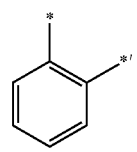

Formula CY1(1)

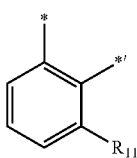

Formula CY1(2)

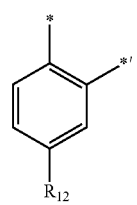

Formula CY1(3)

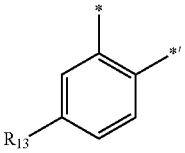

Formula CY1(4)

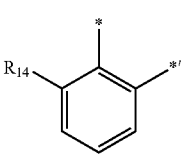

Formula CY1(5)

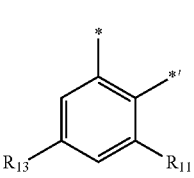

Formula CY1(6)

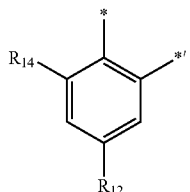

Formula CY1(7)

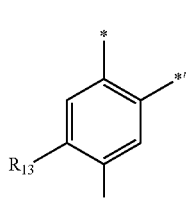

Formula CY1(8)

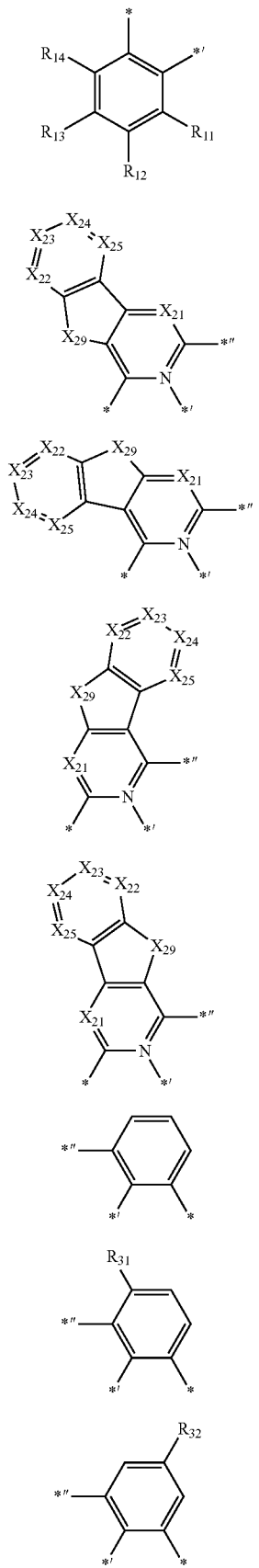
Formula CY1(9)
Formula CY2-1
Formula CY2-2
Formula CY2-3
Formula CY2-4
Formula CY3(1)
Formula CY3(2)
Formula CY3(3)
Formula CY3(4)
Formula CY3(5)
Formula CY3(6)
Formula CY3(7)
Formula CY3(8)
Formula CY3(9)
Formula CY3(10)
Formula CY3(11)

In Formulae CY1(1) to CY1(9), $R_{11}$ to $R_{14}$ may each independently be the same as described herein in connection with $R_1$, wherein none of $R_{11}$ to $R_{14}$ may be hydrogen, in Formulae CY2-1 to CY2-4, $X_{21}$ may be N or $C(R_{21})$, $X_{22}$ may be N or $C(R_{22})$, $X_{23}$ may be $C(R_{23})$, $X_{24}$ may be $C(R_{24})$, and $X_{25}$ may be $C(R_{25})$, $X_{29}$ may be $C(R_{29a})(R_{29b})$, $N(R_{29})$, O, S, or $Si(R_{29a})(R_{29b})$, $R_{21}$ to $R_{25}$, $R_{29}$, and $R_{29a}$ to $R_{29c}$ may each independently be the same as described herein in connection with $R_2$, in Formulae CY3(1) to CY3(14), $X_{39}$ may be $C(R_{39a})(R_{39b})$, $N(R_{39})$, O, S, or $Si(R_{39a})(R_{39b})$, and $R_{31}$ to $R_{33}$, $R_{39}$, $R_{39a}$, and $R_{39b}$ may each independently be the same as described herein in connection with $R_3$, wherein none of $R_{31}$ to $R_{33}$ may be hydrogen, in Formulae CY4(1) to CY4(9), $R_{41}$ to $R_{44}$ may each independently be the same as described herein in connection with $R_4$, wherein none of $R_{41}$ to $R_{44}$ may be hydrogen, in Formulae CY(1) to CY(9), CY2-1 to CY2-4, CY3(1) to CY3(14), and CY4(1) to CY4(9), *, *', and *" each independently indicate a binding site to a neighboring atom.

In various embodiments, the organometallic compound represented by Formula 1 may be represented by one selected from Formulae 1-1 to 1-4:

Formula 1-1

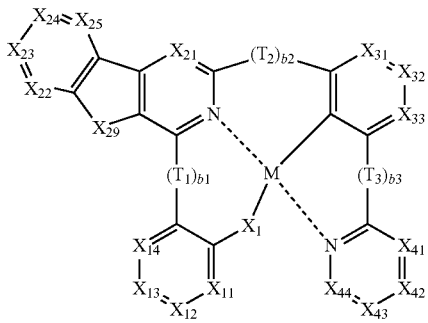

Formula 1-2

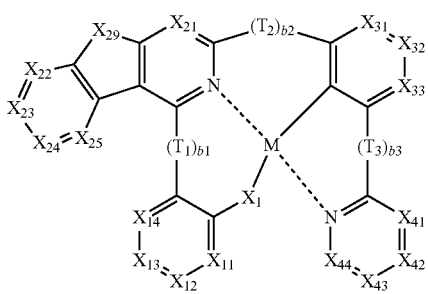

Formula 1-3

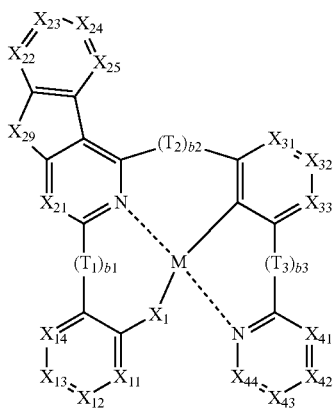

Formula 1-4

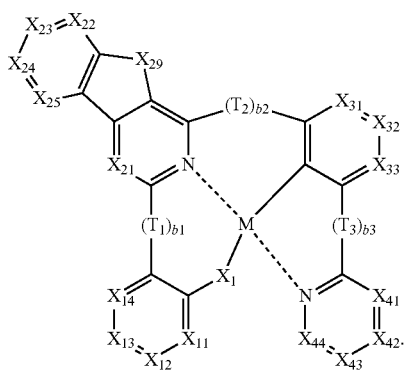

In Formulae 1-1 to 1-4,

M, $X_1$, $T_1$ to $T_3$, and b1 to b3 may be the same as those described herein, $X_{11}$ may be N or $C(R_{11})$, $X_{12}$ may be N or $C(R_{12})$, $X_{13}$ may be N or $C(R_{13})$, and $X_{14}$ may be N or $C(R_{14})$, $X_{21}$ may be N or $C(R_{21})$, $X_{22}$ may be N or $C(R_{22})$, $X_{23}$ may be N or $C(R_{23})$, $X_{24}$ may be N or $C(R_{24})$, and $X_{25}$ may be N or $C(R_{25})$, $X_{31}$ may be N or $C(R_{31})$, $X_{32}$ may be N or $C(R_{32})$, and $X_{33}$ may be N or $C(R_{33})$, $X_{41}$ may be N or $C(R_{41})$, $X_{42}$ may be N or $C(R_{42})$, $X_{43}$ may be N or $C(R_{43})$, and $X_{44}$ may be N or $C(R_{44})$, $R_{11}$ to $R_{14}$ may each independently be the same as described herein in connection with $R_1$, wherein two selected from $R_{11}$ to $R_{14}$ may be optionally linked to form a substituted or unsubstituted $C_5$-$C_{30}$ carbocyclic group or a substituted or unsubstituted $C_1$-$C_{30}$ heterocyclic group, $R_{21}$ to $R_{25}$ may each independently be the same as described herein in connection with $R_2$, wherein two selected from $R_{21}$ to $R_{25}$ may be optionally linked to form a substituted or unsubstituted $C_5$-$C_{30}$ carbocyclic group or a substituted or unsubstituted $C_1$-$C_{30}$ heterocyclic group, $R_{31}$ to $R_{33}$ may each independently be the same as described herein in connection with $R_3$, wherein two selected from $R_{31}$ to $R_{33}$ may be optionally linked to form a substituted or unsubstituted $C_5$-$C_{30}$ carbocyclic group or a substituted or unsubstituted $C_1$-$C_{30}$ heterocyclic group, $R_{41}$ to $R_{44}$ may each independently be the same as described herein in connection with $R_4$, wherein two selected from $R_{41}$ to $R_{44}$ may be optionally linked to form a substituted or unsubstituted $C_5$-$C_{30}$ carbocyclic group or a substituted or unsubstituted $C_1$-$C_{30}$ heterocyclic group and wherein two selected from $R_{11}$ to $R_{14}$, $R_{21}$ to $R_{25}$, $R_{31}$ to $R_{33}$ and $R_{41}$ to $R_{44}$ may be optionally linked to form a substituted or unsubstituted $C_5$-$C_{30}$ carbocyclic group or a substituted or unsubstituted $C_1$-$C_{30}$ heterocyclic group.

For example, in Formulae 1-1 to 1-4, $X_{11}$ may be $C(R_{11})$, $X_{12}$ may be $C(R_{12})$, $X_{13}$ may be $C(R_{13})$, $X_{14}$ may be $C(R_{14})$, $X_{21}$ may be N or $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{31}$ may be $C(R_{31})$, $X_{32}$ may be $C(R_{32})$, $X_{33}$ may be $C(R_{33})$, $X_{41}$ may be $C(R_{41})$, $X_{42}$ may be $C(R_{42})$, $X_{43}$ may be $C(R_{43})$, and $X_{44}$ may be $C(R_{44})$, but embodiments of the present disclosure are not limited thereto.

In an embodiment, in Formulae 1-1 to 1-4, i) a substituted or unsubstituted $C_5$-$C_{30}$ carbocyclic group or a substituted or unsubstituted $C_1$-$C_{30}$ heterocyclic group, formed by optionally linking two selected from $R_{11}$ to $R_{14}$, ii) a substituted or unsubstituted $C_5$-$C_{30}$ carbocyclic group or a substituted or unsubstituted $C_1$-$C_{30}$ heterocyclic group, formed by optionally linking two selected from $R_{21}$ to $R_{25}$, iii) a substituted or unsubstituted $C_5$-$C_{30}$ carbocyclic group or a substituted or unsubstituted $C_1$-$C_{30}$ heterocyclic group, formed by optionally linking two selected from $R_{31}$ to $R_{33}$, iv) a substituted or unsubstituted $C_5$-$C_{30}$ carbocyclic group or a substituted or unsubstituted $C_1$-$C_{30}$ heterocyclic group, formed by optionally linking two selected from $R_{41}$ to $R_{44}$, and v) a substituted or unsubstituted $C_5$-$C_{30}$ carbocyclic group or a substituted or unsubstituted $C_1$-$C_{30}$ heterocyclic group, formed by optionally linking two selected from $R_{11}$ to $R_{14}$, $R_{21}$ to $R_{25}$, $R_{31}$ to $R_{33}$ and $R_{41}$ to $R_{44}$ may each independently be selected from:

a pentadiene group, a cyclohexane group, a cycloheptane group, an adamantane group, a bicyclo-heptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group;

a pentadiene group, a cyclohexane group, a cycloheptane group, an adamantane group, a bicyclo-heptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group, each substituted with at least one $R_{1a}$, but embodiments of the present disclosure are not limited thereto.

$R_{1a}$ may be the same as described herein in connection with $R_1$.

In various embodiments, in Formulae 1-1 to 1-4, $T_3$ may be *—$N(R_5)$—*', b3 may be 1, $X_{41}$ may be $C(R_{41})$, and $R_5$ and $R_{41}$ may be linked via a single bond (for example, see Formula 1(1) below).

In various embodiments, the organometallic compound represented by Formula 1 may be represented by one of Formulae 1(1) and 1(2):

Formula 1(1)

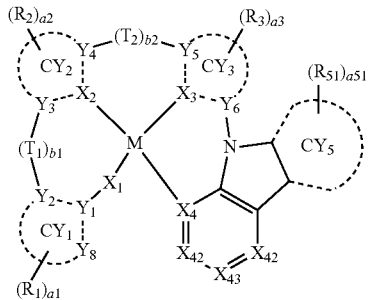

Formula 1(2)

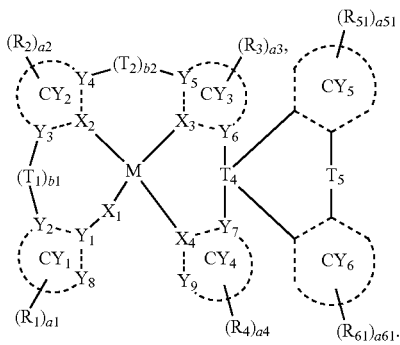

In Formulae 1(1) and 1(2),

M, $X_1$ to $X_4$, $Y_1$ to $Y_9$, CY1 to CY4, $T_1$ to $T_3$, b1 to b3, $R_1$ to $R_4$, and a1 to a4 may be the same as those described herein, $X_{42}$ may be N or $C(R_{42})$, $X_{43}$ may be N or $C(R_{43})$, and $X_{44}$ may be N or $C(R_{44})$, $R_{42}$ to $R_{44}$ may each independently be the same as described herein in connection with $R_4$, wherein two selected from $R_{42}$ to $R_{44}$ may be optionally linked to form a substituted or unsubstituted $C_5$-$C_{30}$ carbocyclic group or a substituted or unsubstituted $C_1$-$C_{30}$ heterocyclic group, $CY_5$ and CY6 may each independently be a $C_5$-$C_{30}$ carbocyclic group or a substituted or unsubstituted $C_1$-$C_{30}$ heterocyclic group, $R_{51}$ and $R_{61}$ may each independently be the same as described herein in connection with $R_1$, a51 and a61 may each independently be 0, 1, 2, or 3, $T_4$ may be C, Si, or Ge, $T_5$ may be selected from a single bond, *—$N[(L_7)_{a7}$-$(R_7)]$—*', *—$B(R_7)$—*', *—$P(R_7)$—*', *—$C(R_7)(R_8)$—*', *—$Si(R_7)(R_8)$—*', *—$Ge(R_7)(R_8)$—*', *—S—*', *—Se—*', *—O—*', *—$C(=O)$—*', *—$S(=O)$—*', *—$S(=O)_2$—*', *—$C(R_7)$=*', *=$C(R_7)$—*', *—$C(R_7)$=$C(R_8)$—*', *—$C(=S)$—*', and *—C≡C—*', $R_7$ and $R_8$ may each independently be the same as described herein in connection with $R_5$, $L_7$ may be the same as described herein in connection with $L_5$, a7 may be the same as described herein in connection with a5, and

* and *' may each independently be a binding site to a neighboring atom.

For example, in Formula 1(1), $X_{42}$ may be $C(R_{42})$, $X_{43}$ may be $C(R_{43})$, and $X_{44}$ may be $C(R_{44})$, but embodiments of the present disclosure are not limited thereto.

In an embodiment, i) a substituted or unsubstituted $C_5$-$C_{30}$ carbocyclic group or a substituted or unsubstituted $C_1$-$C_{30}$ heterocyclic group, formed by optionally linking two selected from $R_{42}$ to $R_{44}$, ii) $CY_5$, and iii) $CY_6$ may each independently be selected from:

a pentadiene group, a cyclohexane group, a cycloheptane group, an adamantane group, a bicyclo-heptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group;

a pentadiene group, a cyclohexane group, a cycloheptane group, an adamantane group, a bicyclo-heptane group, a bicyclo-octane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, an indole group, a benzosilole group, an azabenzothiophene group, an azabenzofuran group, an azaindene group, an azaindole group, and an azabenzosilole group, each substituted with at least one $R_{1a}$, but embodiments of the present disclosure are not limited thereto.

$R_{1a}$ may be the same as described herein in connection with $R_1$.

In an embodiment, the organometallic compound may be selected from Compounds 1 to 240, but embodiments of the present disclosure are not limited thereto:

-continued
| | |
|---|---|
| 1 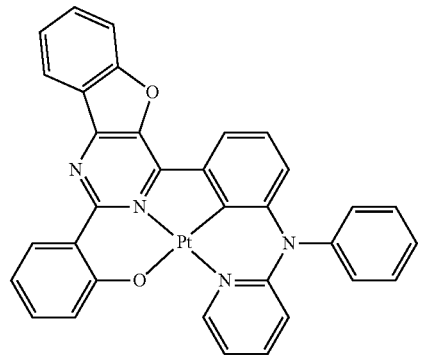 | 5 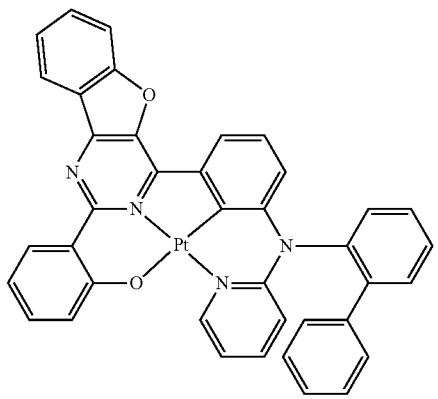 |
| 2 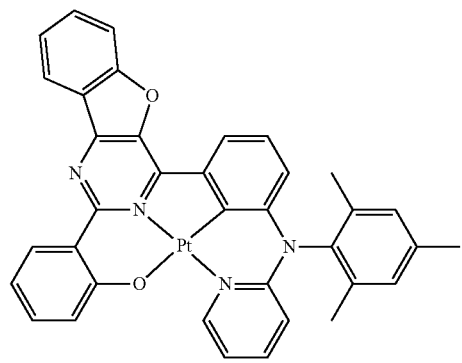 | 6 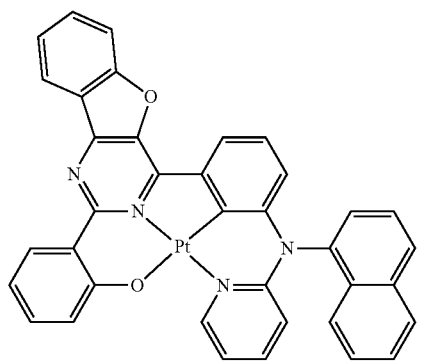 |
| 3 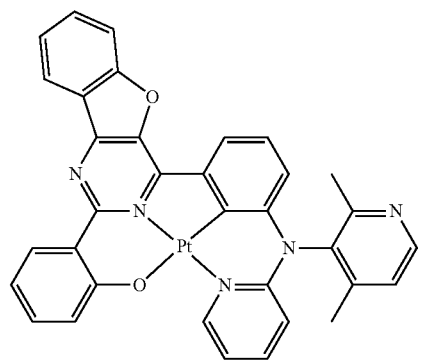 | 7 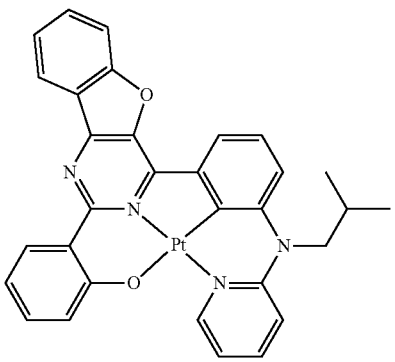 |
| 4 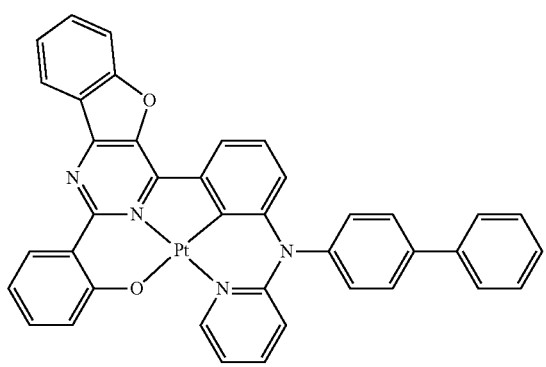 | 8 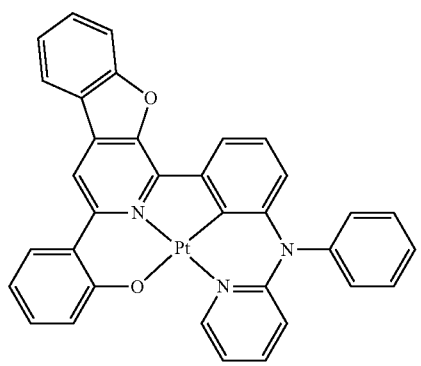 |

9
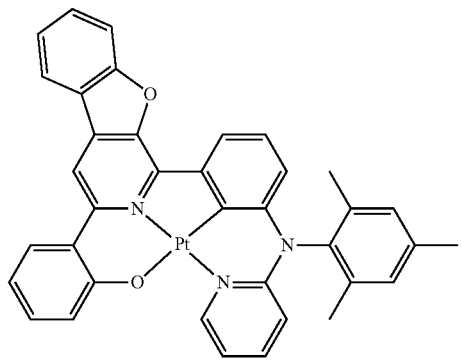
10
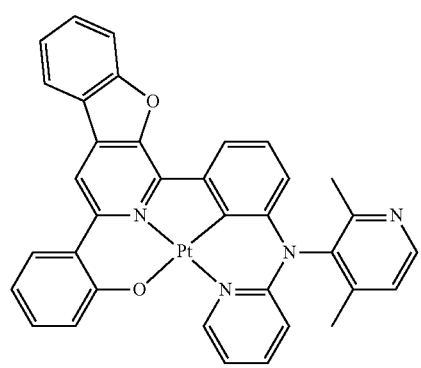
11
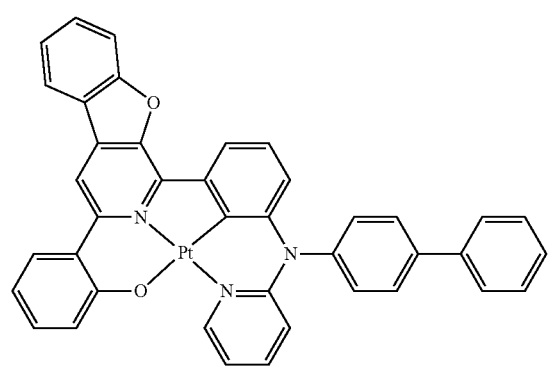
12
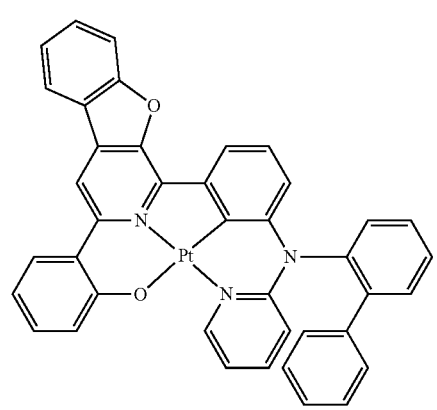
13
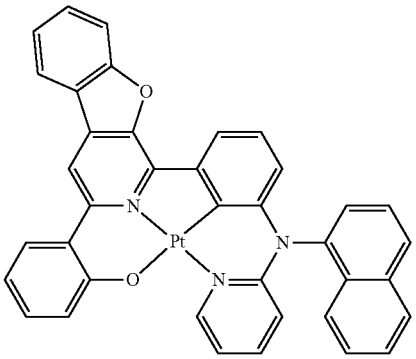
14
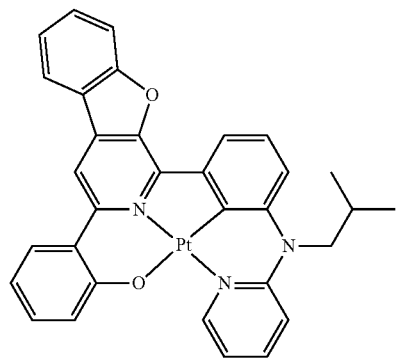
15
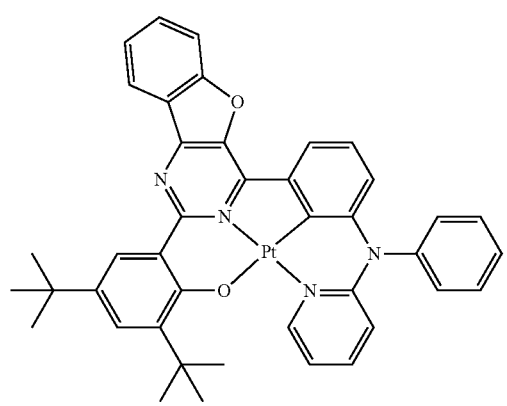
16
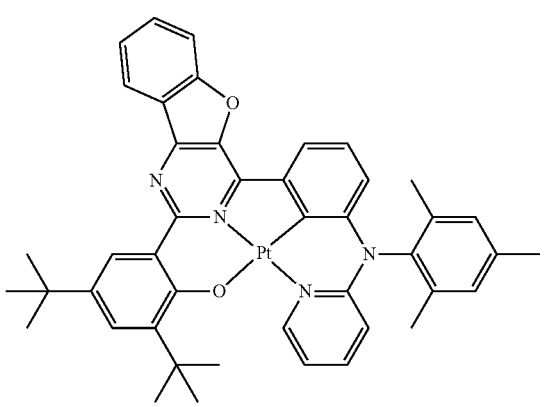

17
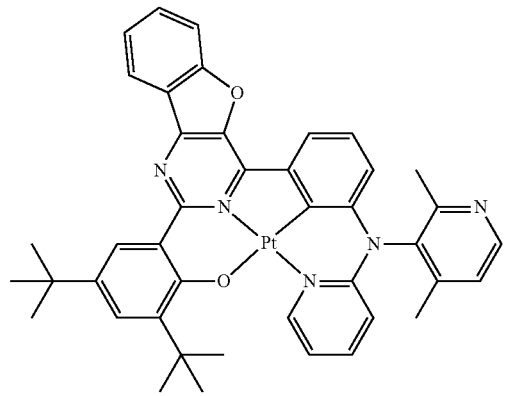
18
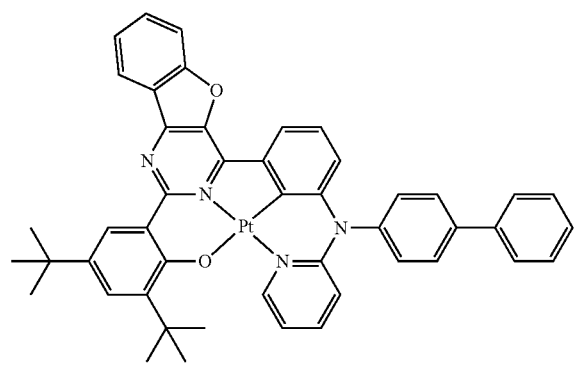
19
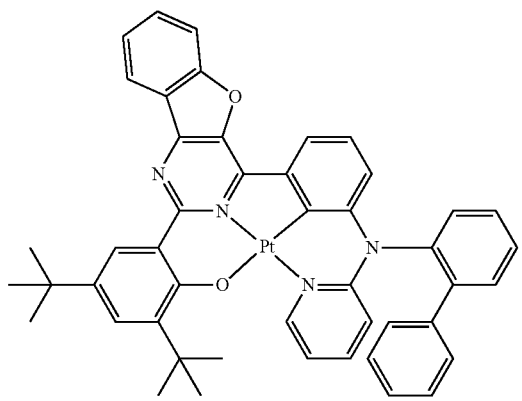
20
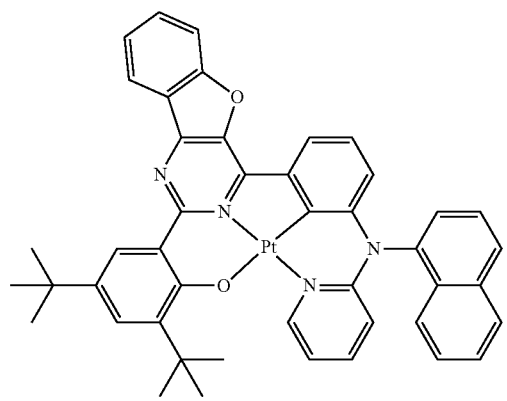
21
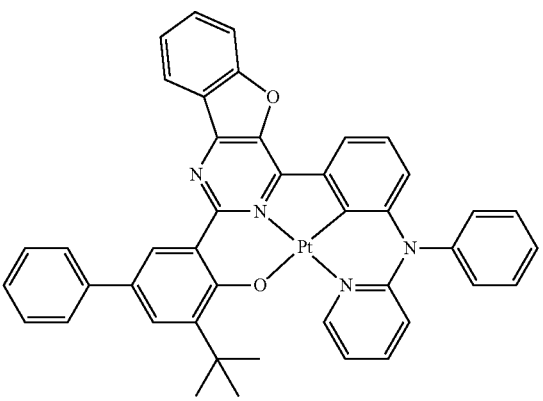
22
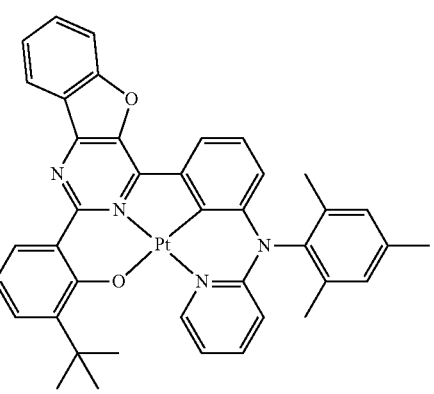
23
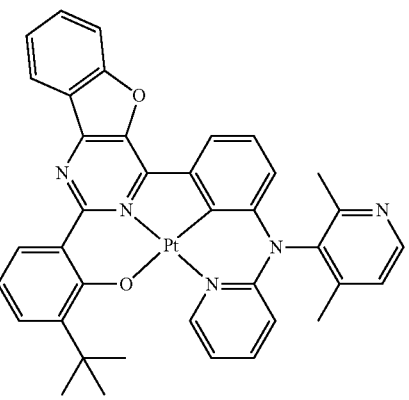
24
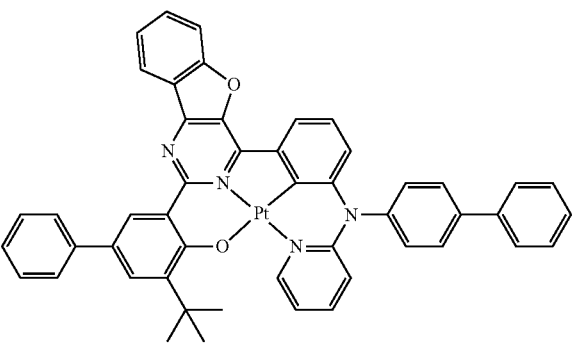

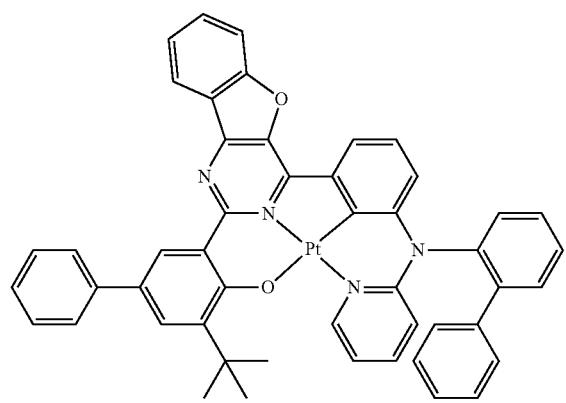
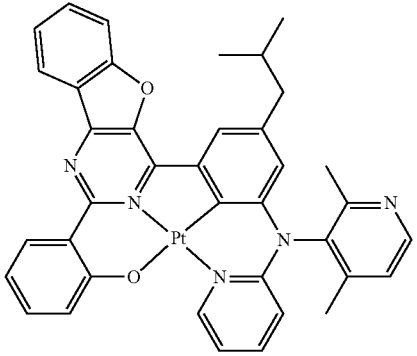
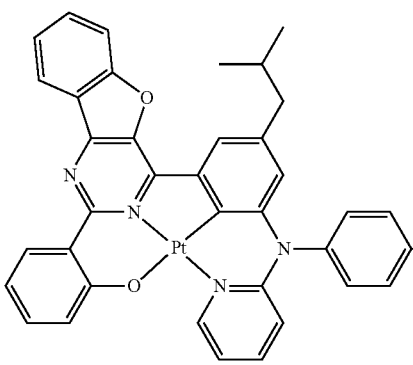
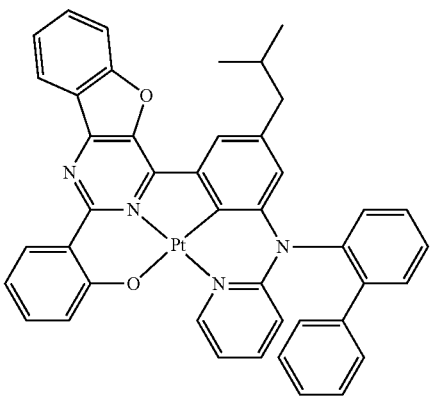
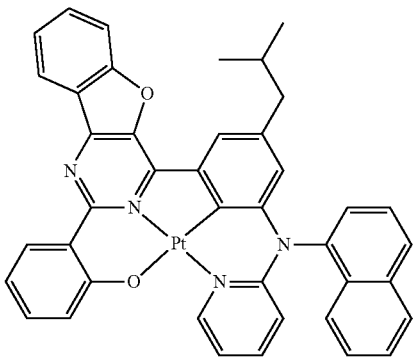

-continued
33
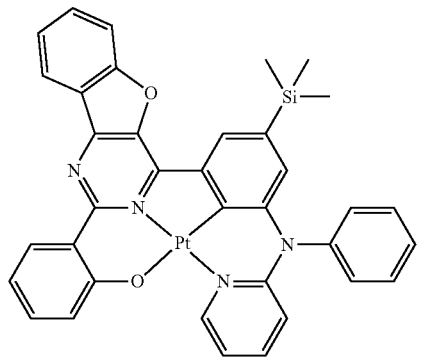
34
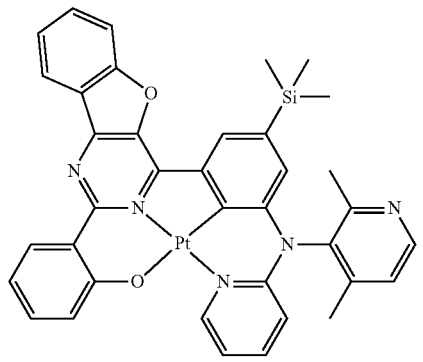
35
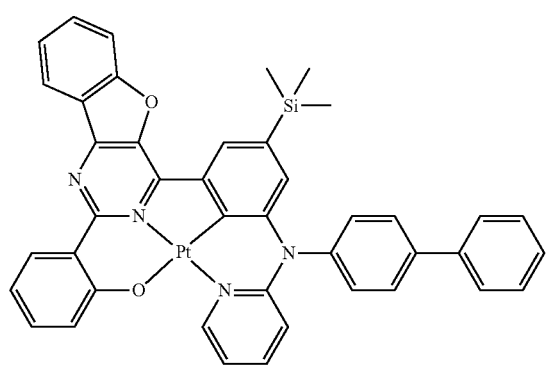
36
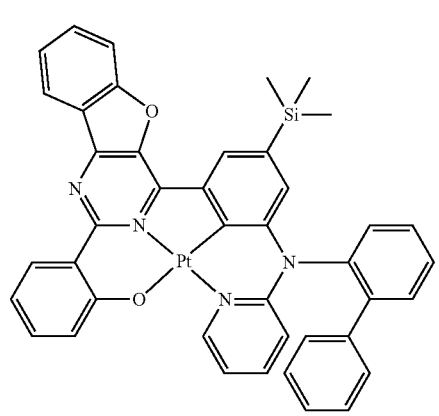
-continued
37
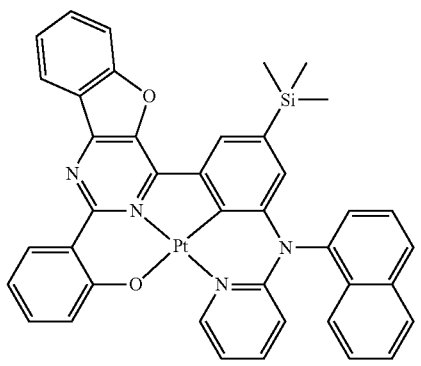
38
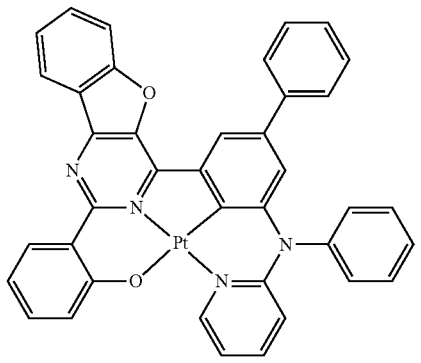
39
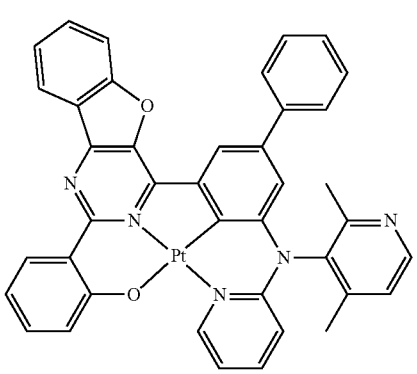
40
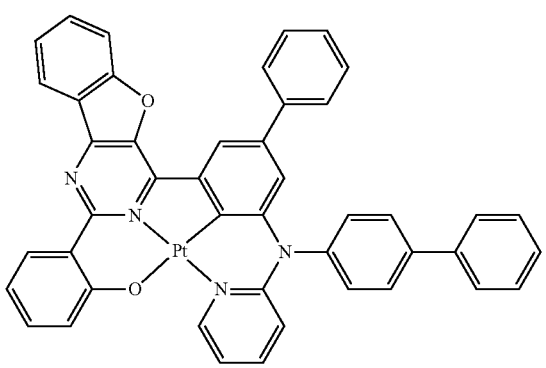

41
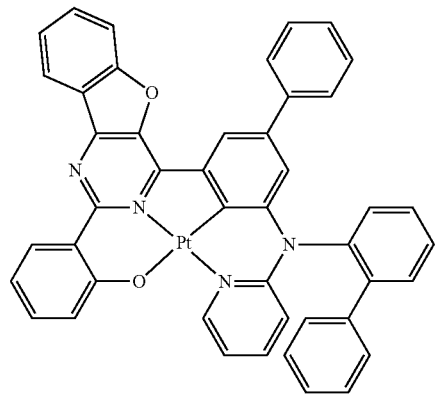
42
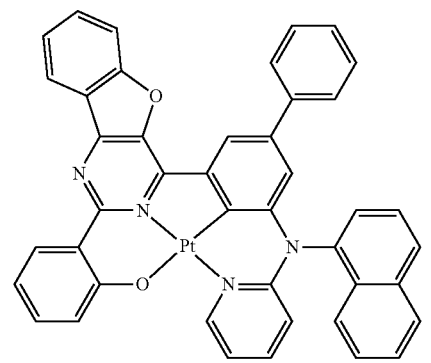
43
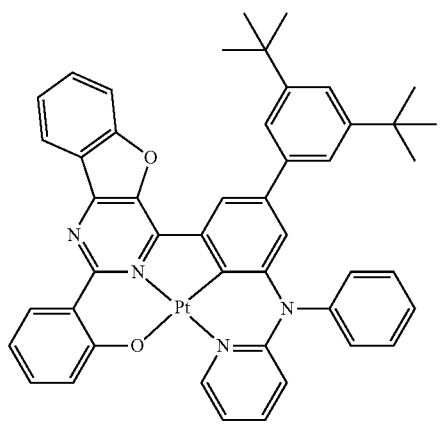
44
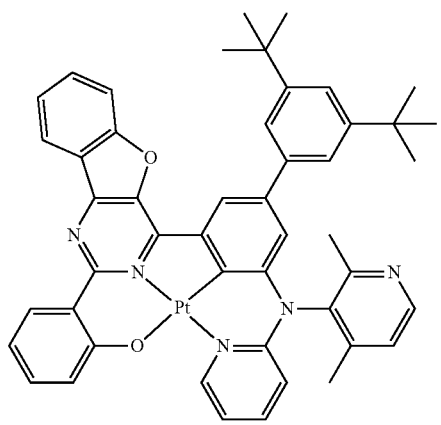
45
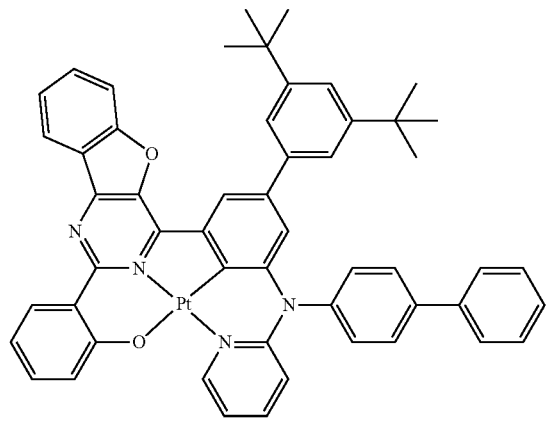
46
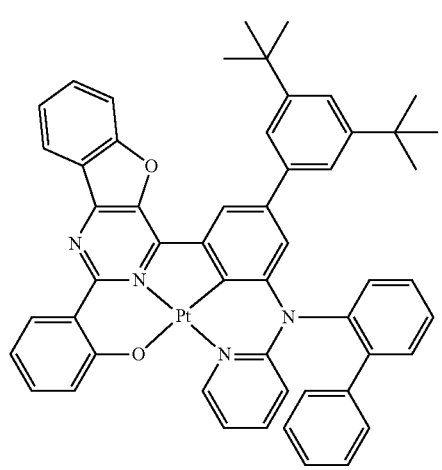
47
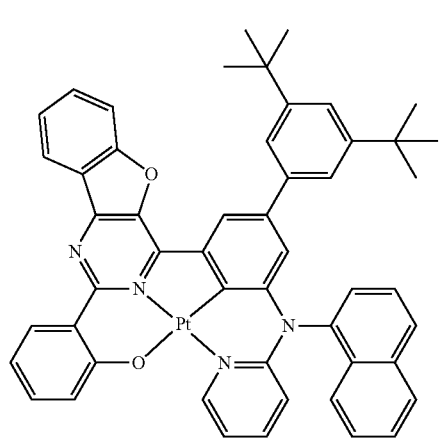

48
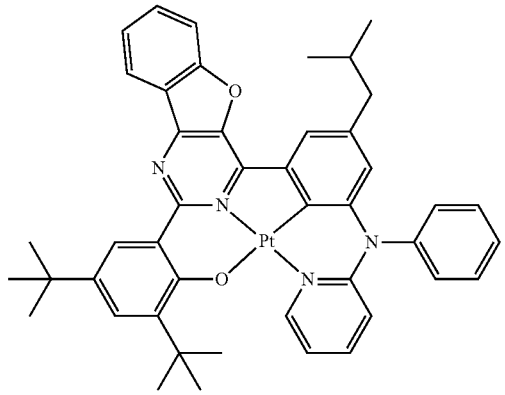
49
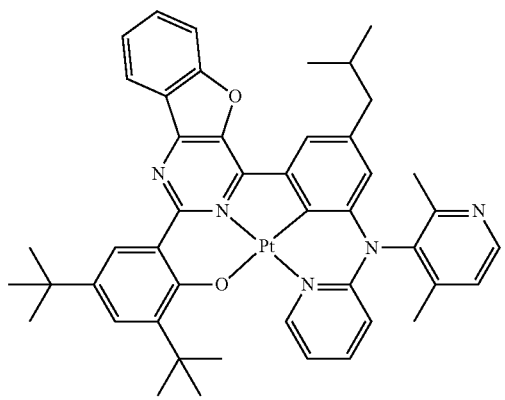
50
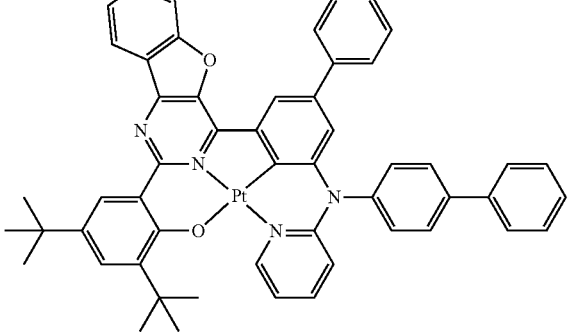
51
52
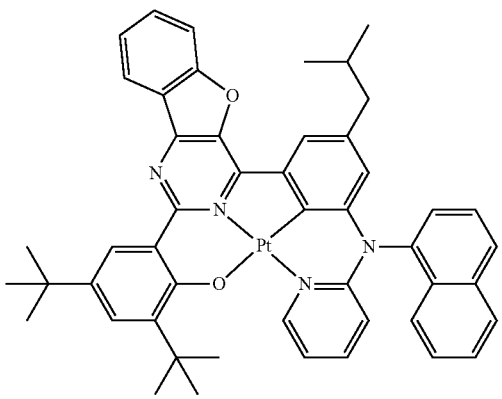
53
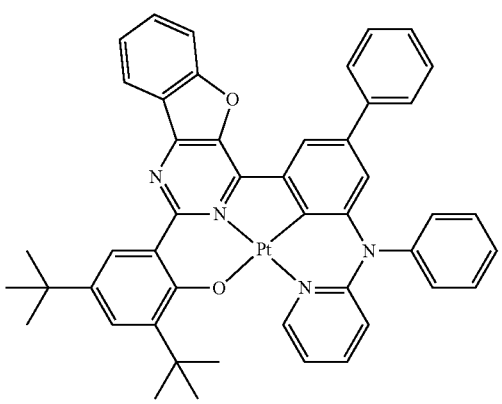
54
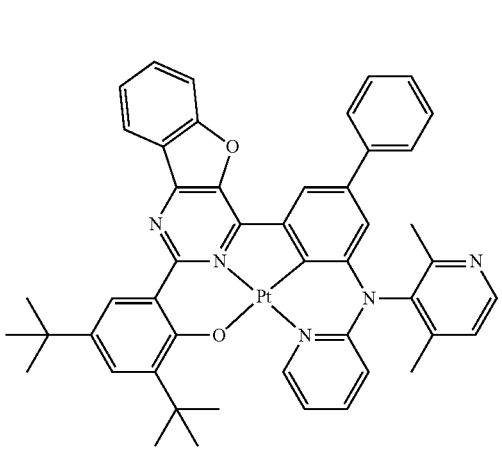
55

56
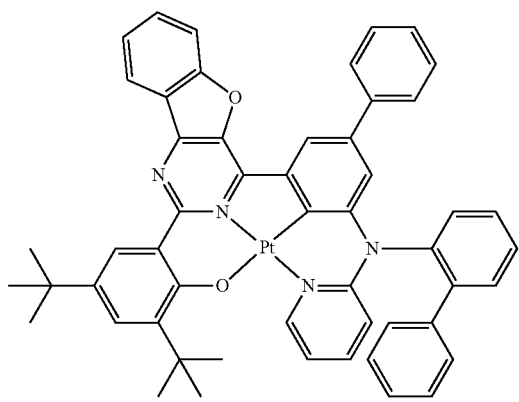
57
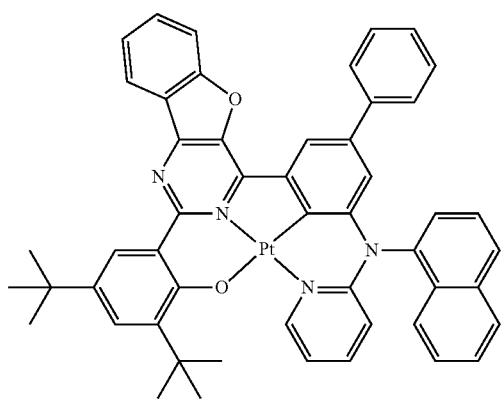
58
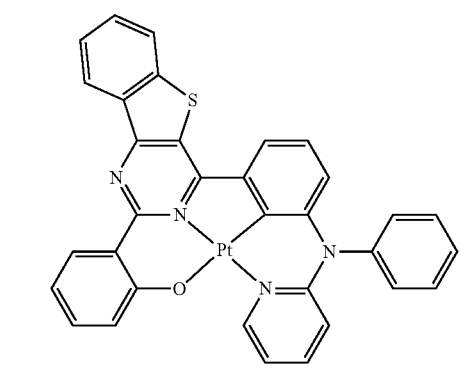
59
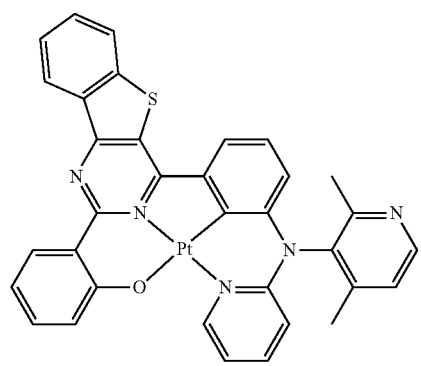
60
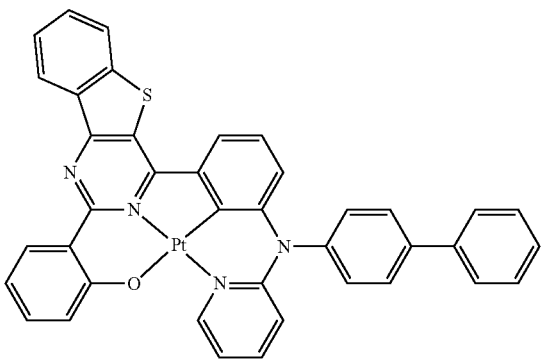
61
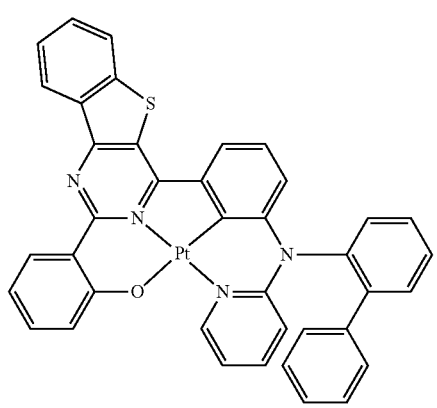
62
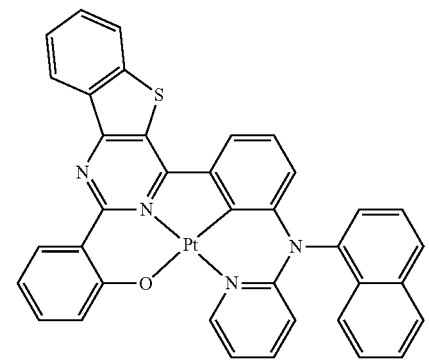
63
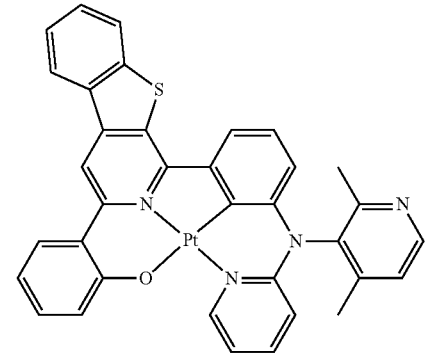

64
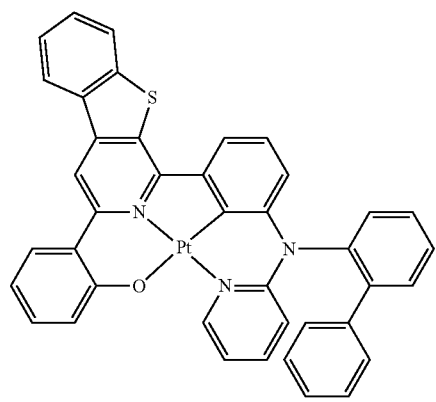
65
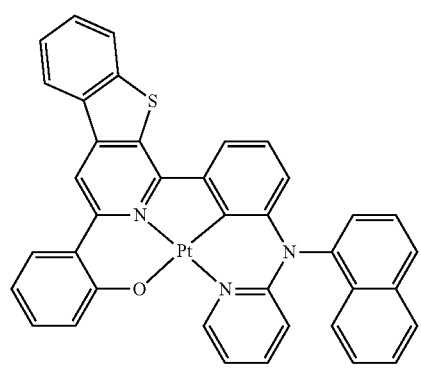
66
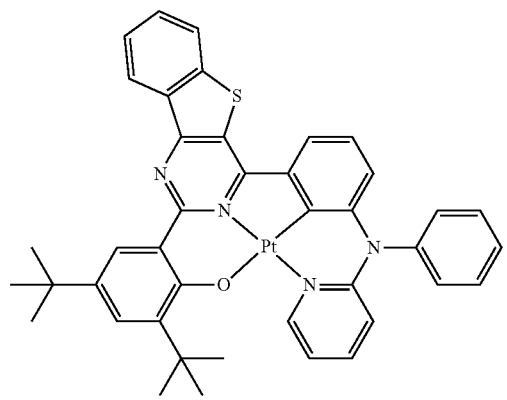
67
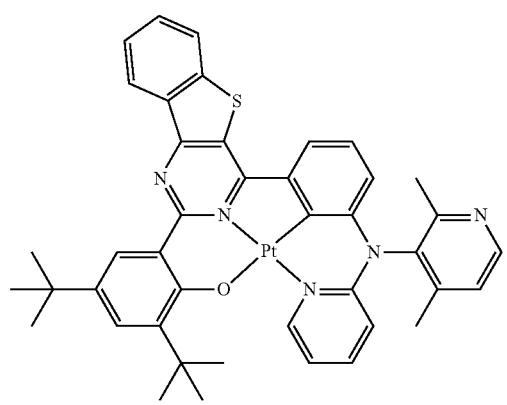
68
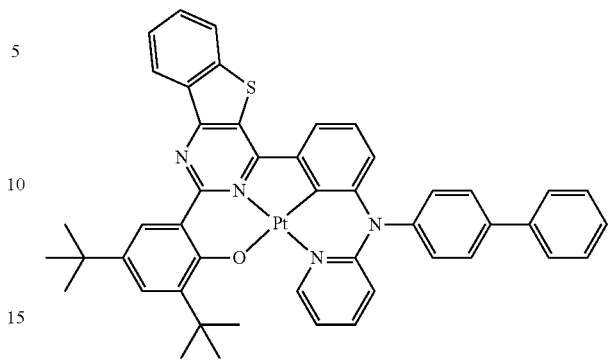
69
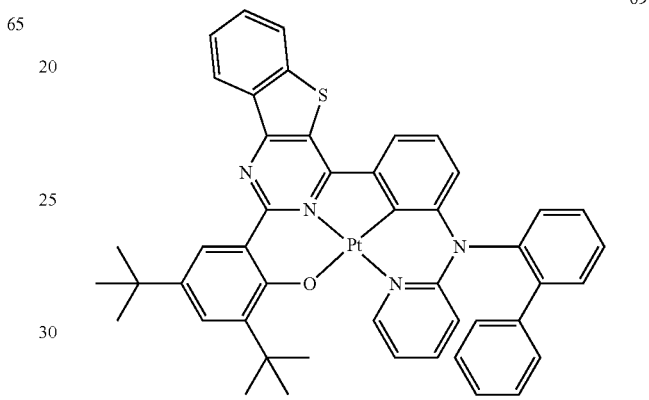
70
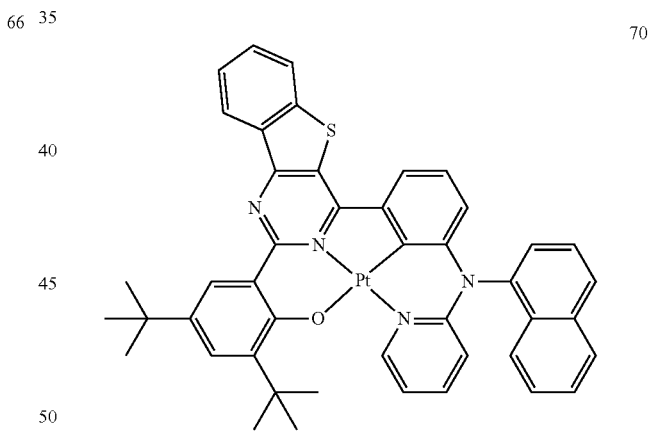
71
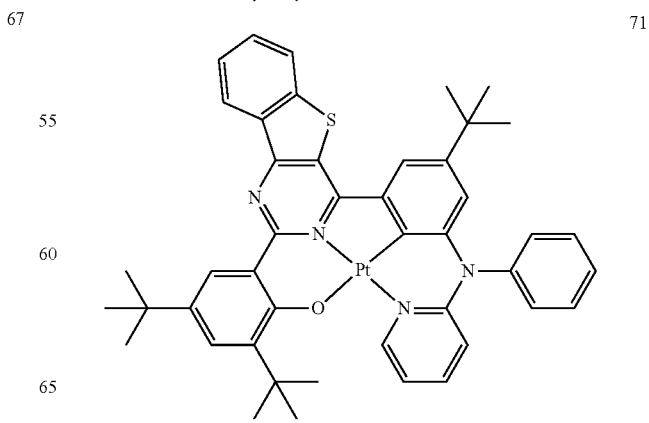

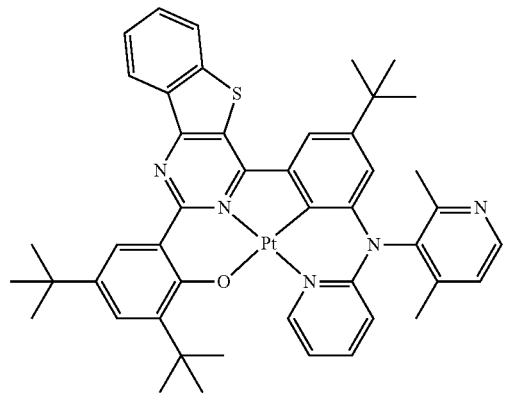
72
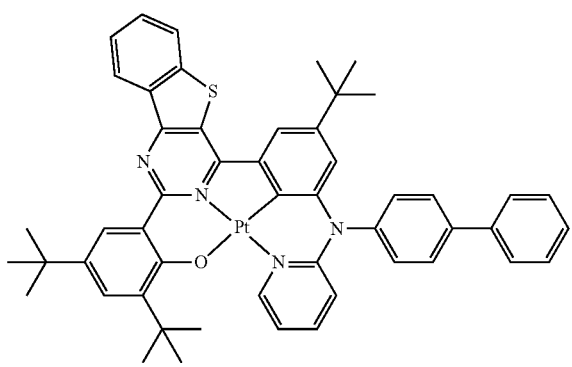
73
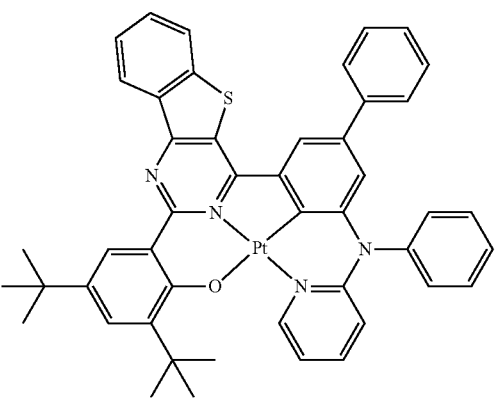
76
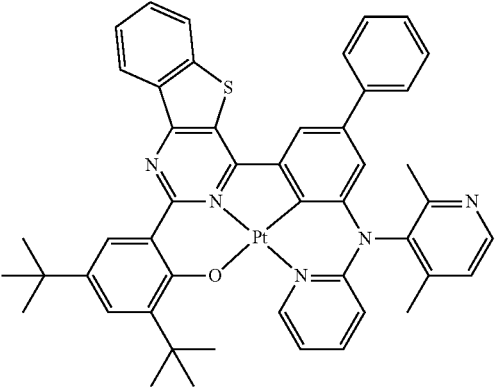
77
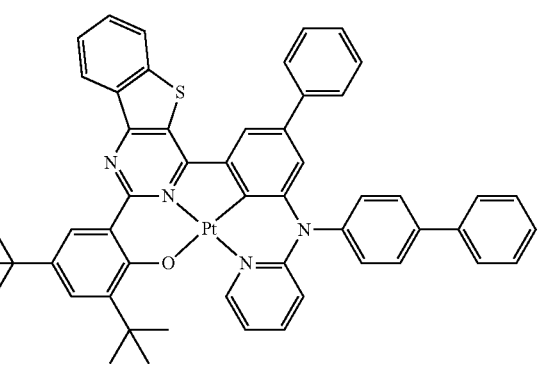
78
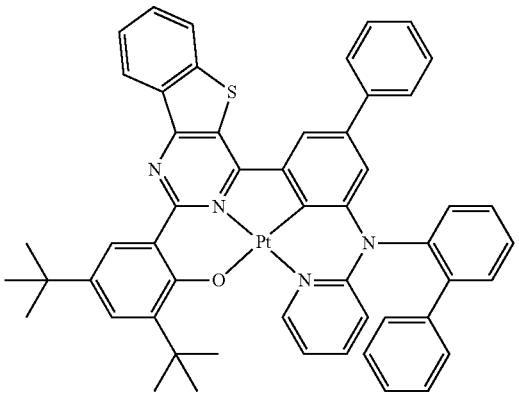
79

80
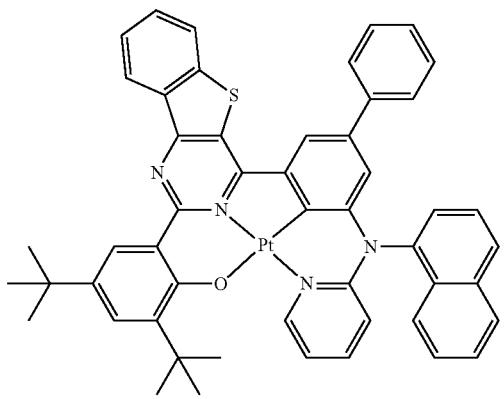
84
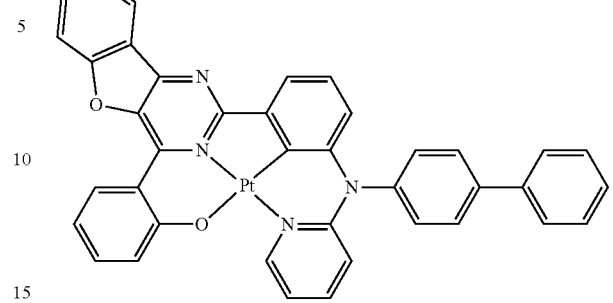
81
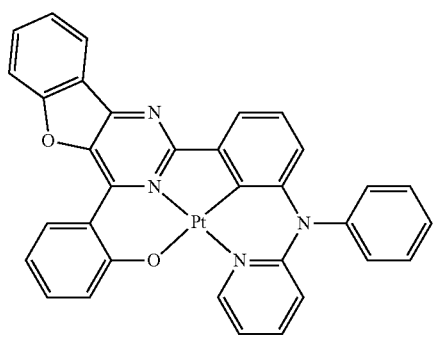
85
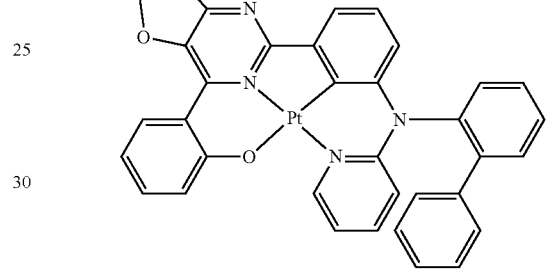
82
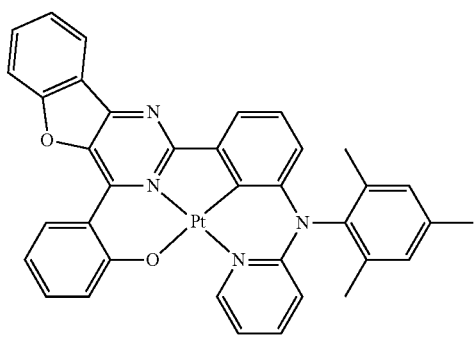
86
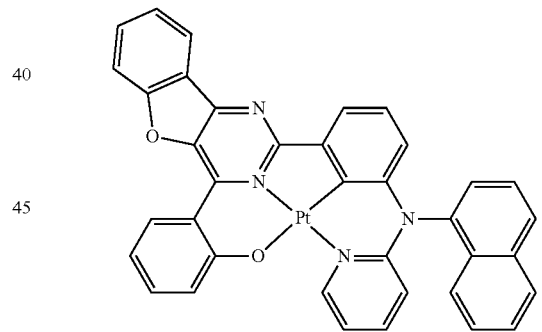
83
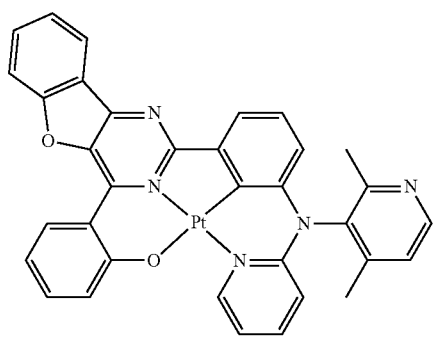
87
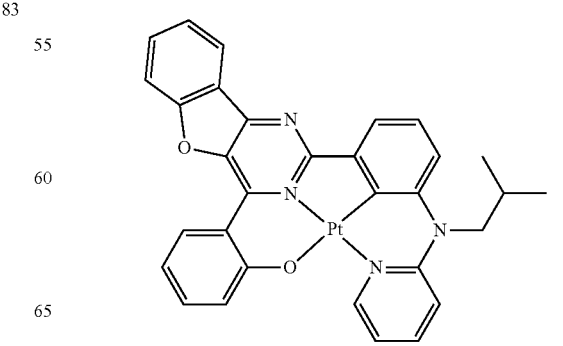

71
-continued
88
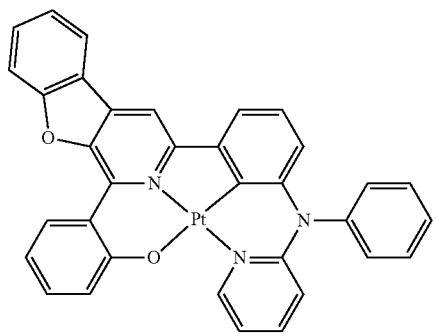
89
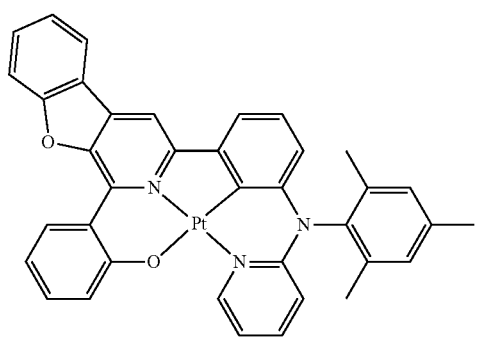
90
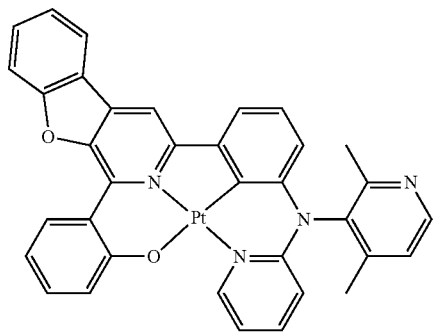
91
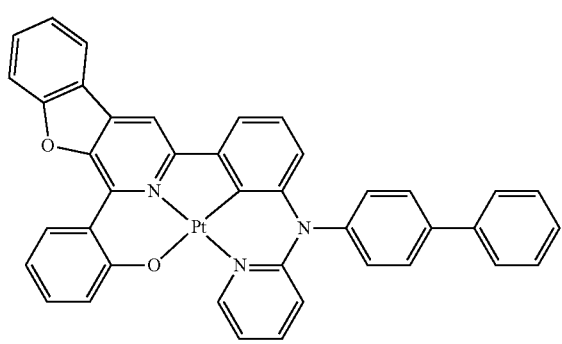
72
-continued
92
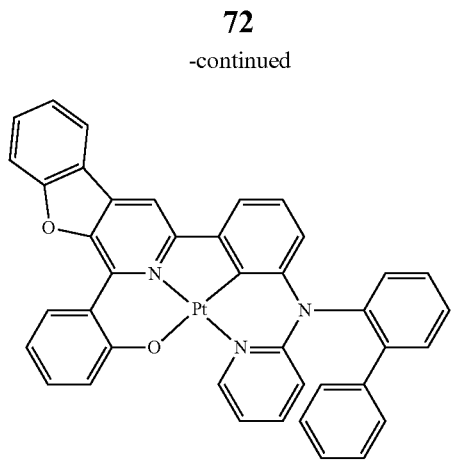
93
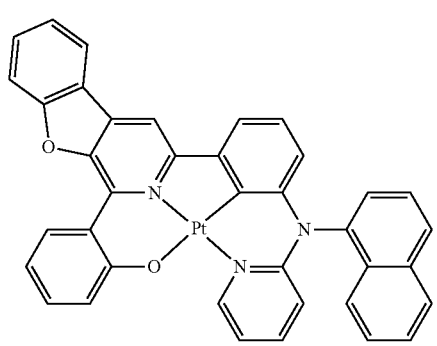
94
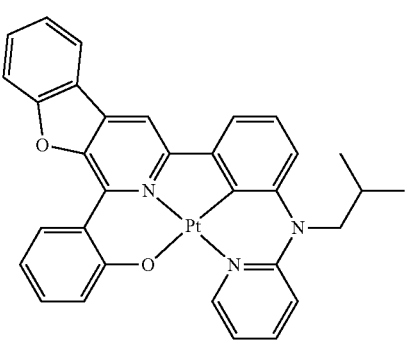
95
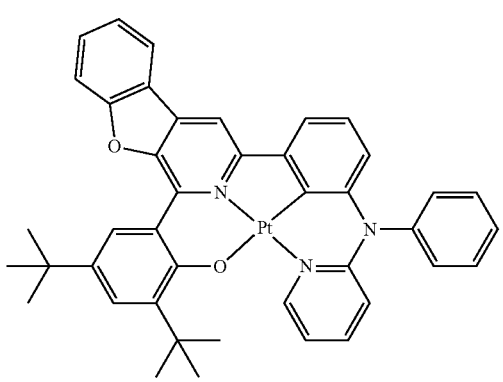

96 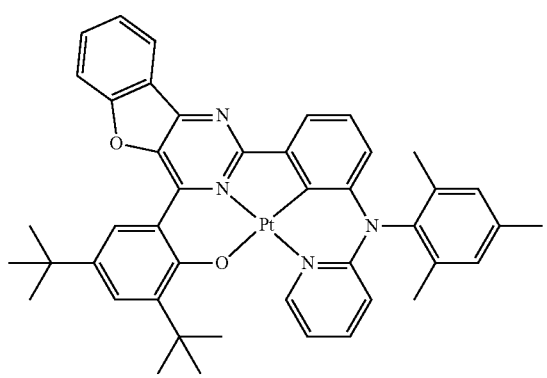
97 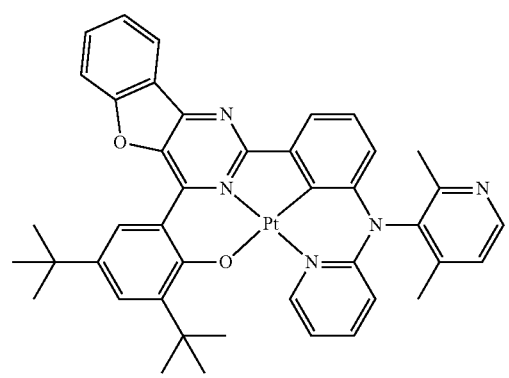
98 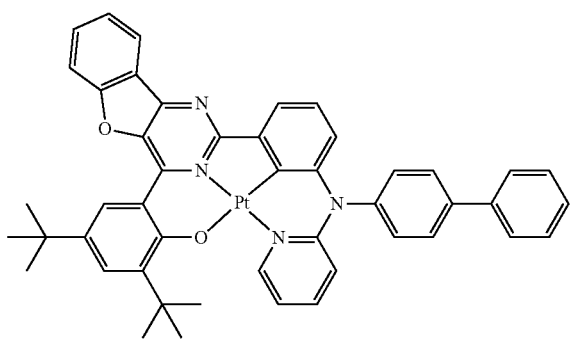
99 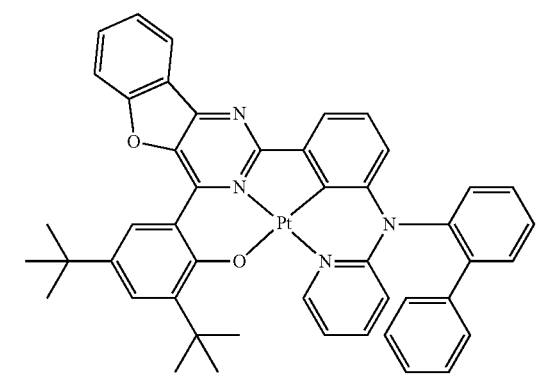
100 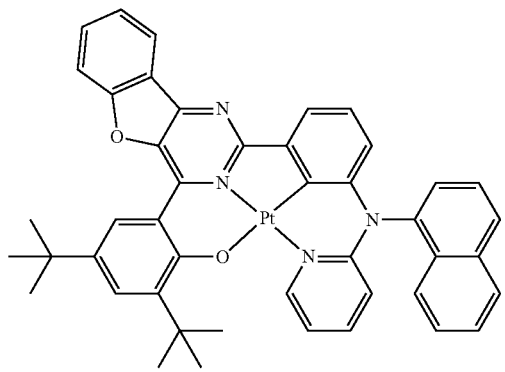
101 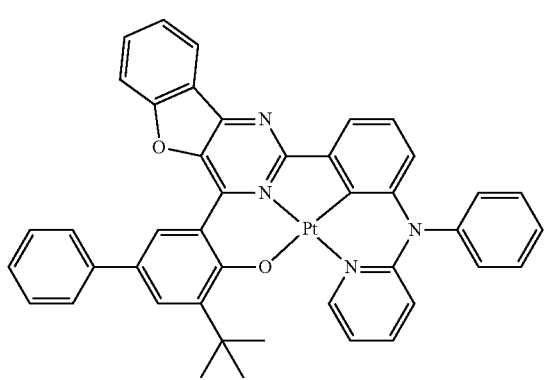
102 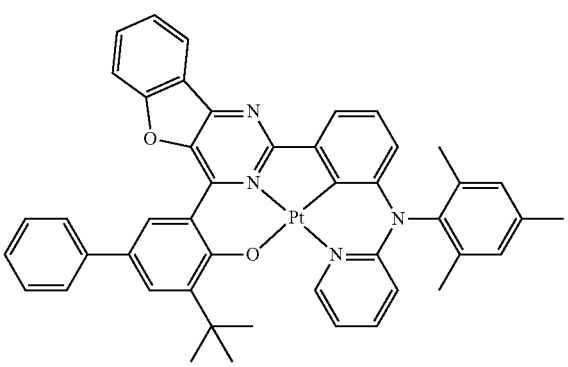
103 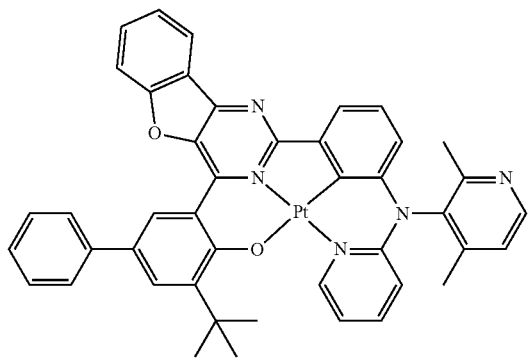

-continued
104
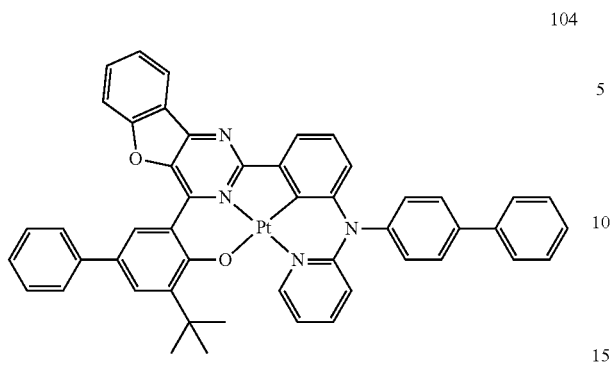
105
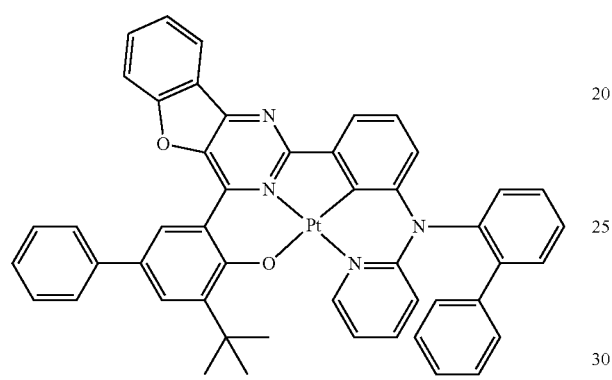
106
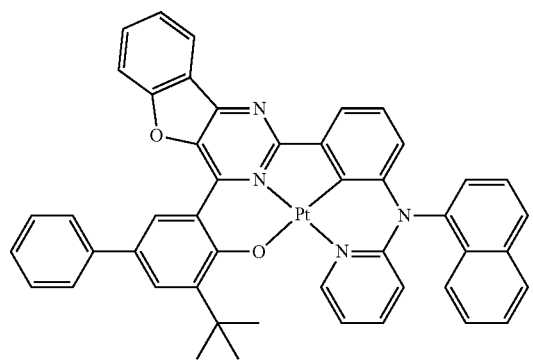
107
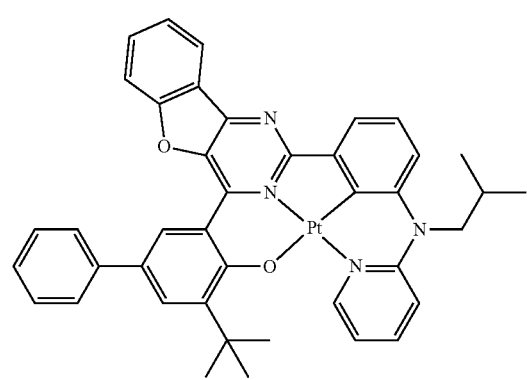
-continued
108
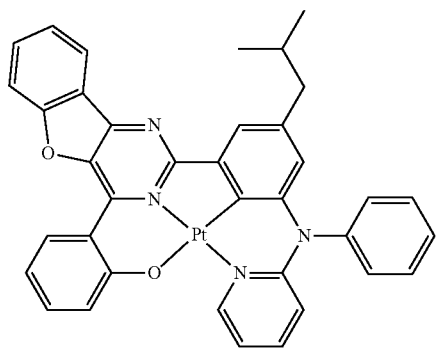
109
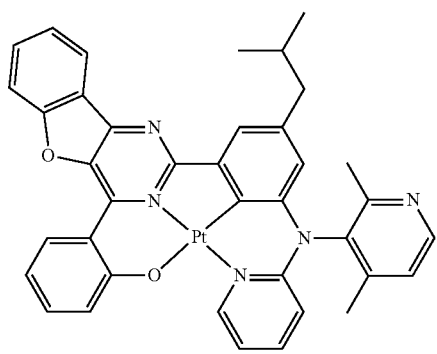
110
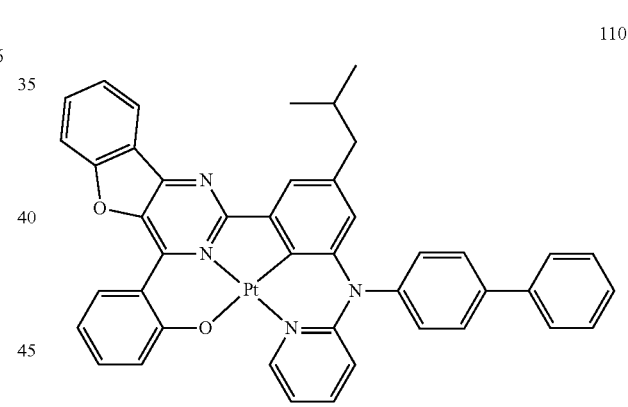
111
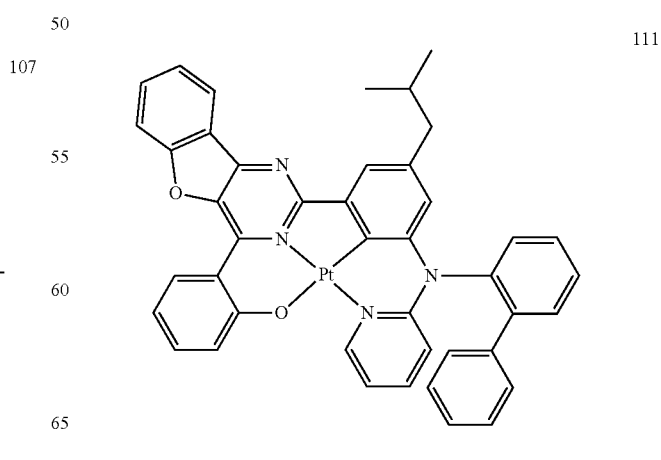

112
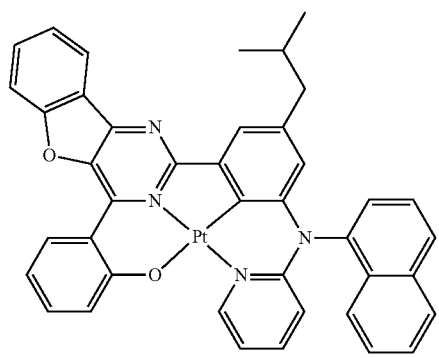
113
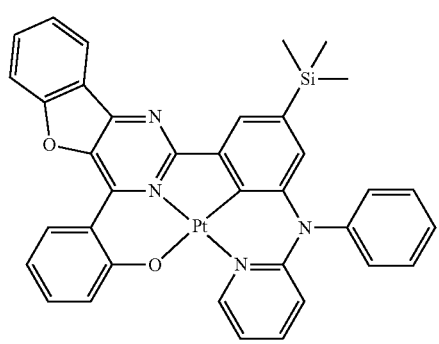
114
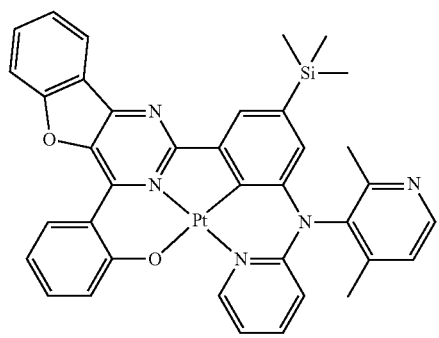
115
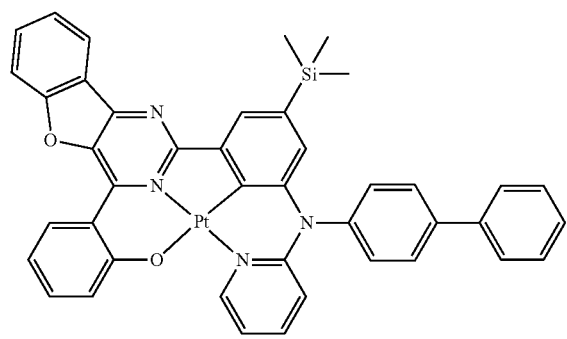
116
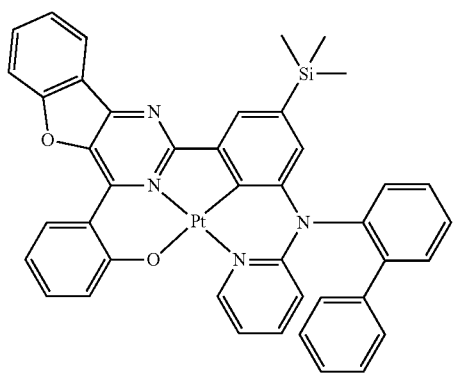
117
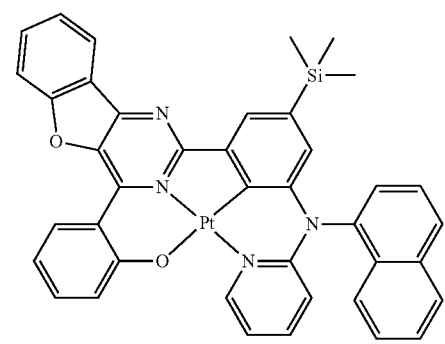
118
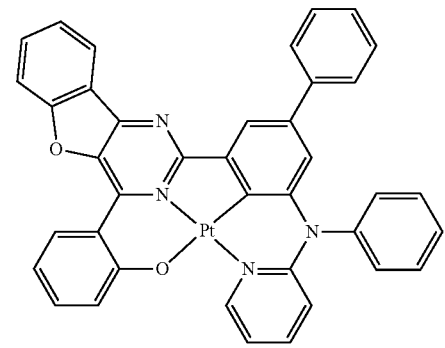
119
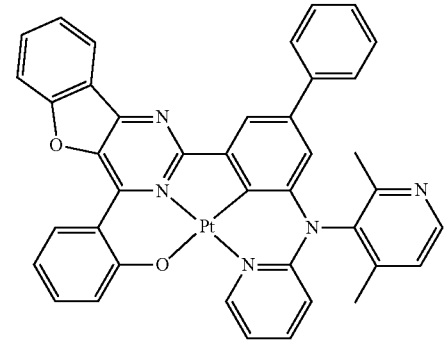

120
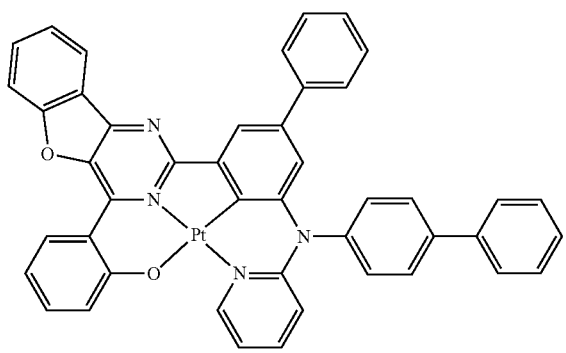
121
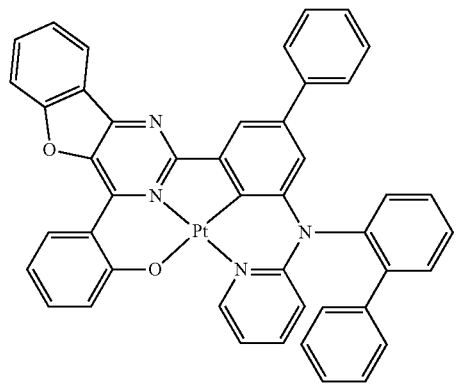
122
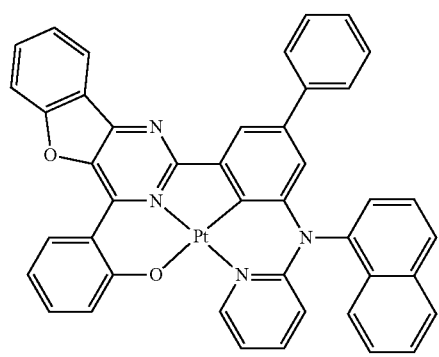
123
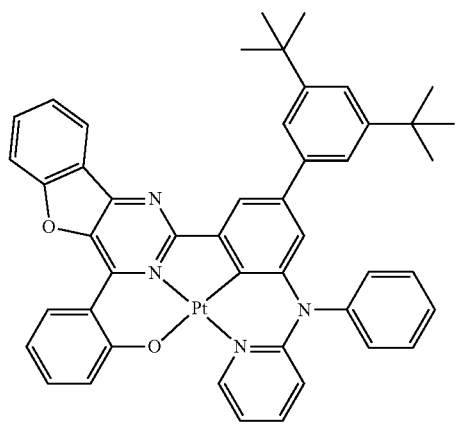
124
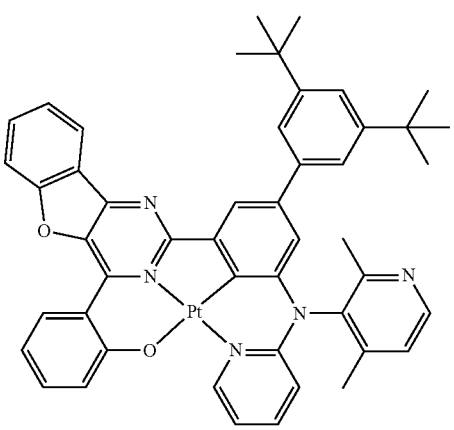
125
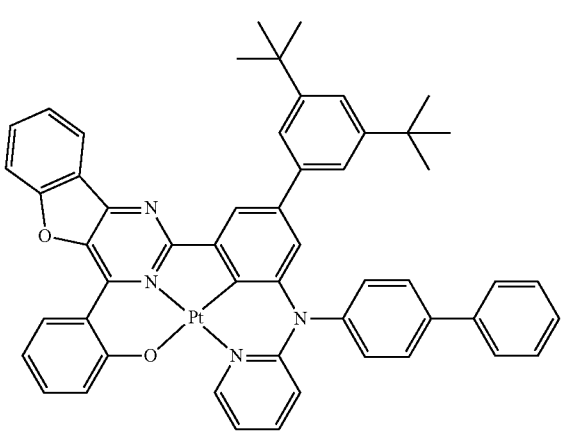
126
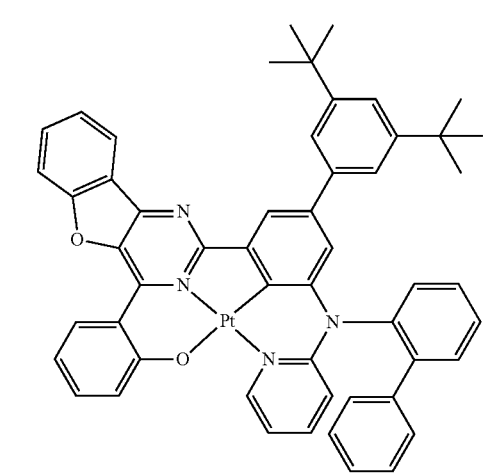

-continued
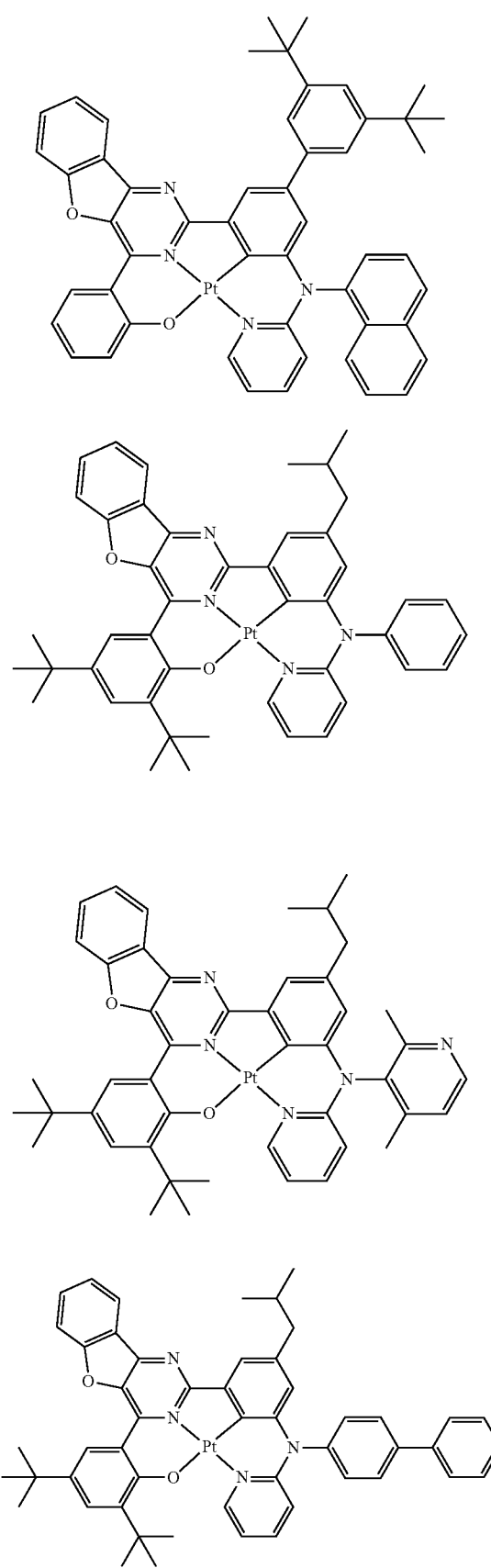
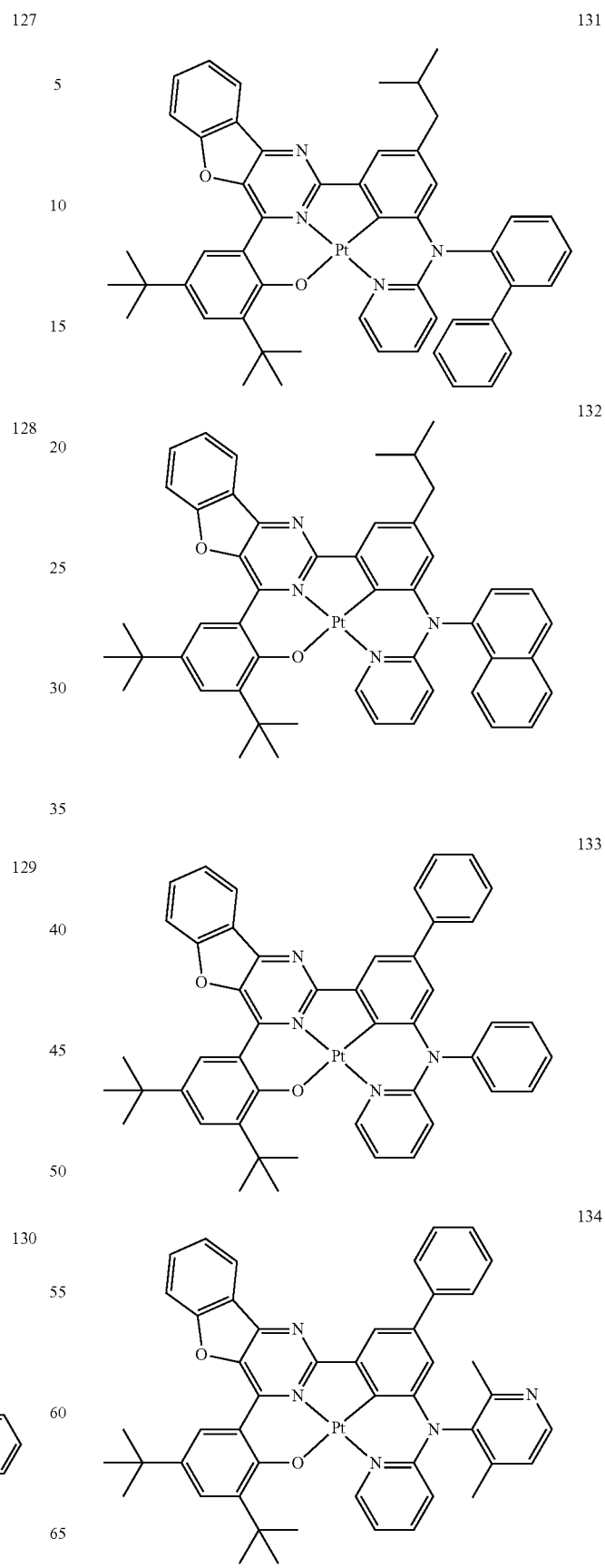

135
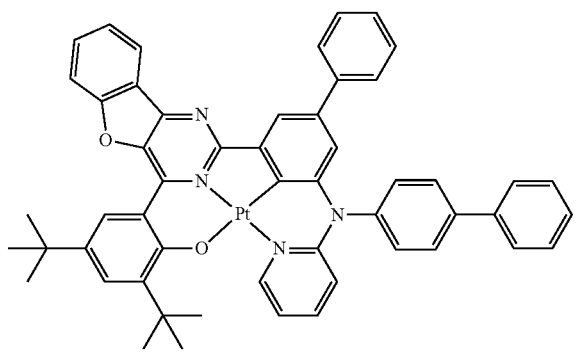
136
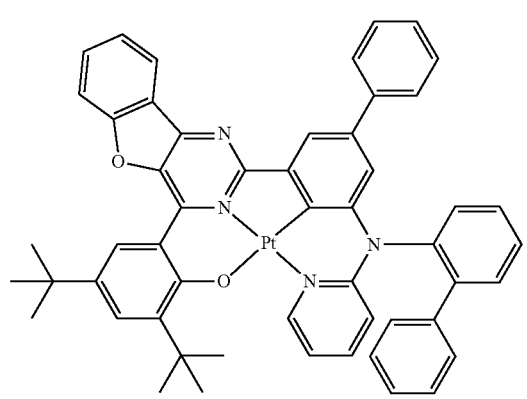
137
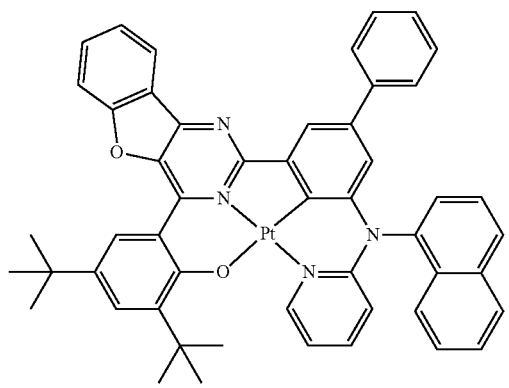
138
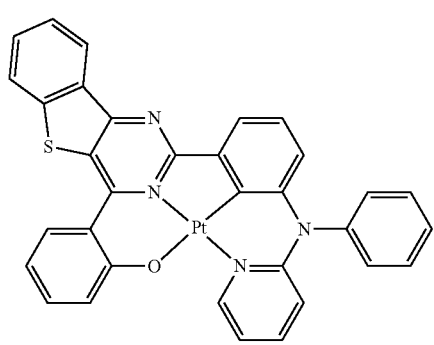
139
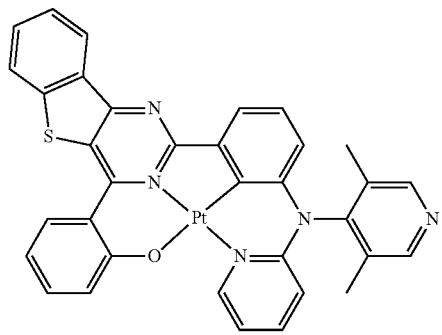
140
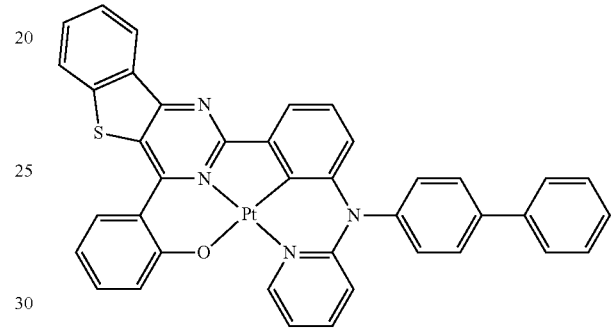
141
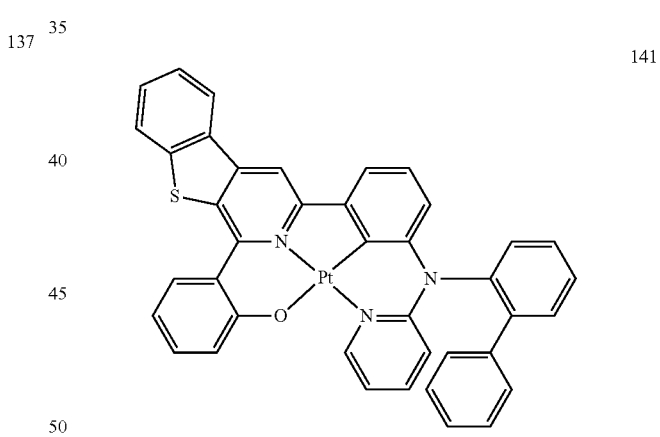
142
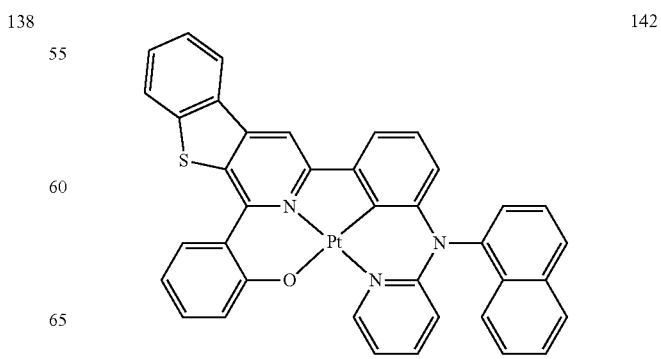

143
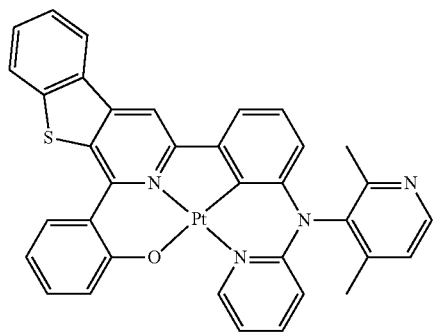
147
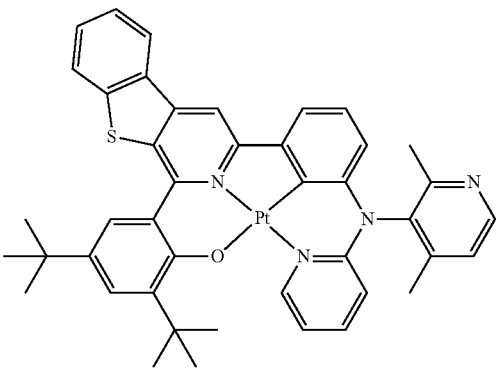
144
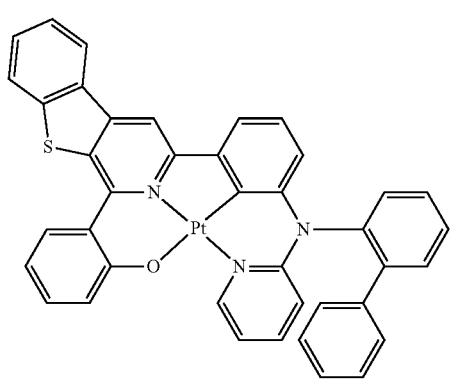
148
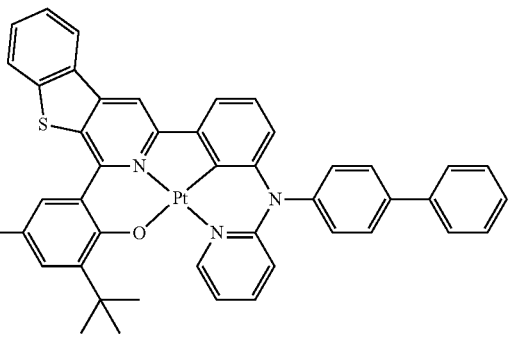
145
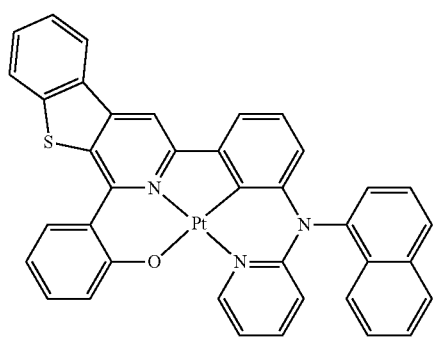
149
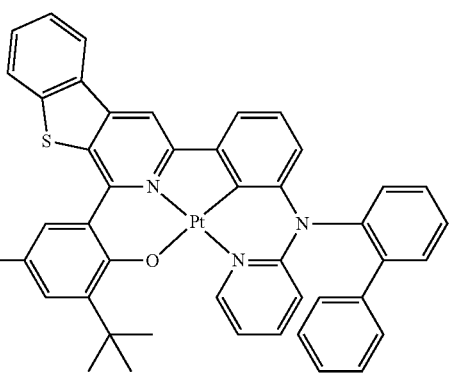
146
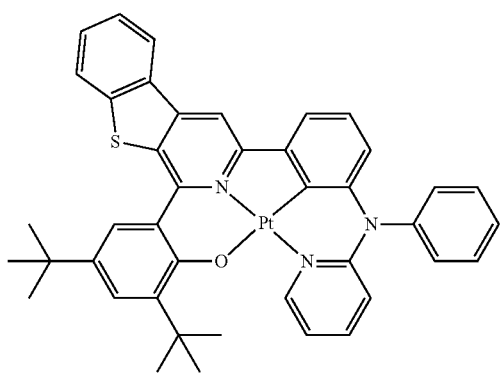
150
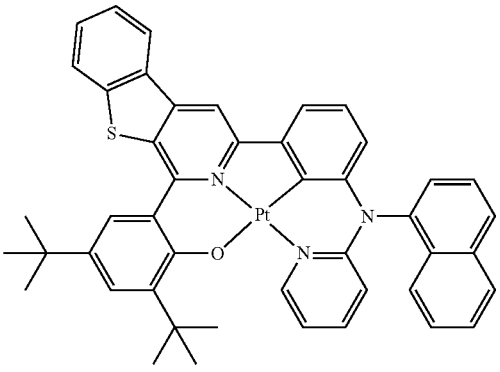

-continued
151
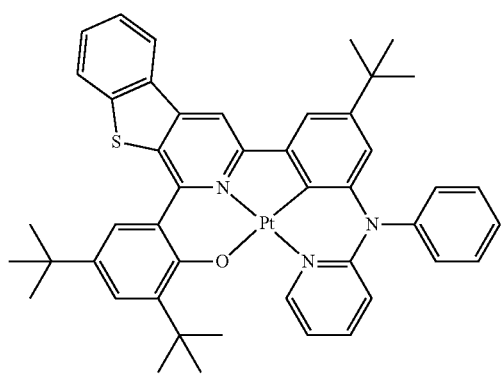
152
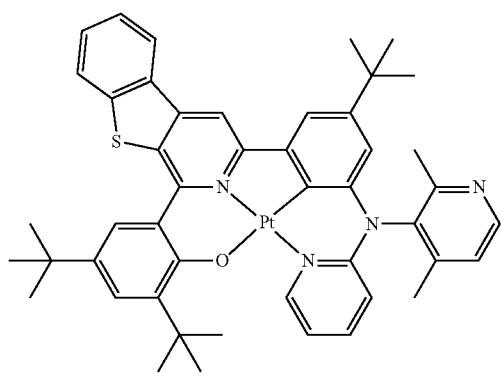
153
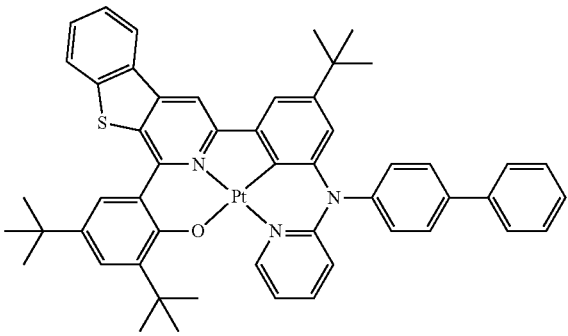
154
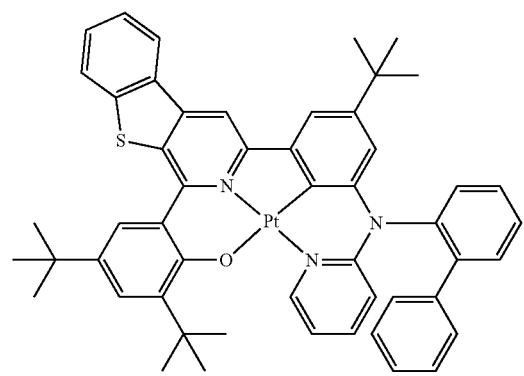
-continued
155
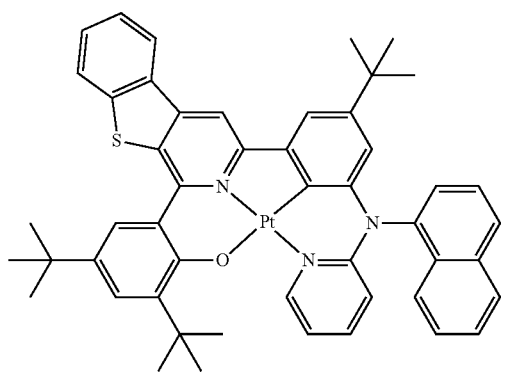
156
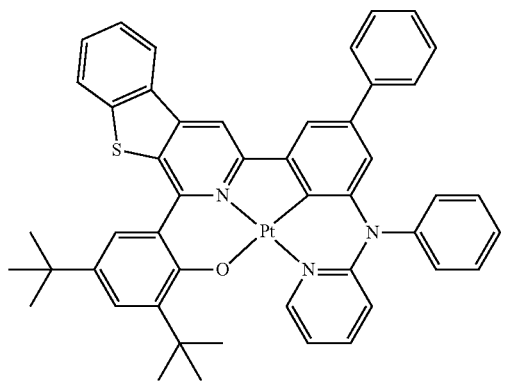
157
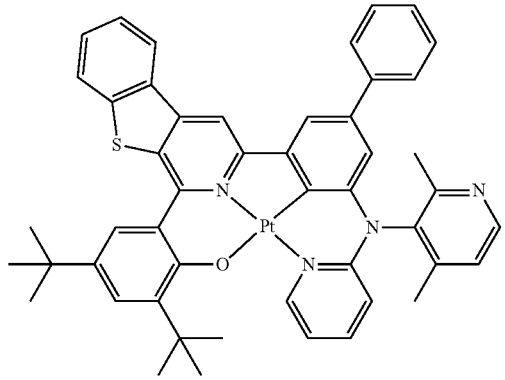
158
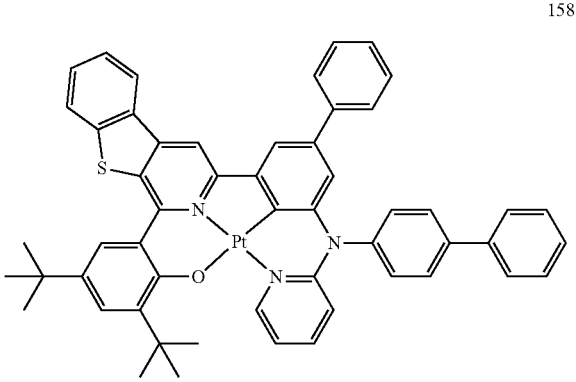

-continued
159
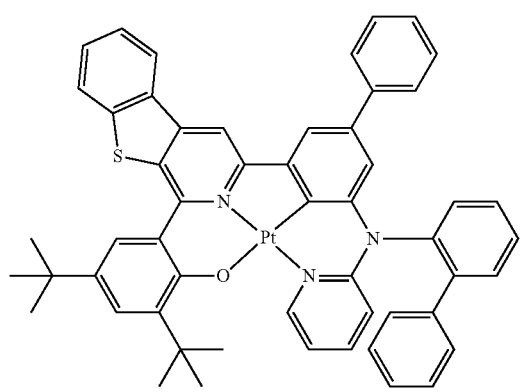
160
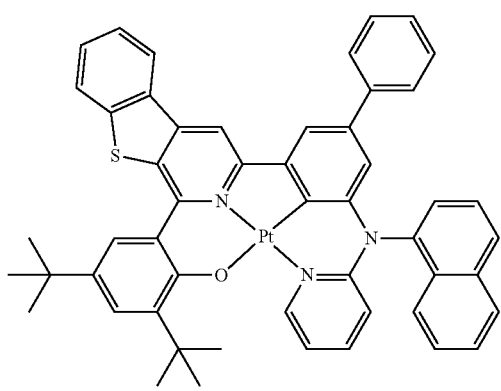
161
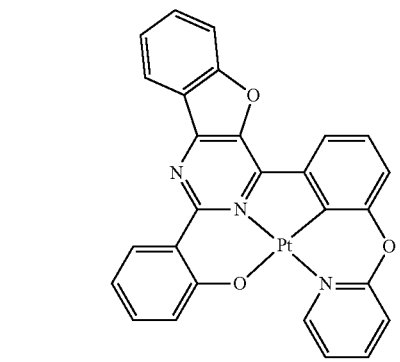
162
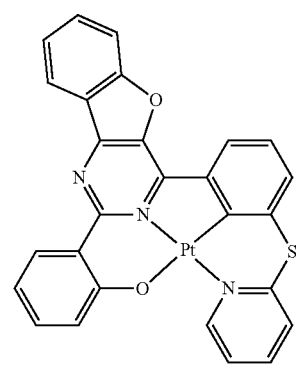
-continued
163
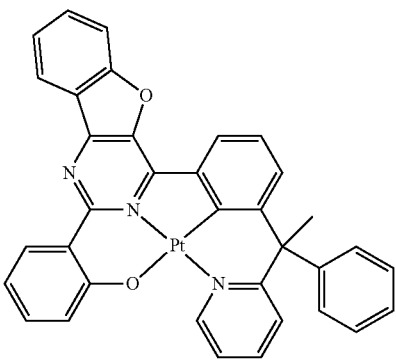
164
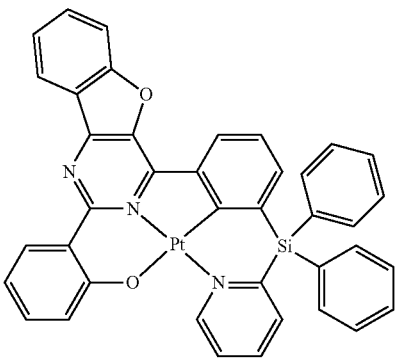
165
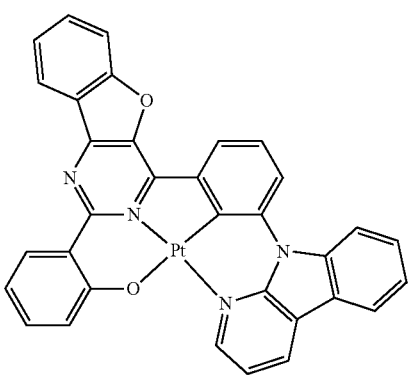
166
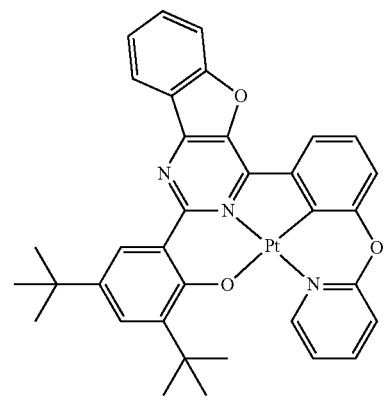

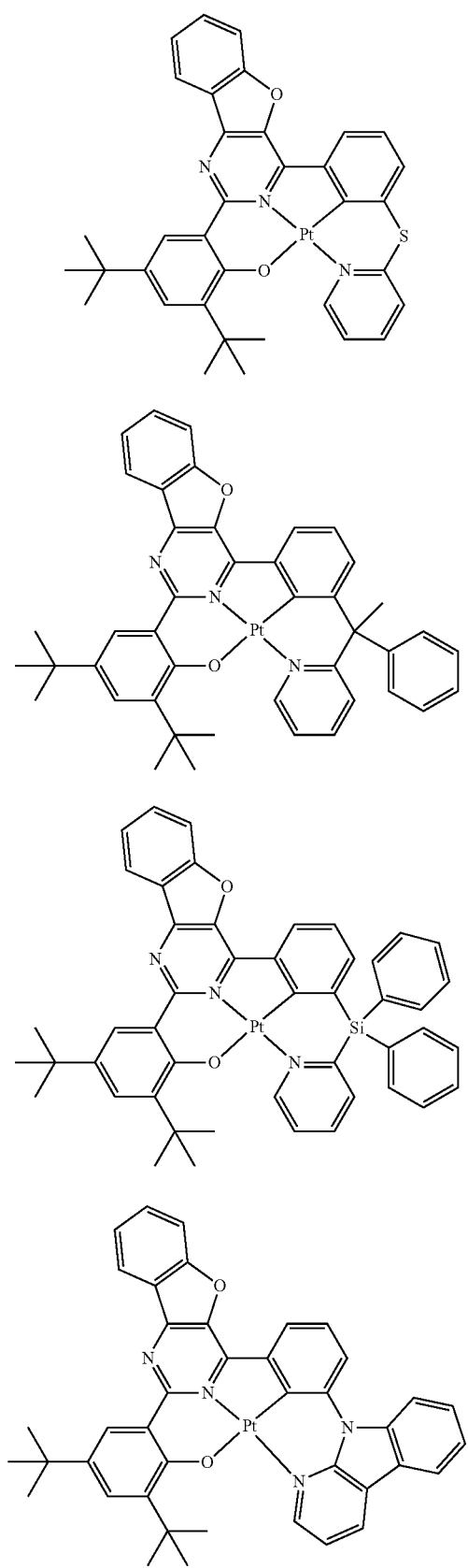
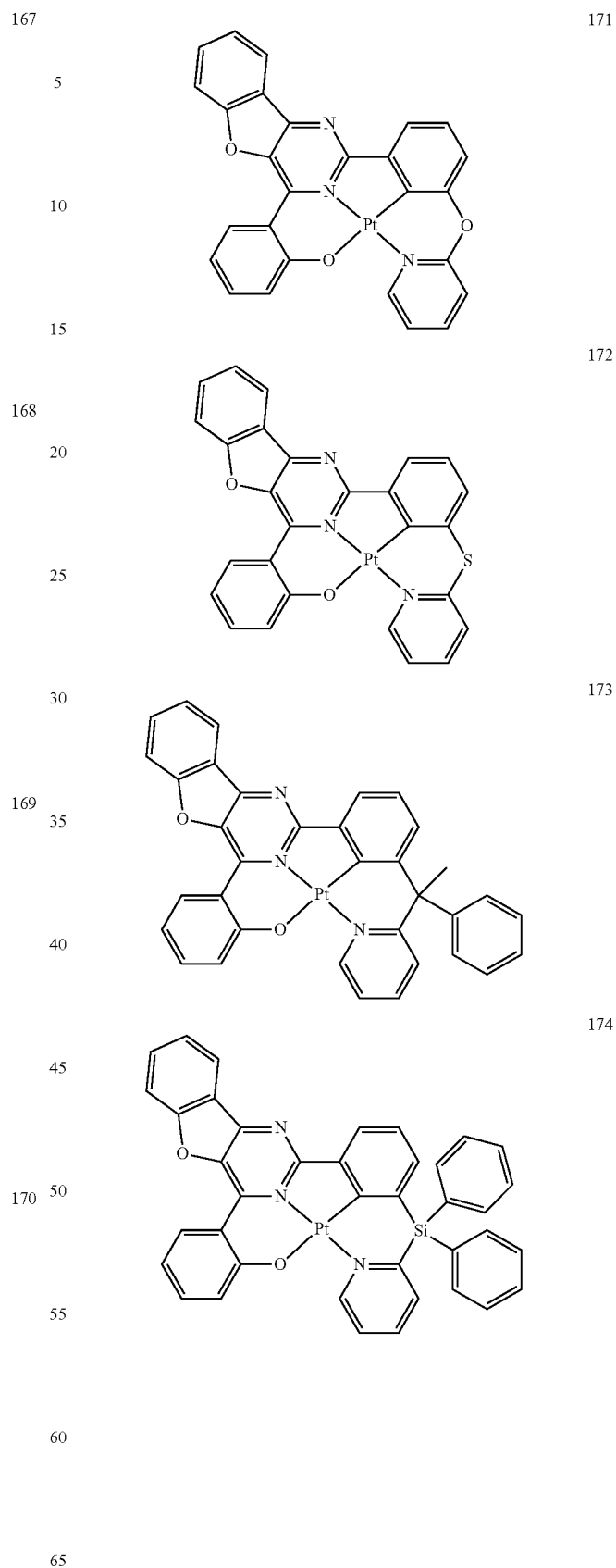

175
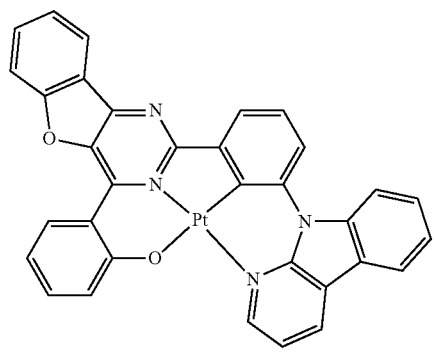
176
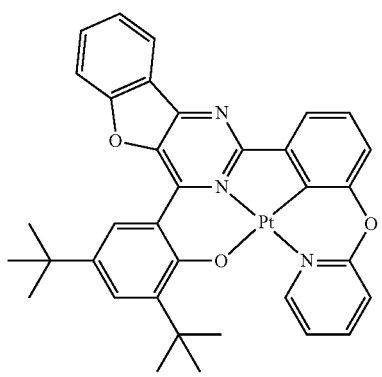
177
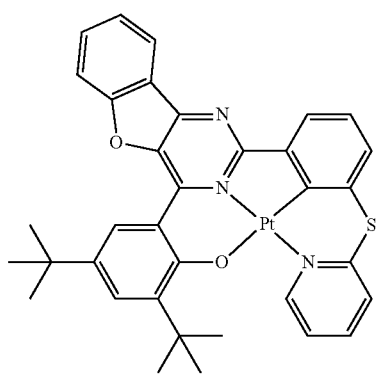
178
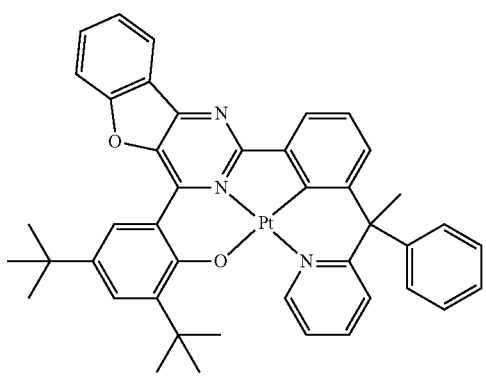
179
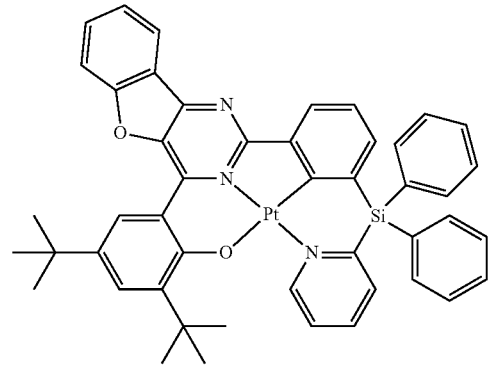
180
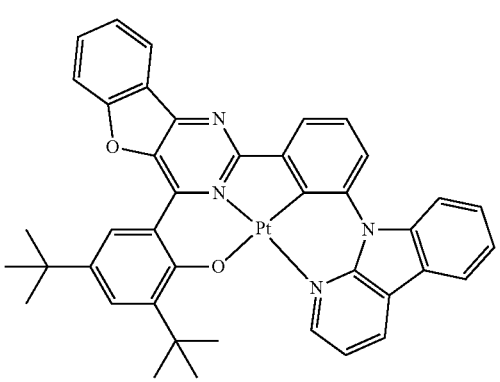
181
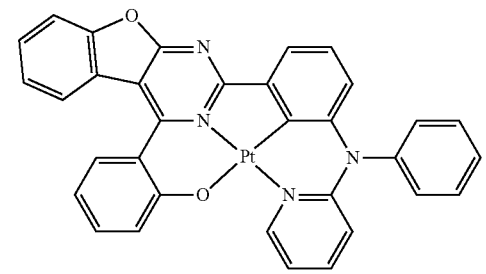
182
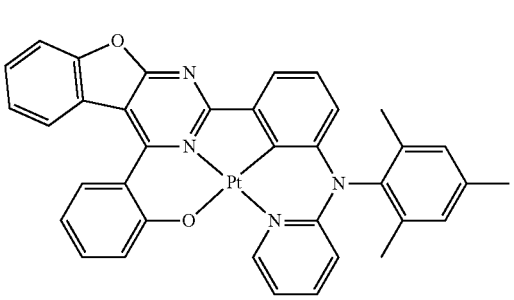
183
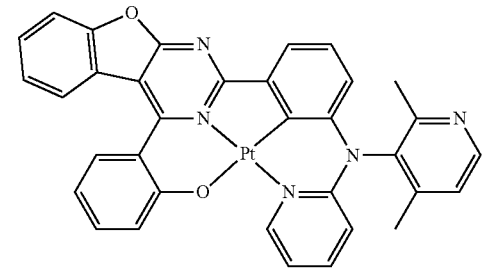

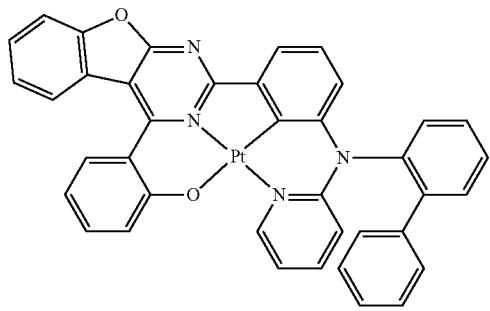
184
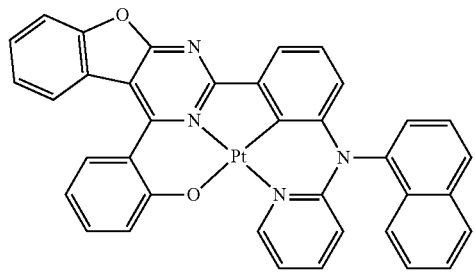
185
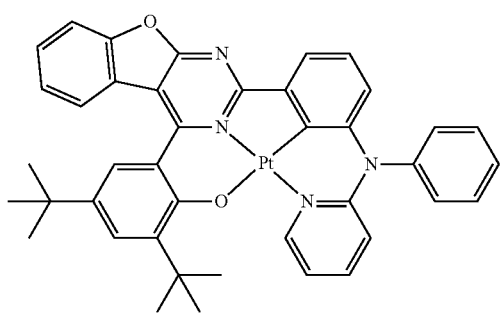
186
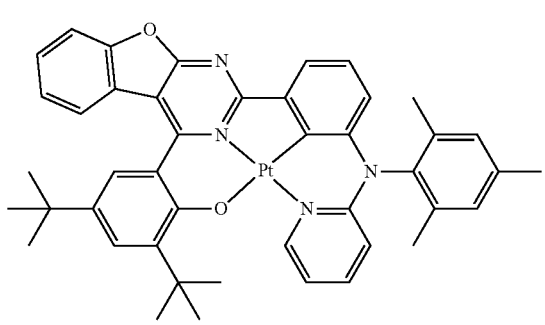
187
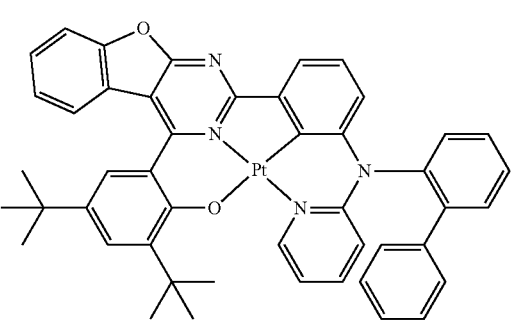
189
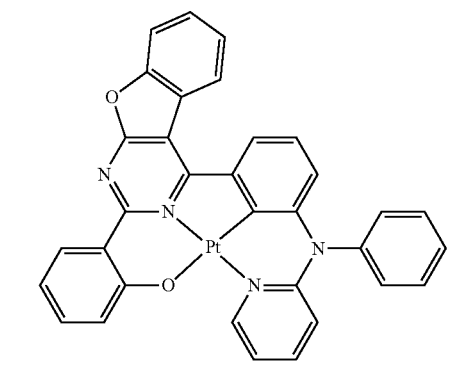
190
188
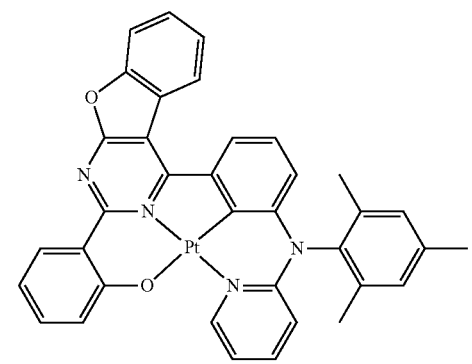
191
192

97
-continued
193
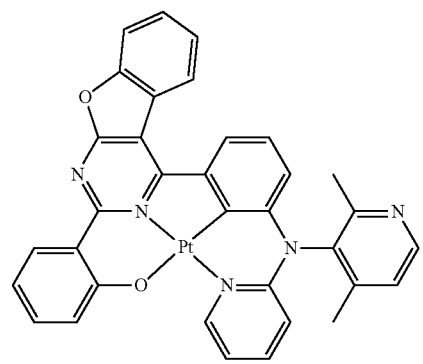
194
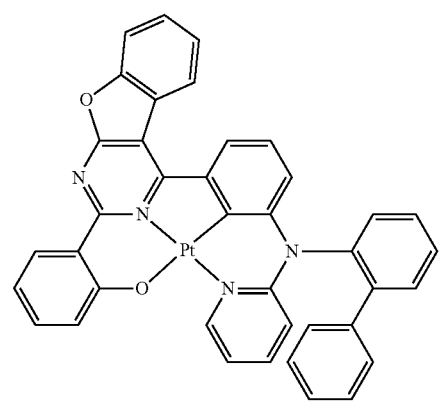
195
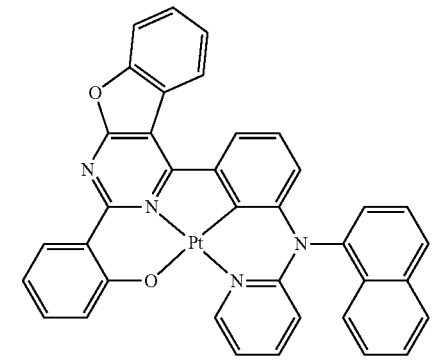
196
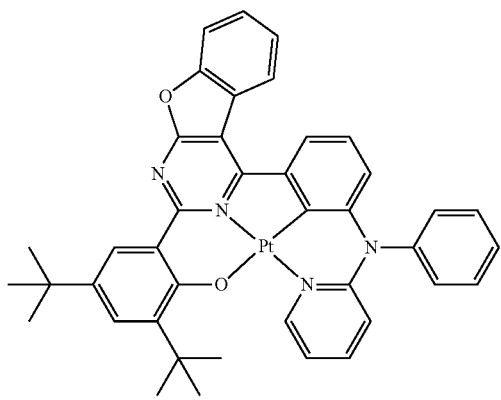
98
-continued
197
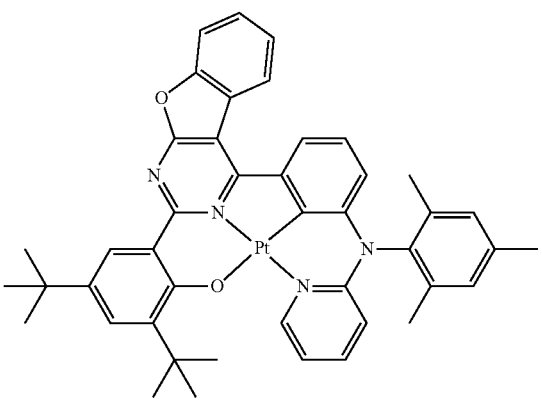
198
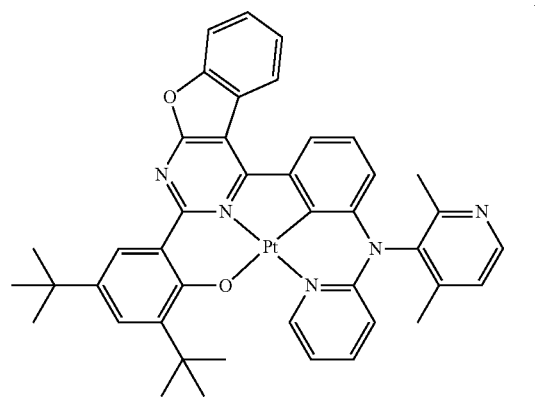
199
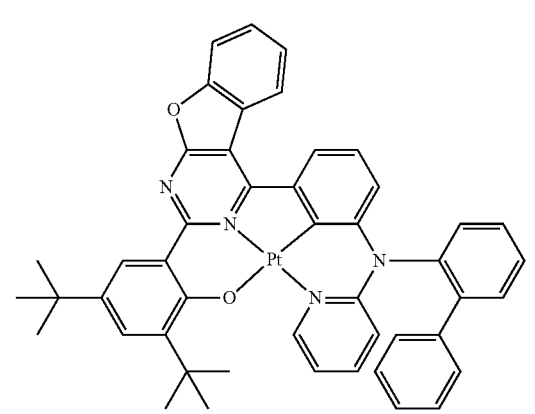
200
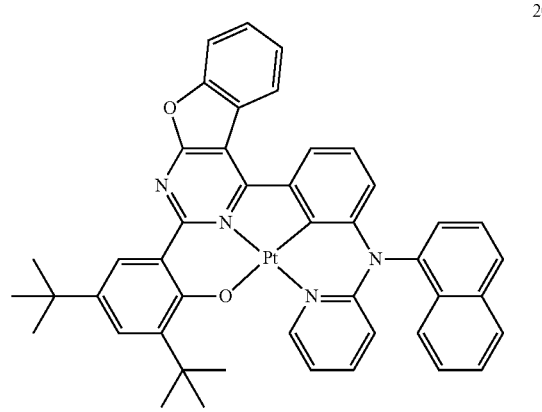

201
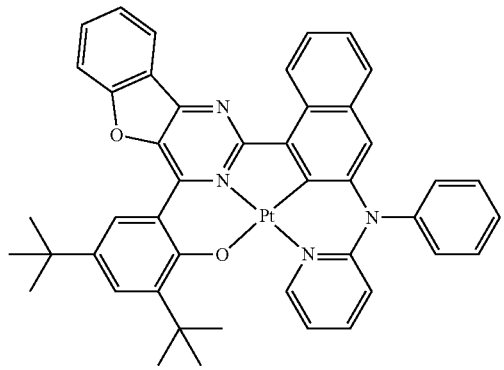
202
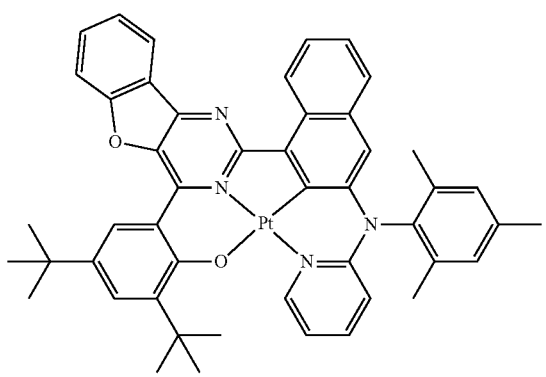
203
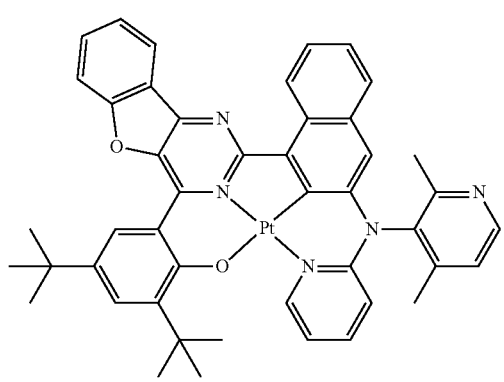
204
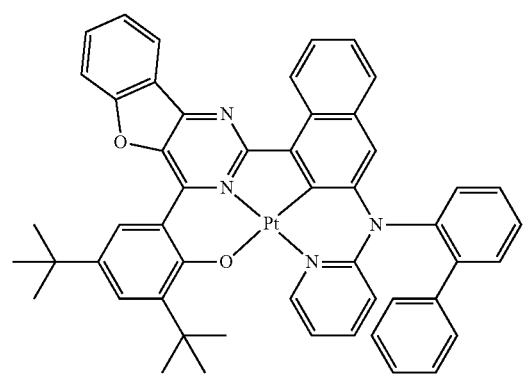
205
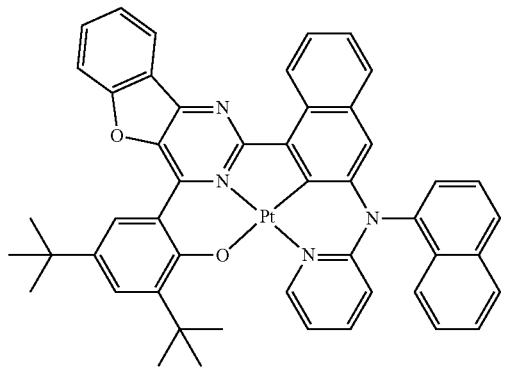
206
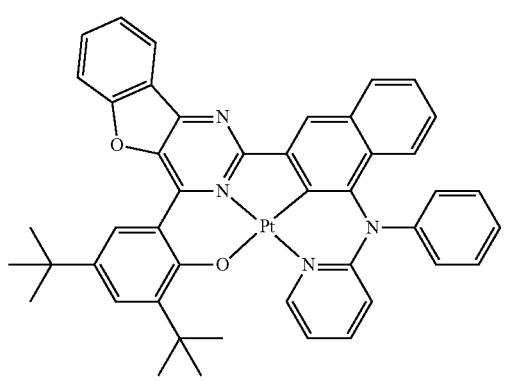
207
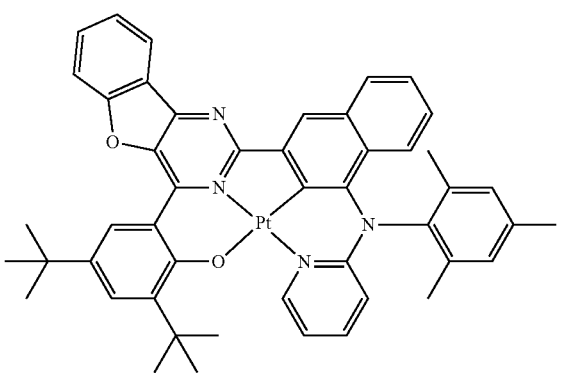
208
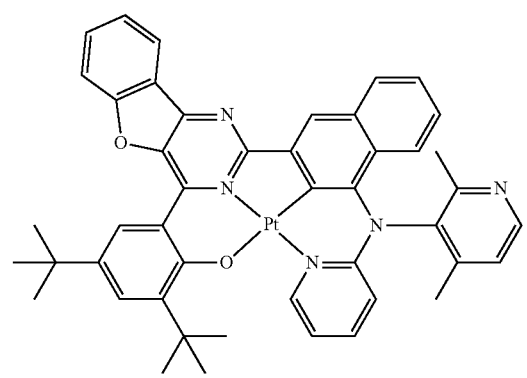

-continued
209
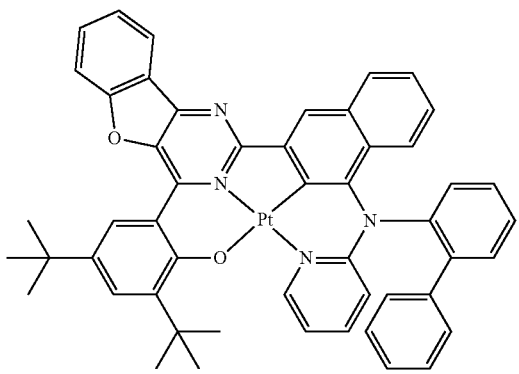
210
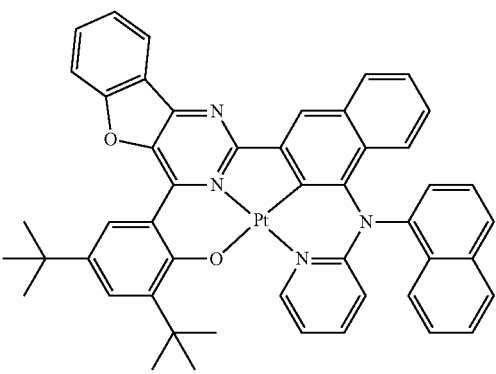
211
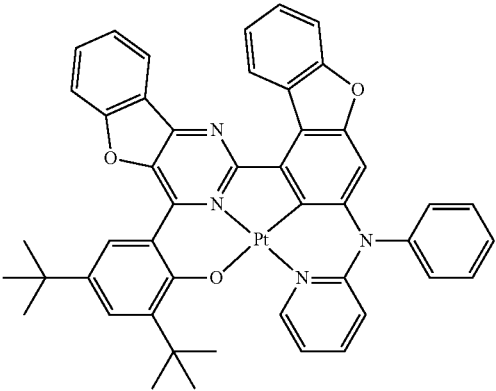
212
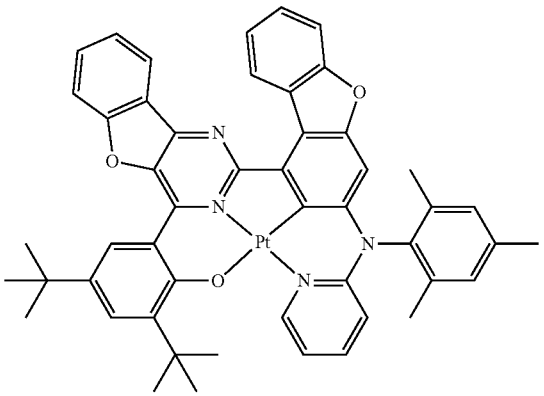
-continued
213
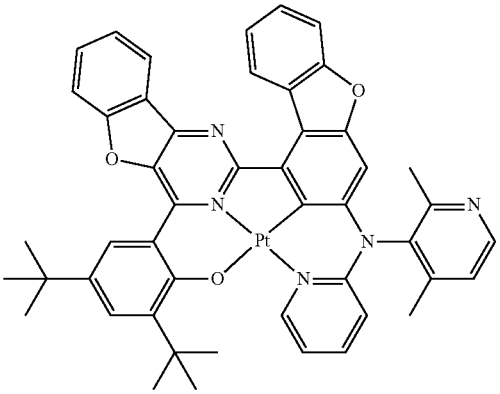
214
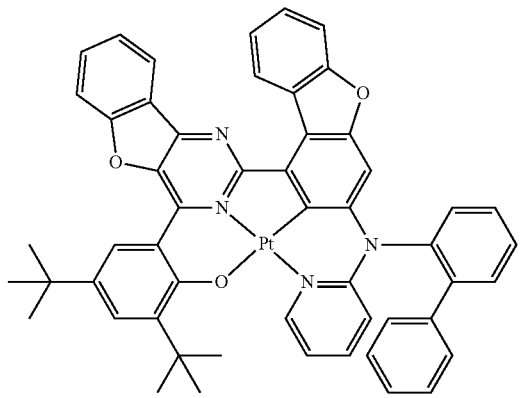
215
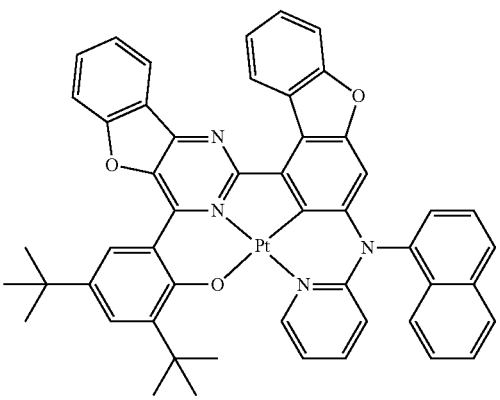
216
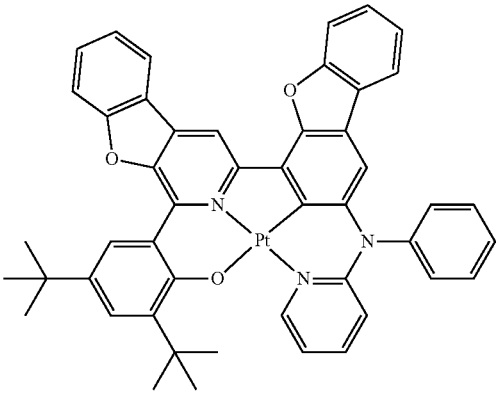

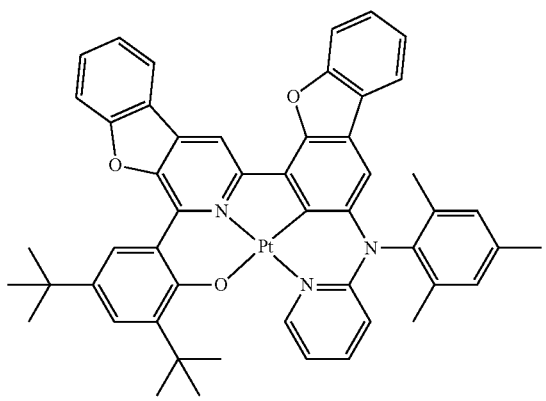
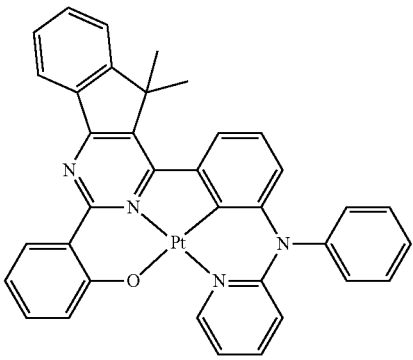
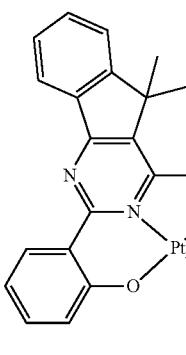
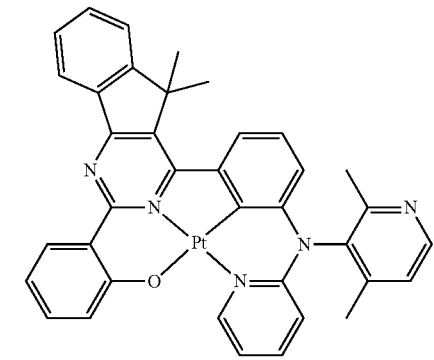
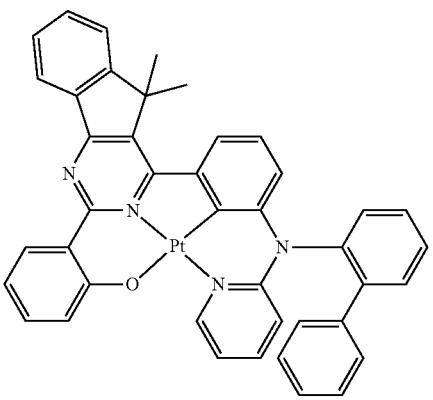

105
-continued
225
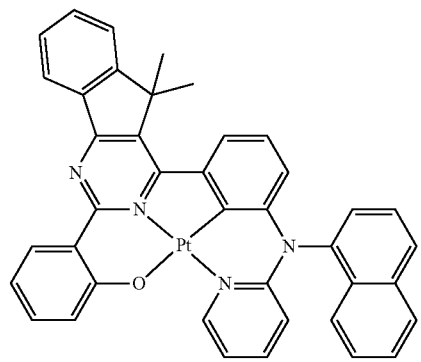
226
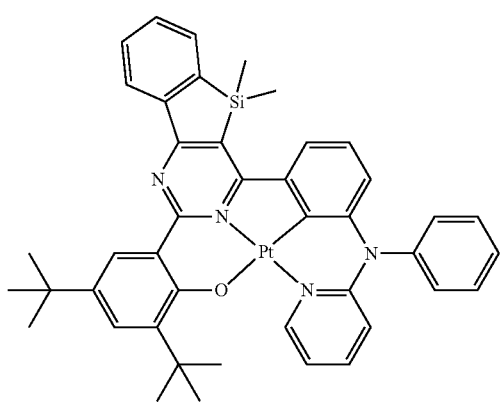
227
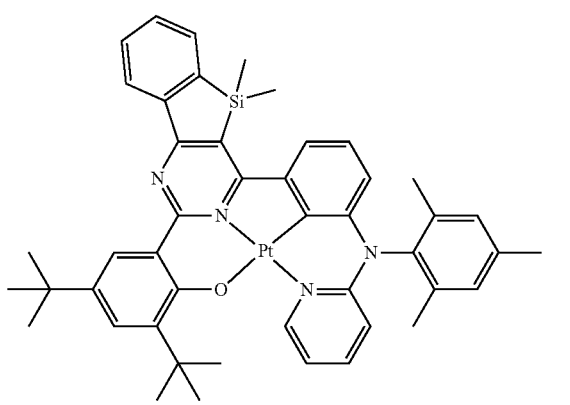
228
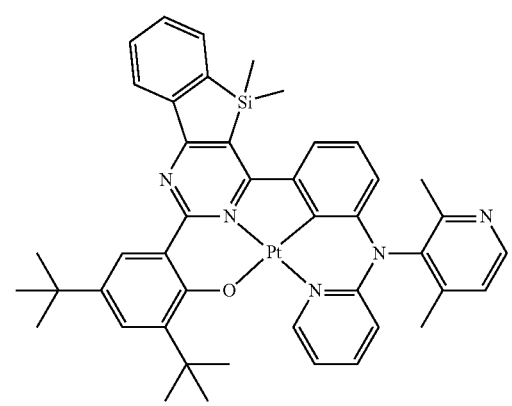
106
-continued
229
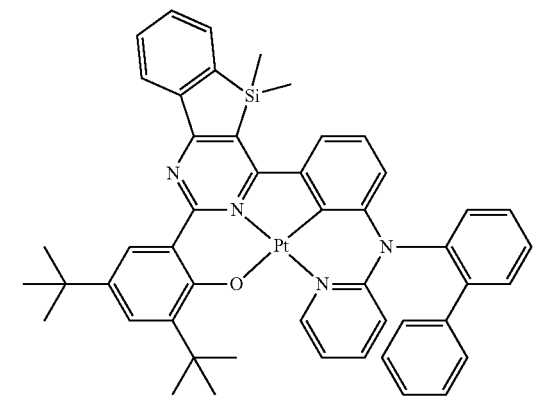
230
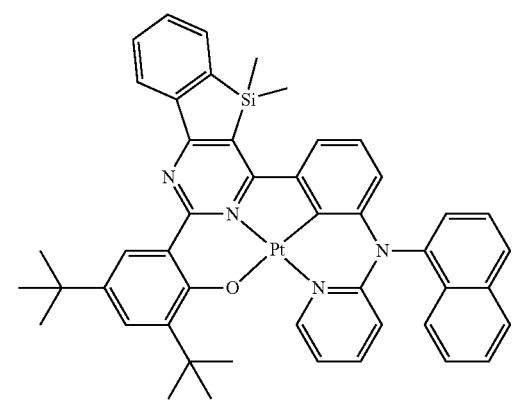
231
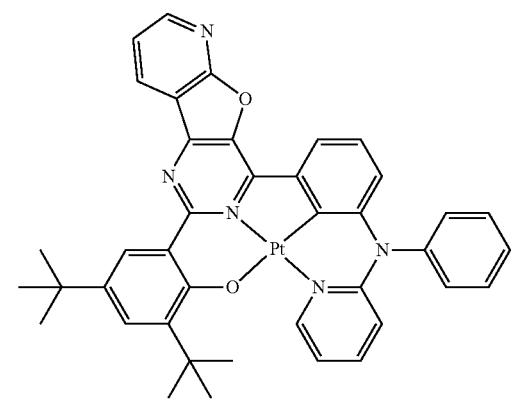
232
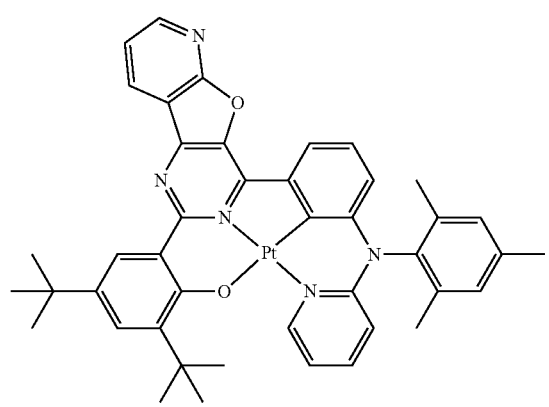

233
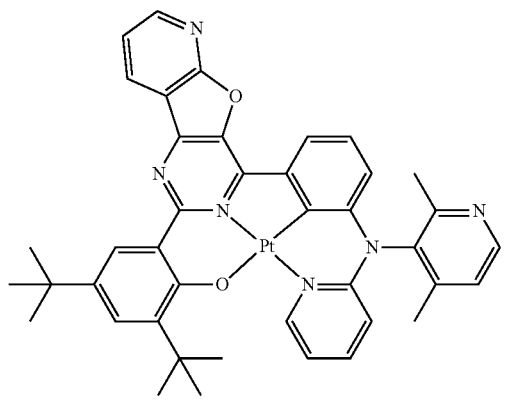
234
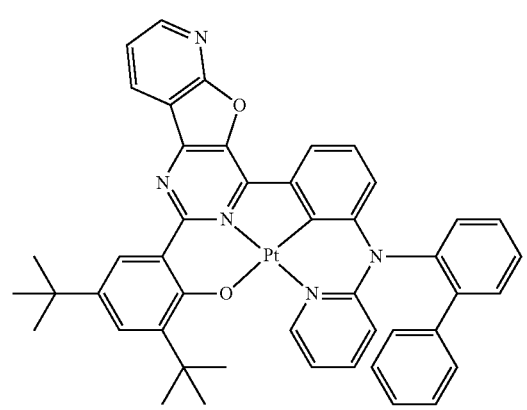
235
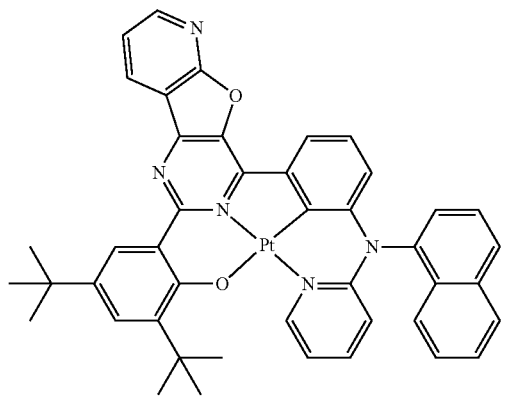
236
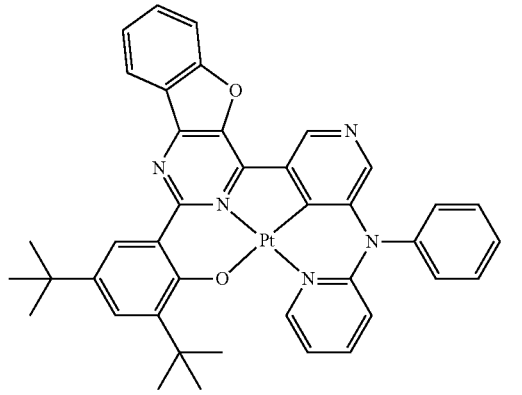
237
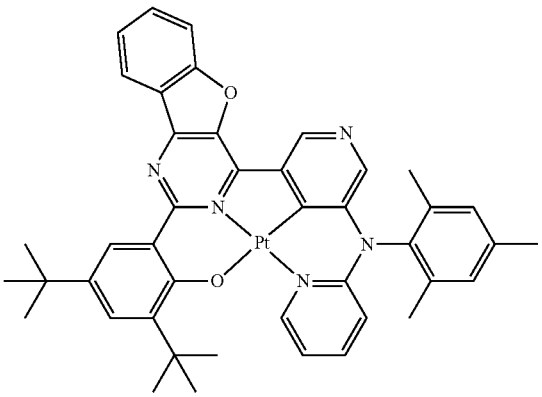
238
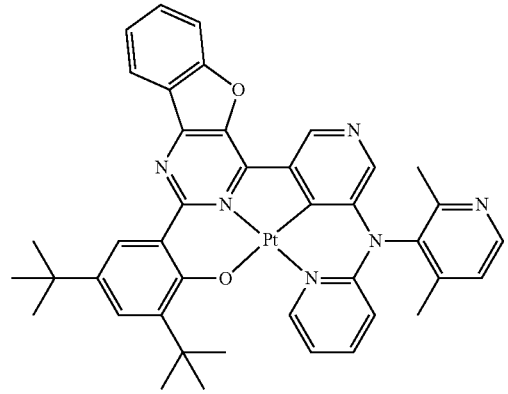
239
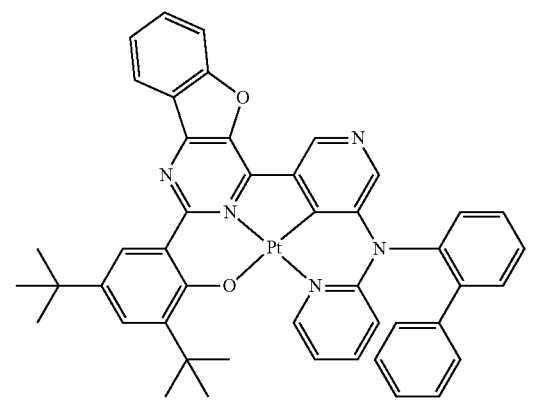
240
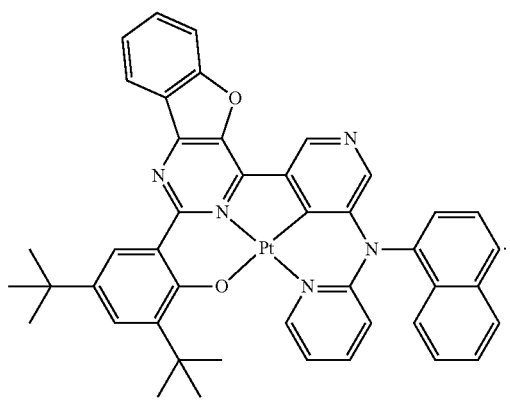

In Formula 1, $X_2$ may be N, and $CY_2$ may be selected from an azacarbazole group, an azadibenzoborol group, an azadibenzophosphol group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, and an azadibenzothiophene 5,5-dioxide group, wherein each of these groups includes at least one N as a ring-forming atom. In this regard, the organometallic compound represented by Formula 1 may have a reduced full width at half maximum (FWHM) in an emission spectrum. Accordingly, an electronic device, for example, an organic light-emitting device, including the organometallic compound represented by Formula 1 may have improved efficiency characteristics.

For example, the highest occupied molecular orbital (HOMO), the lowest unoccupied molecular orbital (LUMO), and singlet ($S_1$) and triplet ($T_1$) energy levels of Compounds 6, 20, 47, 62, 86, 100, 113, 127, 170, and 180 and Compound A may be evaluated by using a density functional theory (DFT) method according to a Gaussian program (structure optimization performed at a degree of B3LYP, and 6-31G(d,p)). The results thereof are shown in Table 1.

TABLE 1

| Compound No. | HOMO (eV) | LUMO (eV) | $S_1$ energy level (eV) | $T_1$ energy level (eV) |
|---|---|---|---|---|
| 6 | −4.627 | −2.034 | 2.017 | 1.849 |
| 20 | −4.516 | −2.055 | 1.901 | 1.764 |
| 47 | −4.612 | −2.038 | 1.997 | 1.828 |
| 62 | −4.668 | −2.030 | 2.053 | 1.885 |
| 86 | −4.790 | −1.798 | 2.461 | 2.047 |
| 100 | −4.710 | −1.767 | 2.428 | 1.993 |
| 113 | −4.792 | −1.802 | 2.462 | 2.047 |
| 127 | −4.765 | −1.809 | 2.423 | 2.036 |
| 170 | −4.658 | −2.177 | 1.923 | 1.780 |
| 180 | −4.837 | −1.914 | 2.423 | 1.993 |
| A | −4.733 | −1.754 | 2.496 | 2.208 |

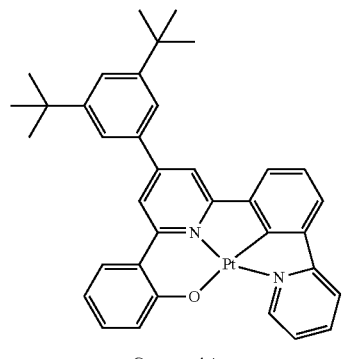

Compound A

Referring to the results of Table 1, it is confirmed that the organometallic compound represented by Formula 1 has suitable electrical characteristics for use as a dopant in an electronic device, such as an organic light-emitting device.

A method of synthesizing the organometallic compound represented by Formula 1 may be apparent to one of ordinary skill in the art by referring to Synthesis Examples provided herein.

The organometallic compound represented by Formula 1 may be suitable for use in an organic layer of an organic light-emitting device, for example, as a dopant in an emission layer of the organic layer. Thus, according to another aspect of the present disclosure, there is provided an organic light-emitting device including:

a first electrode, a second electrode, and an organic layer disposed between the first electrode and the second electrode, wherein the organic layer includes an emission layer and at least one organometallic compound represented by Formula 1.

The organic light-emitting device including the organic layer including the organometallic compound represented by Formula 1 may then have a low driving voltage, high efficiency, high power, high quantum efficiency, a long lifespan, a small roll-off ratio, and excellent color purity.

The organometallic compound represented by Formula 1 may be used in a pair of electrodes in the organic light-emitting device. For example, the organometallic compound represented by Formula 1 may be included in the emission layer. In this case, the organometallic compound may serve as a dopant, and the emission layer may further include a host (that is, an amount of the organometallic compound represented by Formula 1 may be smaller than that of the host).

The expression "(the organic layer) includes at least one organometallic compound" as used herein indicates that "(the organic layer) includes at least one organometallic compound represented by Formula 1, or at least two different organometallic compounds represented by Formula 1".

For example, the organic layer may include Compound 1 only as the organometallic compound. In this case, Compound 1 may be included in the emission layer of the organic light-emitting device. In various embodiments, the organic layer may include Compounds 1 and 2 as the organometallic compounds. In this case, Compounds 1 and 2 may be included in the same layer (for example, Compounds 1 and 2 may be both included in the emission layer).

The first electrode may be an anode, which is a hole injection electrode, and the second electrode may be a cathode, which is an electron injection electrode. In various embodiments, the first electrode may be a cathode, which is an electron injection electrode, and the second electrode may be an anode, which is a hole injection electrode.

For example, in the organic light-emitting device, the first electrode may be an anode, the second electrode may be a cathode, and the organic layer may further include a hole transport region disposed between the first electrode and the emission layer, and an electron transport region disposed between the emission layer and the second electrode, wherein the hole transport region may include a hole injection layer, a hole transport layer, an electron blocking layer, or any combination thereof, and wherein the electron transport region may include a hole blocking layer, an electron transport layer, an electron injection layer, or any combination thereof.

The term "organic layer" as used herein refers to a single and/or a plurality of layers disposed between the first electrode and the second electrode in an organic light-emitting device. The "organic layer" may include not only an organic compound, but also an organometallic complex including a metal.

The FIGURE illustrates a schematic view of an organic light-emitting device 10 according to an embodiment. Hereinafter, a structure and a method of manufacturing an organic light-emitting device according to an embodiment will be described with reference to the FIGURE. The organic light-emitting device 10 may include a first electrode 11, an organic layer 15, and a second electrode 19, which may be sequentially layered in this stated order.

A substrate may be additionally disposed under the first electrode 11 or on the second electrode 19. The substrate may be a conventional substrate used in an organic light-emitting device, and for example, may be a glass substrate or a transparent plastic substrate, each having excellent mechanical strength, thermal stability, transparency, surface smoothness, ease of handling, and water resistance.

The first electrode 11 may be formed by, for example, depositing or sputtering a material for forming the first electrode 11 on the substrate. When the first electrode 11 is an anode, the material for forming the first electrode 11 may be selected from materials with a high work function to facilitate hole injection. The first electrode 11 may be a reflective electrode, a semi-transmissive electrode, or a transmissive electrode. The material for forming the first electrode 11 may be selected from indium tin oxide (ITO), indium zinc oxide (IZO), tin oxide ($SnO_2$), and zinc oxide (ZnO). In various embodiments, the material for forming the first electrode 11 may be a metal selected from magnesium (Mg), aluminum (Al), aluminum-lithium (Al—Li), calcium (Ca), magnesium-indium (Mg—In), and magnesium-silver (Mg—Ag).

The first electrode may have a single-layered structure, or a multi-layered structure including two or more layers. For example, the first electrode 11 may have a three-layered structure of ITO/Ag/ITO, but embodiments of the present disclosure are not limited thereto.

The organic layer 15 may be on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include a hole injection layer only or a hole transport layer only. In various embodiments, the hole transport region may have a hole injection layer/hole transport layer structure or hole injection layer/hole transport layer/electron blocking layer structure, wherein layers of each structure are sequentially stacked on the first electrode 11 in this stated order, but embodiments of the present disclosure are not limited thereto.

When the hole transport region includes a hole injection layer, the hole injection layer may be formed on the first electrode 11 by using one or more suitable methods selected from vacuum deposition, spin coating, casting, and a Langmuir-Blodgett (LB) deposition method.

When the hole injection layer is formed by vacuum deposition, for example, the vacuum deposition may be performed at a deposition temperature of about 100° C. to about 500° C., at a vacuum degree of about $10^{-8}$ torr to about $10^{-3}$ torr, and at a deposition rate of about 0.01 Angstroms per second (Å/sec) to about 100 Å/sec, by taking into account the compound for the hole injection layer to be deposited, and the structure of the hole injection layer to be formed, but embodiments of the present disclosure are not limited thereto.

When the hole injection layer is formed by spin coating, the spin coating may be performed at a rate in a range of about 2,000 revolutions per minute (rpm) to about 5,000 rpm and at a temperature in a range of about 80° C. to about 200° C. to facilitate removal of a solvent after the spin coating, by taking into account the compound for the hole injection layer to be deposited, and the structure and thermal properties of the hole injection layer to be formed, but embodiments of the present disclosure are not limited thereto.

The conditions for forming a hole transport layer and an electron blocking layer may be inferred from the conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201, and a compound represented by Formula 202:

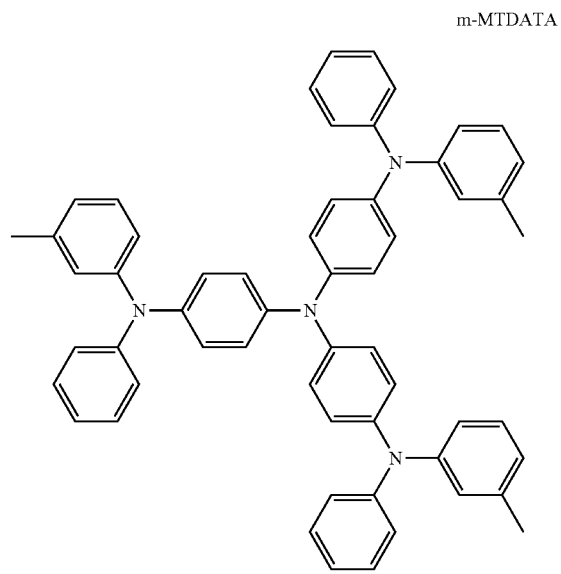

m-MTDATA

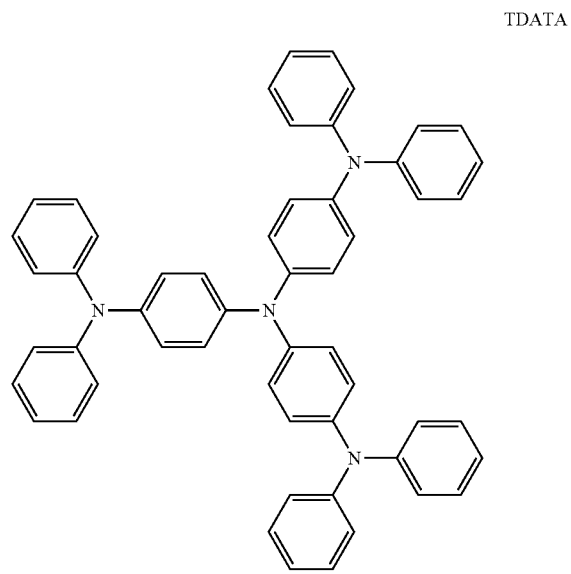

TDATA

2-TNATA
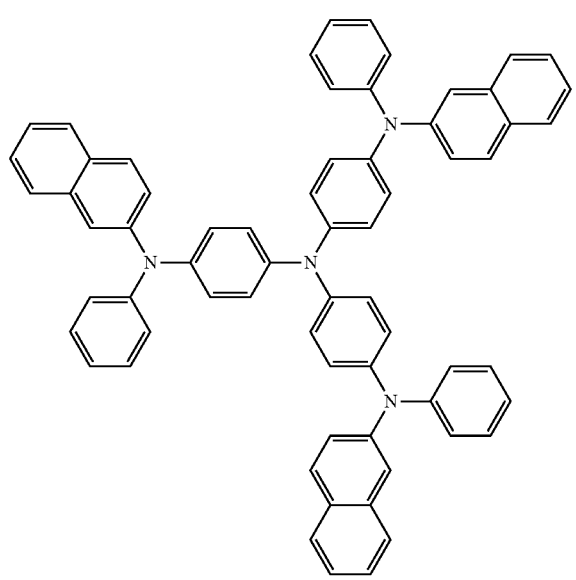
NPB
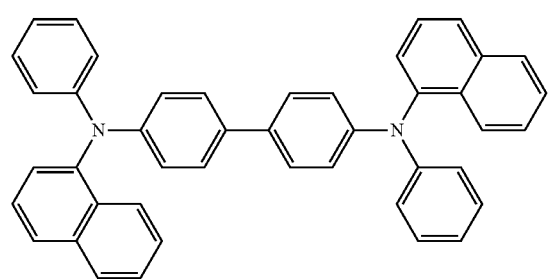
β-NPB
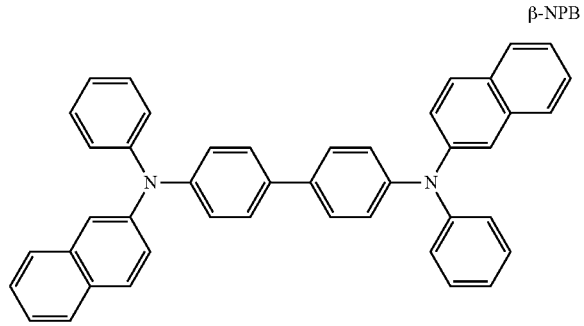
TPD
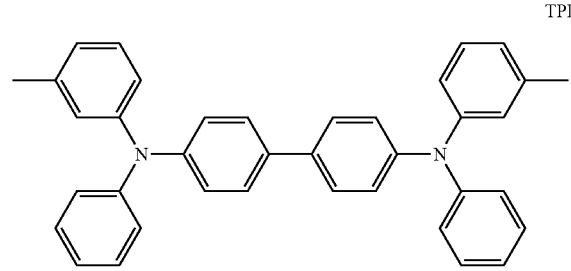
Spiro-TPD
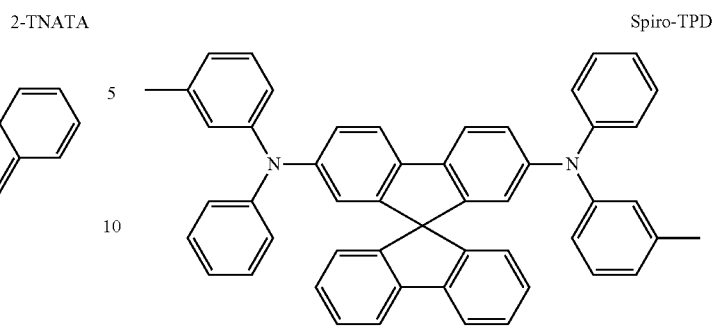
Spiro-NPB
methylated NPB
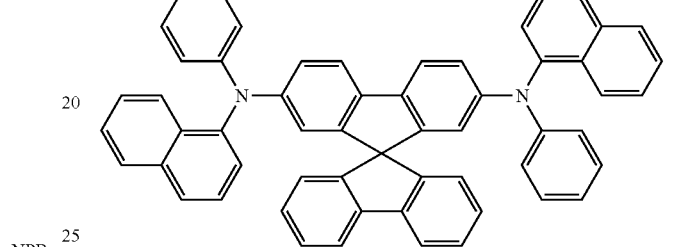
TAPC
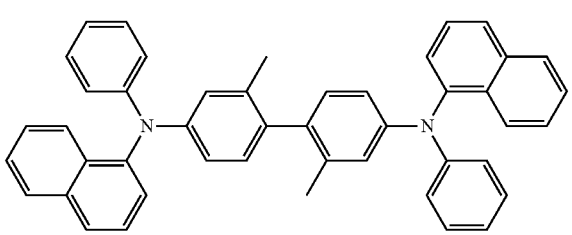
HMTPD
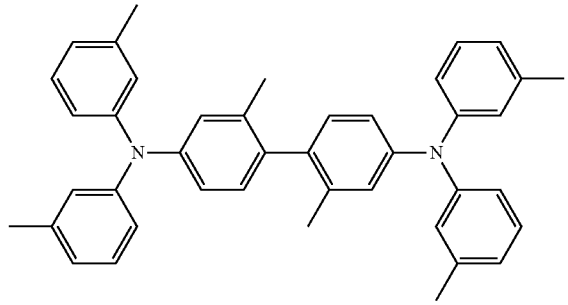
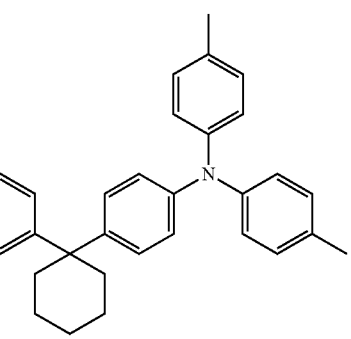

Formula 201

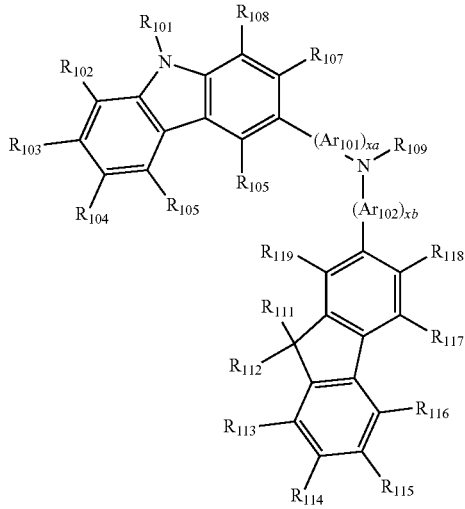

Formula 202

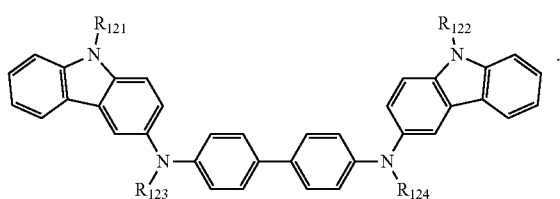

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group.

In Formula 201, xa and xb may each independently be an integer of 0 to 5, or may be 0, 1, or 2. For example, xa may be 1, and xb may be 0, but embodiments of the present disclosure are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, and a hexyl group), and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but embodiments of the present disclosure are not limited thereto:

Formula 201A

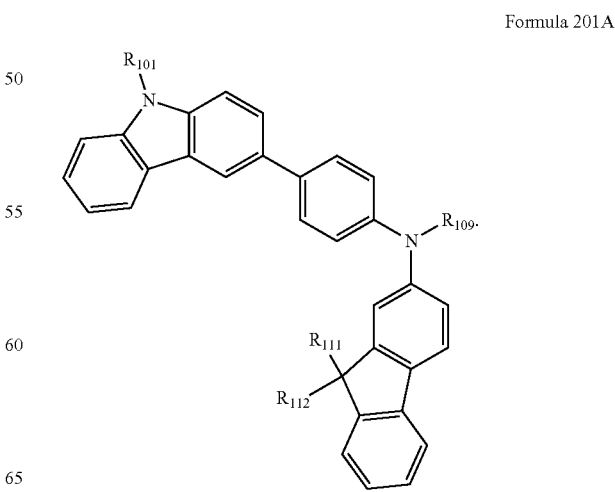

In Formula 201A, $R_{101}$, $R_{111}$, $R_{112}$, and $R_{109}$ may be the same as those described herein.
For example, the compound represented by Formula 201 and the compound represented by Formula 202 may each independently include Compounds HT1 to HT20, but embodiments of the present disclosure are not limited thereto:
HT1
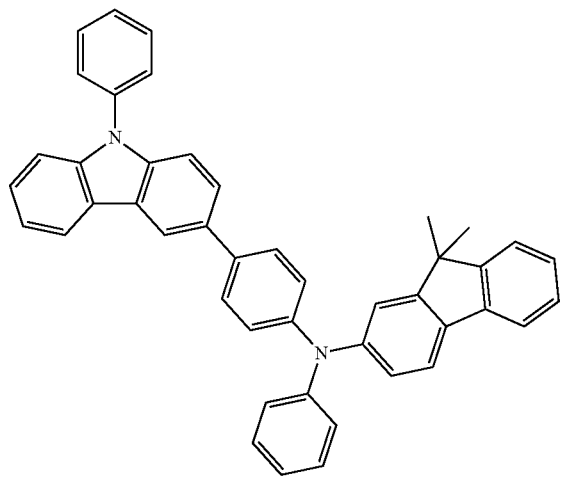
HT2
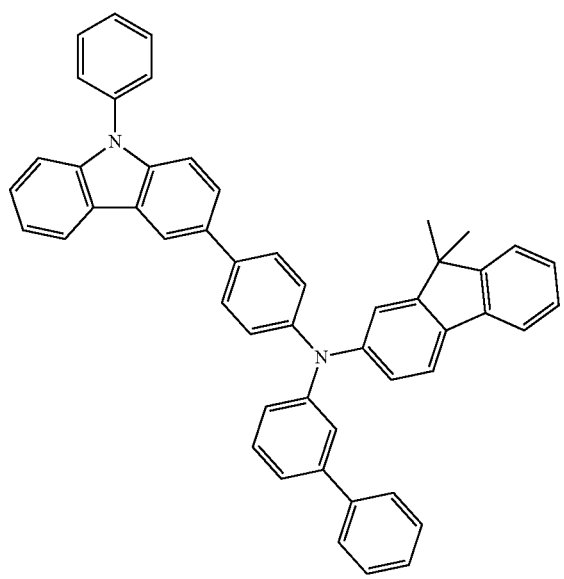
-continued
HT3
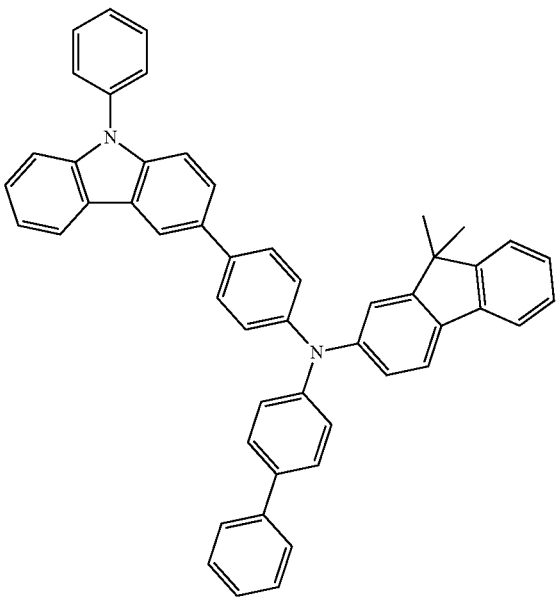
HT4
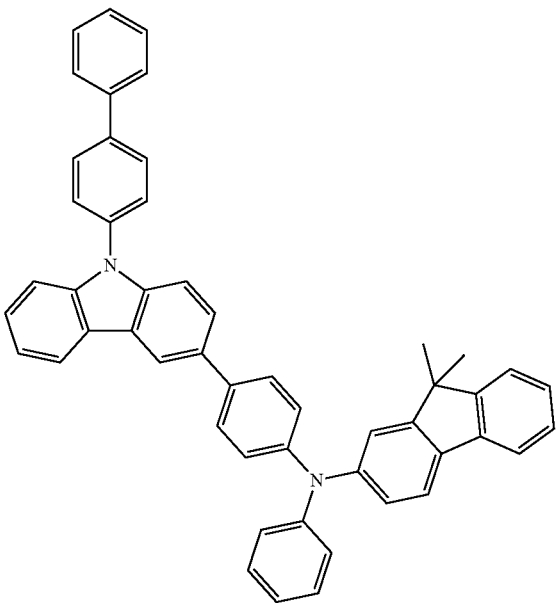

HT5
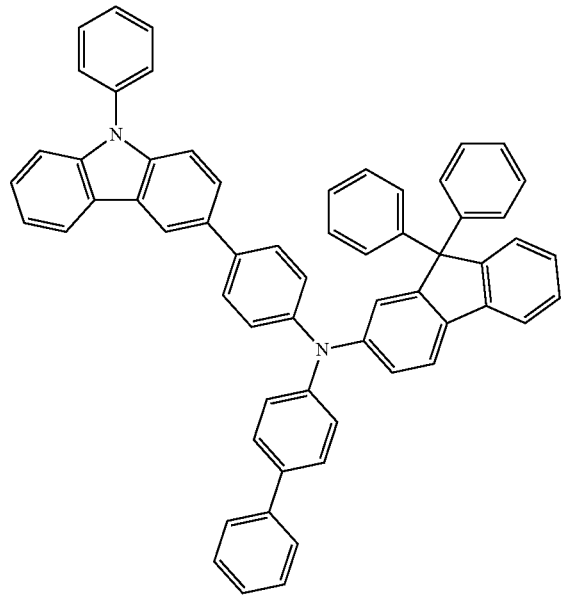
HT6
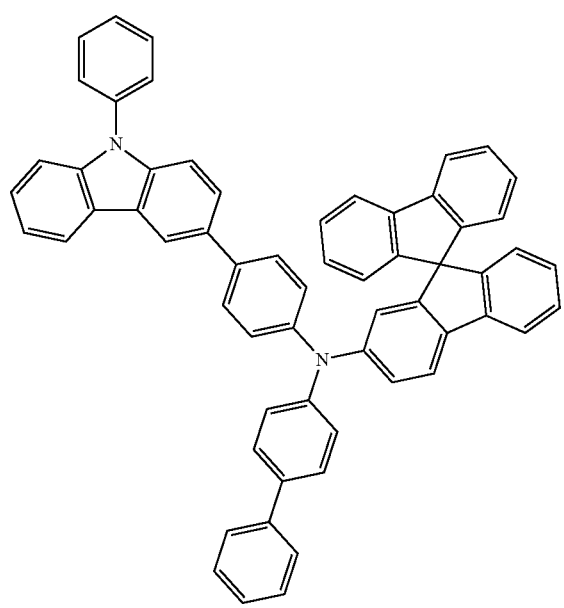
HT7
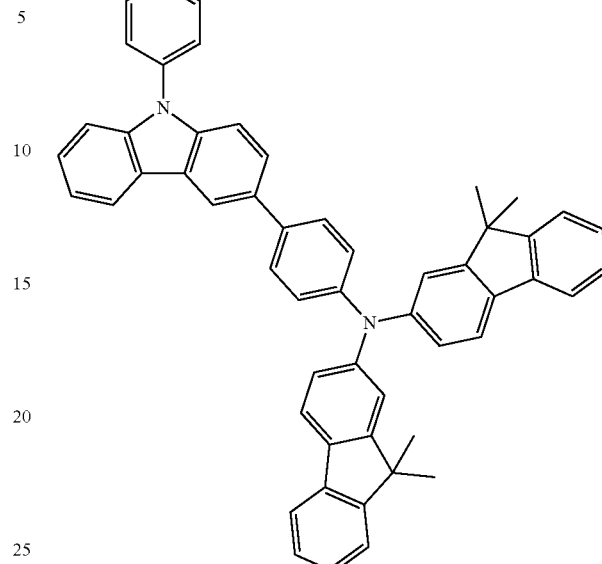
HT8
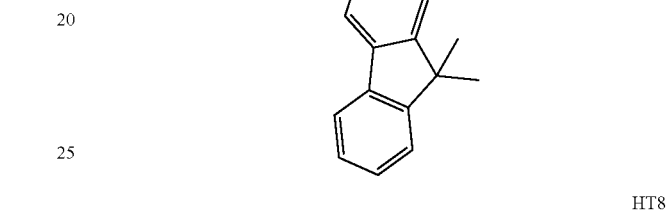
HT9
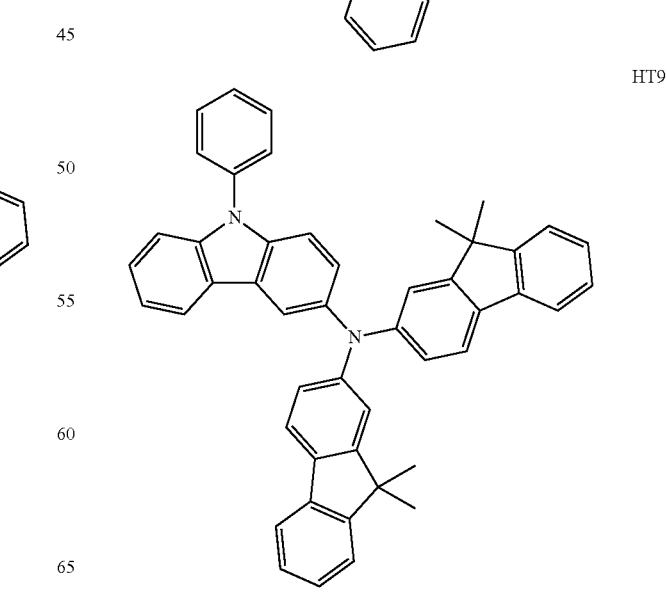

-continued
HT10
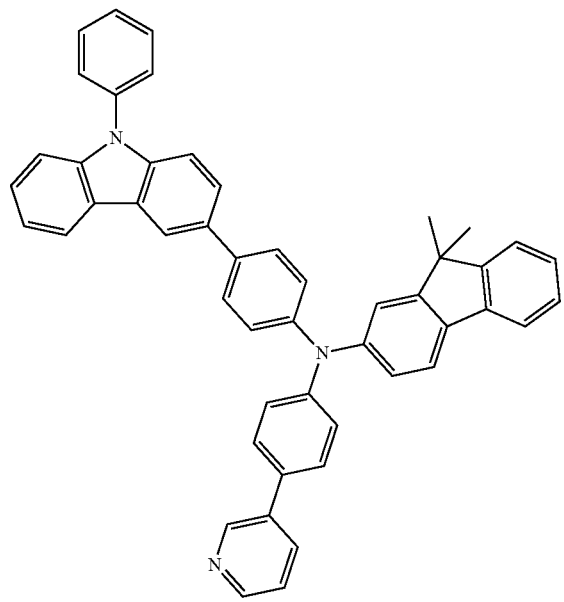
HT12
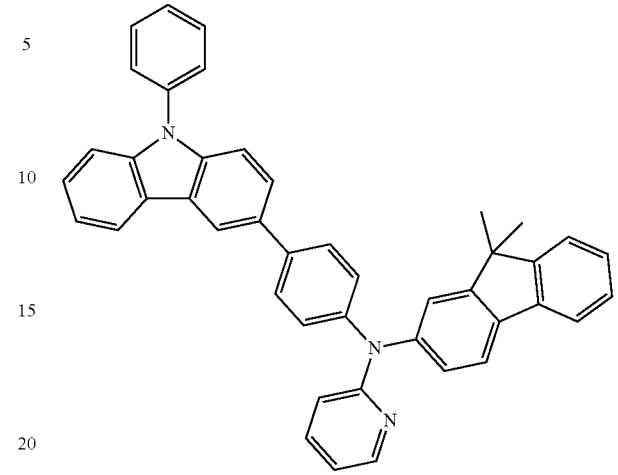
HT13
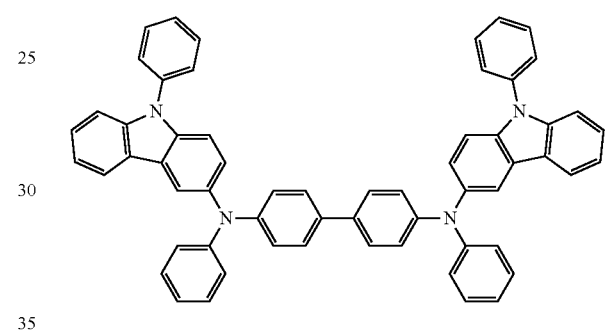
HT11
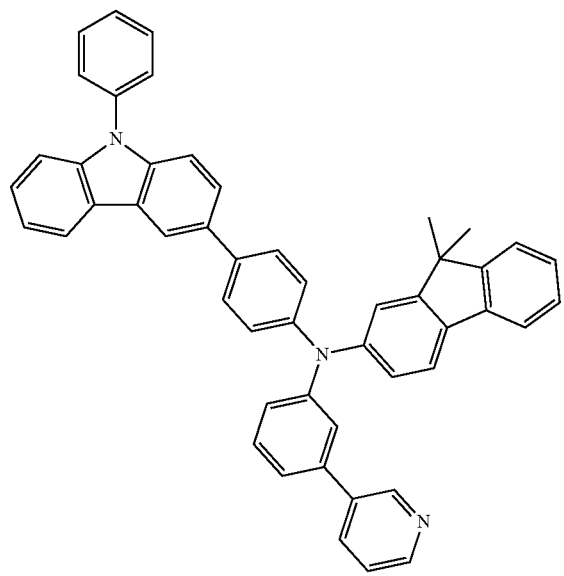
HT14
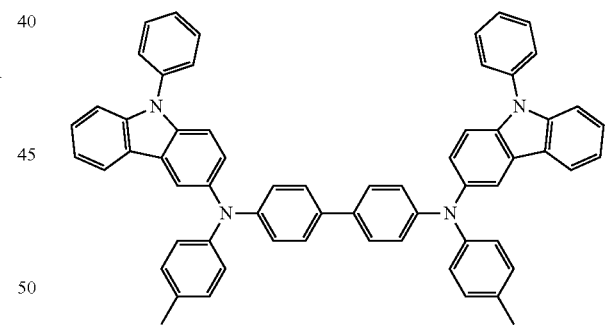
HT15
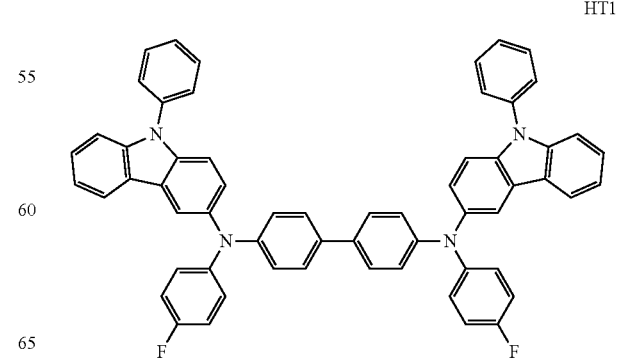

HT16

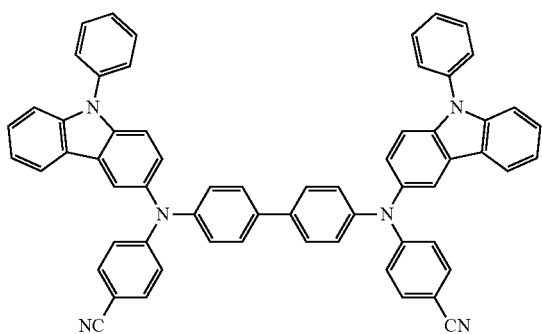

HT20

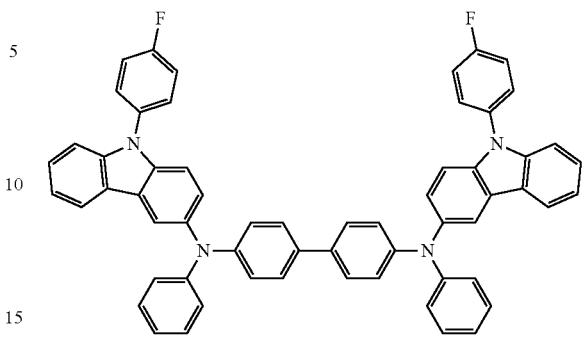

HT17

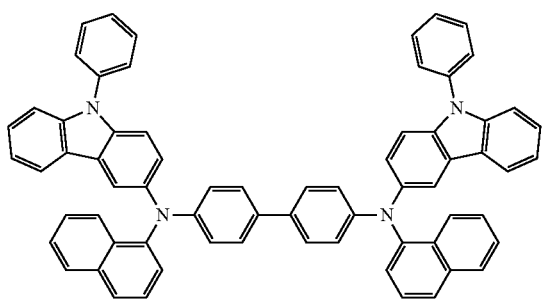

HT18

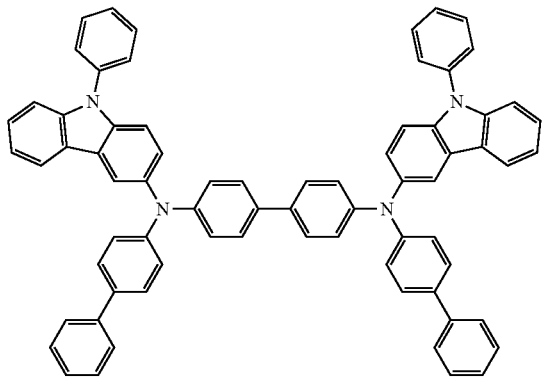

HT19

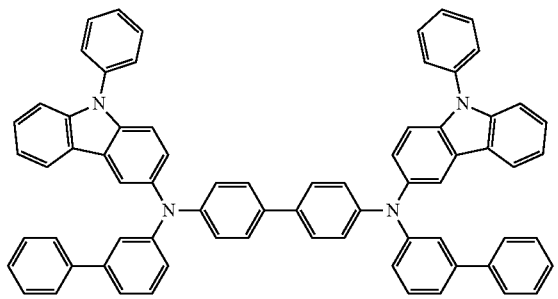

The thickness of the hole transport region may be in a range of about 100 Å to about 10,000 Å, for example, about 100 Å to about 1,000 Å. When the hole transport region includes at least one of a hole injection layer and a hole transport layer, the thickness of the hole injection layer may be in a range of about 100 Å to about 10,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, excellent hole transporting characteristics may be obtained without a substantial increase in driving voltage.

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant. The p-dopant may be selected from a quinone derivative, a metal oxide, and a cyano group-containing compound, but embodiments of the present disclosure are not limited thereto. For example, non-limiting examples of the p-dopant include a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1, but embodiments of the present disclosure are not limited thereto.

HT-D1

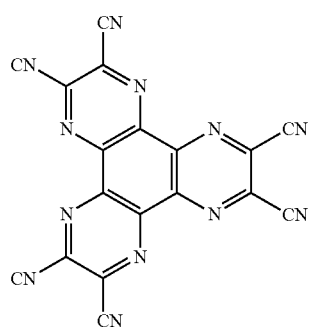

-continued

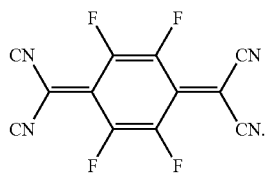

F4-TCNQ

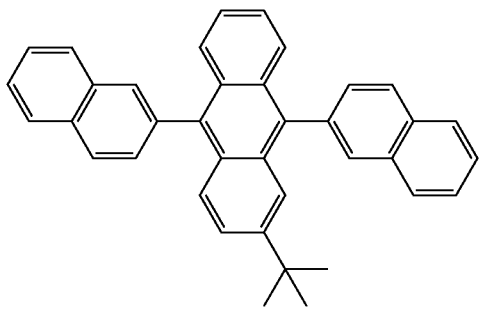

TBADN

The hole transport region may further include a buffer layer.

The buffer layer may compensate for an optical resonance distance depending on a wavelength of light emitted from the emission layer to improve efficiency of an organic light-emitting device.

An emission layer may be formed on the first electrode 11 or the hole transport region by using one or more suitable methods selected from vacuum deposition, spin coating, casting, and an LB deposition method. When the emission layer is formed by vacuum deposition or spin coating, vacuum deposition and coating conditions for the emission layer may be generally similar to the conditions for forming a hole injection layer, though the conditions may vary depending on the compound used.

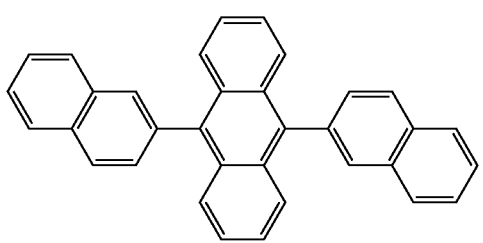

ADN

When the hole transport region includes an electron blocking layer, a material for forming the electron blocking layer may be selected from the materials for forming a hole transport region and host materials described herein, but embodiments of the present disclosure are not limited thereto. For example, when the hole transport region includes an electron blocking layer, mCP described herein may be used for forming the electron blocking layer.

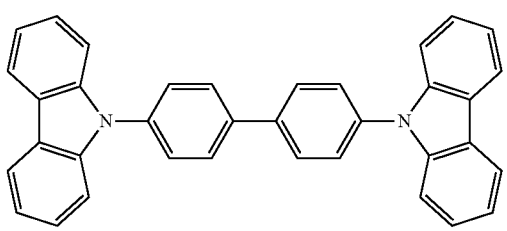

CPB

The emission layer may include a host and a dopant, and the dopant may include the organometallic compound represented by Formula 1.

The host may include at least one selected from TPBi, TBADN, ADN (also referred to as "DNA"), CBP, CDBP, TCP, Mcp, Compound H50, and Compound H51:

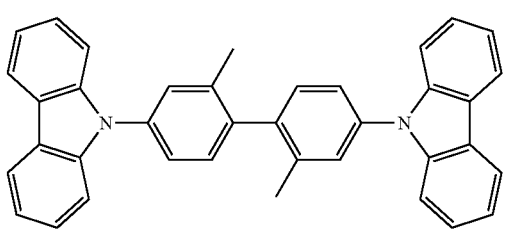

CDBP

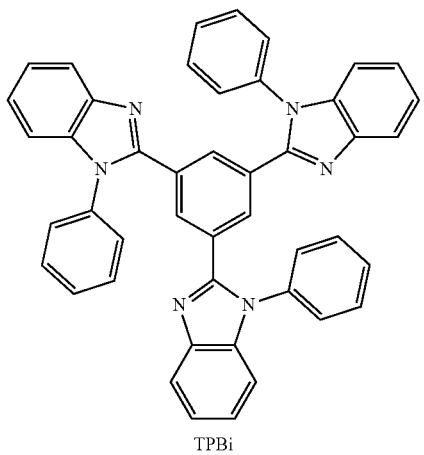

TPBi

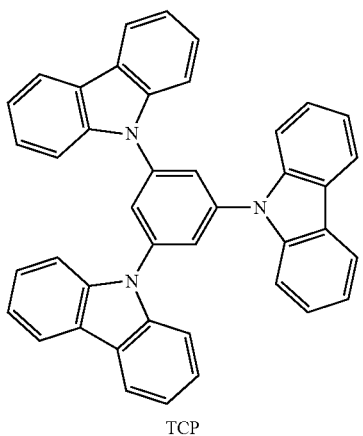

TCP

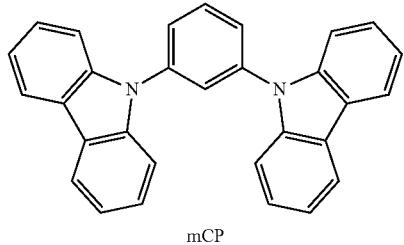

mCP

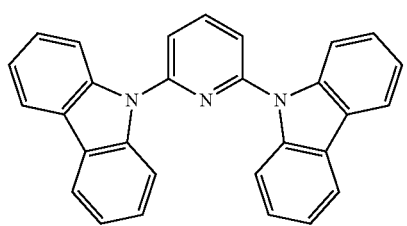

H50

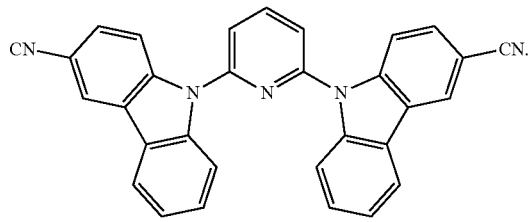

H51

In various embodiments, the host may further include a compound represented by Formula 301:

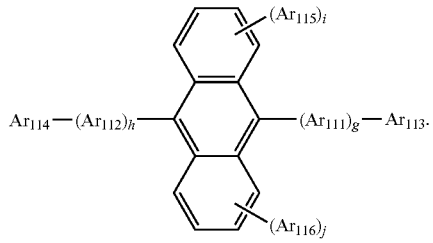

Formula 301

In Formula 301, $Ar_{111}$ and $Ar_{112}$ may each independently be selected from:

a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group.

In Formula 301, $Ar_{113}$ to $Ar_{116}$ may each independently be selected from:

a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one selected from a phenyl group, a naphthyl group, and an anthracenyl group.

In Formula 301, g, h, i, and j may each independently be an integer of 0 to 4, for example, 0, 1, or 2.

In Formula 301, $Ar_{113}$ to $Ar_{116}$ may each independently be selected from:

a $C_1$-$C_{10}$ alkyl group substituted with at least one selected from a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

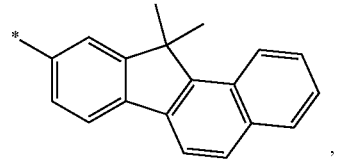 [SMILES: *c1ccc2c(c1)C(C)(C)c1c-2ccc2ccccc12]

, but embodiments of the present disclosure are not limited thereto.

In various embodiments, the host may include a compound represented by Formula 302:

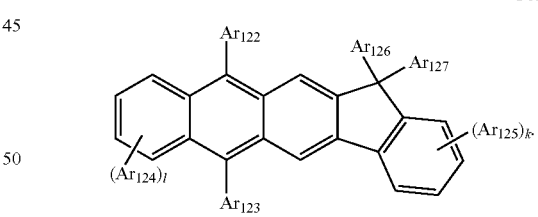

Formula 302

In Formula 302, $Ar_{122}$ to $Ar_{125}$ may each independently be the same as described herein in connection with $Ar_{113}$ of Formula 301.

In Formula 302, $Ar_{126}$ and $Ar_{127}$ may each independently be a $C_1$-$C_{10}$ alkyl group (for example, a methyl group, an ethyl group, or a propyl group).

In Formula 302, k and l may each independently be an integer of 0 to 4. For example, k and l may each independently be 0, 1, or 2.

The compound represented by Formula 301 and the compound represented by Formula 302 may each independently include Compounds H1 to H42, but embodiments of the present disclosure are not limited thereto.

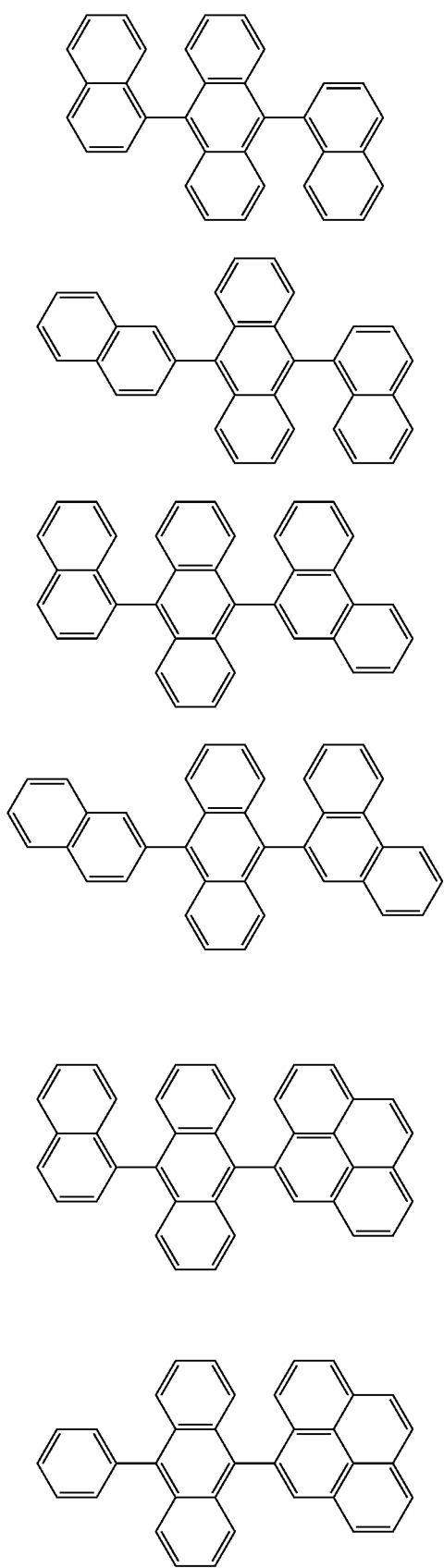
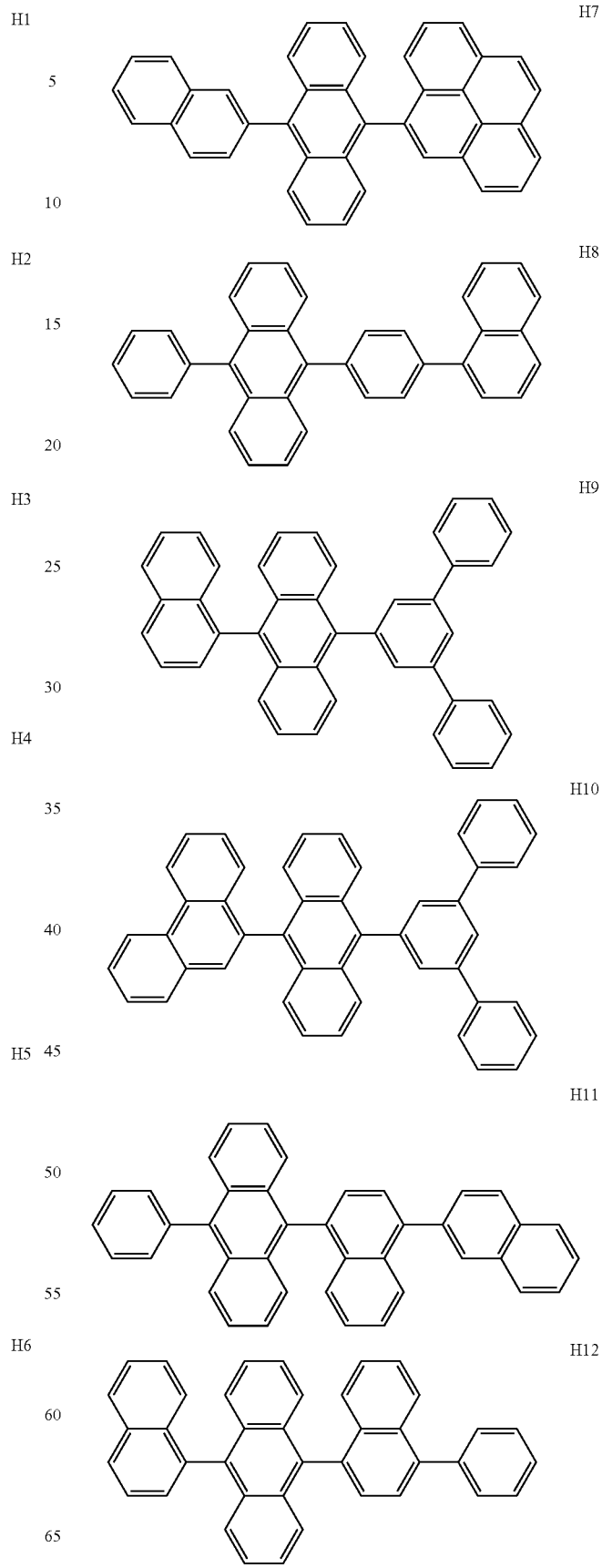

H13
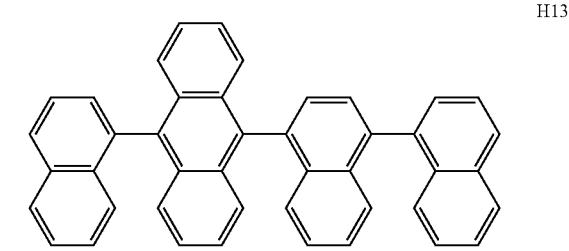
H14
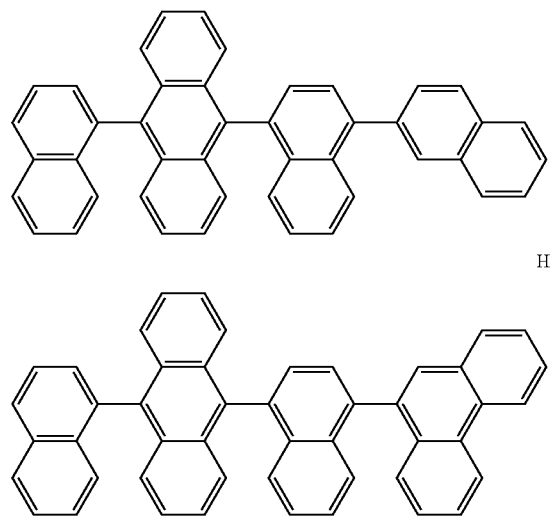
H15
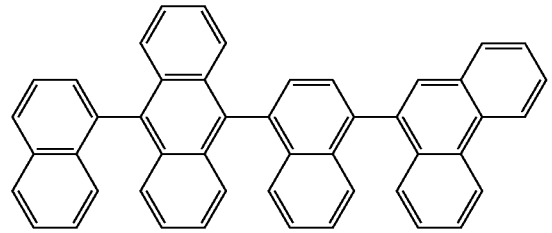
H16
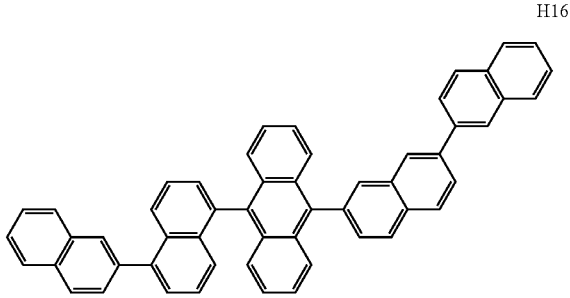
H17
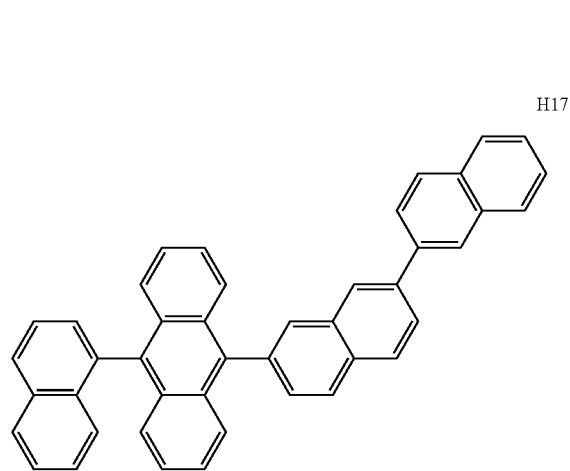
H18
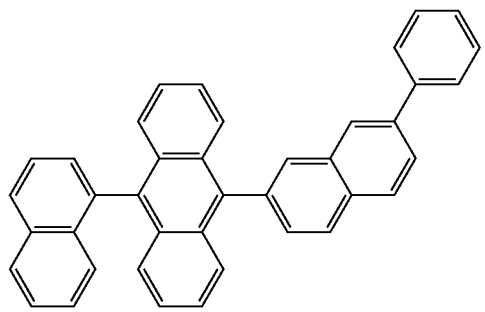
H19
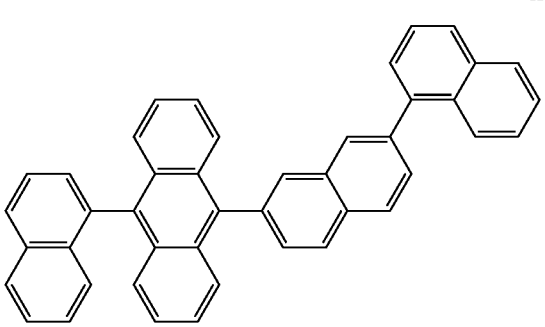
H20
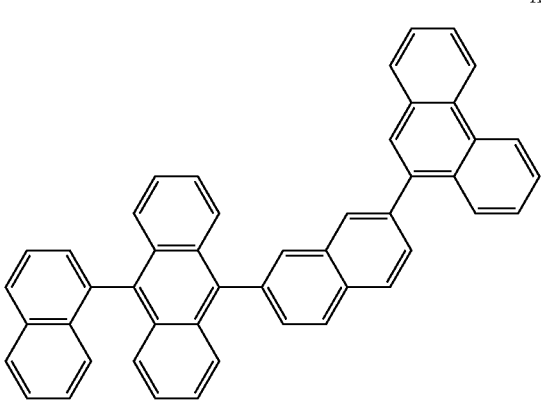
H21
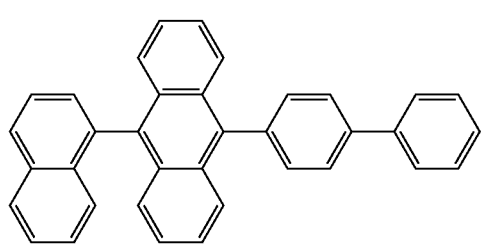
H22
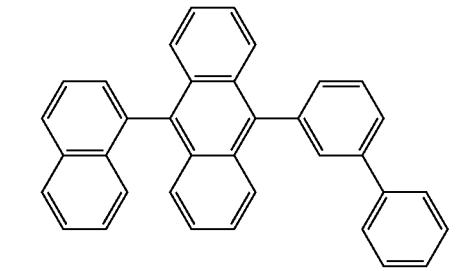

H23
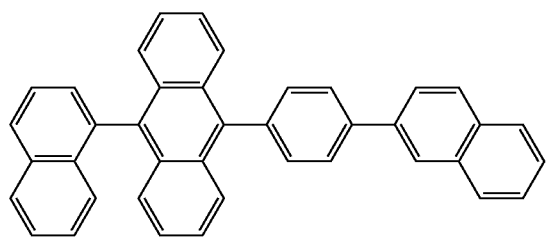
H24
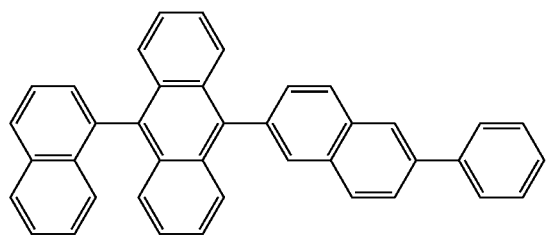
H25
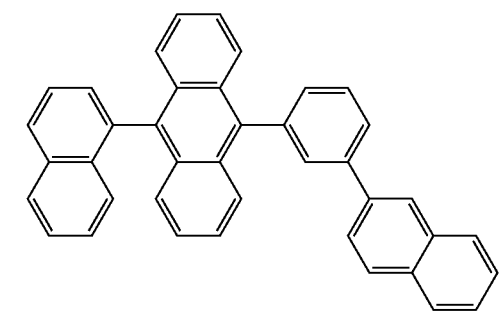
H26
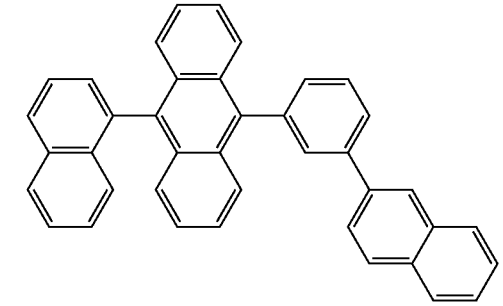
H27
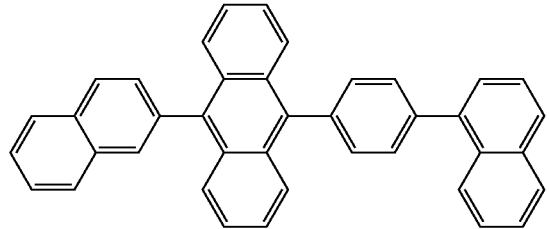
H28
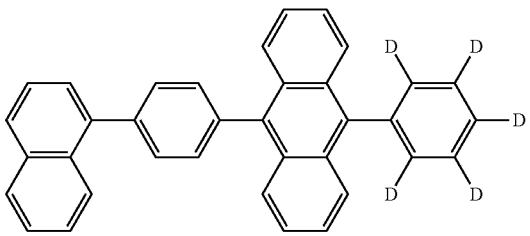
H29
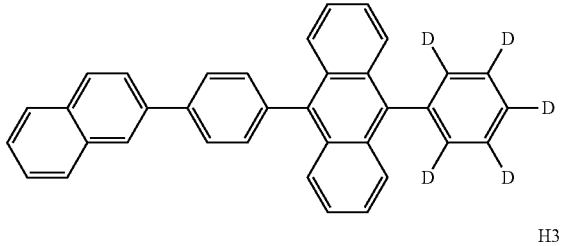
H30
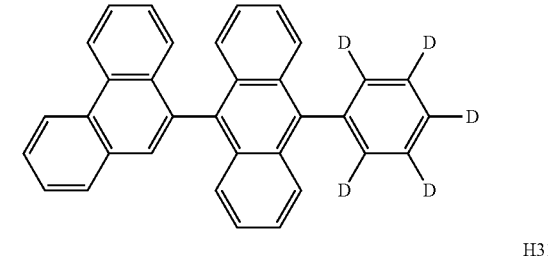
H31
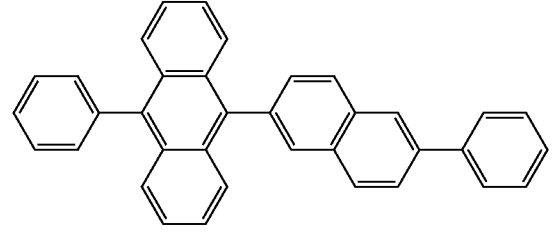
H32
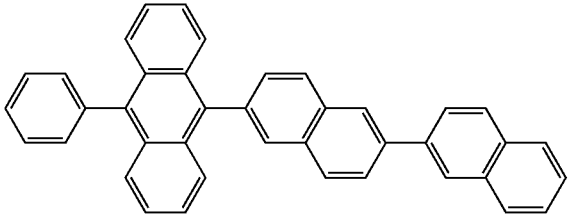
H33
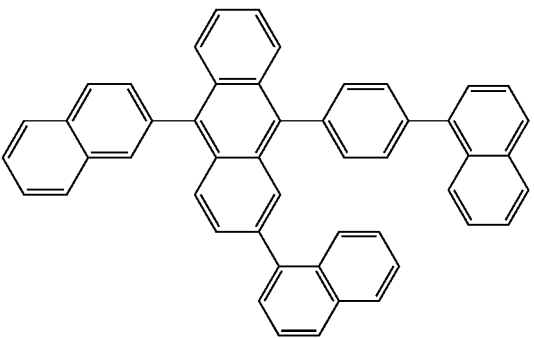

H34
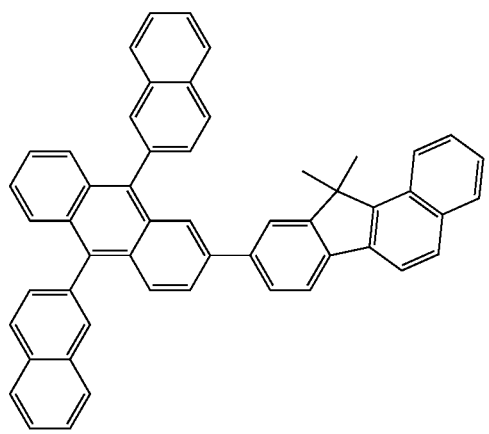
H35
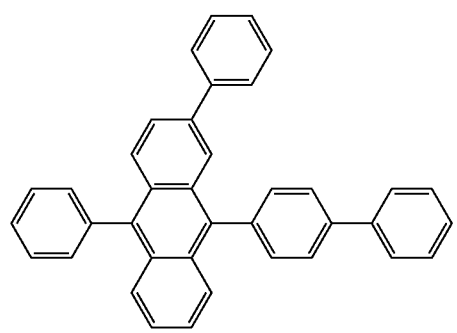
H36
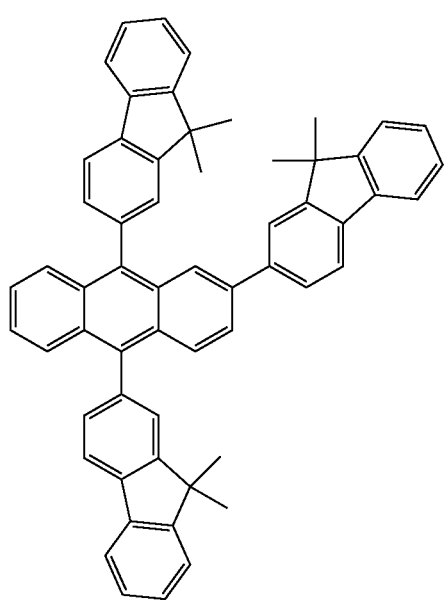
H37
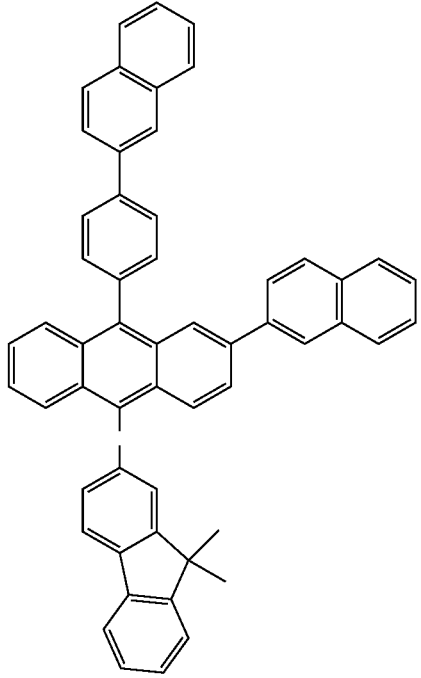
H38
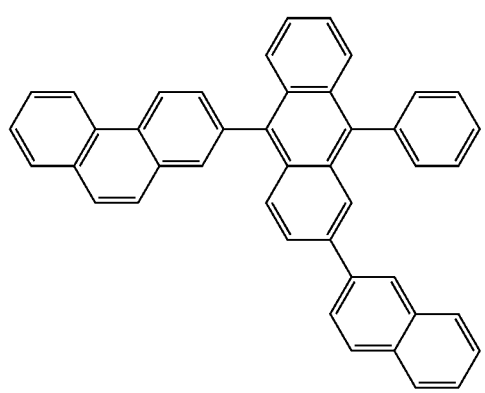
H39
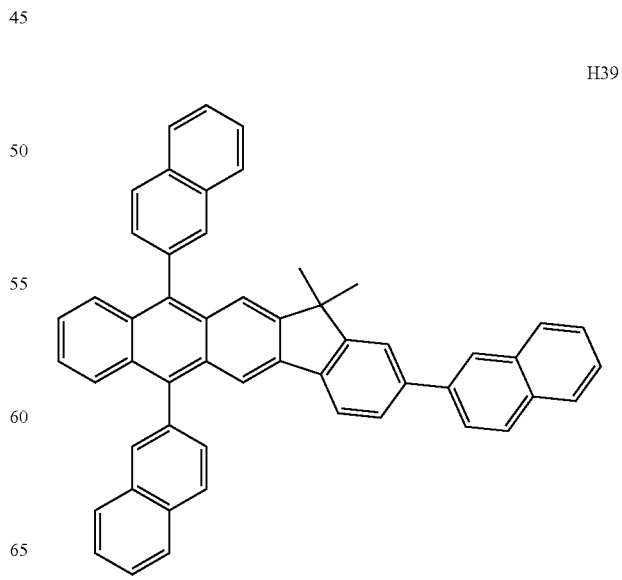

H40

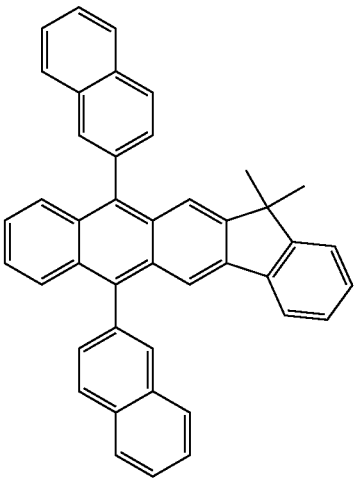

H41

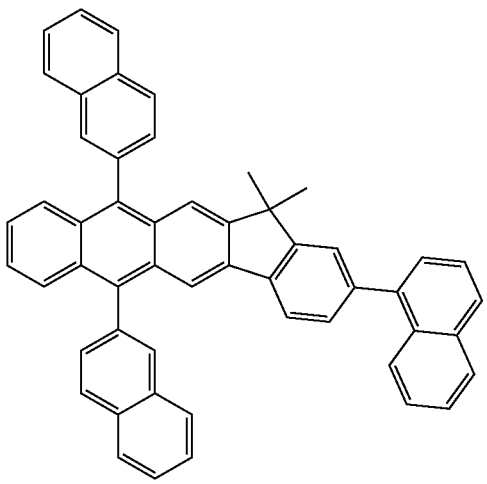

H42

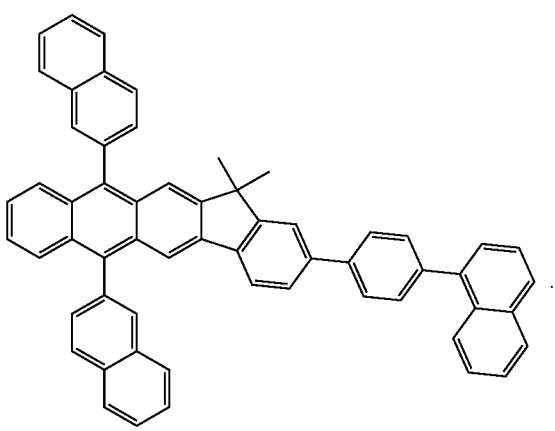

When the organic light-emitting device 10 is a full-color organic light-emitting device, the emission layer may be patterned into a red emission layer, a green emission layer, and a blue emission layer. In various embodiments, the emission layer may have a structure in which the red emission layer, the green emission layer, and/or the blue emission layer are layered so as to emit white light. In various embodiments, the structure of the emission layer may vary.

When the emission layer includes the host and the dopant, an amount of the dopant may be selected from a range of about 0.01 parts to about 15 parts by weight based on about 100 parts by weight of the host, but embodiments of the present disclosure are not limited thereto.

The thickness of the emission layer may be in a range of about 100 Å to about 1,000 Å, for example, about 200 Å to about 600 Å. When the thickness of the emission layer is within any of these ranges, improved luminous characteristics may be obtained without a substantial increase in driving voltage.

Next, an electron transport region may be formed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but embodiments of the present disclosure are not limited thereto. The electron transport layer may have a single-layered structure or a multi-layered structure including two or more different materials.

The conditions for forming a hole blocking layer, an electron transport layer, and an electron injection layer in the electron transport region may be inferred from the conditions for forming the hole injection layer.

When the electron transport region includes a hole blocking layer, the hole blocking layer may include, for example, at least one selected from BOP, Bphen, and BAlq, but embodiments of the present disclosure are not limited thereto.

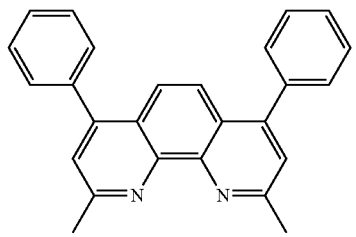

BCP

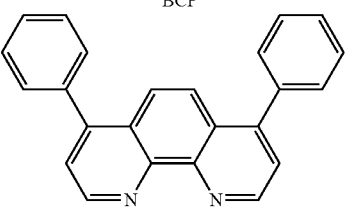

Bphen

The thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, excellent hole blocking characteristics may be obtained without a substantial increase in driving voltage.

The electron transport layer may further include at least one selected from BCP, Bphen, Alq$_3$, BAlq, TAZ, and NTAZ:

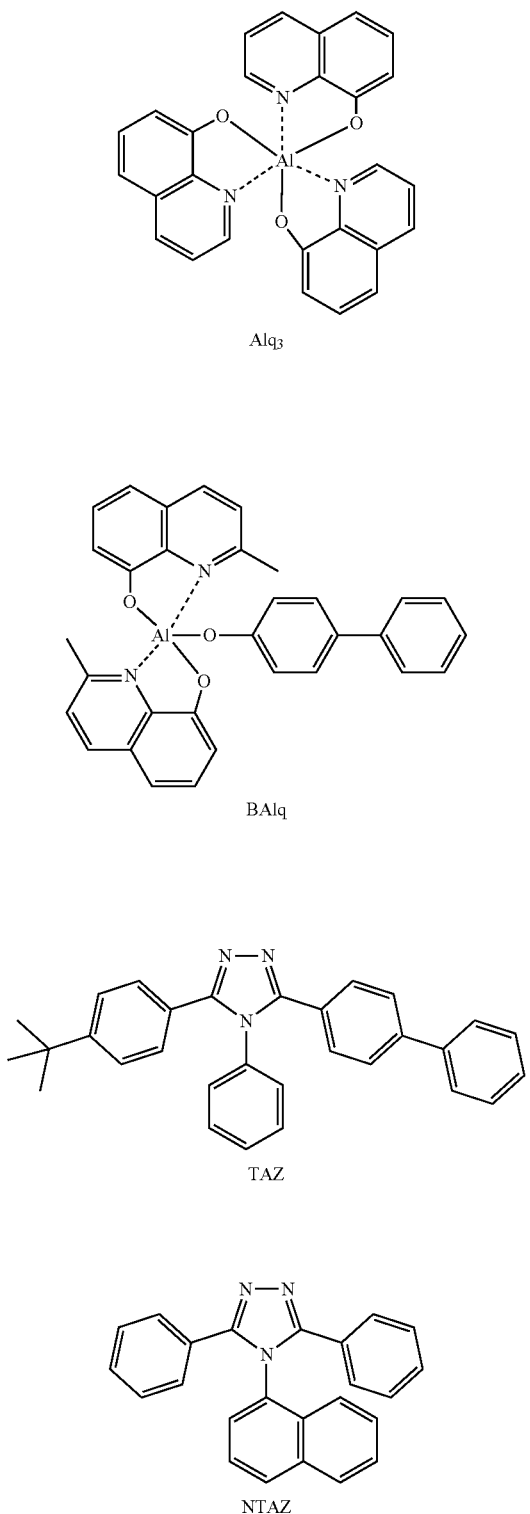

Alq₃

BAlq

TAZ

NTAZ

In various embodiments, the electron transport layer may include at least one of Compounds ET1 and ET2, but embodiments of the present disclosure are not limited thereto:

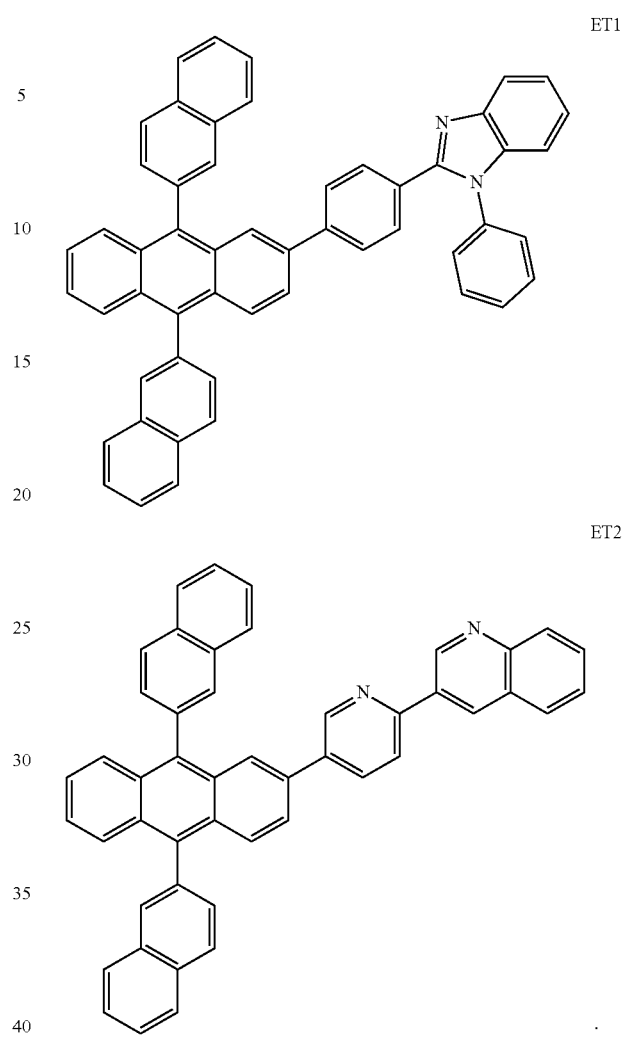

ET1

ET2

The thickness of the electron transport layer may be in a range of about 100 Å to about 1,000 Å, for example, about 150 Å to about 500 Å. While not wishing to be bound by theory, it is understood that when the thickness of the electron transport layer is within any of these ranges, excellent electron transport characteristics may be obtained without a substantial increase in driving voltage.

The electron transport layer may further include a metal-containing material, in addition to the materials described above.

The metal-containing material may include a lithium (Li) complex. The Li complex may include, for example, Compound ET-D1 (lithium quinolate (LiQ)) or Compound ET-D2:

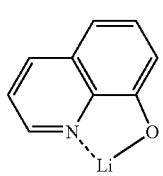

ET-D1

ET-D2

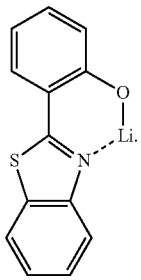

In addition, the electron transport region may include an electron injection layer that facilitates electron injection from the second electrode 19.

The electron injection layer may include at least one selected from LiF, NaCl, CsF, $Li_2O$, and BaO.

The thickness of the electron injection layer may be in a range of about 1 Å to about 100 Å, for example, about 3 Å to about 90 Å. While not wishing to be bound by theory, it is understood that when the thickness of the electron injection layer is within any of these ranges, excellent electron injection characteristics may be obtained without a substantial increase in driving voltage.

The second electrode 19 may be formed on the organic layer 15. The second electrode 19 may be a cathode. A material for forming the second electrode 19 may be a material with a relatively low work function, such as a metal, an alloy, an electrically conductive compound, or a mixture thereof. Examples of the material for forming the second electrode 19 may include Li, Mg, Al, Al—Li, Ca, Mg—In, and Mg—Ag. In various embodiments, ITO or IZO may be used to form a transmissive second electrode 19 to manufacture a top-emission light-emitting device. In various embodiments, the material for forming the second electrode 19 may vary.

Hereinbefore the organic light-emitting device 10 has been described with reference to the FIGURE, but embodiments are not limited thereto.

According to another aspect of the present disclosure, there is provided a diagnostic composition that includes at least one organometallic compound represented by Formula 1.

Since the organometallic compound represented by Formula 1 may provide high emission efficiency, the diagnostic composition including the at least one organometallic compound represented by Formula 1 may also have excellent diagnostic efficiency.

The diagnostic composition may be applied in various ways, such as in a diagnostic kit, a diagnostic reagent, a biosensor, or a biomarker.

The term "$C_1$-$C_{60}$ alkyl group" as used herein refers to a linear or branched saturated aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is a $C_1$-$C_{60}$ alkyl group). Examples thereof include a methoxy group, an ethoxy group, and an iso-propyloxy (iso-propoxy) group.

The term "$C_2$-$C_{60}$ alkenyl group" as used herein refers to a group formed by including at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by including at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the "$C_3$-$C_{10}$ cycloalkyl group".

The term "$C_1$-$C_{10}$ heterocycloalkyl group" as used herein refers to a monovalent monocyclic group including at least one heteroatom selected from N, O, P, Si, and S as a ring-forming atom, 1 to 10 carbon atoms, and at least one carbon-carbon double bond in its ring. Examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, P, Si, and S as a ring-forming atom, 1 to 10 carbon atoms, and at least one carbon-carbon double bond in its ring. Examples of the $C_1$-$C_{10}$ heterocycloalkenyl group include a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

The term "$C_1$-$C_{60}$ heteroaryl group" as used herein refers to a monovalent group having a cyclic aromatic system having at least one heteroatom selected from N, O, P, Si, and S as a ring-forming atom, and 1 to 60 carbon atoms. The term "$C_1$-$C_{60}$ heteroarylene group" as used herein refers to a divalent group having a cyclic aromatic system having at least one heteroatom selected from N, O, P, and S as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein indicates —$OA_{102}$ (wherein $A_{102}$ is the $C_6$-$C_{60}$ aryl group), the term "$C_6$-$C_{60}$ arylthio group" as used herein indicates —$SA_{103}$ (wherein $A_{103}$ is the $C_6$-$C_{60}$ aryl group), and a $C_7$-$C_{60}$ arylalkyl group as used herein indicates -$A_{104}A_{105}$ (wherein $A_{104}$ is the $C_6$-$C_{59}$ aryl group and $A_{105}$ is the $C_1$-$C_{53}$ alkyl group).

The term "monovalent non-aromatic condensed polycyclic group" as used herein refers to a monovalent group that has two or more condensed rings and only carbon atoms (for example, the number of carbon atoms may be in a range of 8 to 60) as ring-forming atoms, wherein the molecular structure as a whole is non-aromatic. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group that has two or more condensed rings, and a heteroatom selected from N, O, P, Si, and S and carbon atoms (e.g., the number of carbon atoms may be in a range of 1 to 60) as ring-forming atoms, wherein the molecular structure as a whole is non-aromatic. The monovalent non-aromatic condensed heteropolycyclic group may include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group including 5 to 30 carbon atoms only as ring-forming atoms. The $C_5$-$C_{30}$ carbocyclic group may be a monocyclic group or a polycyclic group.

The term "$C_1$-$C_{30}$ heterocyclic group" as used herein refers to saturated or unsaturated cyclic group including 1 to 30 carbon atoms and at least one heteroatom selected from N, O, P, Si, and S as ring-forming atoms. The $C_1$-$C_{30}$ heterocyclic group may be a monocyclic group or a polycyclic group.

At least one substituent of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_2$-$C_{60}$ heteroaryloxy group, the substituted $C_2$-$C_{60}$ heteroarylthio group, the substituted $C_3$-$C_{60}$ heteroarylalkyl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and
—$N(Q_{31})(Q_{32})$, —$Si(Q_{33})(Q_{34})(Q_{35})$, —$B(Q_{36})(Q_{37})$, and —$P(=O)(Q_{38})(Q_{39})$, and $Q_1$ to $Q_9$, $Q_{11}$ to $Q_{19}$, $Q_{21}$ to $Q_{29}$, and $Q_{31}$ to $Q_{39}$ may each independently be selected from a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group and a monovalent non-aromatic condensed heteropolycyclic group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group, and a $C_6$-$C_{60}$ aryl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Hereinafter, a compound and an organic light-emitting device according to an embodiment will be described in detail with reference to Synthesis Examples and Examples, however, the present disclosure is not limited thereto. The wording "B was used instead of A" used in describing Synthesis Examples means that an identical molar equivalent of B was used in place of A.

EXAMPLES

Synthesis Example 1

Synthesis of Compound 20

Synthesis of Intermediate L1-1

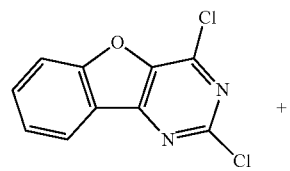

+

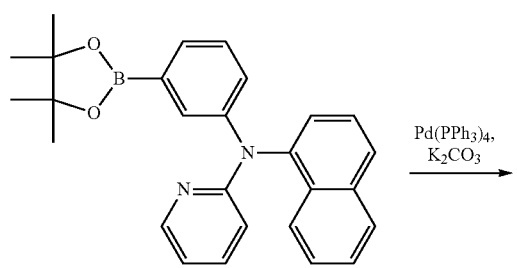

Intermediate L1-2

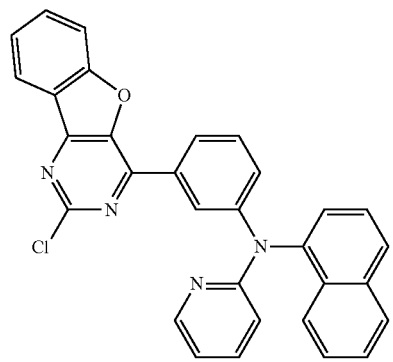

Intermediate L1-1

4.79 g (grams) (20.04 millimoles, mmol) of 2,4-dichlorobenzofuro[3,2-d]pyrimidine, 8.89 g (21.04 mmol) of Intermediate L1-2, 1.16 g (1.00 mmol) of Pd(PPh$_3$)$_4$, and 8.31 g (60.13 mmol) of potassium carbonate were added to 200 milliliters (mL) of toluene, and the mixture was stirred under reflux for 12 hours. The reaction mixture was cooled to room temperature and extracted by using water and methylene chloride. The organic layer was separated, and the solvent was removed therefrom. The resulting residue was then purified by column chromatography using hexane:acetyl acetate at a ratio of 8:2, thereby obtaining 5.22 g (yield: 52%) of Intermediate L1-1, which was then identified by using HPLC.

Synthesis of Intermediate L1

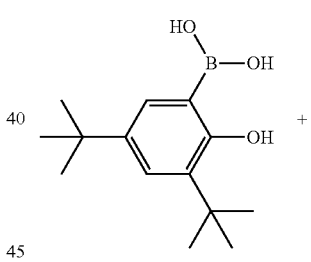

+

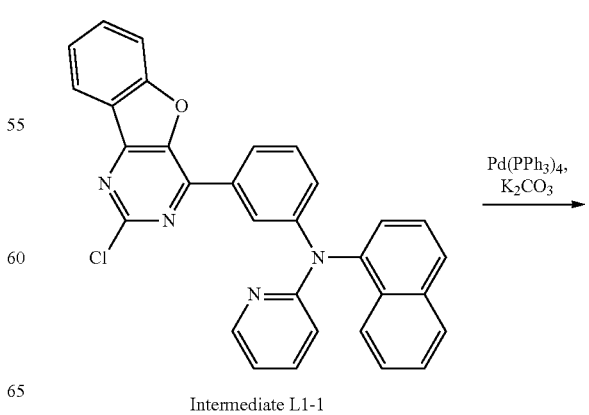

Intermediate L1-1

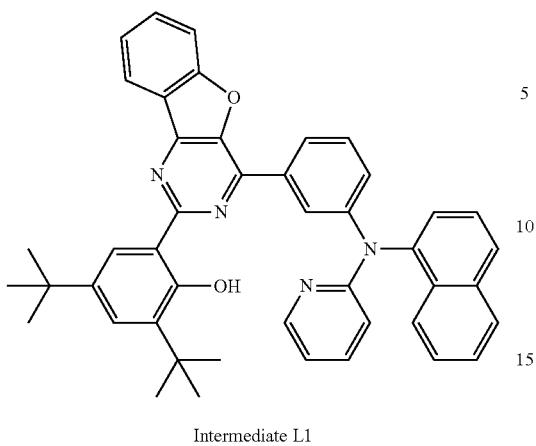

Intermediate L1

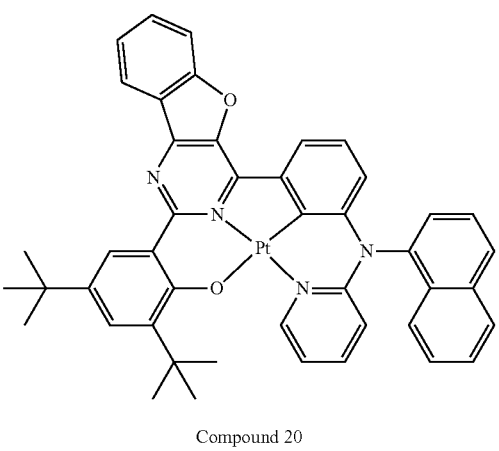

Compound 20

1.55 g (2.32 mmol) of Intermediate L1, 1.21 g (2.55 mmol) of PtCl$_2$(NCPh)$_2$, and 20 mL of benzonitrile were mixed together, and the mixture was stirred under reflux for 12 hours. The reaction mixture was cooled to room temperature, and the solvent was removed therefrom. The resulting residue was then purified by column chromatography using hexane:methylene chloride at a ratio of 7:3, thereby obtaining 0.54 g (yield: 27%) of Compound 20, which was then identified by using mass spectrometry and HPLC.

HRMS (MALDI) calcd. for C$_{45}$H$_{38}$N$_4$O$_2$Pt: m/z 861.2643, Found: 861.2649.

Synthesis Example 2

Synthesis of Compound 47

Synthesis of Intermediate L2-1

3.93 g (15.70 mmol) of 3,5-di-tert-butyl-2-hydroxyl phenyl boronic acid, 5.22 g (10.47 mmol) of Intermediate L1-1, 0.61 g (0.52 mmol) of Pd(PPh$_3$)$_4$, and 4.34 g (31.40 mmol) of potassium carbonate were added to a solution in which 90 mL of tetrahydrofuran and 30 mL of water were mixed, and the mixture was stirred under reflux for 12 hours. The reaction mixture was then cooled to room temperature and extracted by using water and methylene chloride. The organic layer was separated, and the solvent was removed therefrom. The resulting residue was then purified by column chromatography using hexane:acetyl acetate at a ratio of 85:15, thereby obtaining 4.00 g (yield: 57%) of Intermediate L1, which was then identified by using HPLC.

Synthesis of Compound 20

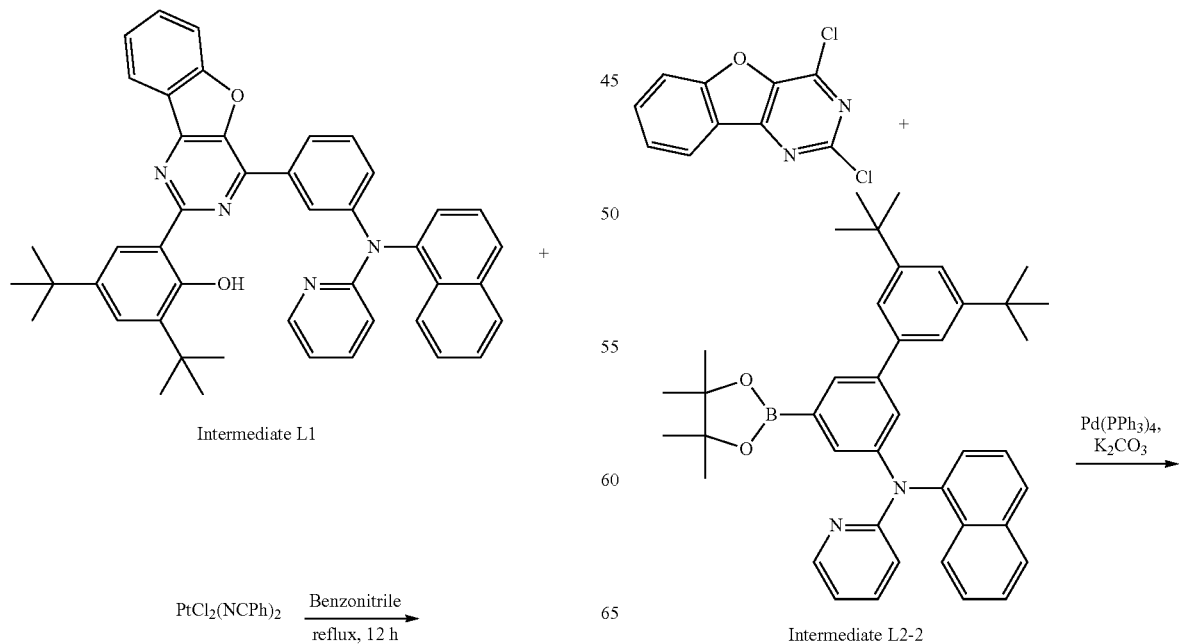

-continued

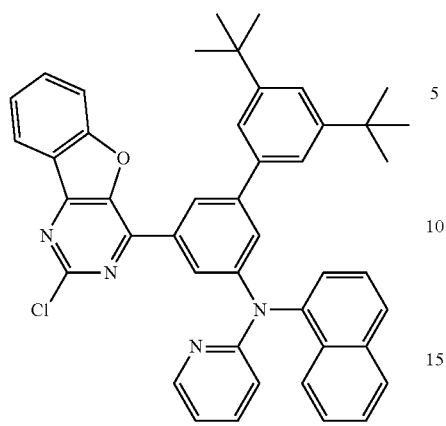

Intermediate L2-1

3.48 g (14.55 mmol) of 2,4-dichlorobenzofuro[3,2-d]pyrimidine, 9.33 g (15.28 mmol) of Intermediate L2-2, 0.84 g (0.73 mmol) of Pd(PPh$_3$)$_4$, and 6.03 g (43.65 mmol) of potassium carbonate were added to 200 mL of toluene, and the mixture was stirred under reflux for 12 hours. The reaction mixture was cooled to room temperature and extracted by using water and methylene chloride. The organic layer was separated, and the solvent was removed therefrom. The resulting residue was then purified by column chromatography using hexane:acetyl acetate at a ratio of 8:2, thereby obtaining 6.50 g (yield: 65%) of Intermediate L2-1, which was then identified by using HPLC.

Synthesis of Intermediate L2

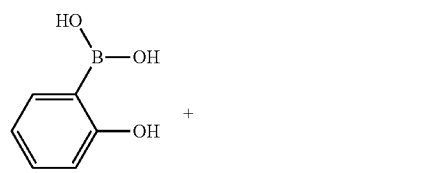

+

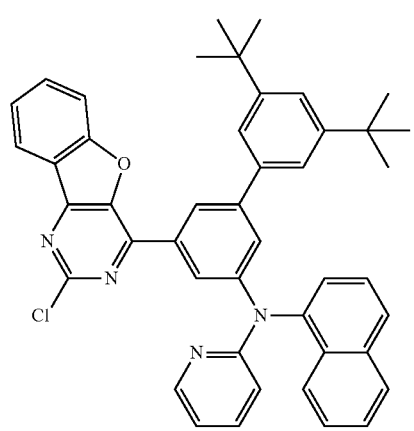

Intermediate L2-1

Pd(PPh$_3$)$_4$, K$_2$CO$_3$
→

-continued

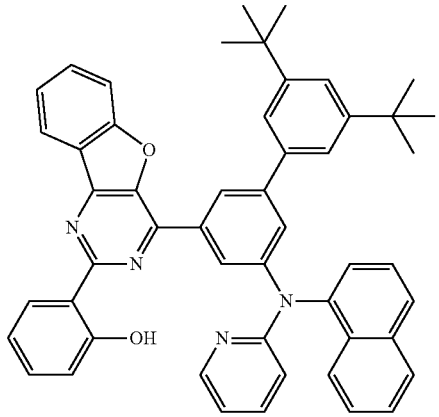

Intermediate L2

1.94 g (14.10 mmol) of 2-hydroxyl phenyl boronic acid, 6.46 g (9.40 mmol) of Intermediate L2-1, 0.54 g (0.47 mmol) of Pd(PPh$_3$)$_4$, and 3.90 g (28.19 mmol) of potassium carbonate were added to a solution in which 90 mL of tetrahydrofuran and 30 mL of water were mixed, and the mixture was stirred under reflux for 12 hours. The reaction mixture was cooled to room temperature and extracted by using water and methylene chloride. The organic layer was separated, and the solvent was removed therefrom. The resulting residue was then purified by column chromatography using hexane:acetyl acetate at a ratio of 85:15, thereby obtaining 4.85 g (yield: 69%) of Intermediate L2, which was then identified by using HPLC.

Synthesis of Compound 47

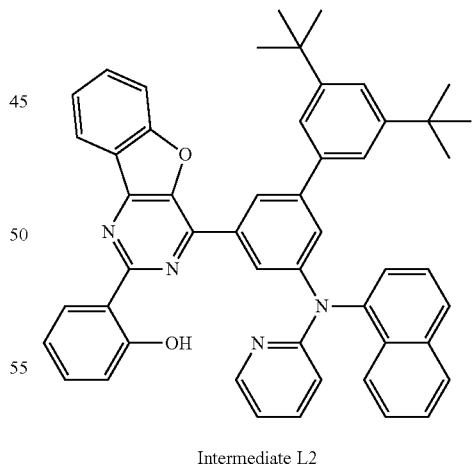

+

Intermediate L2

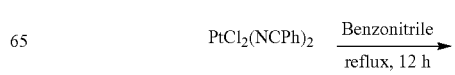

PtCl$_2$(NCPh)$_2$ $\xrightarrow{\text{Benzonitrile}}{\text{reflux, 12 h}}$

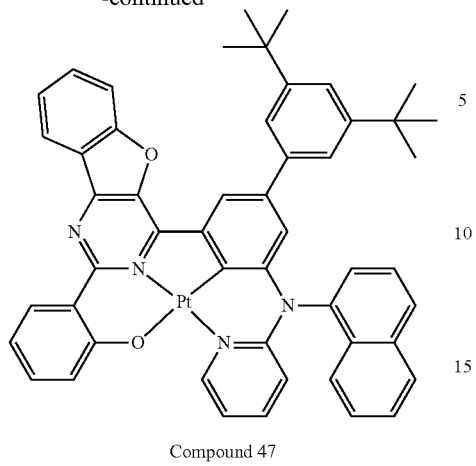

Compound 47

1.59 g (2.13 mmol) of Intermediate L2, 1.11 g (2.35 mmol) of PtCl$_2$(NCPh)$_2$, and 20 mL of benzonitrile were mixed together, and the mixture was stirred under reflux for 12 hours. The reaction mixture was cooled to room temperature, and the solvent was removed therefrom. The resulting residue was then purified by column chromatography using hexane:methylene chloride at a ratio of 8:2, thereby obtaining 0.32 g (yield: 16%) of Compound 47, which was then identified by using Mass and HPLC.

HRMS (MALDI) calcd. for C$_{51}$H$_{42}$N$_4$O$_2$Pt: m/z 937.2956, Found: 937.2950.

Synthesis Example 3

Synthesis of Compound 100

Synthesis of Intermediate L3

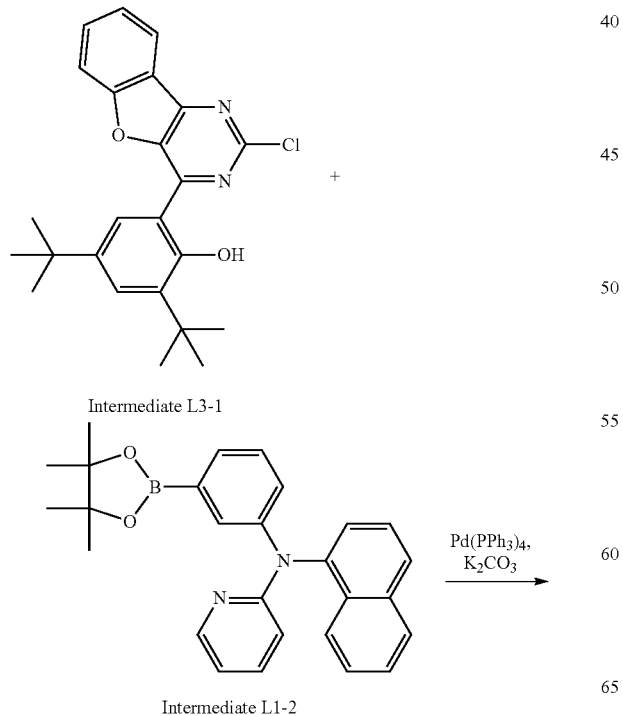

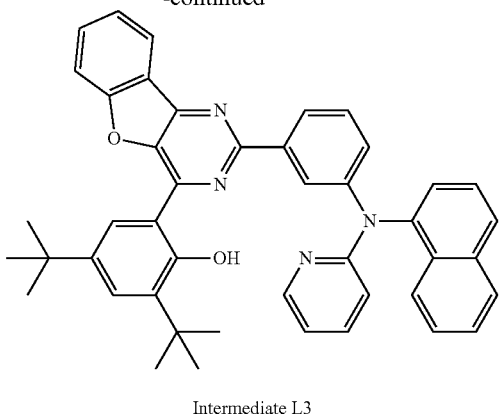

Intermediate L3

2.45 g (5.98 mmol) of Intermediate L3-1, 2.65 g (6.28 mmol) of Intermediate L1-2, 0.35 g (0.30 mmol) of Pd(PPh$_3$)$_4$, and 2.48 g (17.94 mmol) of potassium carbonate were added to a solution in which 60 mL of tetrahydrofuran and 20 mL of water were mixed, and the mixture was stirred under reflux for 12 hours. The reaction mixture was cooled to room temperature and extracted by using water and methylene chloride. The organic layer was separated, and the solvent was removed therefrom. The resulting residue was then purified by column chromatography using hexane: acetyl acetate at a ratio of 85:15, thereby obtaining 2.76 g (yield: 69%) of Intermediate L3, which was then identified by using HPLC.

Synthesis of Compound 100

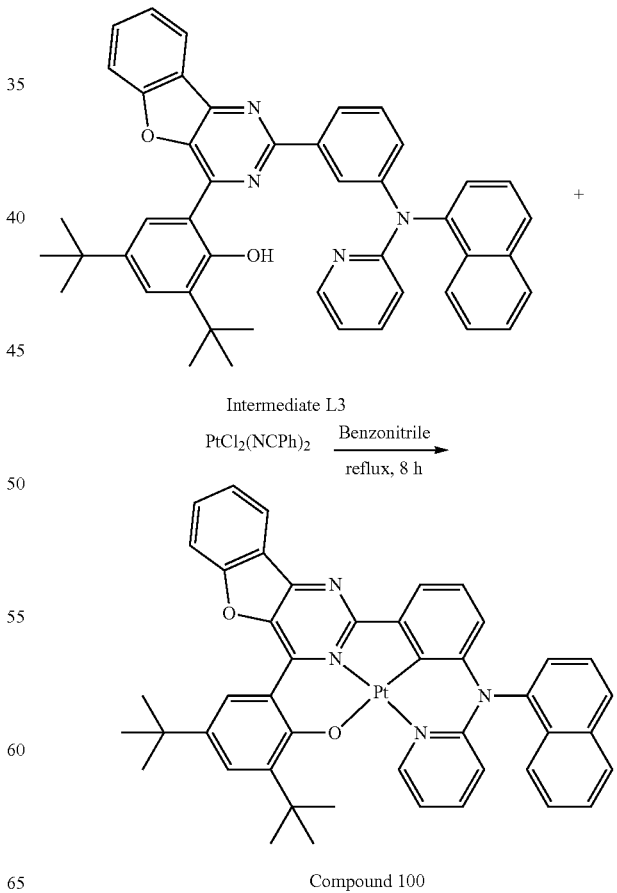

Compound 100

1.19 g (1.60 mmol) of Intermediate L3, 0.83 g (1.76 mmol) of PtCl$_2$(NCPh)$_2$, and 15 mL of benzonitrile were mixed together, and the mixture was stirred under reflux for 8 hours. The reaction mixture was cooled to room temperature, and the solvent was removed therefrom. The resulting residue was then purified by column chromatography using hexane:methylene chloride at a ratio of 8:2, thereby obtaining 0.41 g (yield: 27%) of Compound 100, which was then identified by using Mass and HPLC.

HRMS (MALDI) calcd. for C$_{45}$H$_{38}$N$_4$O$_2$Pt: m/z 861.2643, Found: 861.2635.

Synthesis Example 4

Synthesis of Compound 180

Synthesis of Intermediate L4

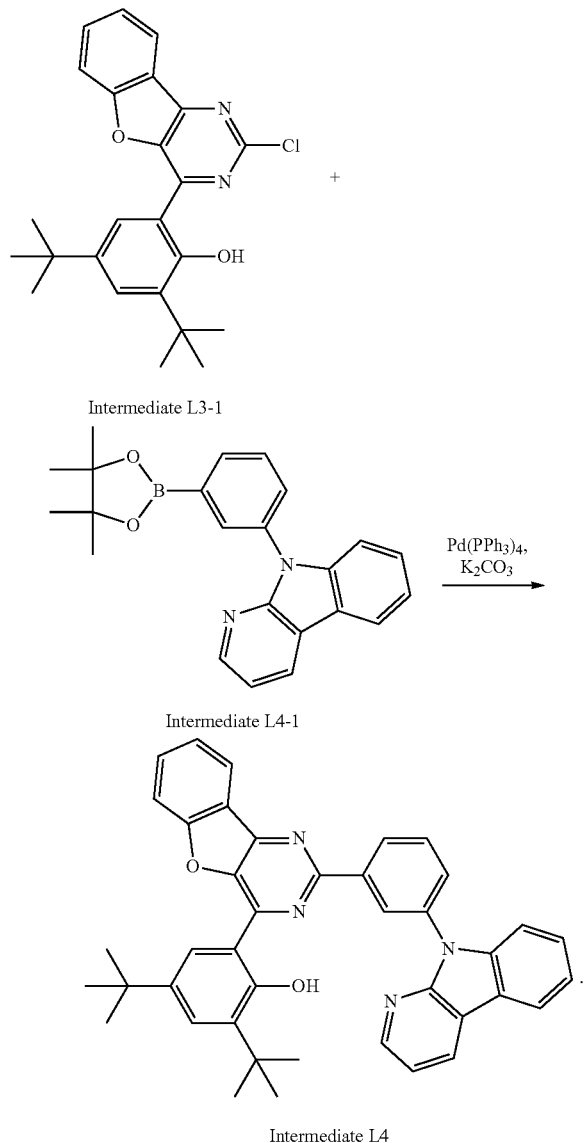

2.65 g (6.49 mmol) of Intermediate L3-1, 2.52 g (6.81 mmol) of Intermediate L4-1, 0.38 g (0.32 mmol) of Pd(PPh$_3$)$_4$, and 2.69 g (19.46 mmol) of potassium carbonate were added to a solution in which 60 mL of tetrahydrofuran and 20 mL of water were mixed, and the mixture was stirred under reflux for 12 hours. The reaction mixture was cooled to room temperature and extracted by using water and methylene chloride. The organic layer was separated, and the solvent was removed therefrom. The resulting residue was then purified by column chromatography using hexane: acetyl acetate at a ratio of 85:15, thereby obtaining 2.21 g (yield: 55%) of Intermediate L4, which was then identified by using HPLC.

Synthesis of Compound 180

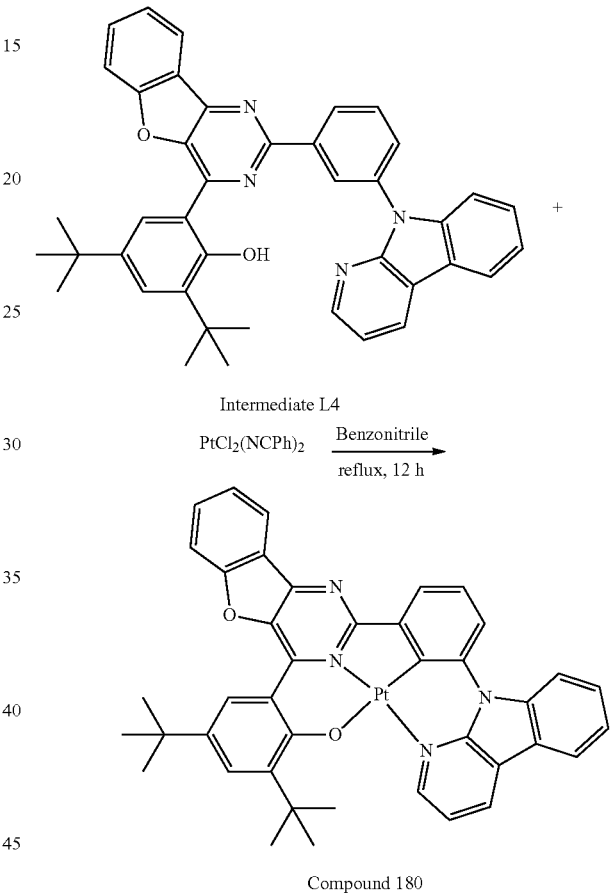

1.90 g (3.09 mmol) of Intermediate L4, 1.60 g (3.40 mmol) of PtCl$_2$(NCPh)$_2$, and 20 mL of benzonitrile were mixed together, and the mixture was stirred under reflux for 12 hours. The reaction mixture was cooled to room temperature, and the solvent was removed therefrom. The resulting residue was then purified by column chromatography using hexane:methylene chloride at a ratio of 7:3, thereby obtaining 0.58 g (yield: 23%) of Compound 180, which was then identified by using Mass and HPLC.

HRMS (MALDI) calcd. for C$_{41}$H$_{34}$N$_4$O$_2$Pt: m/z 809.2330, Found: 809.2338.

Example 1

An ITO glass substrate was cut to a size of 50 millimeters (mm)×50 mm×0.5 mm. Then, the glass substrate was sonicated in acetone, iso-propyl alcohol, and pure water for about 15 minutes each, and cleaned by exposure to ultraviolet rays and ozone for 30 minutes.

Thereafter, a hole injection layer was formed to have a thickness of about 600 Angstroms (Å) on the ITO electrode (anode) on the glass substrate by depositing m-MTDATA at a rate of about 1 Angstroms per second (Å/sec). A hole transport layer was formed to have a thickness of about 250 Å on the hole injection layer by depositing α-NPD at a rate of about 1 Å/sec.

An emission layer was formed to have a thickness of about 400 Å on the hole transport layer by co-depositing Compound 20 (as a dopant) and CBP (as a host) at a rate of about 0.1 Å/sec and 1 Å/sec, respectively.

A hole blocking layer was formed on the emission layer by depositing BAlq at a rate of 1 Å/sec to have a thickness of about 50 Å. Then, an electron transport layer was formed on the hole blocking layer by depositing $Alq_3$ to have a thickness of about 300 Å. An electron injection layer was formed on the electron transport layer by depositing LiF to have a thickness of about 10 Å. A second electrode (cathode) was formed on the electron injection layer by vacuum-depositing Al to have a thickness of about 1,200 Å. Therefore, the manufacture of an organic light-emitting device was completed, in which the organic light-emitting device included an ITO/m-MTDATA (600 Å)/α-NPD (250 Å)/CBP+10% Compound 20 (400 Å)/BAlq (50 Å)/$Alq_3$ (300 Å)/LiF (10 Å)/Al (1,200 Å) structure.

Examples 2 to 4 and Comparative Example 1

Organic light-emitting devices were each manufactured in substantially the same manner as in Example 1, except that Compounds listed in Table 2 were used instead of Compound 20 as a dopant in the formation of the emission layer.

Evaluation Example 1

Evaluation of Characteristics of Organic Light-emitting Device

The driving voltage, color purity, quantum efficiency, and lifespan ($T_{95}$) of the organic light-emitting devices manufactured in Examples 1 to 4 and Comparative Example 1 were evaluated, and the results of the experiment are shown in Table 2. A Keithley 2400 current voltmeter and a luminance meter (Minolta Cs-1000A) were used for the evaluation. The lifespan ($T_{95}$, at 6,000 nit) refers to time required for the initial luminance (100%) of the organic light-emitting device to reduce by 95%.

TABLE 2

| | Dopant | Driving voltage (V) | CIEx | CIEy | Quantum efficiency (%) | Lifespan (hr) ($T_{95}$) |
|---|---|---|---|---|---|---|
| Example 1 | Compound 20 | 5.1 | 0.628 | 0.356 | 16.5 | 140 h |
| Example 2 | Compound 47 | 4.9 | 0.669 | 0.329 | 17.5 | 155 h |
| Example 3 | Compound 100 | 4.4 | 0.519 | 0.472 | 18.3 | 255 h |
| Example 4 | Compound 180 | 4.8 | 0.523 | 0.468 | 18.8 | 110 h |

TABLE 2-continued

| | Dopant | Driving voltage (V) | CIEx | CIEy | Quantum efficiency (%) | Lifespan (hr) ($T_{95}$) |
|---|---|---|---|---|---|---|
| Comparative Example 1 | Compound A | 5.8 | 0.311 | 0.622 | 14.1 | 20 h |

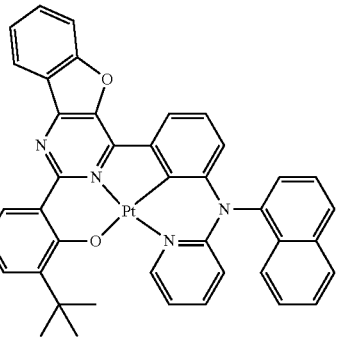

Compound 20

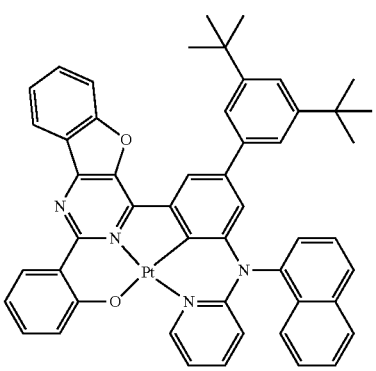

Compound 47

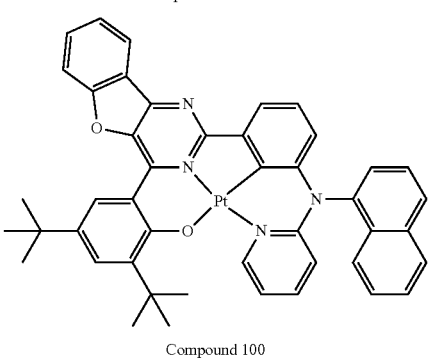

Compound 100

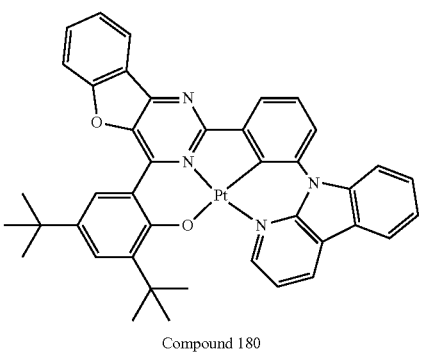

Compound 180

TABLE 2-continued

| Dopant | Driving voltage (V) | CIEx | CIEy | Quantum efficiency (%) | Lifespan (hr) ($T_{95}$) |
|---|---|---|---|---|---|

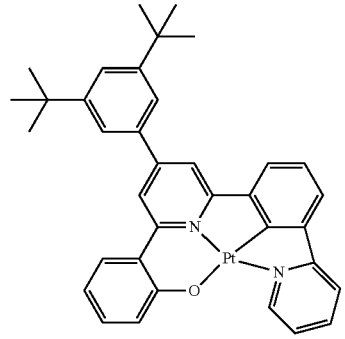

Compound A

Referring to Table 2, it was confirmed that the organic light-emitting device of Examples 1 to 4 exhibited excellent driving voltage, quantum efficiency, and lifespan characteristics, as compared with those characteristics of the organic light-emitting device of Comparative Example 1.

As described above, the organometallic compound has excellent electrical characteristics and thermal stability. Accordingly, an organic light-emitting device employing the organometallic compound has a low driving voltage, high efficiency, high power, high color purity, and excellent lifespan characteristics. In addition, the organometallic compound has excellent phosphorescent luminosity, and thus, a diagnostic composition including the organometallic compound may also have high diagnostic efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. An organometallic compound represented by Formula 1:

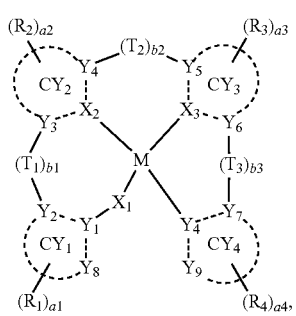

Formula 1 wherein, in Formula 1,

M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), $X_1$ is O or S, wherein a bond between $X_1$ and M is a covalent bond, $X_2$ is N, wherein a bond between $X_2$ and M is a coordinate bond, $X_3$ and $X_4$ are each independently C or N, one of a bond between $X_3$ and M and a bond between $X_4$ and M is a covalent bond, and the other thereof is a coordinate bond, a moiety represented by

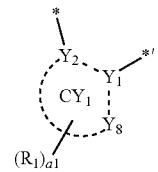

in Formula 1 is selected from groups represented by Formulae CY1-1 to CY1-16, a moiety represented by

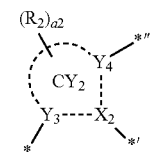

in Formula 1 is selected from groups represented by Formulae CY2-1 to CY2-4, a moiety represented by

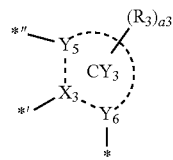

in Formula 1 is selected from groups represented by Formulae CY3-1 to CY3-22, a moiety represented by

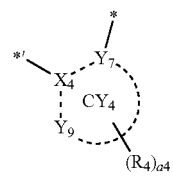

in Formula 1 is selected from groups represented by Formulae CY4-1 to CY4-8, $T_1$ to $T_3$ are each independently selected from *—N[$(L_5)_{a5}$-$(R_5)$]—*', *—B($R_5$)—*', *—P($R_5$)—*', \*—C(R$_5$)(R$_6$)—\*', \*—Si(R$_5$)(R$_6$)—\*', \*—Ge(R$_5$)(R$_6$)—\*', \*—S—\*', \*—Se—\*', \*—O—\*', \*—C(=O)—\*', \*—S(=O)—\*', \*—S(=O)$_2$—\*', \*—C(R$_5$)=\*', \*=C(R$_5$)—\*', \*—C(R$_5$)=C(R$_6$)—\*', \*—C(=S)—\*', and \*—C≡C—\*', L$_5$ is selected from a single bond, a substituted or unsubstituted C$_5$-C$_{30}$ carbocyclic group, and a substituted or unsubstituted C$_1$-C$_{30}$ heterocyclic group, a5 is selected from 1 to 3, wherein, when a5 is two or more, two or more of groups L$_5$ are identical to or different from each other, R$_5$ and R$_6$ are optionally linked via a first linking group to form a substituted or unsubstituted C$_5$-C$_{30}$ carbocyclic group or a substituted or unsubstituted C$_1$-C$_{30}$ heterocyclic group, b1 to b3 are each independently 0 or 1, provided that at least one selected from b1 to b3 is 1, wherein, when b1 is 0, \*-(T$_1$)$_{b1}$-\*' is a single bond, when b2 is 0, \*-(T$_2$)$_{b2}$-\*' is a single bond, and when b3 is 0, \*-(T$_3$)$_{b3}$-\*' is a single bond:

Formula CY1-1

Formula CY1-2

Formula CY1-3

Formula CY1-4

Formula CY1-5

Formula CY1-6

Formula CY1-7

Formula CY1-8

Formula CY1-9

Formula CY1-10

Formula CY1-11

-continued

Formula CY1-12

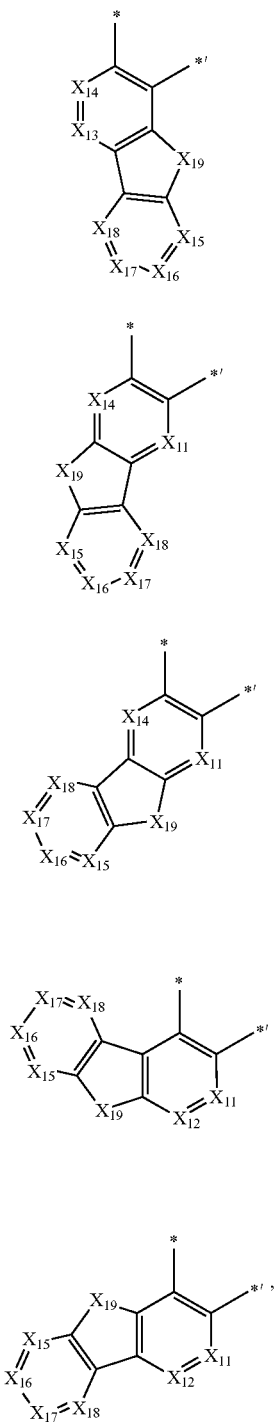

Formula CY1-13

Formula CY1-14

Formula CY1-15

Formula CY1-16 wherein, in Formulae CY1-1 to CY1-16, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, $X_{18}$ is N or $C(R_{18})$, $X_{19}$ is $C(R_{19a})(R_{19b})$, $N(R_{19})$, O, S, or $Si(R_{19a})(R_{19b})$, and

* and *' each independently indicate a binding site to a neighboring atom,

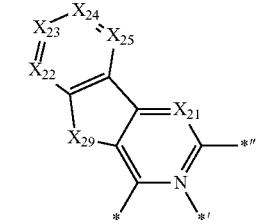

Formula CY2-1

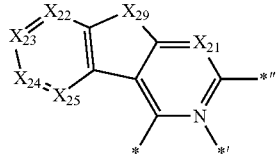

Formula CY2-2

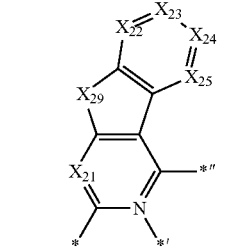

Formula CY2-3

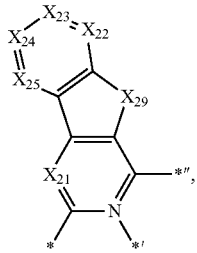

Formula CY2-4 wherein, in Formulae CY2-1 to CY2-4, $X_{21}$ is N or $C(R_{21})$, $X_{22}$ is N or $C(R_{22})$, $X_{23}$ is N or $C(R_{23})$, $X_{24}$ is N or $C(R_{24})$, $X_{25}$ is N or $C(R_{25})$, $X_{29}$ is $C(R_{29a})(R_{29b})$, $N(R_{29})$, O, S, or $Si(R_{29a})(R_{29b})$, and

*, *', and *" each independently indicate a binding site to a neighboring atom,

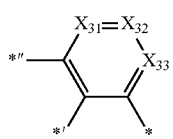

Formula CY3-1

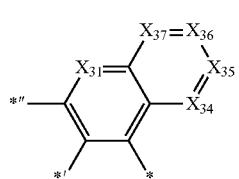

Formula CY3-2

Formula CY3-3
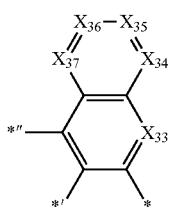
Formula CY3-4
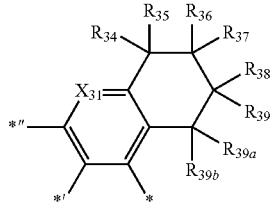
Formula CY3-5
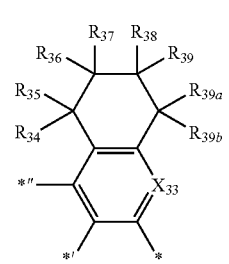
Formula CY3-6
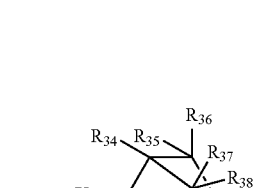
Formula CY3-7
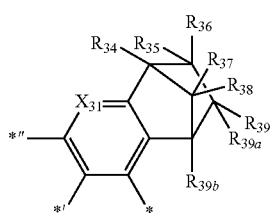
Formula CY3-8
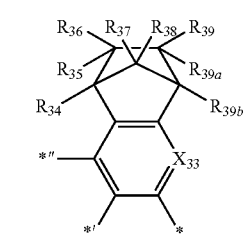
Formula CY3-9
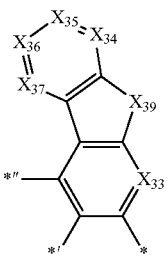
Formula CY3-10
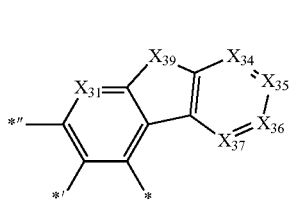
Formula CY3-11
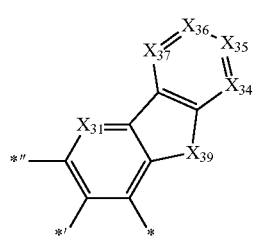
Formula CY3-12
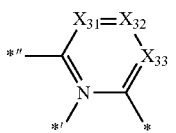
Formula CY3-13
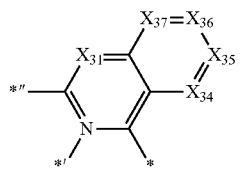
Formula CY3-14
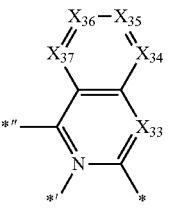
Formula CY3-15
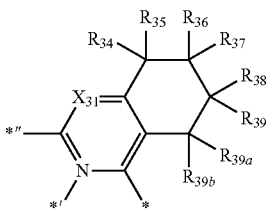

-continued

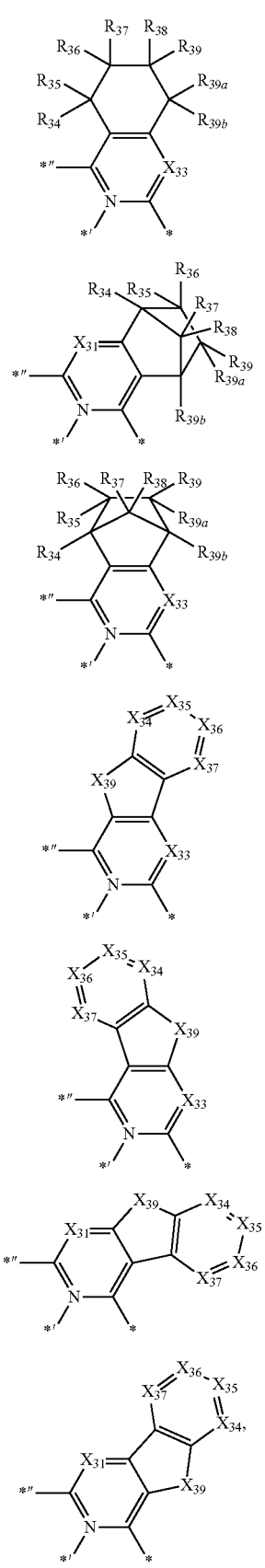

Formula CY3-16

Formula CY3-17

Formula CY3-18

Formula CY3-19

Formula CY3-20

Formula CY3-21

Formula CY3-22 wherein, in Formulae CY3-1 to CY3-22, $X_{31}$ is N or $C(R_{31})$, $X_{32}$ is N or $C(R_{32})$, $X_{33}$ is N or $C(R_{33})$, $X_{34}$ is N or $C(R_{34})$, $X_{35}$ is N or $C(R_{35})$, $X_{36}$ is N or $C(R_{36})$, $X_{37}$ is N or $C(R_{37})$, and $X_{39}$ is $C(R_{39a})(R_{39b})$, $N(R_{39})$, O, S, or $Si(R_{39a})(R_{39b})$, and

*, *', and *" each independently indicate a binding site to a neighboring atom,

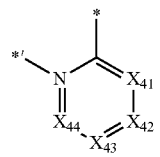

Formula CY4-1

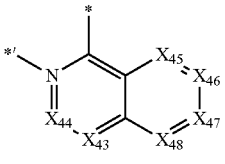

Formula CY4-2

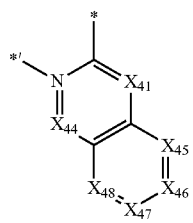

Formula CY4-3

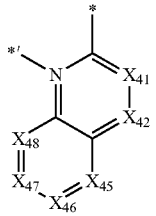

Formula CY4-4

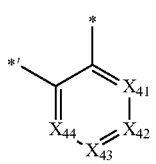

Formula CY4-5

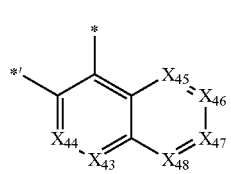

Formula CY4-6

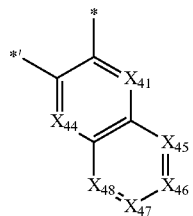

Formula CY4-7

Formula CY4-8

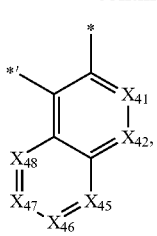

wherein, in Formulae CY4-1 to CY4-8,
$X_{41}$ is N or $C(R_{41})$, $X_{42}$ is N or $C(R_{42})$, $X_{43}$ is N or $C(R_{43})$, $X_{44}$ is N or $C(R_{44})$, $X_{45}$ is N or $C(R_{45})$, $X_{46}$ is N or $C(R_{46})$, $X_{47}$ is N or $C(R_{47})$, and $X_{48}$ is N or $C(R_{48})$, and
* and *' each independently indicate a binding site to a neighboring atom,
wherein
$R_5$, $R_6$, $R_{11}$ to $R_{19}$, $R_{19a}$ to $R_{19c}$, $R_{21}$ to $R_{25}$, $R_{29}$, $R_{29a}$ to $R_{29b}$, $R_{31}$ to $R_{39}$, $R_{39a}$ to $R_{39b}$ and $R_{41}$ to $R_{48}$ are each independently selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$),
two of $R_{11}$ to $R_{19}$ and $R_{19a}$ to $R_{19c}$ are optionally linked to form a substituted or unsubstituted $C_5$-$C_{30}$ carbocyclic group or a substituted or unsubstituted $C_1$-$C_{30}$ heterocyclic group,
two groups of $R_{21}$ to $R_{25}$, $R_{29}$, $R_{29a}$ to $R_{29b}$ are optionally linked to form a substituted or unsubstituted $C_5$-$C_{30}$ carbocyclic group or a substituted or unsubstituted $C_1$-$C_{30}$ heterocyclic group,
two groups of $R_{31}$ to $R_{39}$, $R_{39a}$ to $R_{39b}$ are optionally linked to form a substituted or unsubstituted $C_5$-$C_{30}$ carbocyclic group or a substituted or unsubstituted $C_1$-$C_{30}$ heterocyclic group,
two groups of $R_{41}$ to $R_{48}$ are optionally linked to form a substituted or unsubstituted $C_5$-$C_{30}$ carbocyclic group or a substituted or unsubstituted $C_1$-$C_{30}$ heterocyclic group,
one of $R_5$ and $R_6$ is optionally linked with one of $R_{11}$ to $R_{19}$, $R_{19a}$ to $R_{19c}$, $R_{21}$ to $R_{25}$, $R_{29}$, $R_{29a}$ to $R_{29b}$, $R_{31}$ to $R_{39}$, $R_{39a}$ to $R_{39b}$ and $R_{41}$ to $R_{48}$ to form a substituted or unsubstituted $C_5$-$C_{30}$ carbocyclic group or a substituted or unsubstituted $C_1$-$C_{30}$ heterocyclic group,
at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_2$-$C_{60}$ heteroaryloxy group, the substituted $C_2$-$C_{60}$ heteroarylthio group, the substituted heteroarylalkyl group, the substituted monovalent non-aromatic condensed polycyclic group, and the substituted monovalent non-aromatic condensed heteropolycyclic group is selected from:
deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), and —P(=O)(Q$_{18}$)(Q$_{19}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_2$-C$_{60}$ heteroaryloxy group, a C$_2$-C$_{60}$ heteroarylthio group, a C$_3$-C$_{60}$ heteroarylalkyl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), and, Q$_1$ to Q$_9$, Q$_{11}$ to Q$_{19}$, Q$_{21}$ to Q$_{29}$, and Q$_{31}$ to Q$_{39}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryl group substituted with at least one of a C$_1$-C$_{60}$ alkyl group and a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a substituted or unsubstituted C$_2$-C$_{60}$ heteroaryloxy group, a substituted or unsubstituted C$_2$-C$_{60}$ heteroarylthio group, a substituted or unsubstituted C$_3$-C$_{60}$ heteroarylalkyl group, a monovalent non-aromatic condensed polycyclic group, and a monovalent non-aromatic condensed heteropolycyclic group.

2. The organometallic compound of claim 1, wherein T$_1$ to T$_3$ are each independently selected from *—N[(L$_5$)$_{a5}$-(R$_5$)]—*', *—C(R$_5$)(R$_6$)—*', *—Si(R$_5$)(R$_6$)—*', *—S—*', and *—O—*'.

3. The organometallic compound of claim 1, wherein T$_1$ to T$_3$ are each independently selected from *—C(R$_5$)(R$_6$)—*', *—Si(R$_5$)(R$_6$)—*', and *—Ge(R$_5$)(R$_6$)—*', R$_5$ and R$_6$ are linked via a first linking group, the first linking group is selected from a single bond, *—N[(L$_9$)$_{a9}$-(R$_9$)]—', *—B(R$_9$)—*', *—P(R$_9$)—*', *—C(R$_9$)(R$_{10}$)—*', *—Si(R$_9$)(R$_{10}$)—*', *—Ge(R$_9$)(R$_{10}$)—*', *—S—*', *—Se—*', *—O—*', *—C(=O)—*', *—S(=O)—*', *—S(=O)$_2$—*', *—C(R$_9$)=*', *=C(R$_9$)—*', *—C(R$_9$)=C(R$_{10}$)—*', *—C(=S)—*', and *—C≡C—*', R$_9$ and R$_{10}$ are each independently the same as described in connection with R$_5$ in claim 1, L$_9$ is the same as described in connection with L$_5$ in claim 1, a9 is the same as described in connection with a5 in claim 1, and

* and *' each independently indicate a binding site to a neighboring atom.

4. The organometallic compound of claim 1, wherein
b1 is 1, and b2 and b3 are each 0;
b2 is 1, and b1 and b3 are each 0; or
b3 is 1, and b1 and b2 are each 0.

5. The organometallic compound of claim 1, wherein R$_5$, R$_6$, R$_{11}$ to R$_{19}$, R$_{19a}$ to R$_{19c}$, R$_{21}$ to R$_{25}$, R$_{29}$, R$_{29a}$ to R$_{29b}$, R$_{31}$ to R$_{39}$, R$_{39a}$ to R$_{39b}$ and R$_{41}$ to R$_{48}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, afluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), and $Q_1$ to $Q_9$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$ and —$CD_2CDH_2$;

an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

6. The organometallic compound of claim 1, wherein $R_5$, $R_6$, $R_{11}$ to $R_{19}$, $R_{19a}$ to $R_{19c}$, $R_{21}$ to $R_{25}$, $R_{29}$, $R_{29a}$ to $R_{29b}$, $R_{31}$ to $R_{39}$, $R_{39a}$ to $R_{39b}$ and $R_{41}$ to $R_{48}$ are each independently selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group; and —N($Q_1$)($Q_2$), —Si($Q_3$)($Q_4$)($Q_5$), —B($Q_6$)($Q_7$), and —P(=O)($Q_8$)($Q_9$), and $Q_1$ to $Q_9$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$ and —$CD_2CDH_2$;

an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

7. The organometallic compound of claim 1, wherein $R_5$, $R_6$, $R_{11}$ to $R_{19}$, $R_{19a}$ to $R_{19c}$, $R_{21}$ to $R_{25}$, $R_{29}$, $R_{29a}$ to $R_{29b}$, $R_{31}$ to $R_{39}$, $R_{39a}$ to $R_{39b}$ and $R_{41}$ to $R_{48}$ are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-142, and —$Si(Q_3)(Q_4)(Q_5)$:

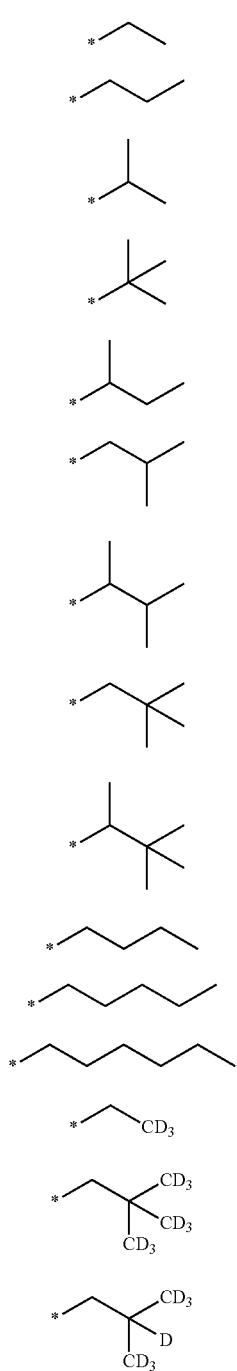

Formula 9-1
Formula 9-2
Formula 9-3
Formula 9-4
Formula 9-5
Formula 9-6
Formula 9-7
Formula 9-8
Formula 9-9
Formula 9-10
Formula 9-11
Formula 9-12
Formula 9-13
Formula 9-14
Formula 9-15

-continued

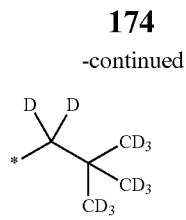

Formula 9-16

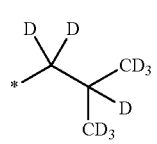

Formula 9-17

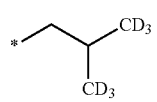

Formula 9-18

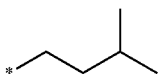

Formula 9-19

Formula 10-1

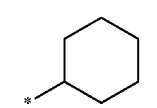

Formula 10-2

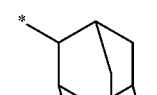

Formula 10-3

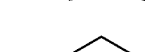

Formula 10-4

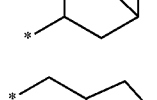

Formula 10-5

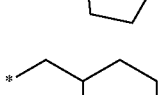

Formula 10-6

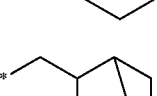

Formula 10-7

Formula 10-8

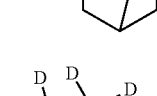

Formula 10-9

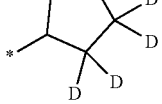

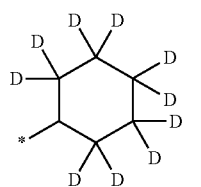 Formula 10-10
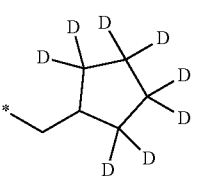 Formula 10-11
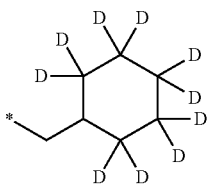 Formula 10-12
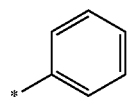 Formula 10-13
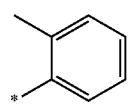 Formula 10-14
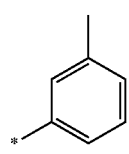 Formula 10-15
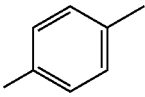 Formula 10-16
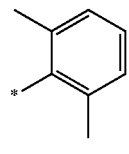 Formula 10-17
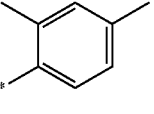 Formula 10-18
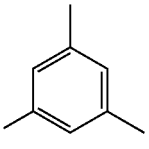 Formula 10-19
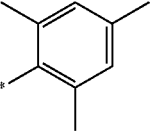 Formula 10-20
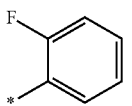 Formula 10-21
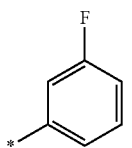 Formula 10-22
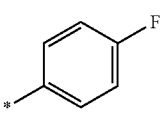 Formula 10-23
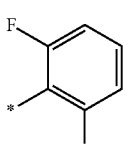 Formula 10-24
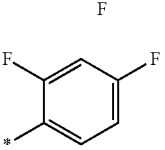 Formula 10-25
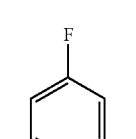 Formula 10-26
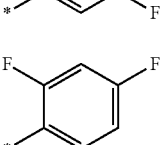 Formula 10-27
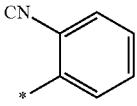 Formula 10-28
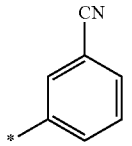 Formula 10-29
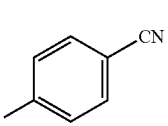 Formula 10-30
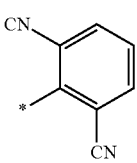 Formula 10-31

| | | |
|---|---|---|
| 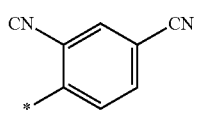 | Formula 10-32 | |
| 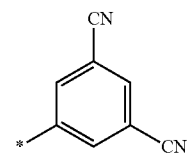 | Formula 10-33 | |
| 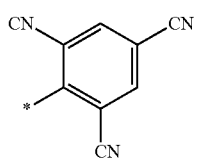 | Formula 10-34 | |
| 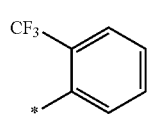 | Formula 10-35 | |
| 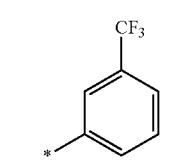 | Formula 10-36 | |
| 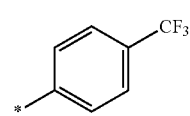 | Formula 10-37 | |
| 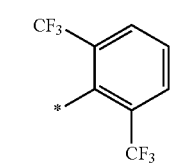 | Formula 10-38 | |
| 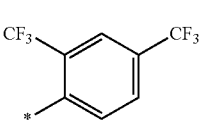 | Formula 10-39 | |
| 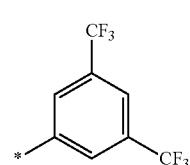 | Formula 10-40 | |
| 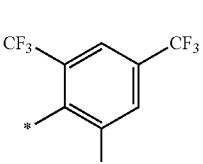 | Formula 10-41 | |
| 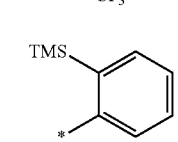 | Formula 10-42 | |
| 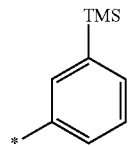 | Formula 10-43 | |
| 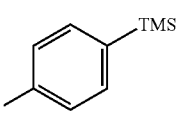 | Formula 10-44 | |
| 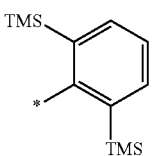 | Formula 10-45 | |
| 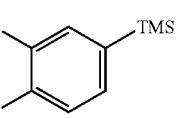 | Formula 10-46 | |
| 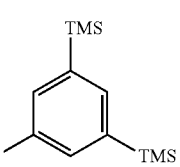 | Formula 10-47 | |
| 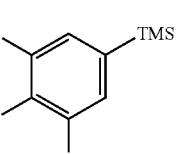 | Formula 10-48 | |
| 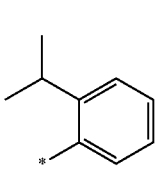 | Formula 10-49 | |
| 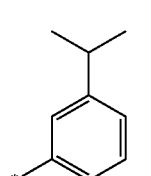 | Formula 10-50 | |
| 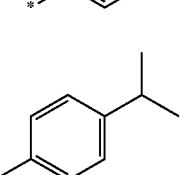 | Formula 10-51 | |
| 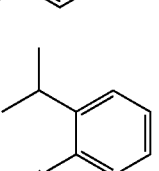 | Formula 10-52 | |

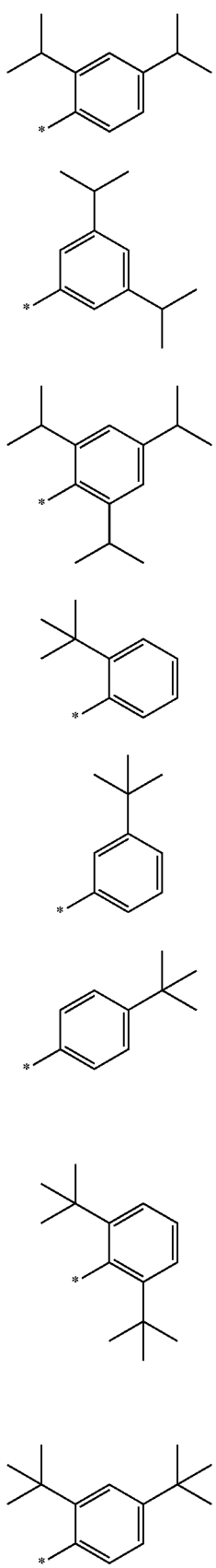
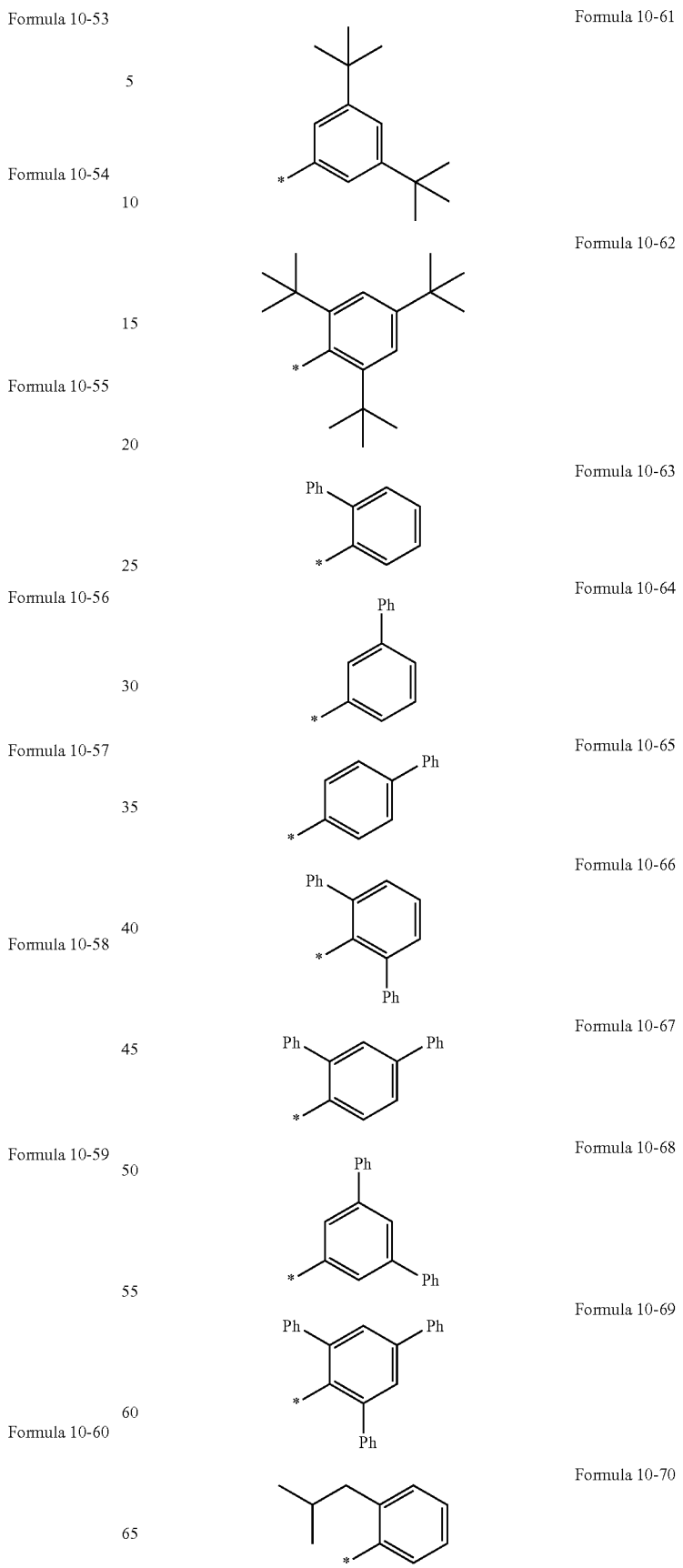
Formula 10-53
Formula 10-54
Formula 10-55
Formula 10-56
Formula 10-57
Formula 10-58
Formula 10-59
Formula 10-60
Formula 10-61
Formula 10-62
Formula 10-63
Formula 10-64
Formula 10-65
Formula 10-66
Formula 10-67
Formula 10-68
Formula 10-69
Formula 10-70

US 10,400,003 B2
181
-continued
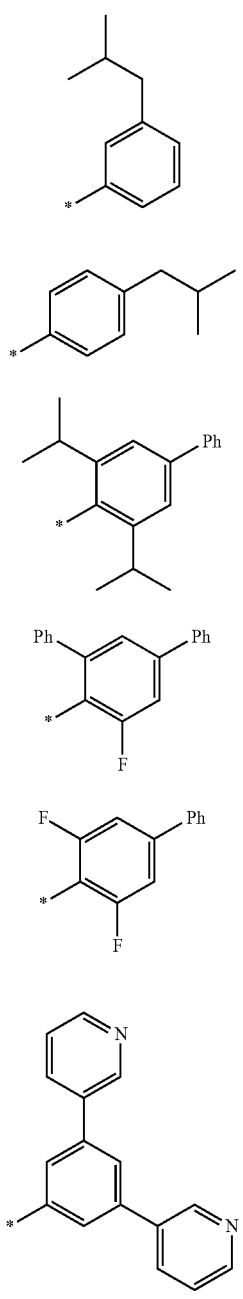
Formula 10-71
Formula 10-72
Formula 10-73
Formula 10-74
Formula 10-75
Formula 10-76
Formula 10-77
182
-continued
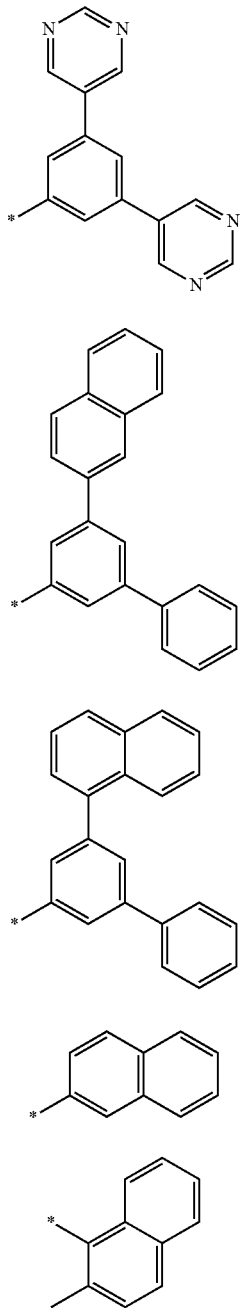
Formula 10-78
Formula 10-79
Formula 10-80
Formula 10-81
Formula 10-82
Formula 10-83
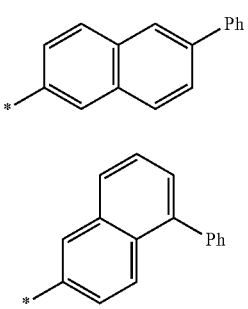
Formula 10-84

-continued
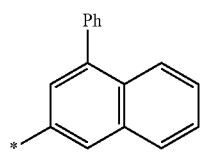
Formula 10-85
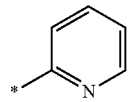
Formula 10-86
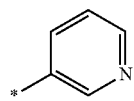
Formula 10-87
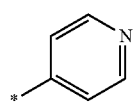
Formula 10-88
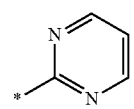
Formula 10-89
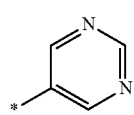
Formula 10-90
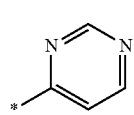
Formula 10-91
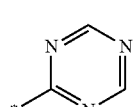
Formula 10-92
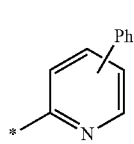
Formula 10-93
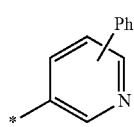
Formula 10-94
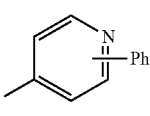
Formula 10-95
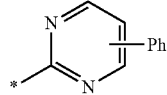
Formula 10-96
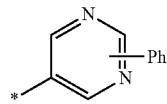
Formula 10-97
-continued
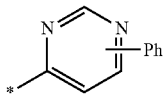
Formula 10-98
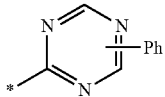
Formula 10-99
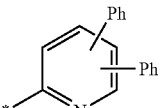
Formula 10-100
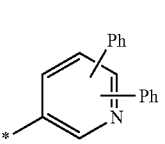
Formula 10-101
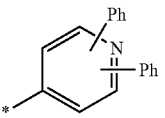
Formula 10-102
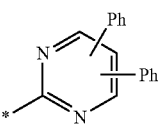
Formula 10-103
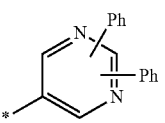
Formula 10-104
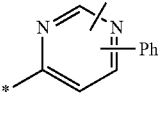
Formula 10-105
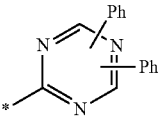
Formula 10-106
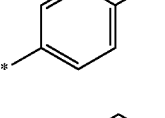
Formula 10-107
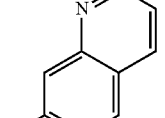
Formula 10-108

Formula 10-109
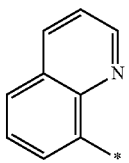
Formula 10-110
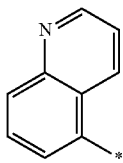
Formula 10-111
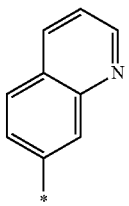
Formula 10-112
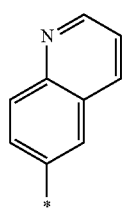
Formula 10-113
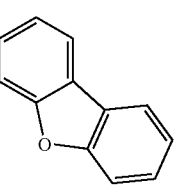
Formula 10-114
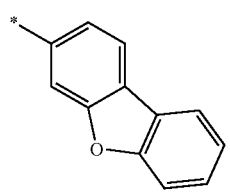
Formula 10-115
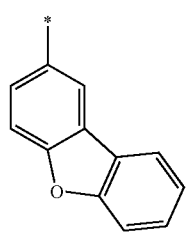
Formula 10-116
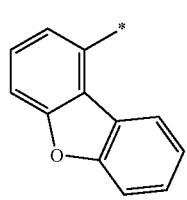
Formula 10-117
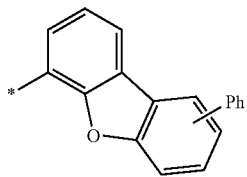
Formula 10-118
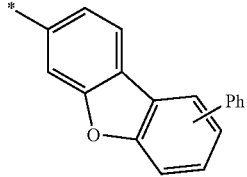
Formula 10-119
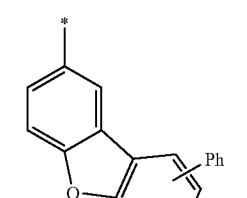
Formula 10-120
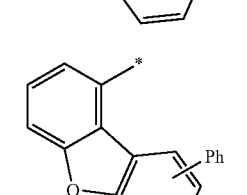
Formula 10-121
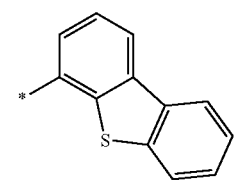
Formula 10-122
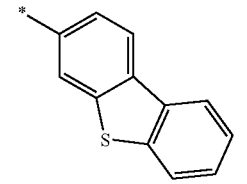
Formula 10-123
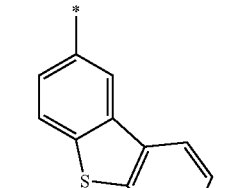
Formula 10-124
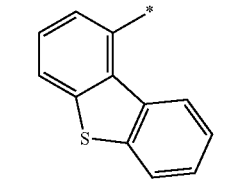

-continued
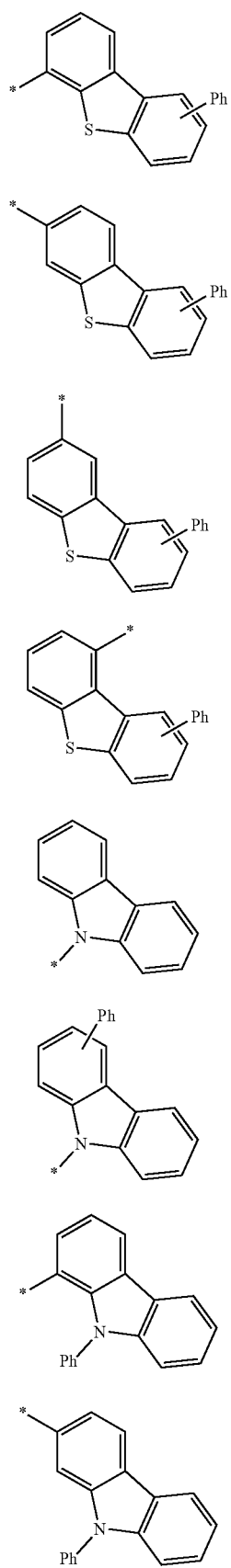
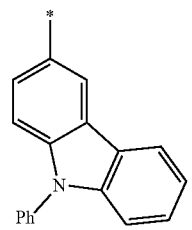
Formula 10-133
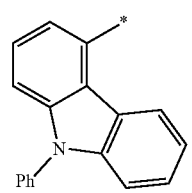
Formula 10-134
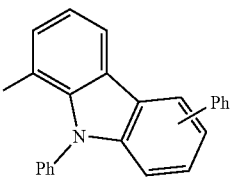
Formula 10-135
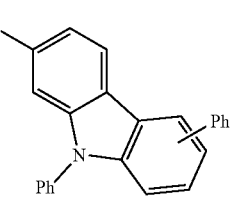
Formula 10-136
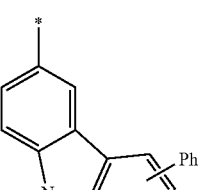
Formula 10-137
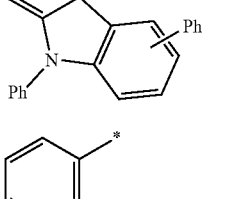
Formula 10-138
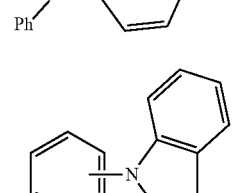
Formula 10-139
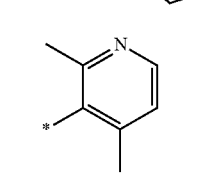
Formula 10-140

-continued

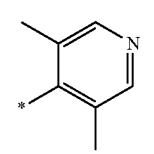
Formula 10-141

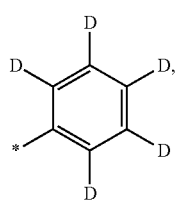
Formula 10-142 wherein, in Formulae 9-1 to 9-19 and 10-1 to 10-142,
* indicates a binding site to a neighboring atom,
the term "Ph" refers to a phenyl group, and
the term "TMS" refers to a trimethylsilyl group.

8. An organometallic compound represented by Formula 1:

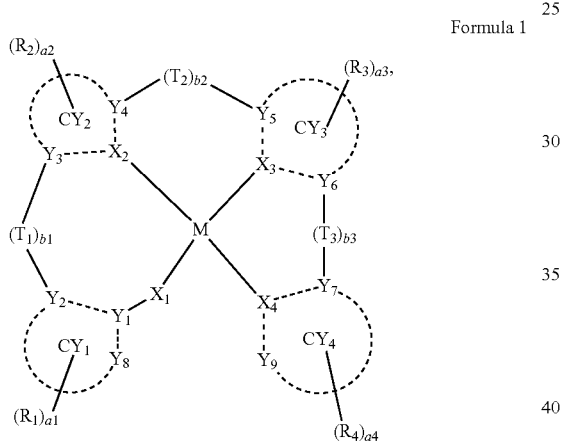
Formula 1 wherein, in Formula 1,

M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), $X_1$ is O or S, wherein a bond between $X_1$ and M is a covalent bond, $X_2$ is N, wherein a bond between $X_2$ and M is a coordinate bond, $X_3$ is C, wherein a bond between $X_3$ and M is a covalent bond, and $X_4$ is N, wherein a bond between $X_4$ and M is a coordinate bond, $Y_1$ to $Y_9$ are each C, $CY_1$ is selected from groups represented by Formulae CY1(1) to CY1(9), $CY_2$ is selected from groups represented by Formulae CY2-1 to CY2-4, $CY_3$ is selected from groups represented by Formulae CY3(1) to CY3(14), $CY_4$ is selected from groups represented by Formulae CY4(1) to CY4(9):

b1 and b2 are 0 and b3 is 1, wherein, *-$(T_1)_{b1}$-*' is a single bond, *-$(T_2)_{b2}$-*' is a single bond, and *-$(T_3)_{b3}$-*' is selected from *—N[$(L_5)_{a5}$-$(R_5)$]—*', *—B($R_5$)—*', *—P($R_5$)—*', *—C($R_5$)($R_6$)—*', *—Si($R_5$)($R_6$)—*', *—Ge($R_5$)($R_6$)—*', *—S—*', *—Se—*', *—O—*', *—C(=O)—*', *—S(=O)—*', *—S(=O)$_2$—*', *—C($R_5$)=*', *=C($R_5$)—*', *—C($R_5$)=C($R_6$)—*', *—C(=S)—*', and *—C≡C—*', $L_5$ is selected from a single bond, a substituted or unsubstituted $C_5$-$C_{30}$ carbocyclic group, and a substituted or unsubstituted $C_1$-$C_{30}$ heterocyclic group, a5 is selected from 1 to 3, wherein, when a5 is two or more, two or more of groups $L_5$ are identical to or different from each other, $R_5$ and $R_6$ are optionally linked via a first linking group to form a substituted or unsubstituted $C_5$-$C_{30}$ carbocyclic group or a substituted or unsubstituted $C_1$-$C_{30}$ heterocyclic group:

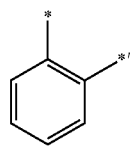
Formula CY1(1)

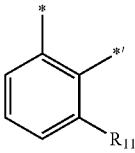
Formula CY1(2)

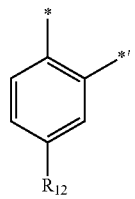
Formula CY1(3)

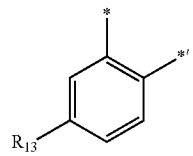
Formula CY1(4)

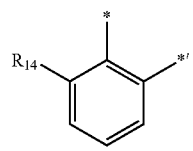
Formula CY1(5)

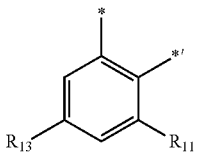
Formula CY1(6)

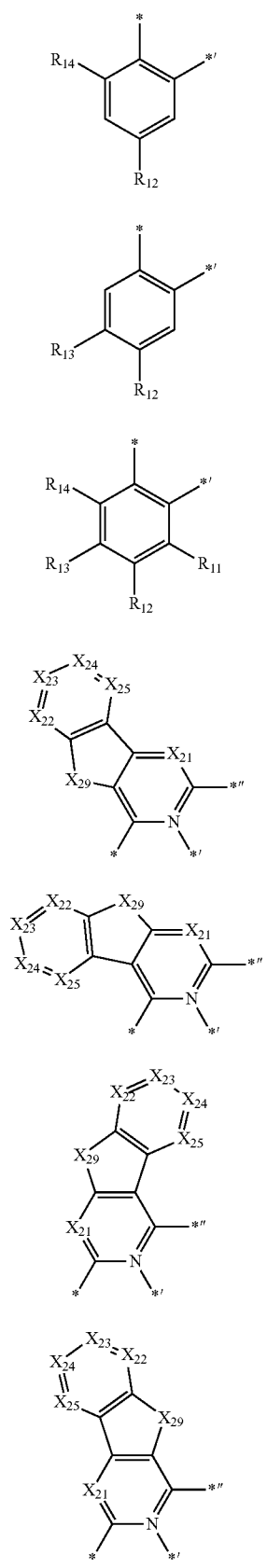

-continued

Formula CY3(11)

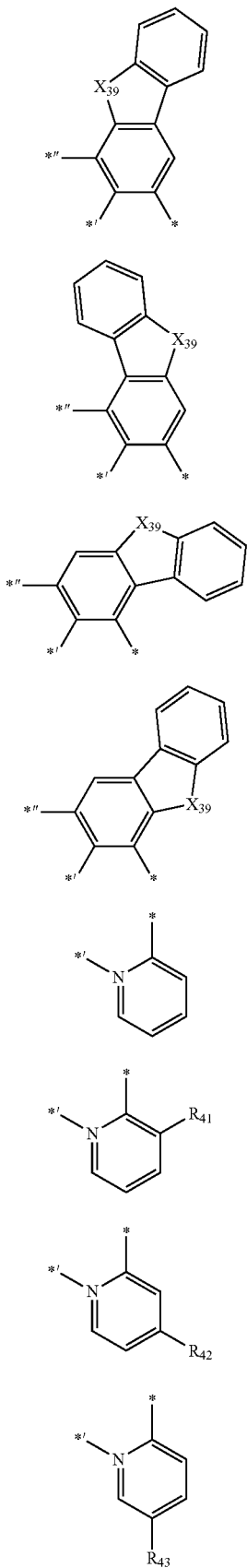

Formula CY3(12)

Formula CY3(13)

Formula CY3(14)

Formula CY4(1)

Formula CY4(2)

Formula CY4(3)

Formula CY4(4)

-continued

Formula CY4(5)

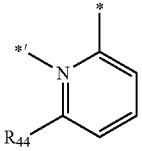

Formula CY4(6)

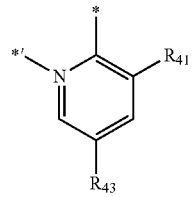

Formula CY4(7)

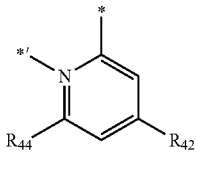

Formula CY4(8)

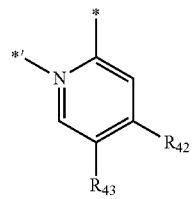

Formula CY4(9)

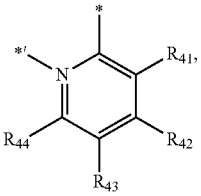

wherein, in Formulae CY2-1 to CY2-4, $X_{21}$ is N or $C(R_{21})$, $X_{22}$ is N or $C(R_{22})$, $X_{23}$ is $C(R_{23})$, $X_{24}$ is $C(R_{24})$, $X_{25}$ is $C(R_{25})$, $X_{29}$ is $C(R_{29a})(R_{29b})$, $N(R_{29})$, O, S, or $Si(R_{29a})(R_{29b})$, in Formulae CY3(1) to CY3(14), $X_{39}$ is $C(R_{39a})(R_{39b})$, $N(R_{39})$, O, S, or $Si(R_{39a})(R_{39b})$, wherein $R_5$, $R_6$, $R_{11}$ to $R_{14}$, $R_{21}$ to $R_{25}$, $R_{29}$, $R_{29a}$ to $R_{29b}$, $R_{31}$ to $R_{33}$, $R_{39}$, $R_{39a}$, $R_{39b}$ and $R_{41}$ to $R_{44}$ are each independently selected from hydrogen, deuterium, —F, —Cl, —Br, —I, —SF$_5$, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), provided that, none of $R_{11}$ to $R_{14}$ is hydrogen, none of $R_{31}$ to $R_{33}$ is hydrogen and none of $R_{41}$ to $R_{44}$ is hydrogen, two of $R_{11}$ to $R_{14}$ are optionally linked to form a substituted or unsubstituted $C_5$-$C_{30}$ carbocyclic group or a substituted or unsubstituted $C_1$-$C_{30}$ heterocydic group, two of $R_{21}$ to $R_{25}$, $R_{29}$ and $R_{29a}$ to $R_{29b}$ are optionally linked to form a substituted or unsubstituted $C_5$-$C_{30}$ carbocyclic group or a substituted or unsubstituted $C_1$-$C_{30}$ heterocyclic group, two of $R_{31}$ to $R_{33}$, $R_{39}$, $R_{39a}$ and $R_{39b}$ are optionally linked to form a substituted or unsubstituted $C_5$-$C_{30}$ carbocyclic group or a substituted or unsubstituted $C_1$-$C_{30}$ heterocyclic group, two of $R_{41}$ to $R_{44}$ are optionally linked to form a substituted or unsubstituted $C_5$-$C_{30}$ carbocyclic group or a substituted or unsubstituted $C_1$-$C_{30}$ heterocydic group, one of $R_5$ and $R_6$ is optionally linked with one of $R_{11}$ to $R_{14}$, $R_{21}$ to $R_{25}$, $R_{29}$, $R_{29a}$ to $R_{29b}$, $R_{31}$ to $R_{33}$, $R_{39}$, $R_{39a}$, $R_{39b}$ and $R_{41}$ to $R_{44}$ to form a substituted or unsubstituted $C_5$-$C_{30}$ carbocyclic group or a substituted or unsubstituted $C_1$-$C_{30}$ heterocyclic group, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_2$-$C_{60}$ heteroaryloxy group, the substituted $C_2$-$C_{60}$ heteroarylthio group, the substituted heteroarylalkyl group, the substituted monovalent non-aromatic condensed polycyclic group, and the substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycydic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxy group, a cyano group, a nitro group, an amidino group, a hydrazine group, a hydrazone group, a carboxylic acid group or a salt thereof, a sulfonic add group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxy group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group and a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a monovalent non-aromatic condensed polycyclic group, and a monovalent non-aromatic condensed heteropolycyclic group, and

*, *', and *" each independently indicate a binding site to a neighboring atom.

9. The organometallic compound of claim 1, wherein the organometallic compound is represented by one of Formulae 1(1) and 1(2):

Formula 1(1)

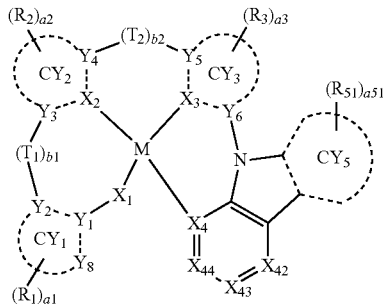

Formula 1(2)

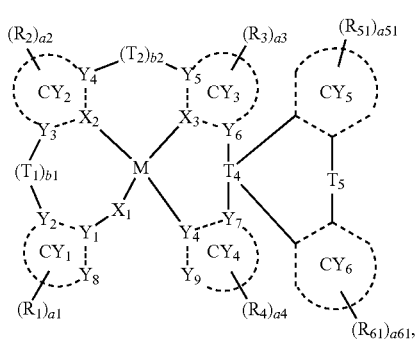

wherein, in Formulae 1(1) and 1(2),

M, $X_1$ to $X_4$, $T_1$ to $T_3$, and b1 to b3 are each independently the same as described in claim 1, a moiety represented by

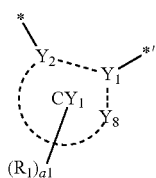

is the same as described in claim 1, a moiety represented by

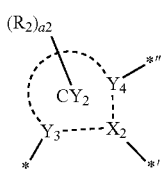

is the same as described in claim 1, a moiety represented by

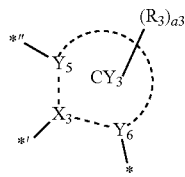

is the same as described in claim 1, a moiety represented by

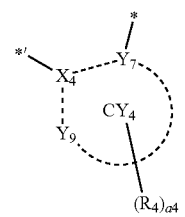

is the same as described in claim 1, $X_{42}$ is N or $C(R_{42})$, $X_{43}$ is N or $C(R_{43})$, and $X_{44}$ is N or $C(R_{44})$, $R_{42}$ to $R_{44}$ are each independently the same as described in connection with $R_{41}$ in claim 1, wherein two selected from $R_{42}$ to $R_{44}$ are optionally linked to form a substituted or unsubstituted $C_5$-$C_{30}$ carbocyclic group or a substituted or unsubstituted $C_1$-$C_{30}$ heterocyclic group, $CY_5$ and $CY_6$ are each independently a $C_5$-$C_{30}$ carbocyclic group or a substituted or unsubstituted $C_1$-$C_{30}$ heterocyclic group, $R_{51}$ and $R_{61}$ are each independently the same as described in connection with $R_{11}$ in claim 1, a51 and a61 are each independently 0, 1, 2, or 3, $T_4$ is C, Si, or Ge, $T_5$ is selected from a single bond, *—N[$(L_7)_{a7}$-$(R_7)$]—*', *—B($R_7$)—*', *—P($R_7$)—*', *—C($R_7$)($R_8$)—*', *—Si($R_7$)($R_8$)—*', *—Ge($R_7$)($R_8$)—*', *—S—*', *—Se—*', *—O—*', *—C(=O)—*', *—S(=O)—*', *—S(=O)$_2$—*', *—C($R_7$)=*', *=C($R_7$)—*', *—C($R_7$)=C($R_8$)—*', *—C(=S)—*', and *—C≡C—*', $R_7$ and $R_8$ are each independently the same as described in connection with $R_5$ in claim 1, $L_7$ is the same as described in connection with $L_5$ in claim 1, a7 is the same as described in connection with a5 in claim 1, and

* and *' each independently indicate a binding site to a neighboring atom.

10. The organometallic compound of claim 1, wherein the organometallic compound is selected from Compounds 1 to 240:

-continued
1
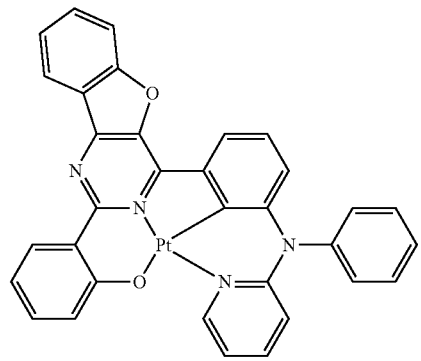
2
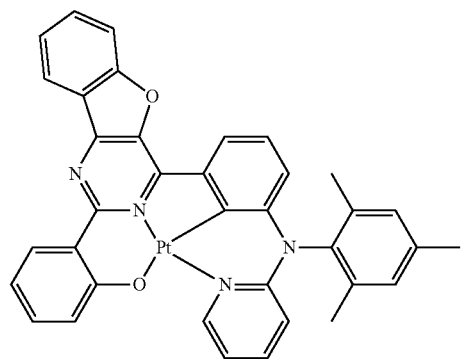
3
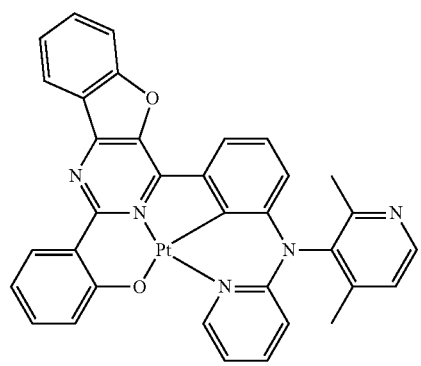
4
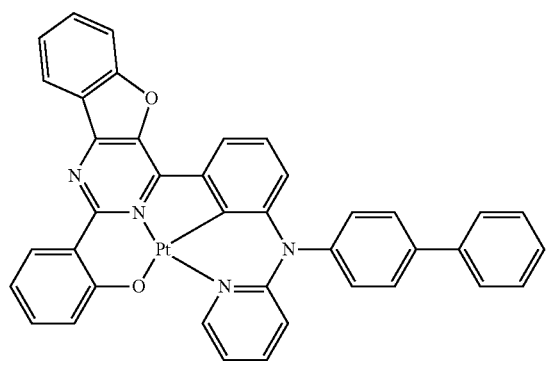
5
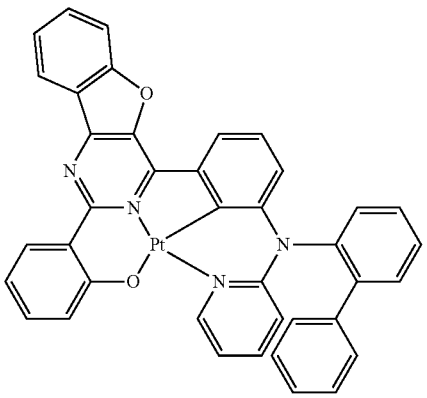
6
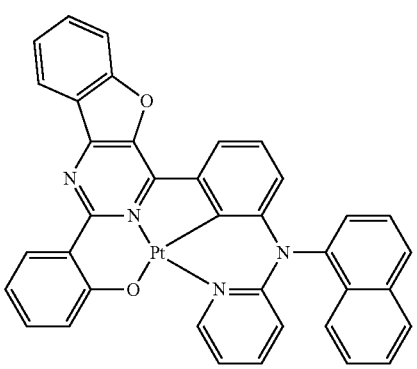
7
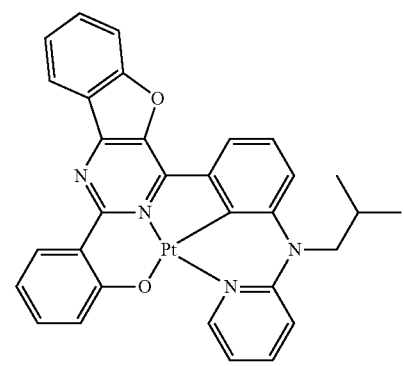
8
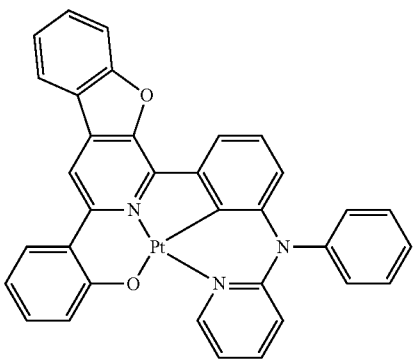

-continued
9
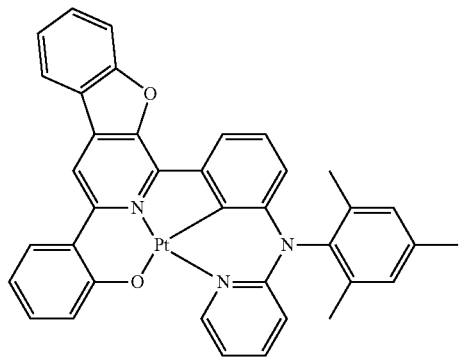
10
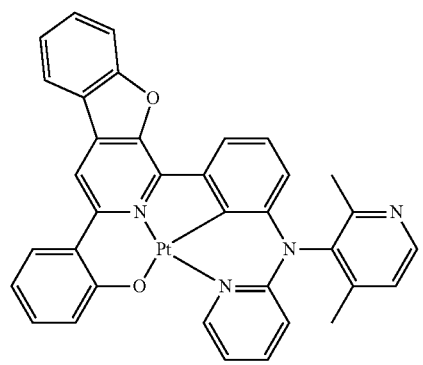
11
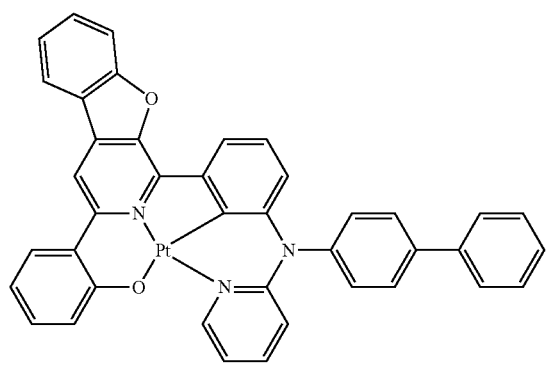
12
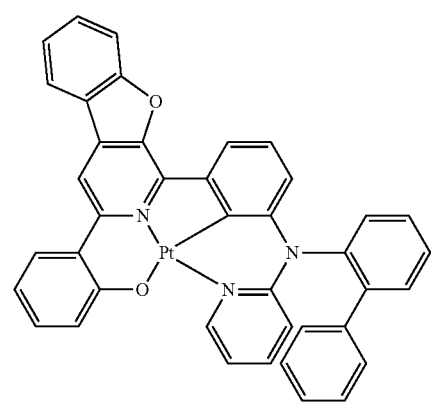
-continued
13
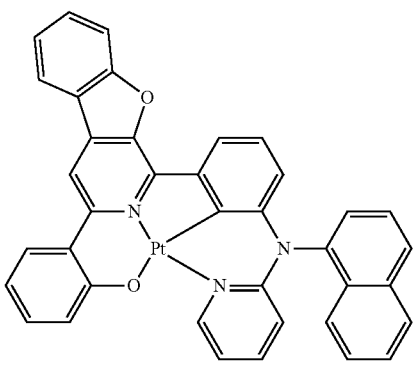
14
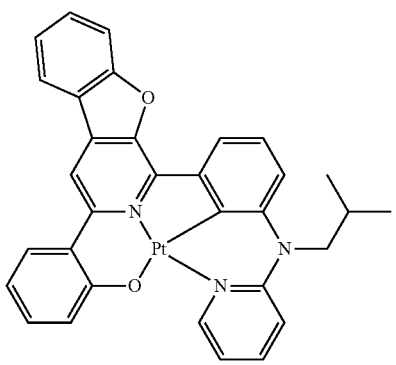
15
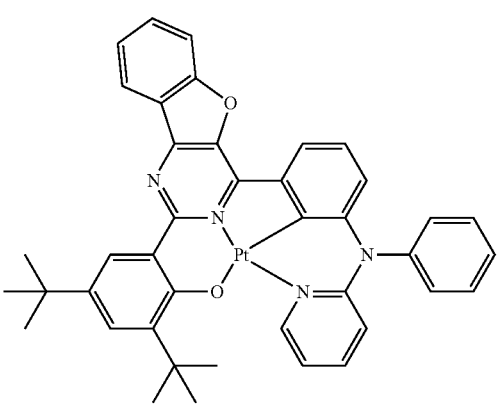
16
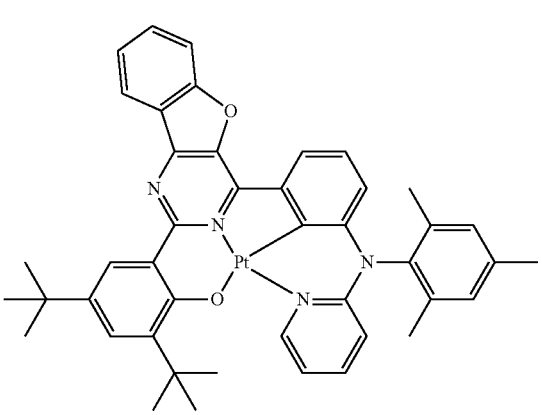

17
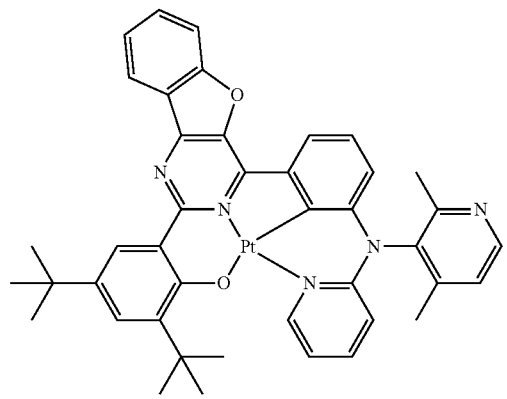
18
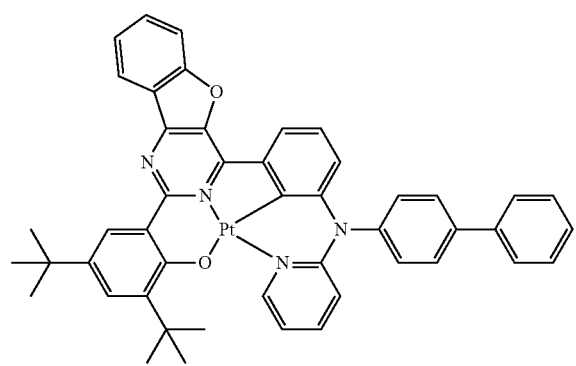
19
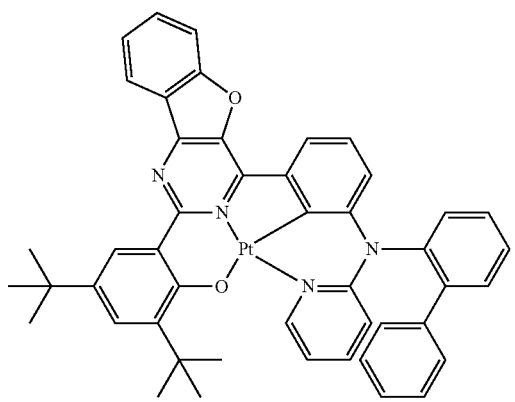
20
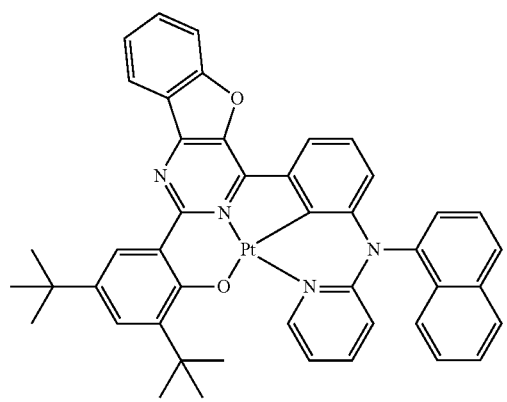
21
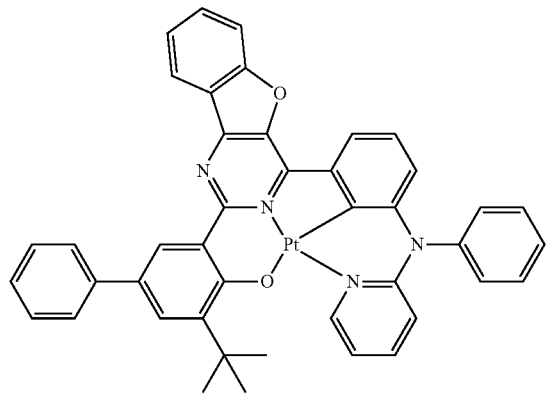
22
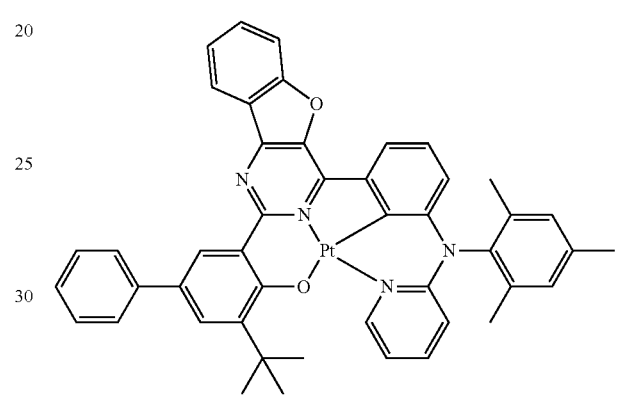
23
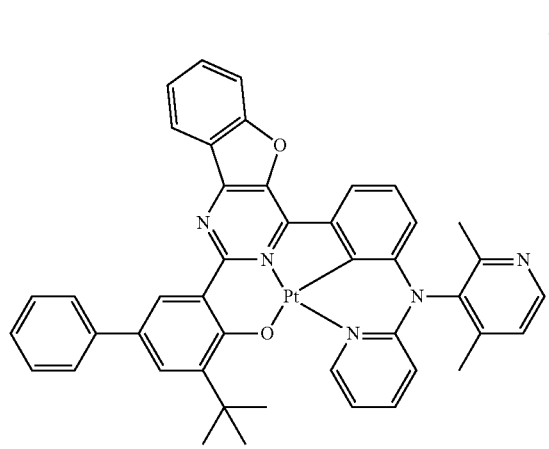
24
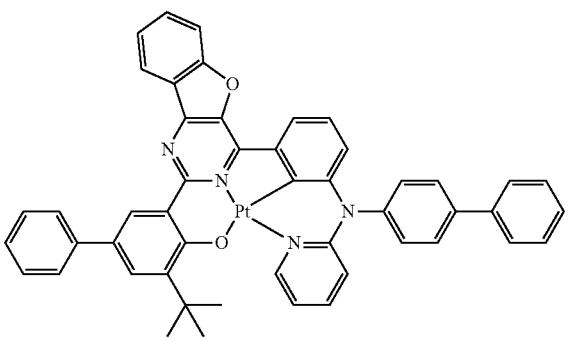

205
-continued
25
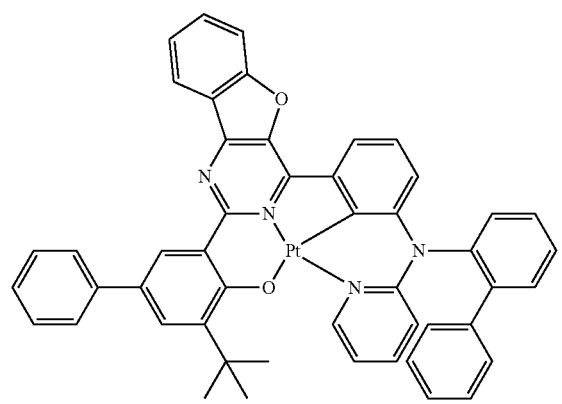
26
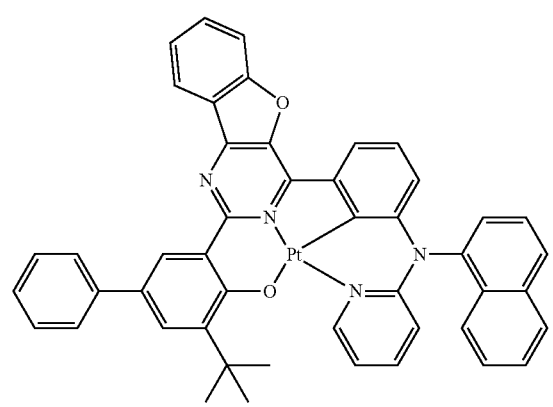
27
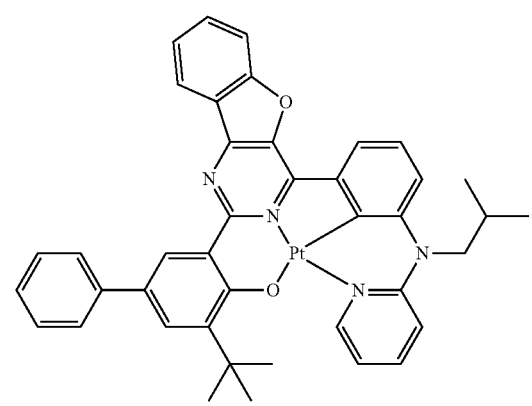
28
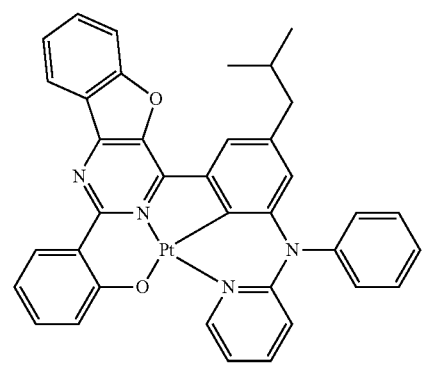
206
-continued
29
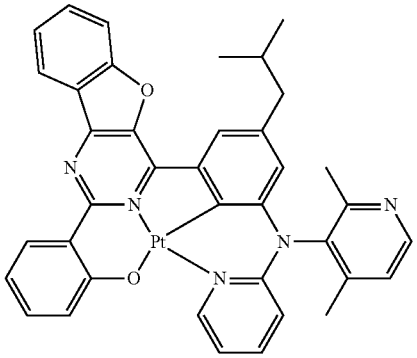
30
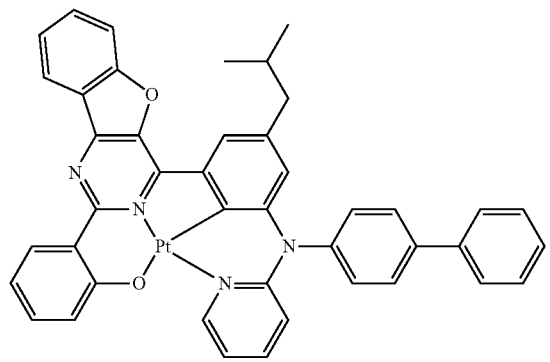
31
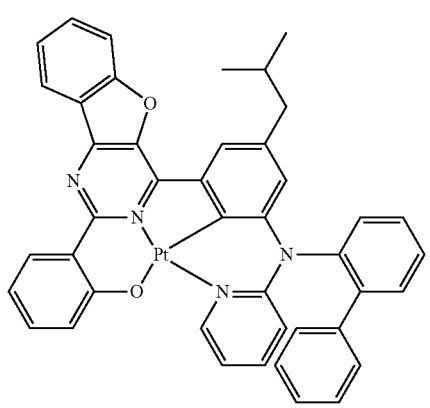
32
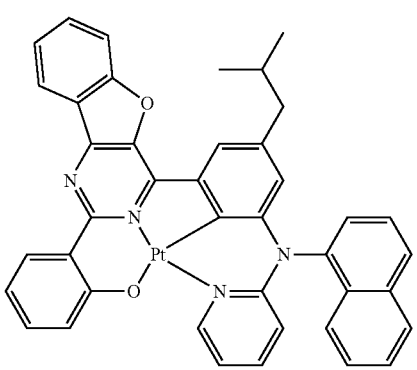

207
-continued
33
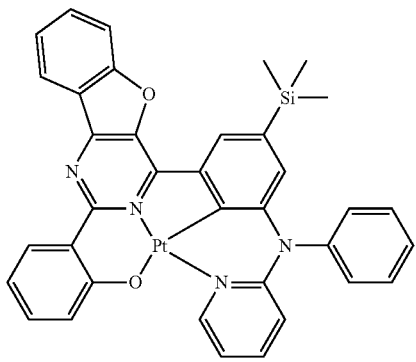
34
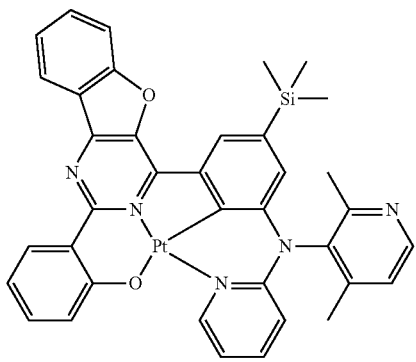
35
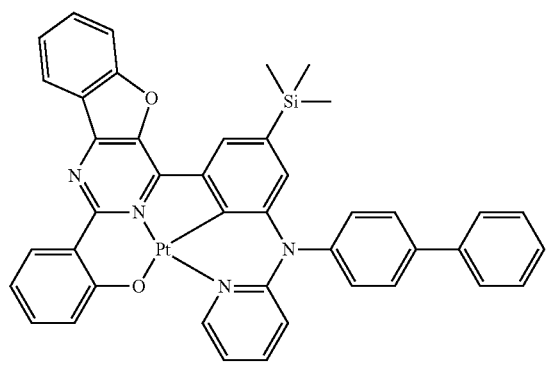
36
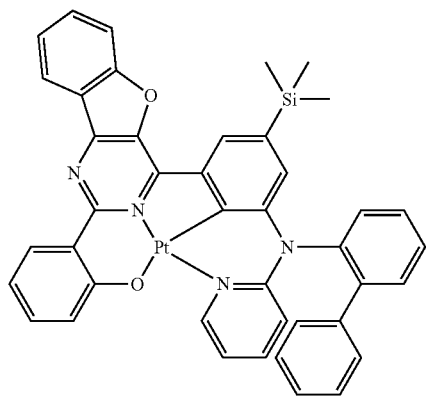
208
-continued
37
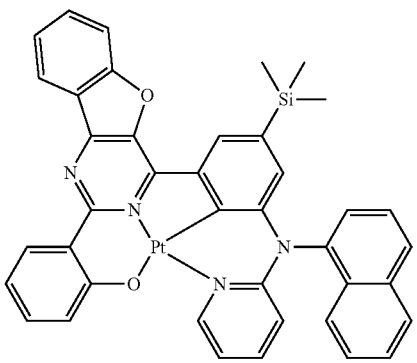
38
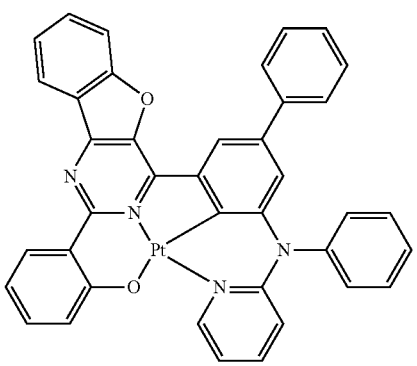
39
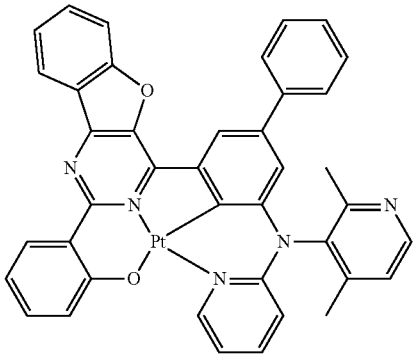
40
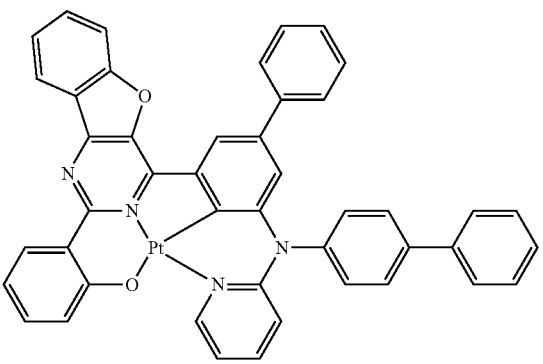

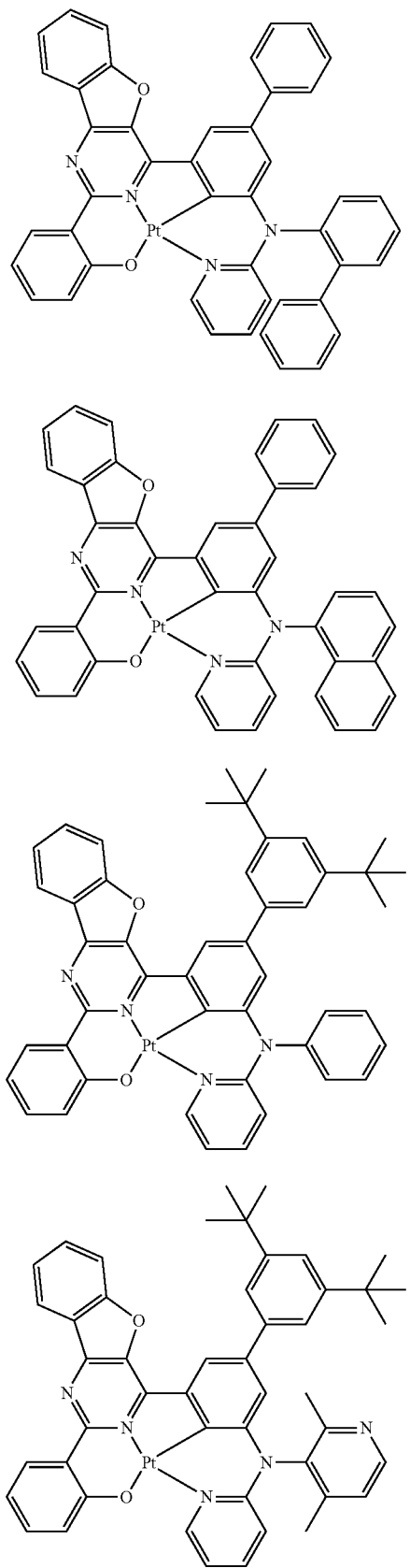
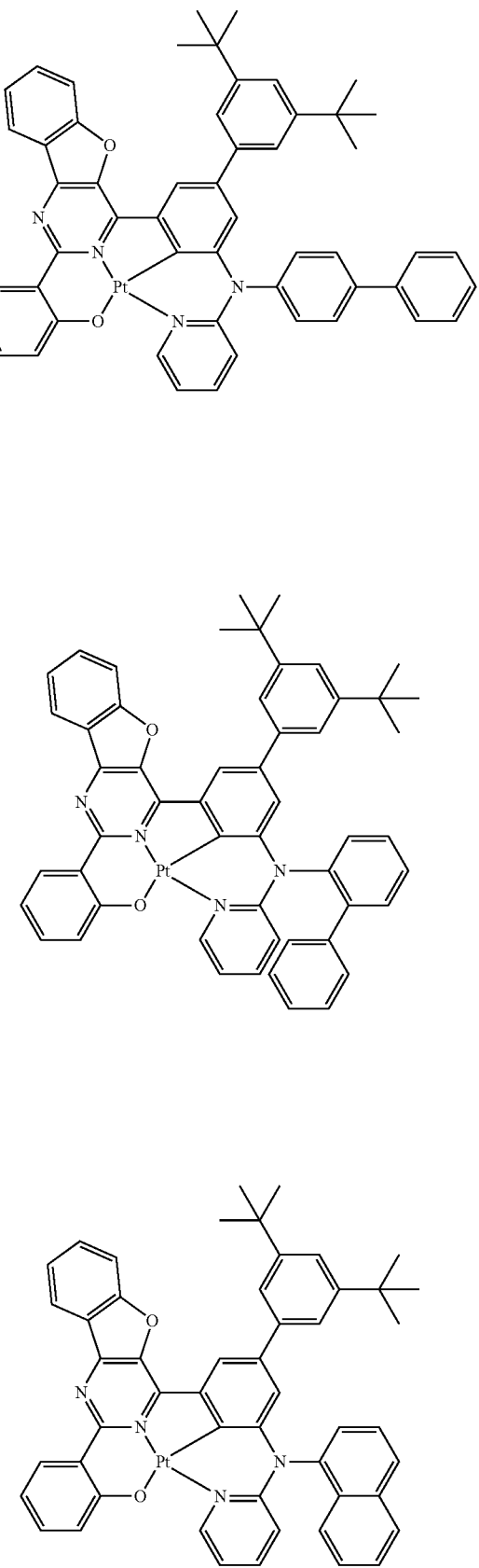

211
-continued
48
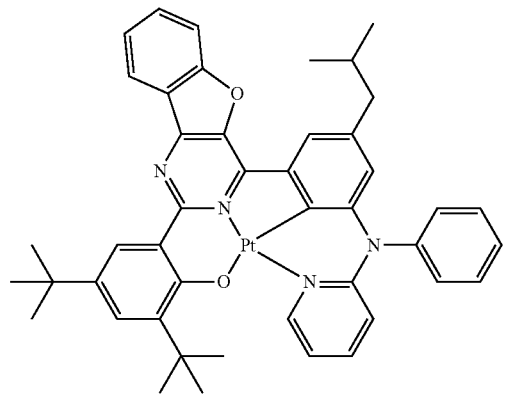
49
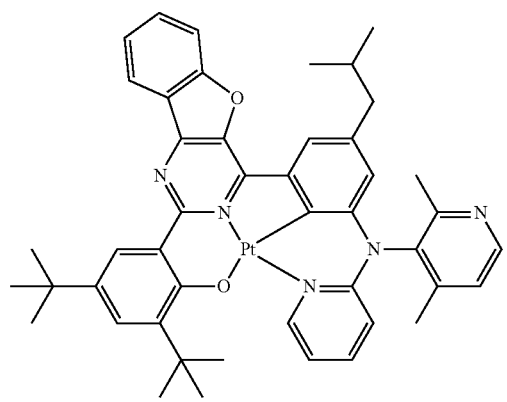
50
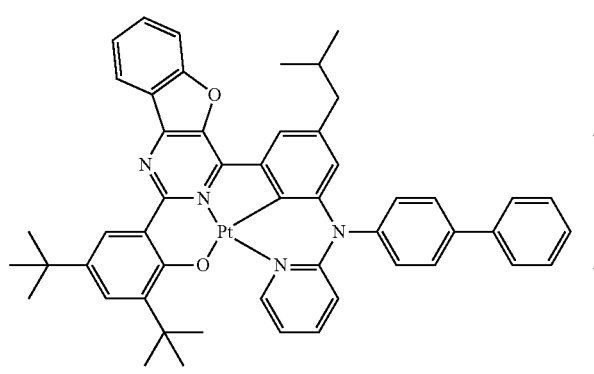
51
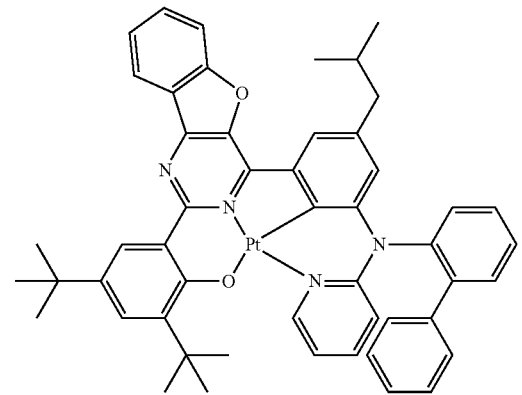
212
-continued
52
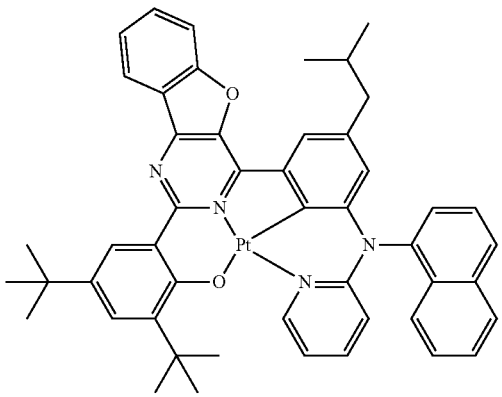
53
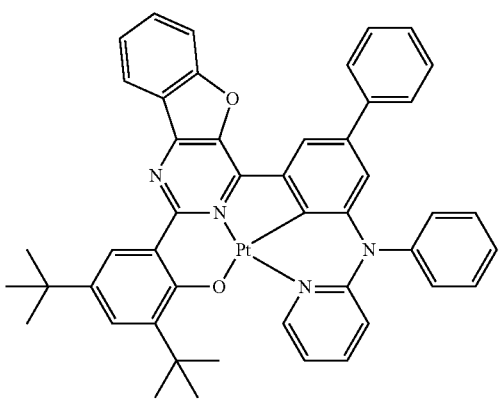
54
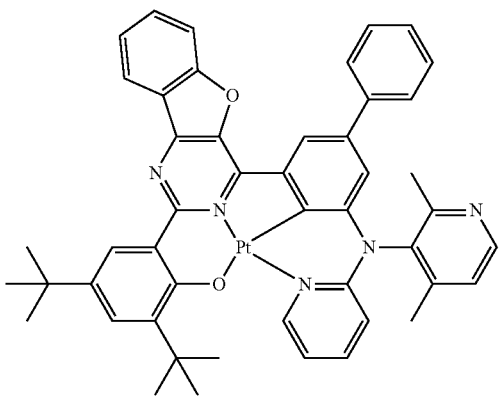
55
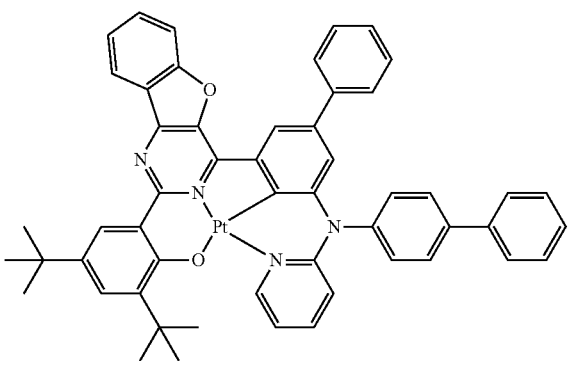

56
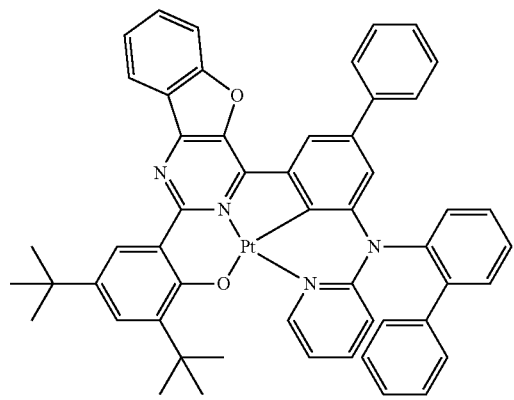
57
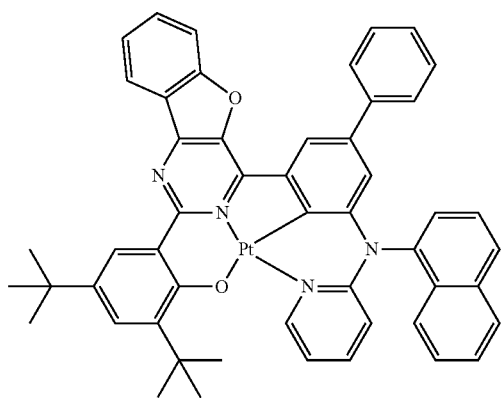
58
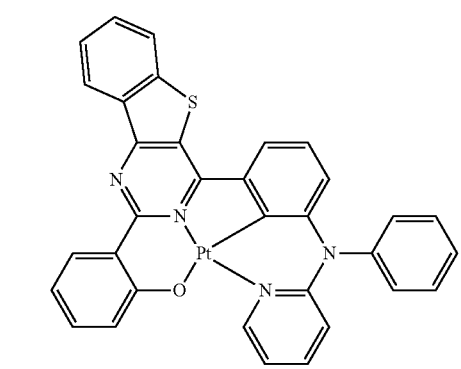
59
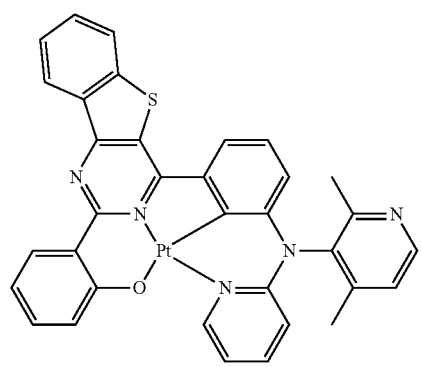
60
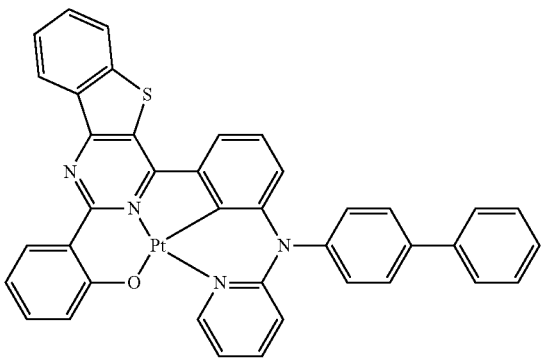
61
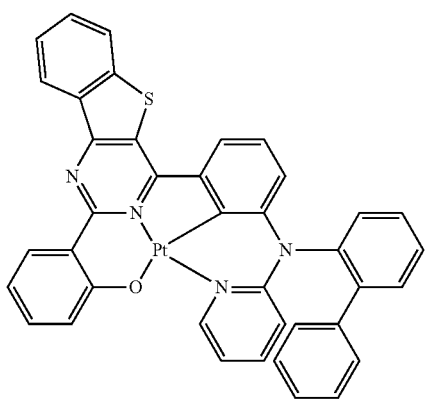
62
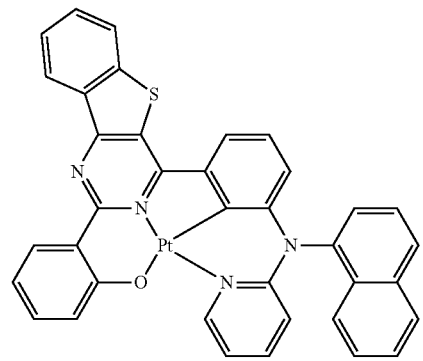
63
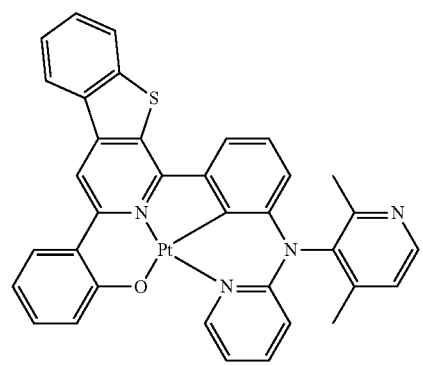

215
-continued
64
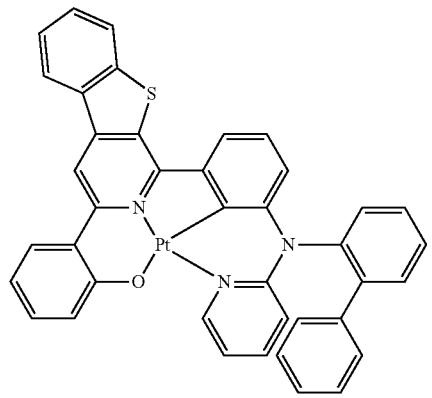
65
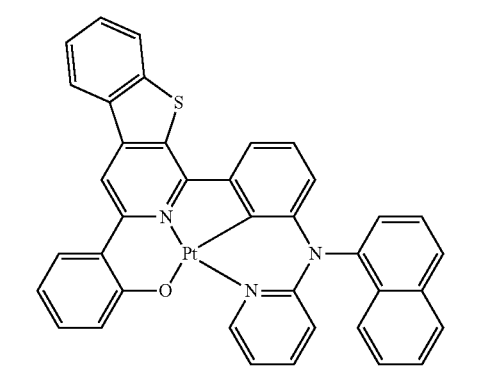
66
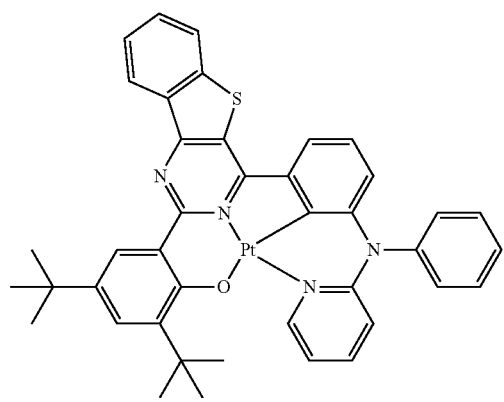
67
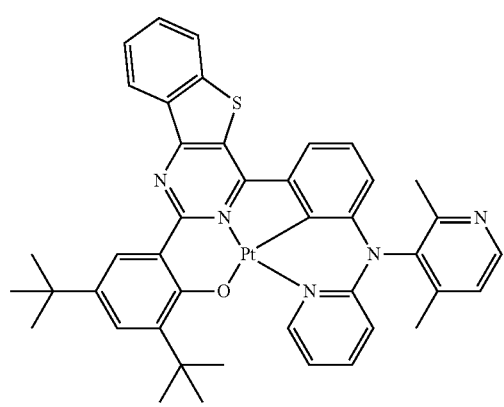
216
-continued
68
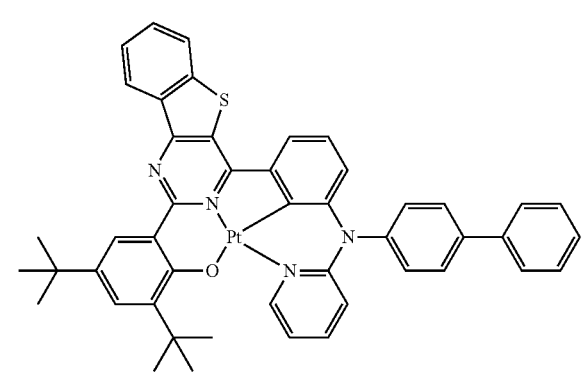
69
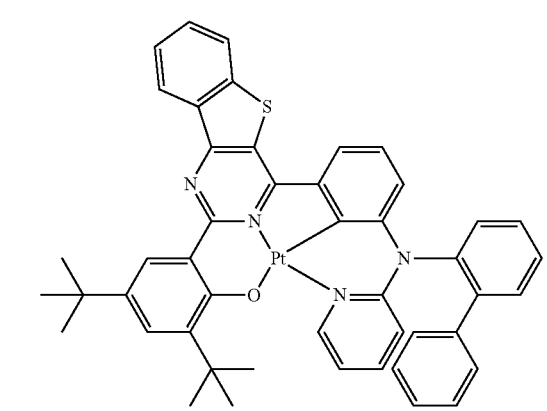
70
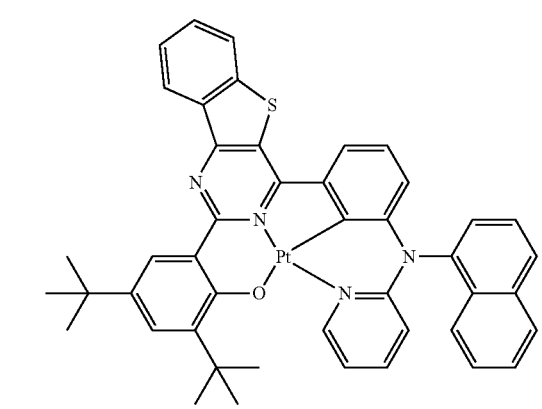
71
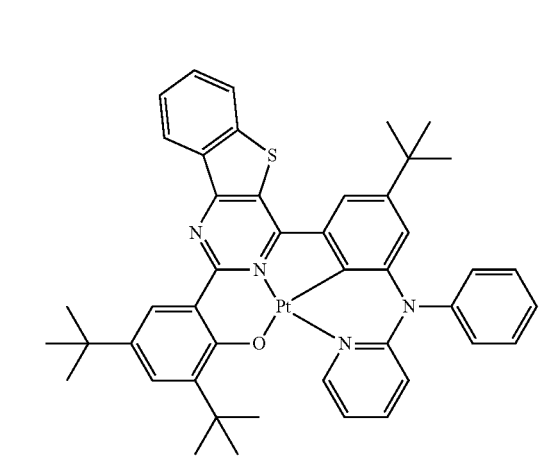

217
-continued
72
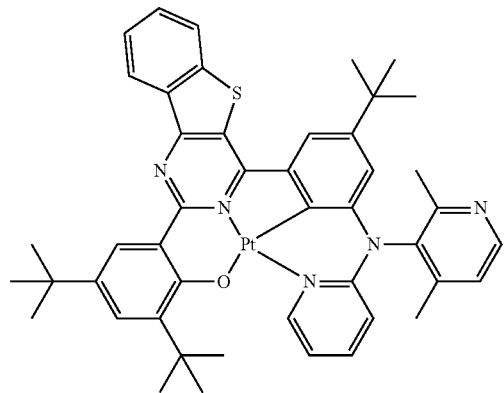
73
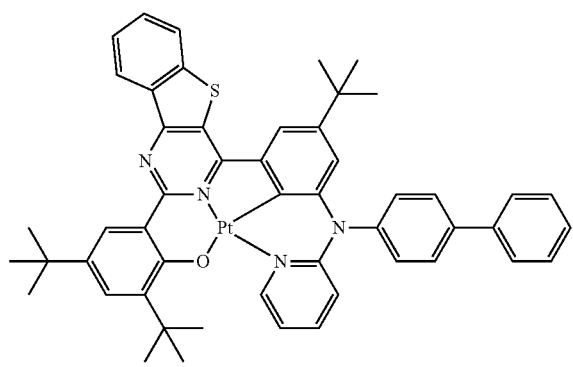
74
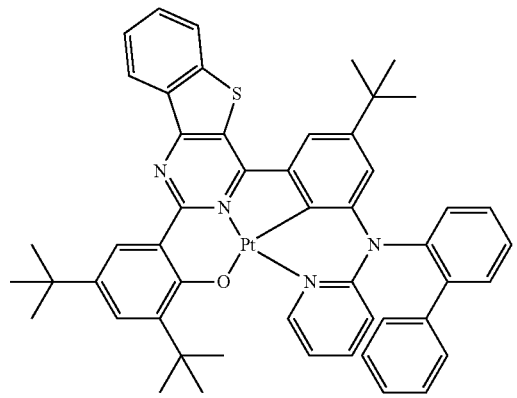
75
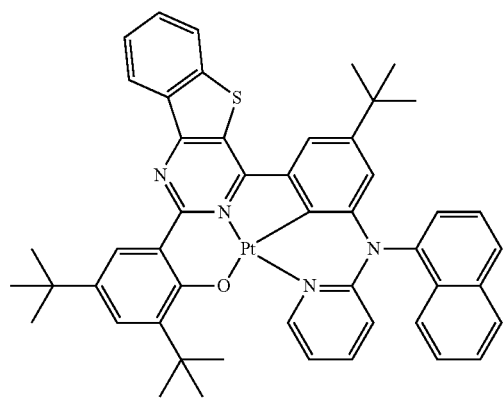
218
-continued
76
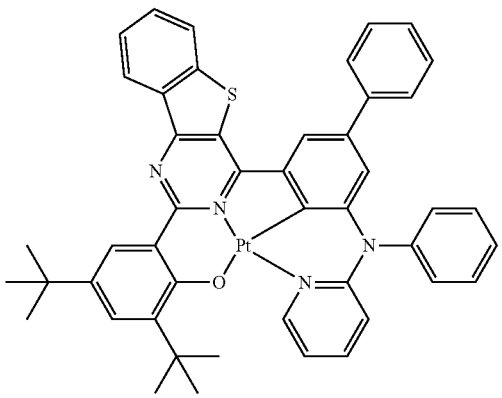
77
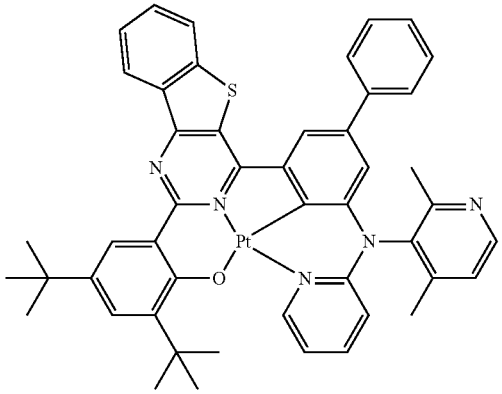
78
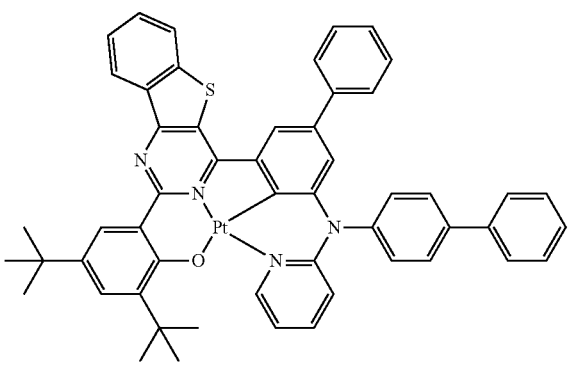
79
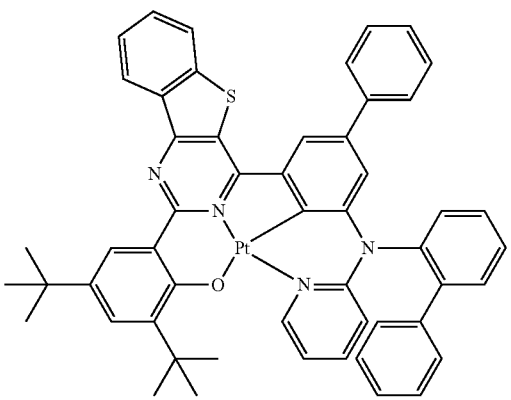

219
-continued
80
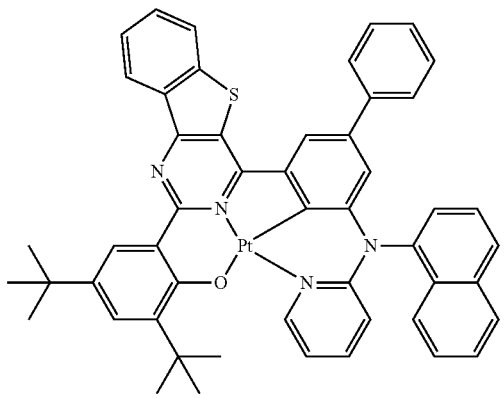
81
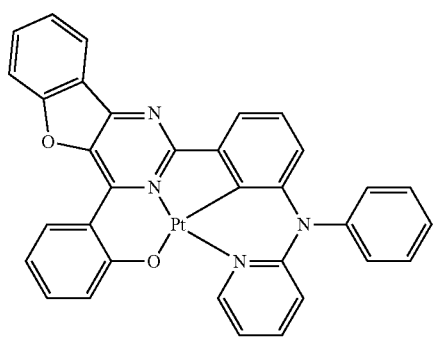
82
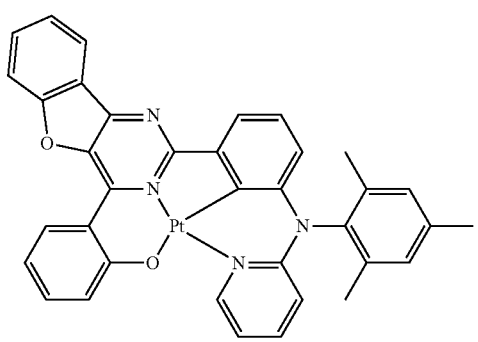
83
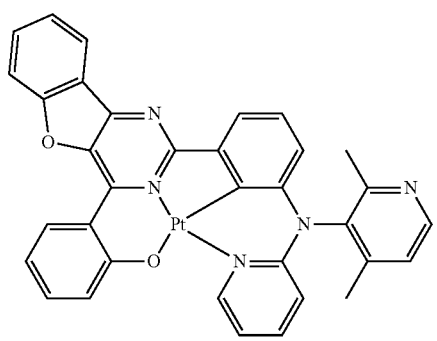
220
-continued
84
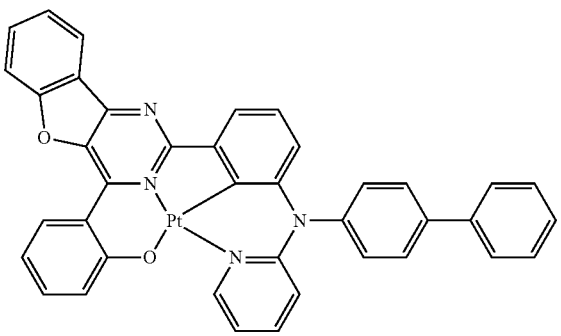
85
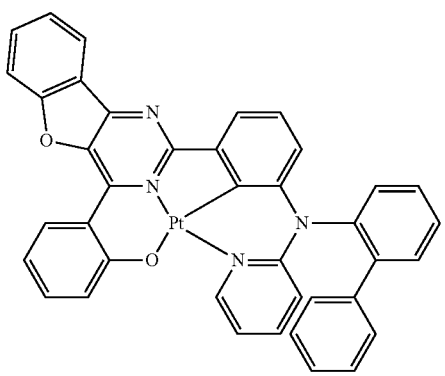
86
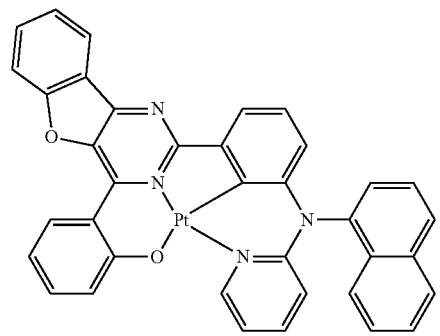
87
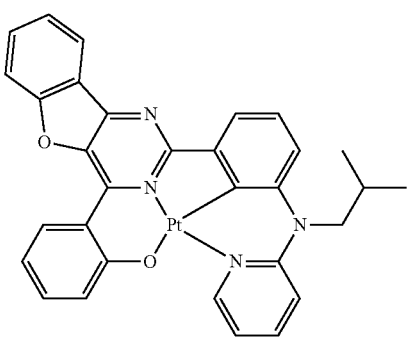

221
-continued
88
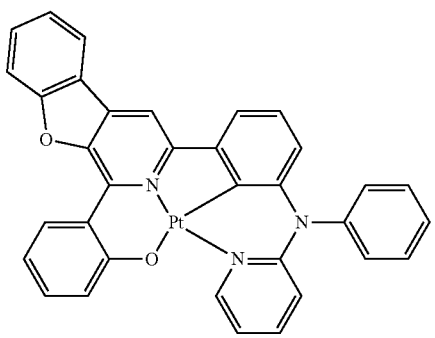
89
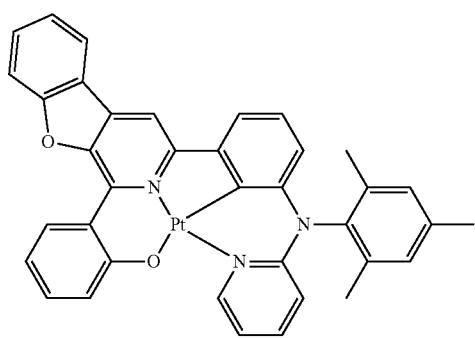
90
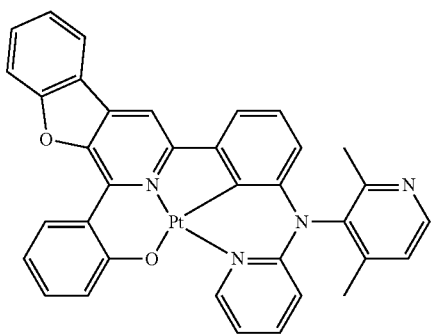
91
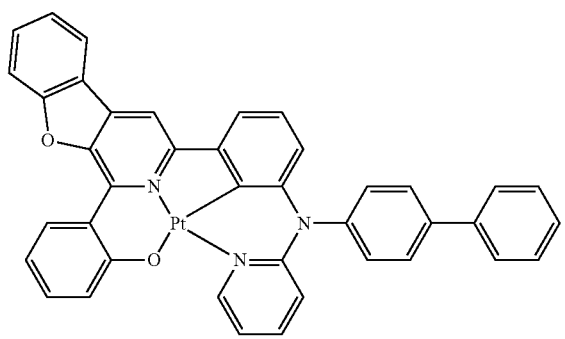
222
-continued
92
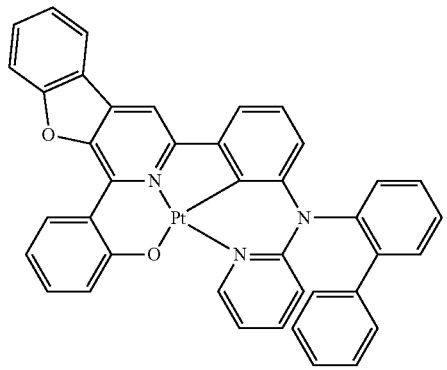
93
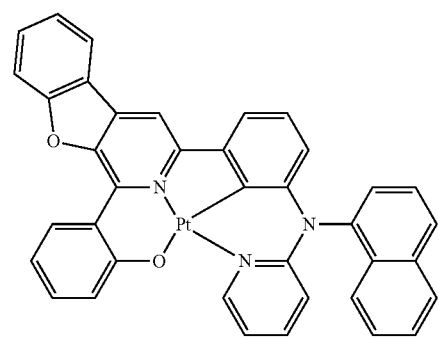
94
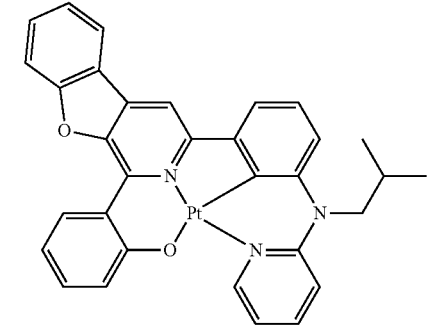
95
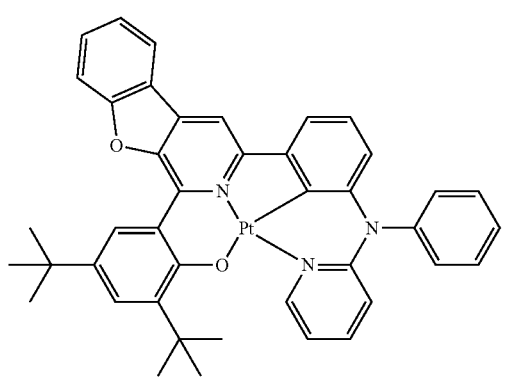

223
-continued
96
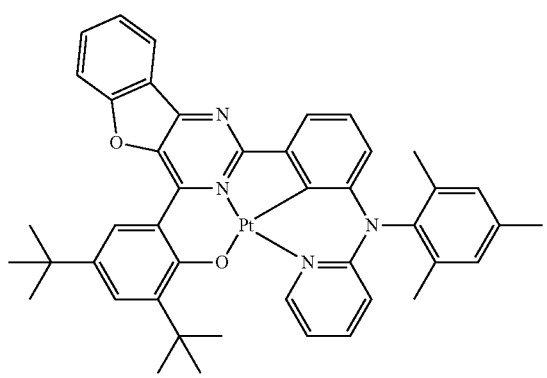
97
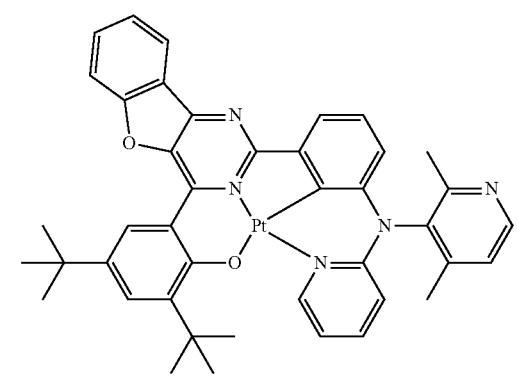
98
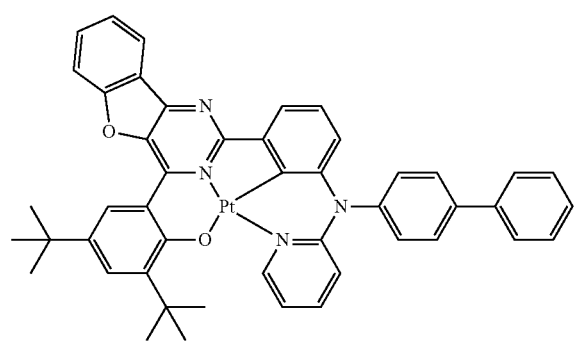
99
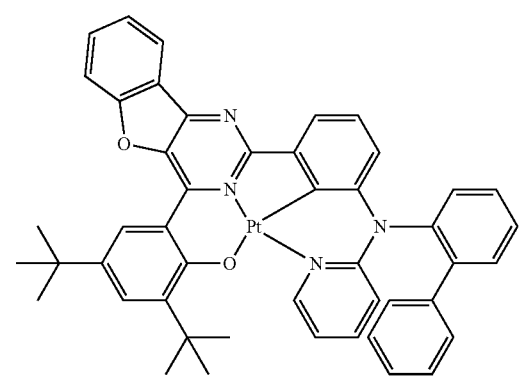
224
-continued
100
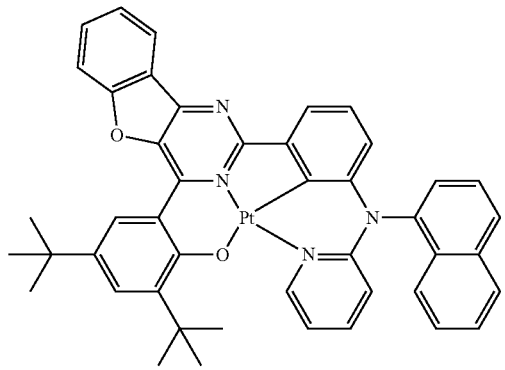
101
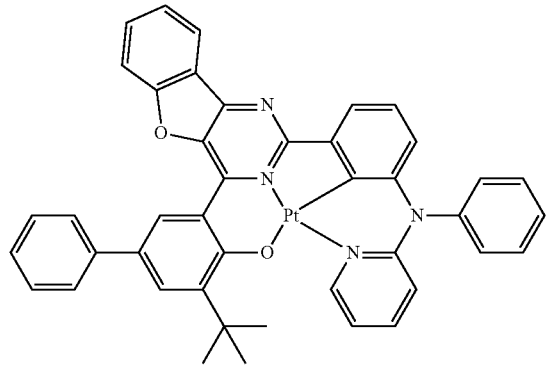
102
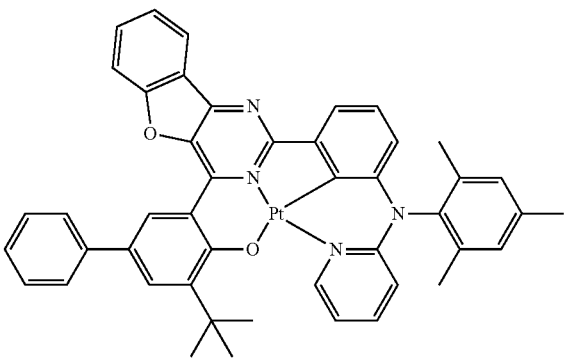
103
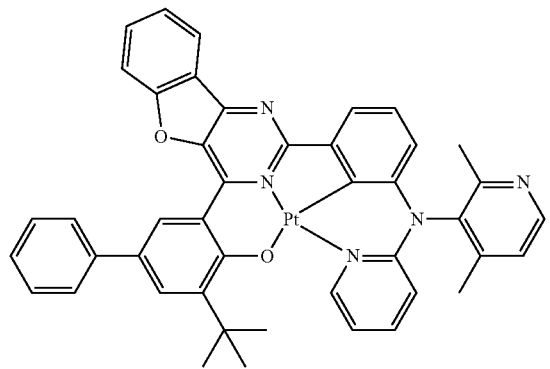

225
-continued
104
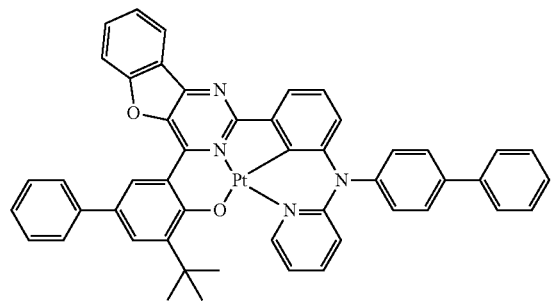
105
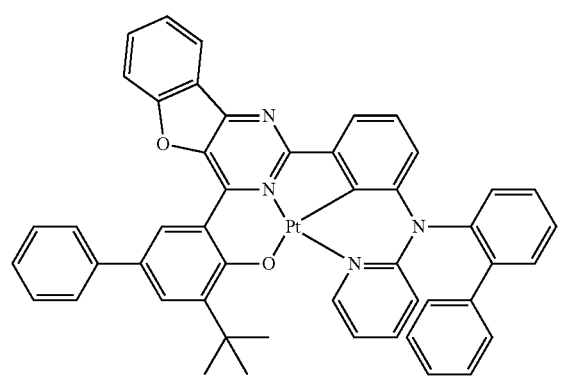
106
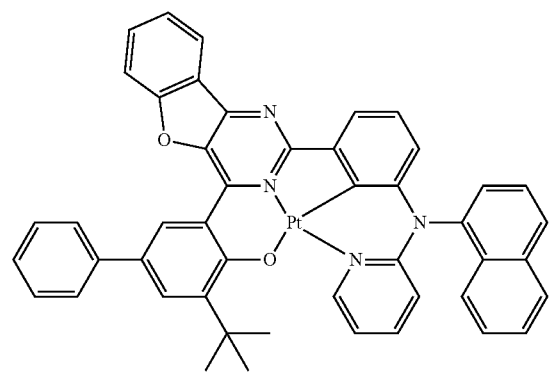
107
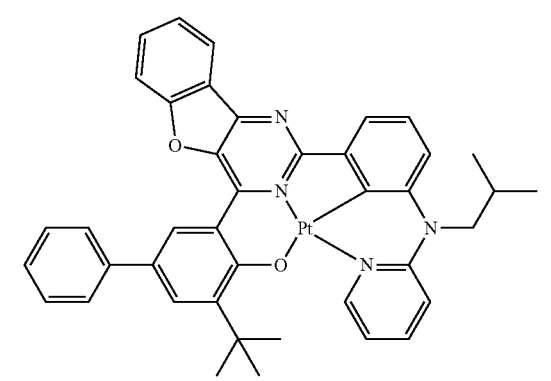
226
-continued
108
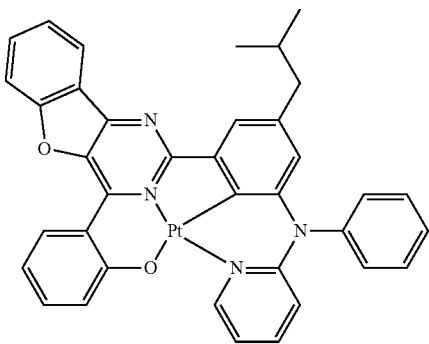
109
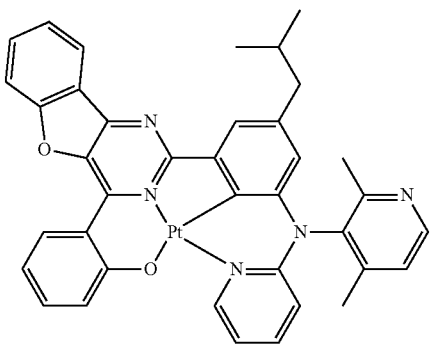
110
111
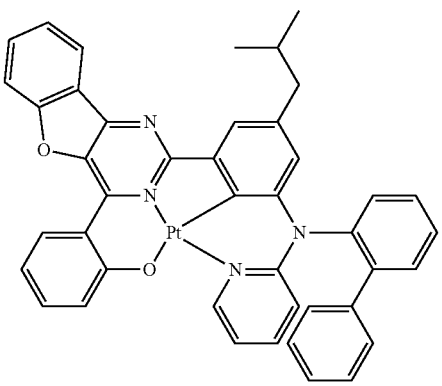

227
-continued
112
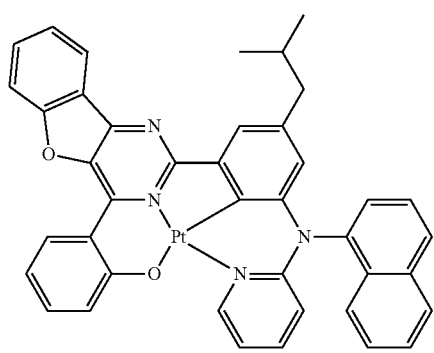
113
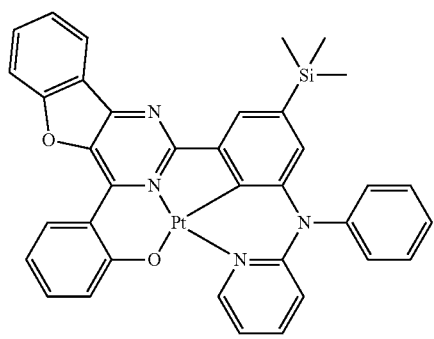
114
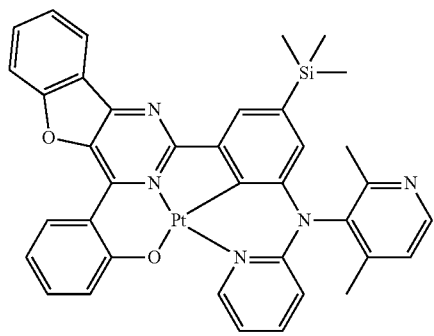
115
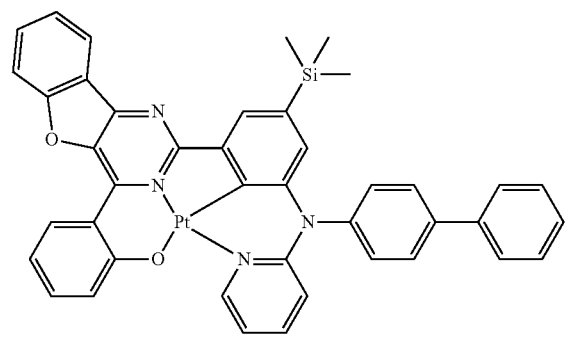
228
-continued
116
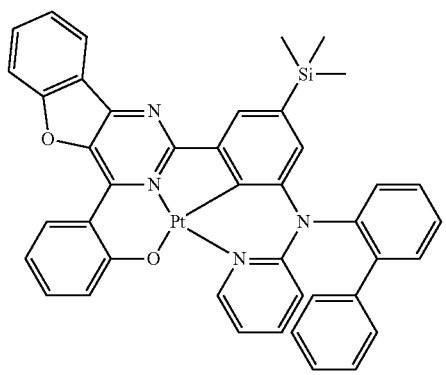
117
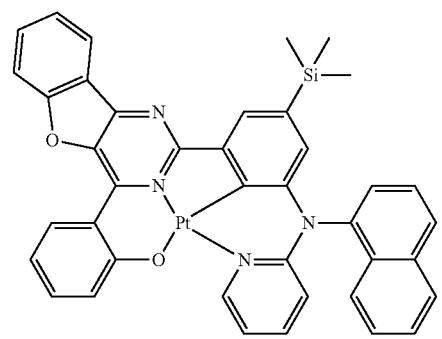
118
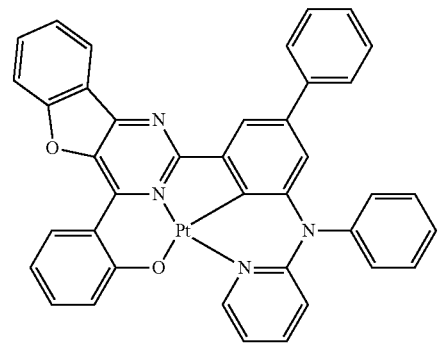
119
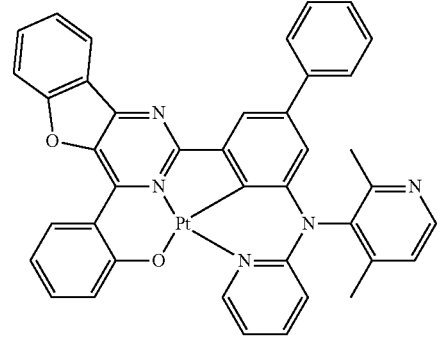

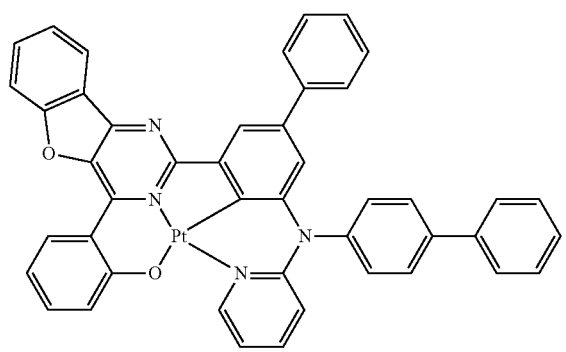
120
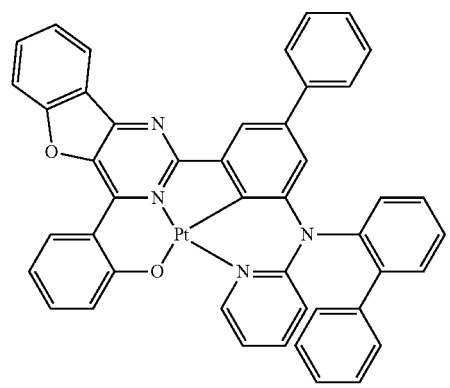
121
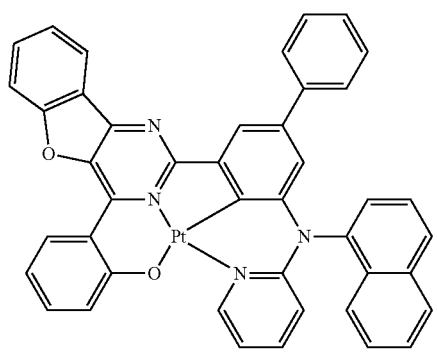
122
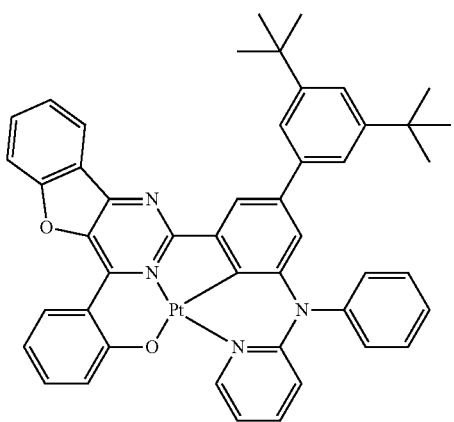
123
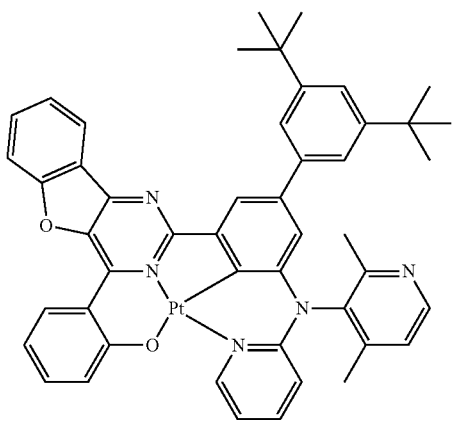
124
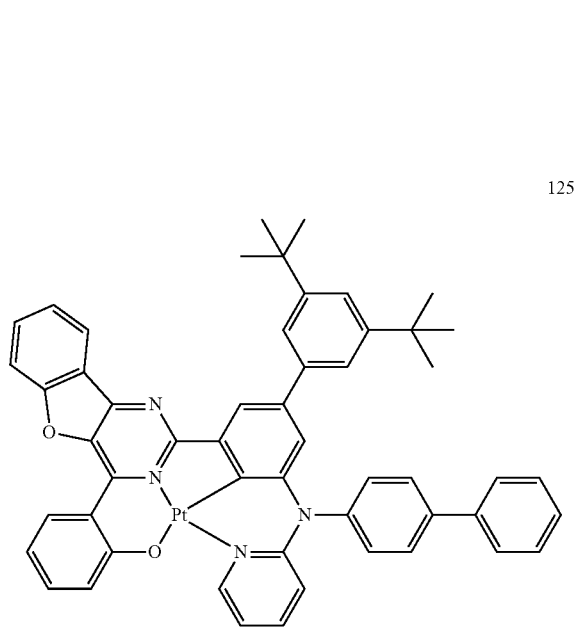
125
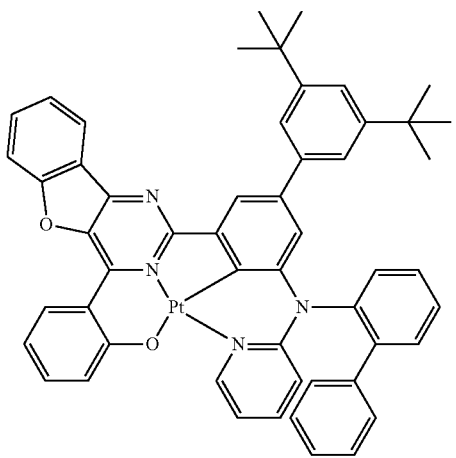
126

231
-continued
127
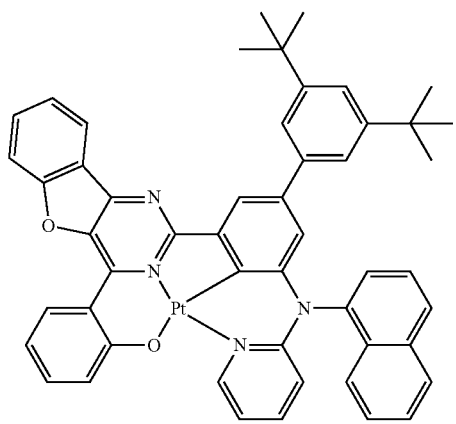
128
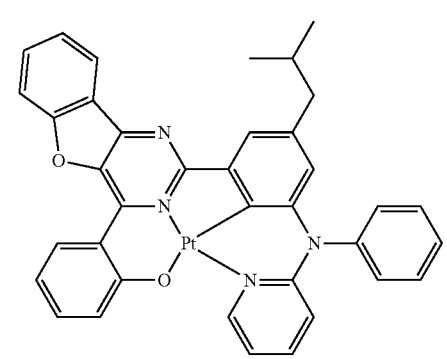
129
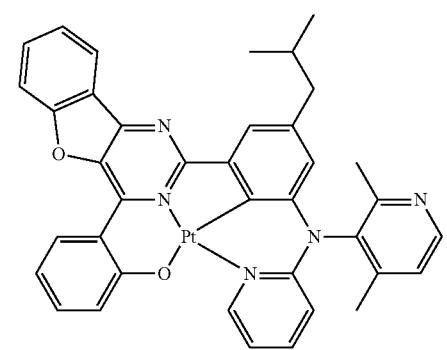
130
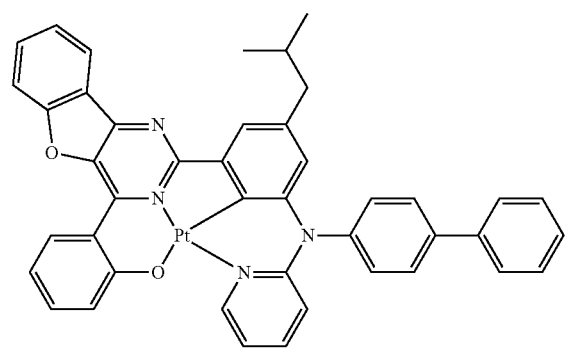
232
-continued
131
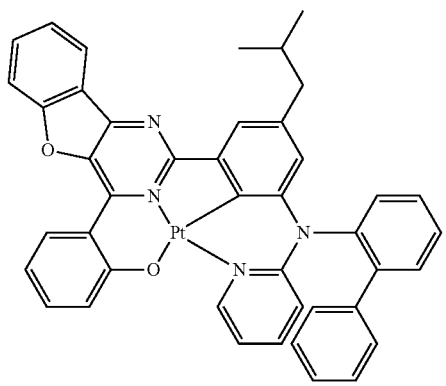
132
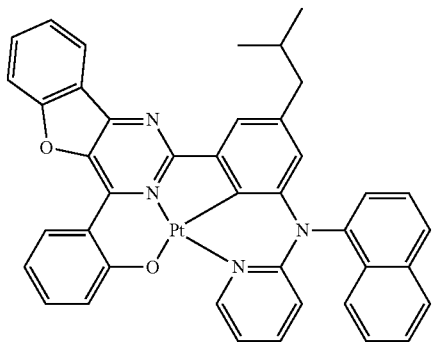
133
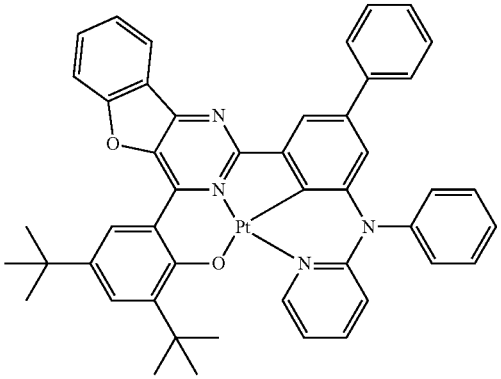
134
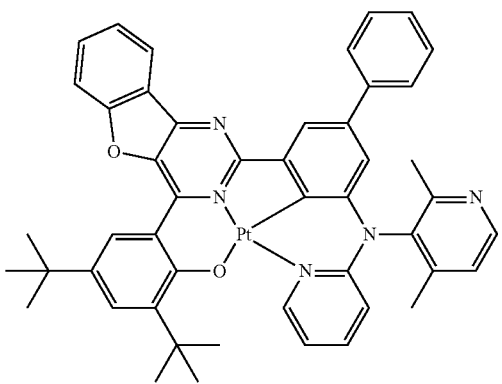

-continued
135
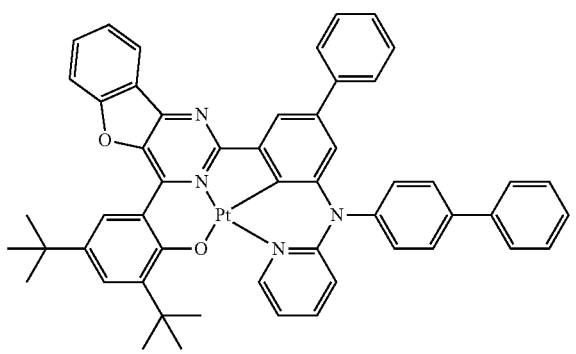
136
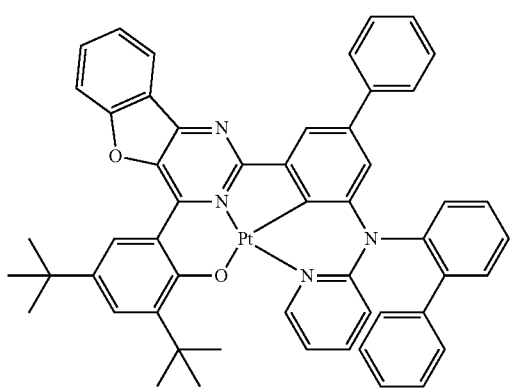
137
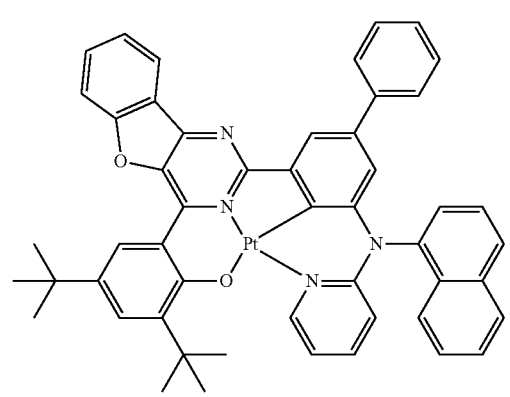
138
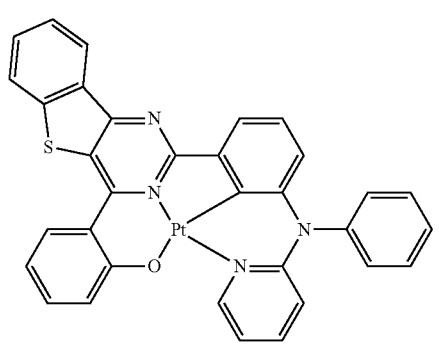
-continued
139
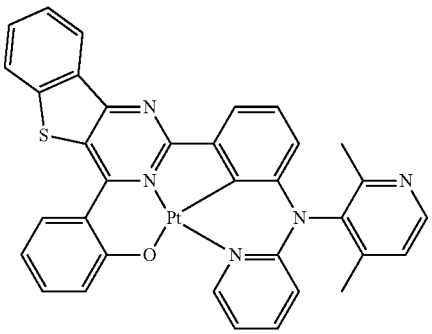
140
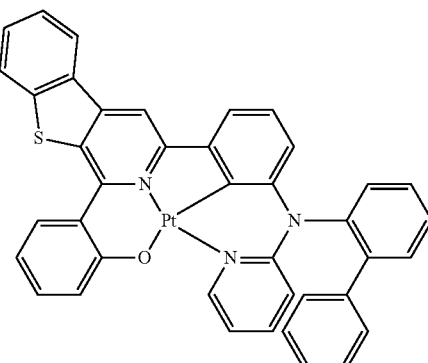
141
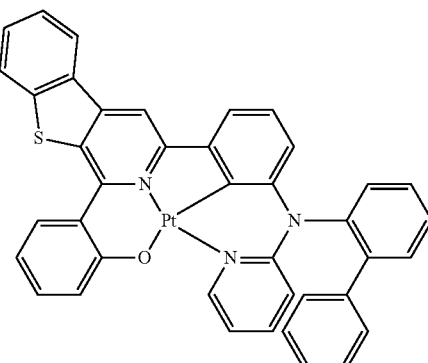
142
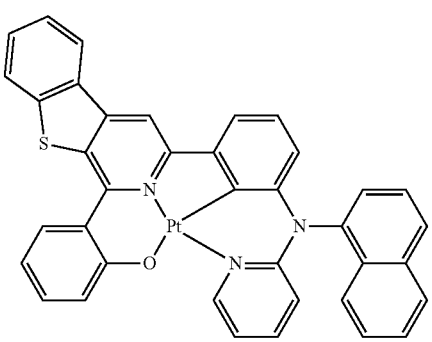

235
-continued
143
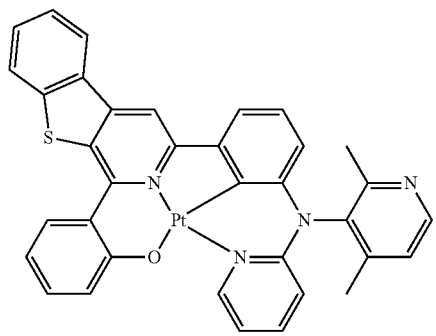
144
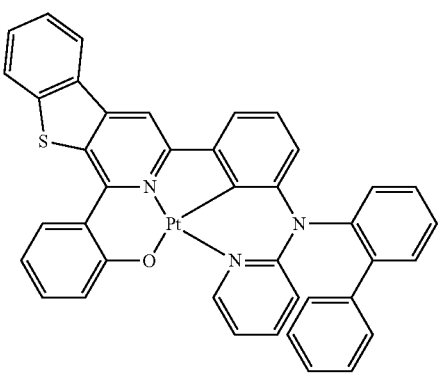
145
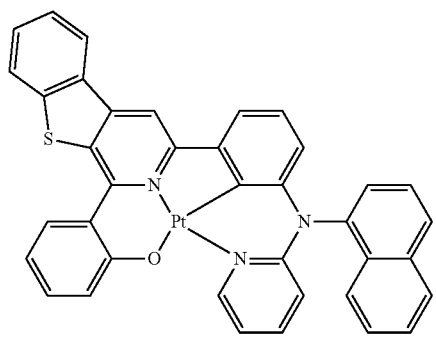
146
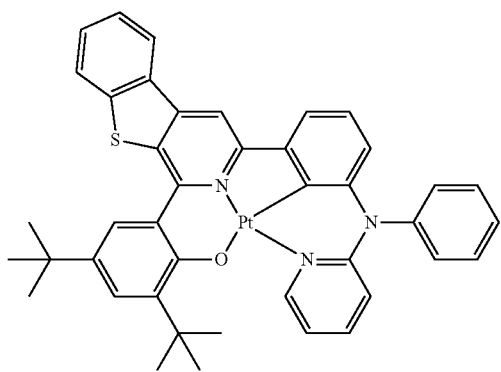
236
-continued
147
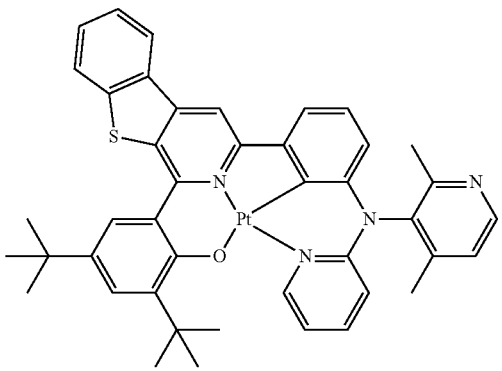
148
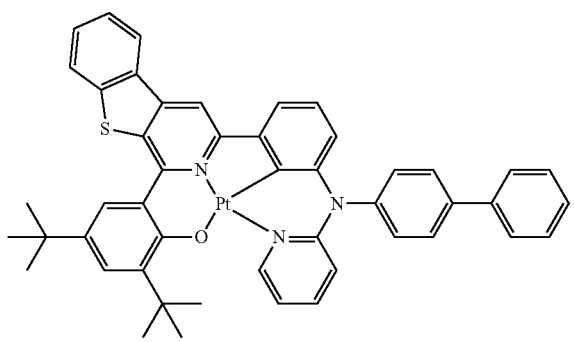
149
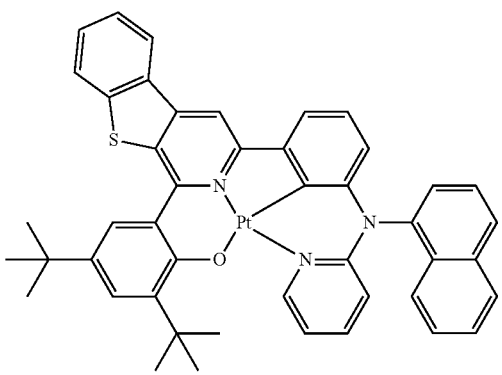
150

151
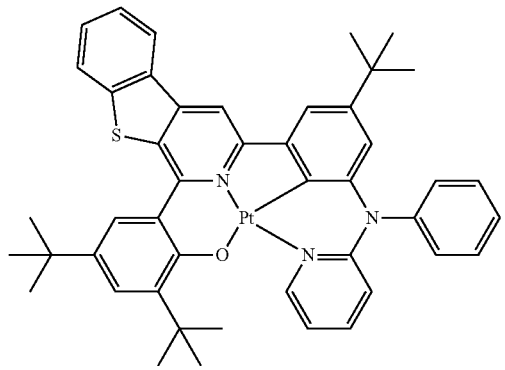
152
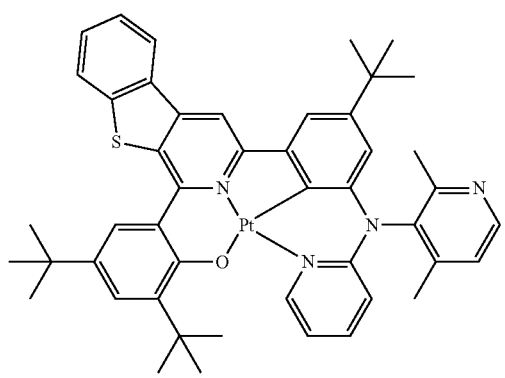
153
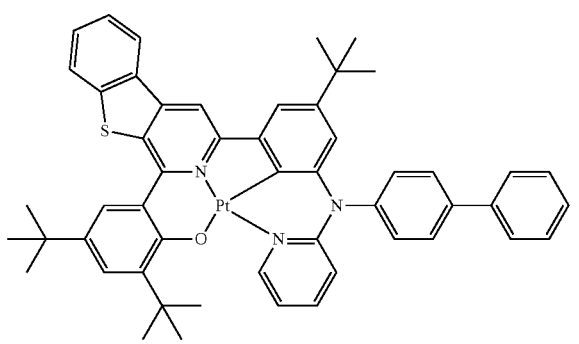
154
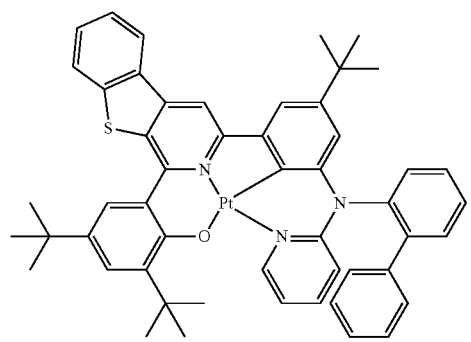
155
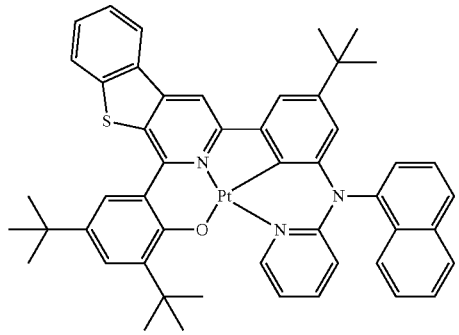
156
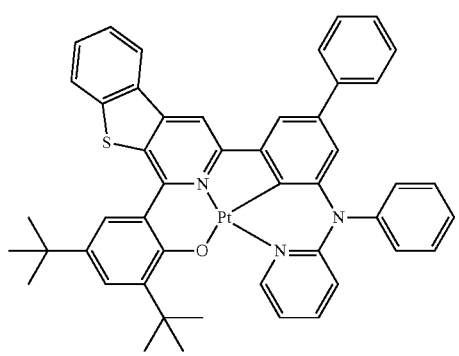
157
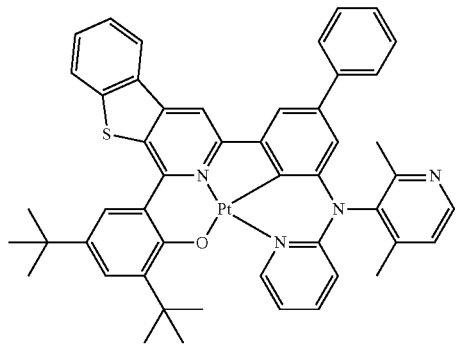
158
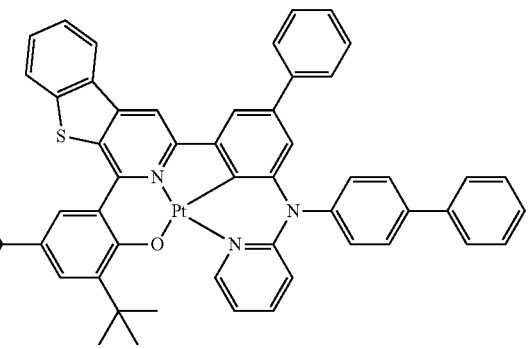

159
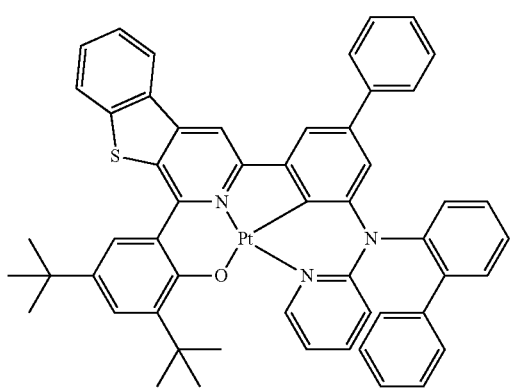
160
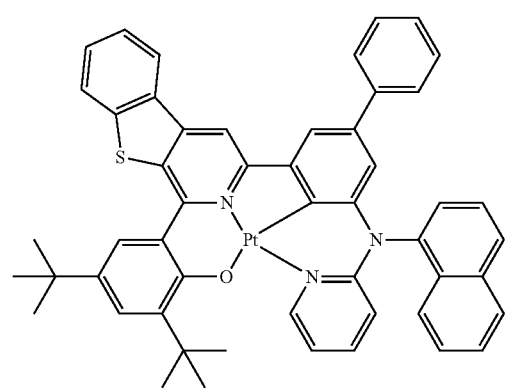
161
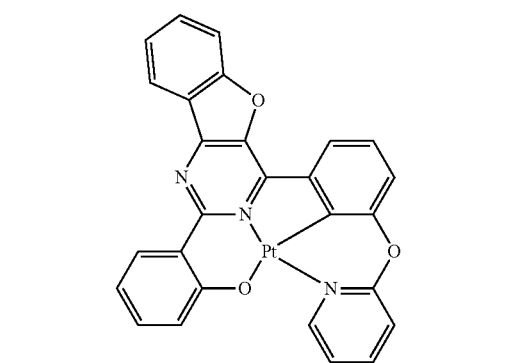
162
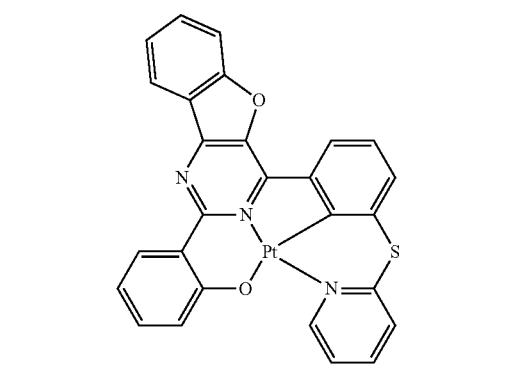
163
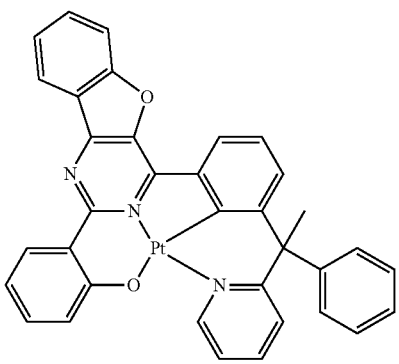
164
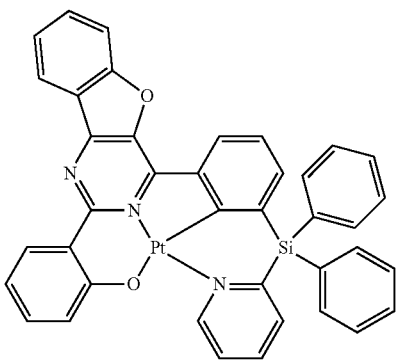
165
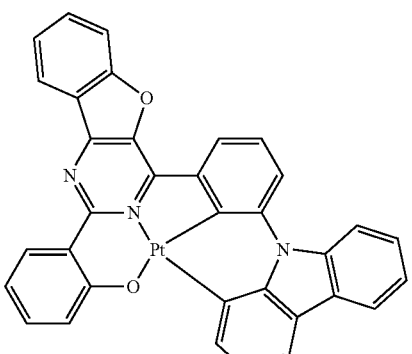
166
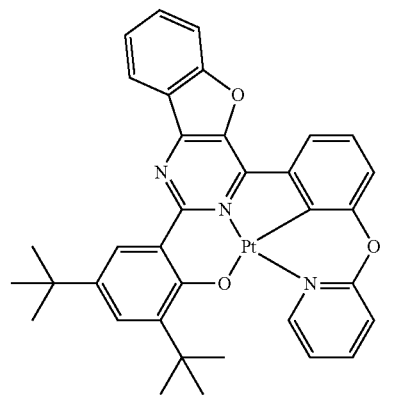

167
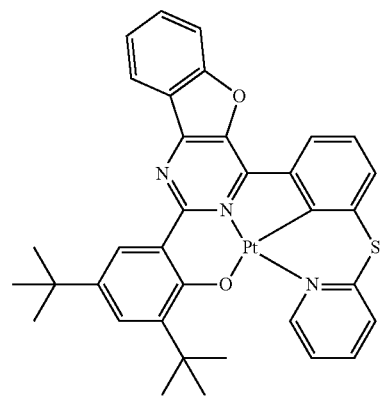
168
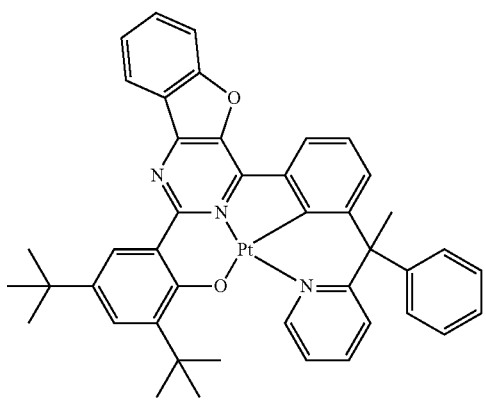
169
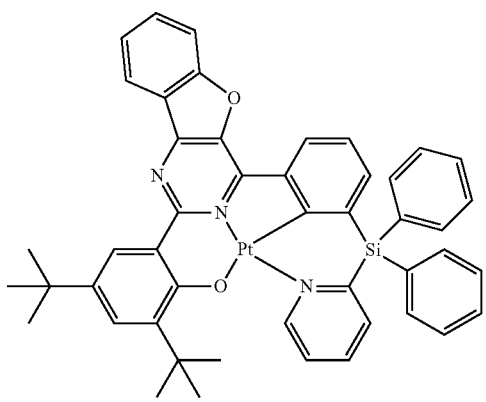
170
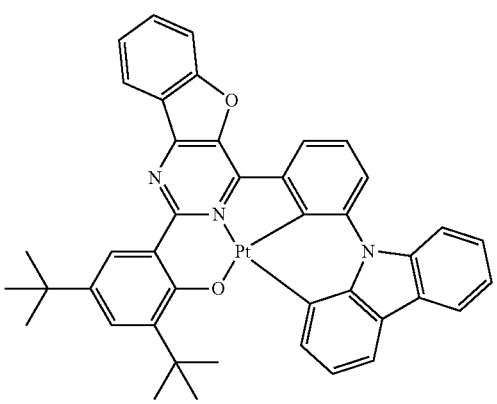
171
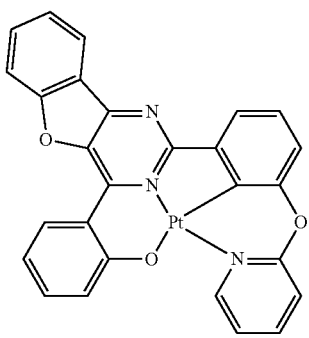
172
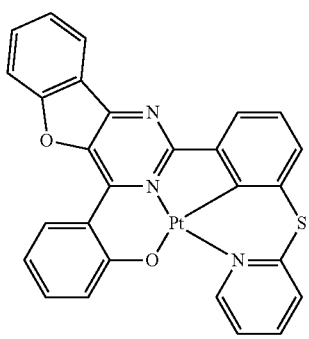
173
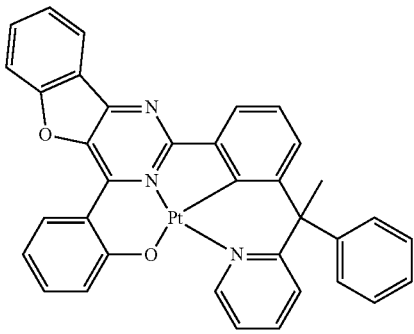
174
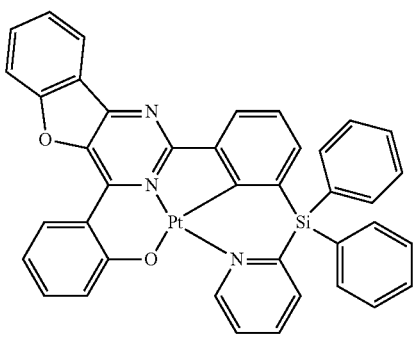

-continued
175
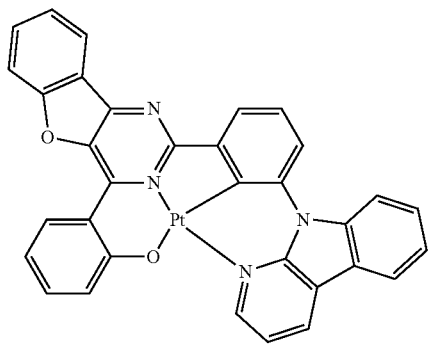
176
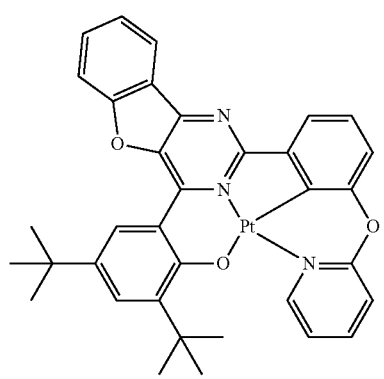
177
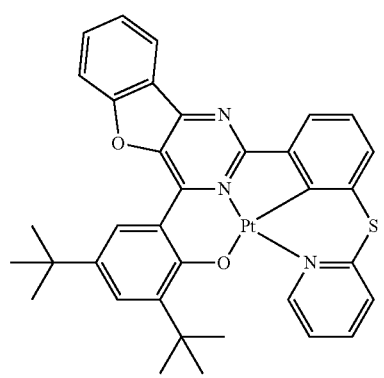
178
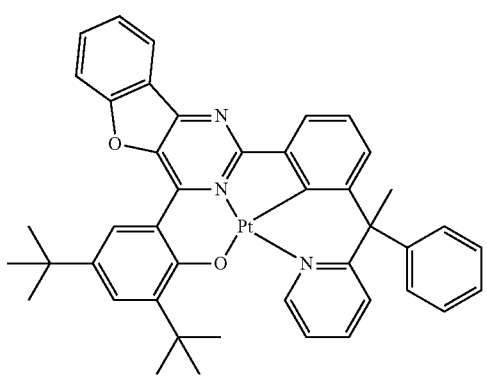
-continued
179
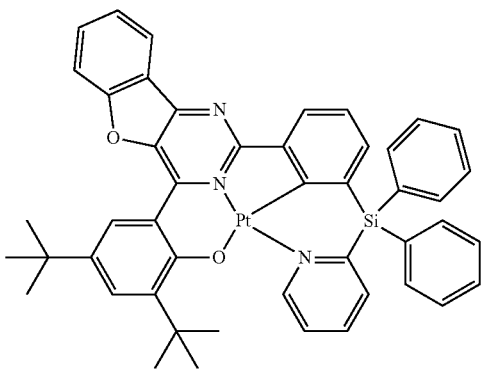
180
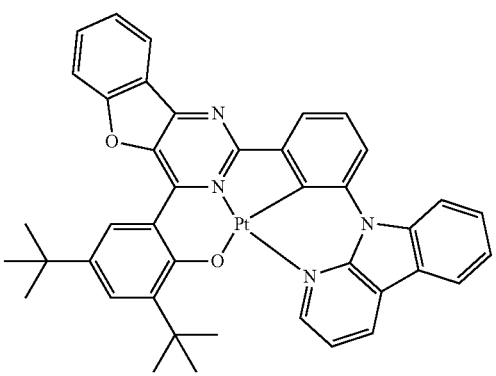
181
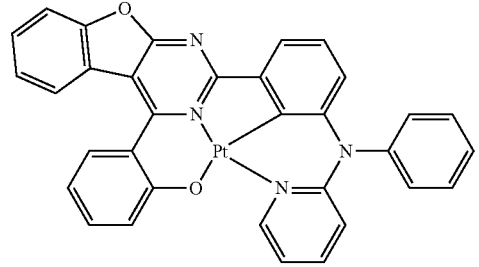
182
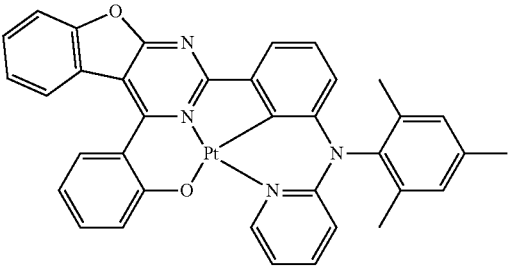
183
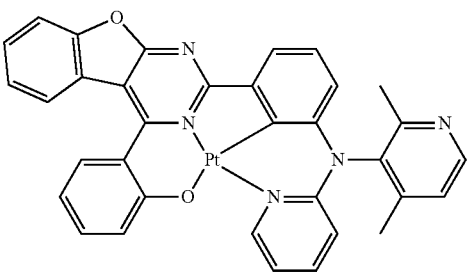

184
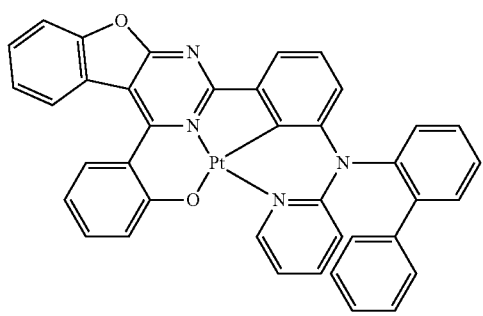
185
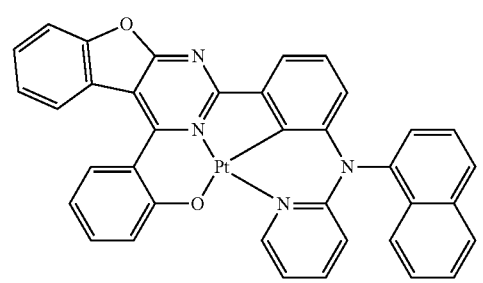
186
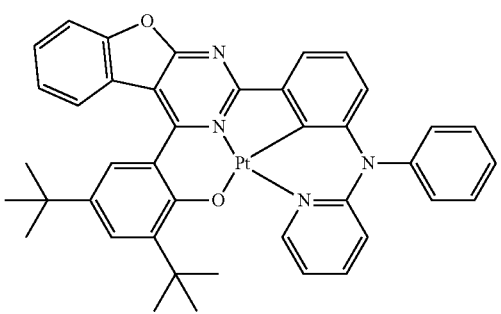
187
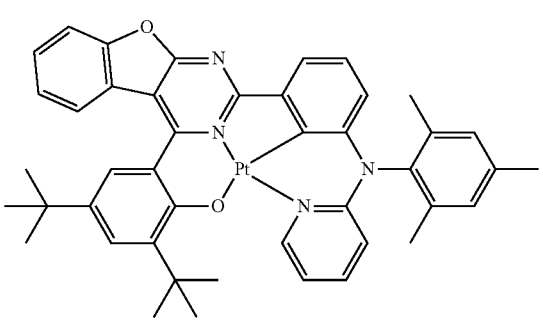
188
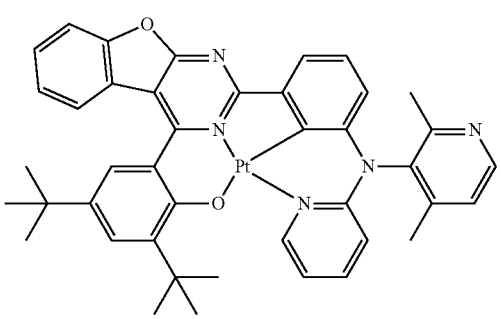
189
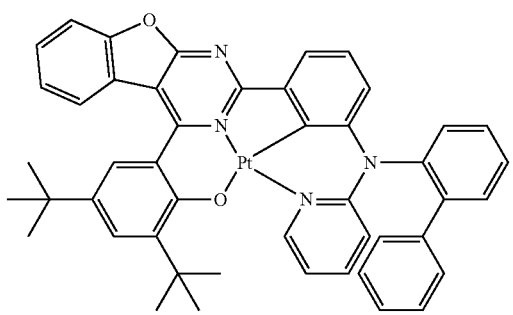
190
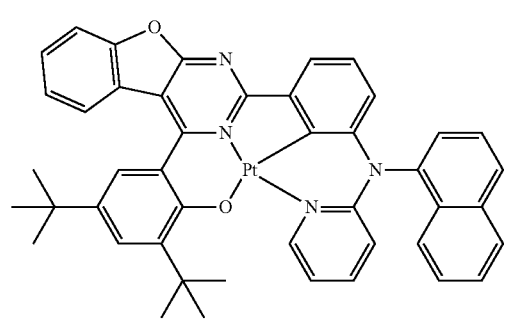
191
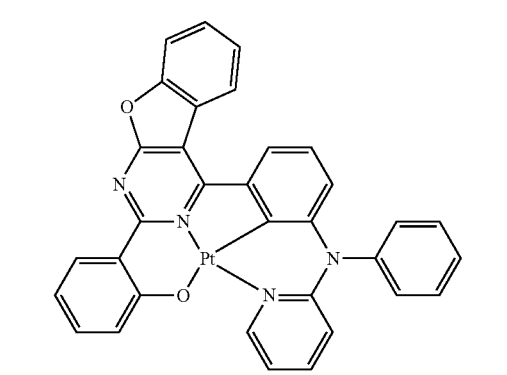
192
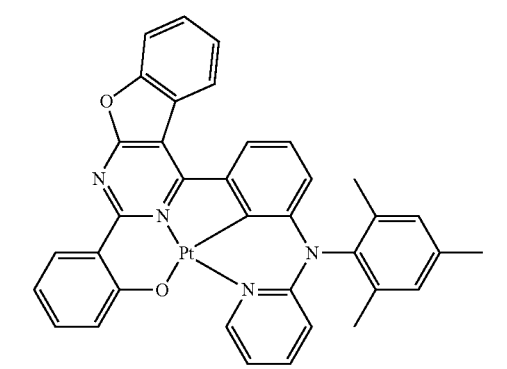

193
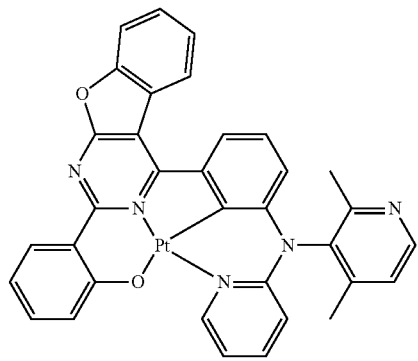
194
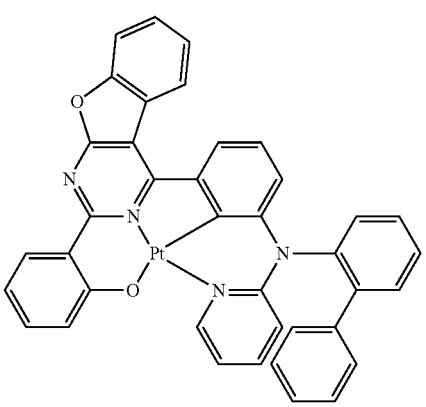
195
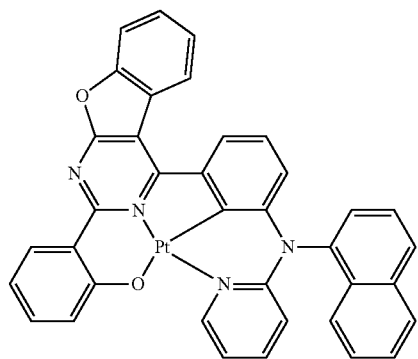
196
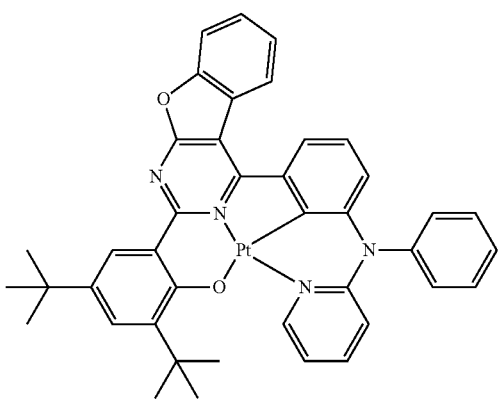
197
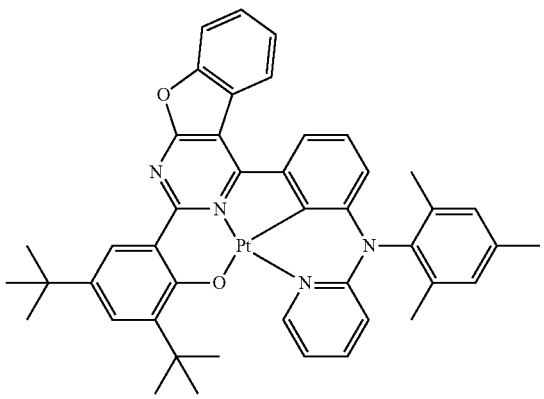
198
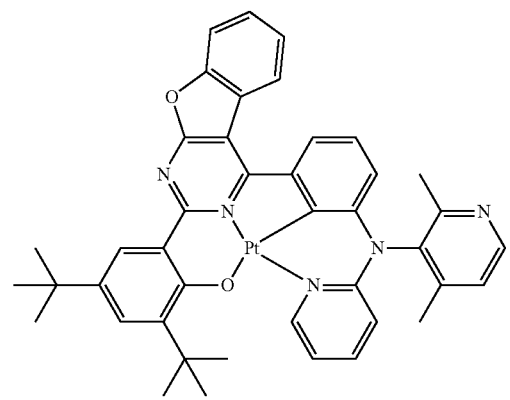
199
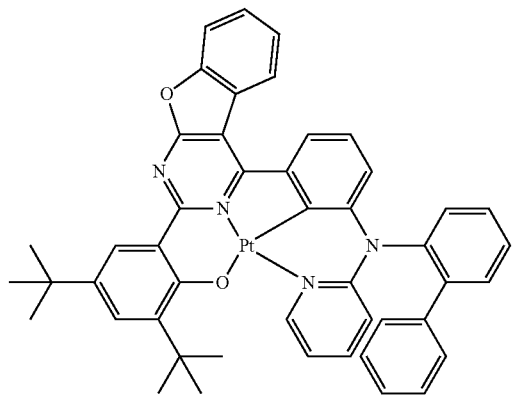
200
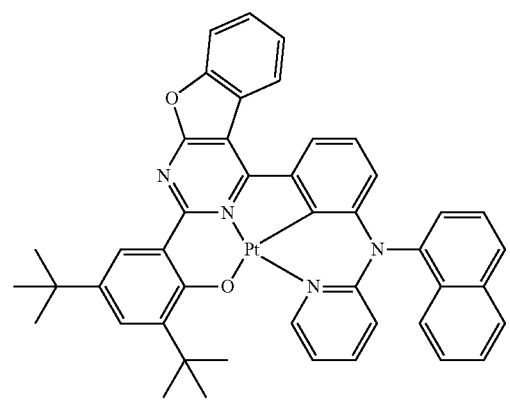

201 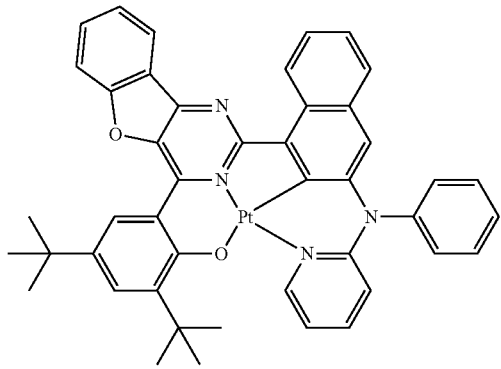
202 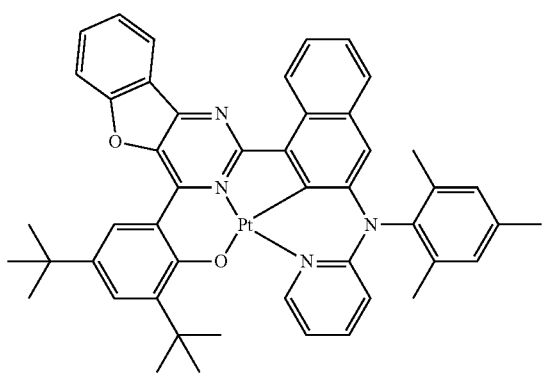
203 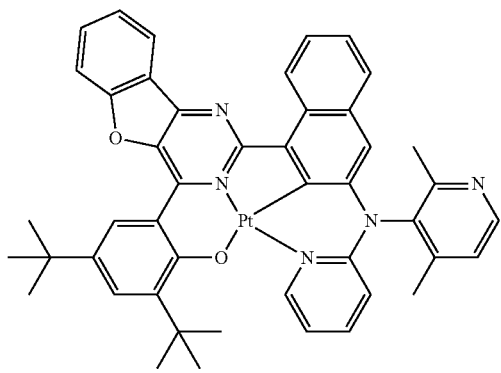
204 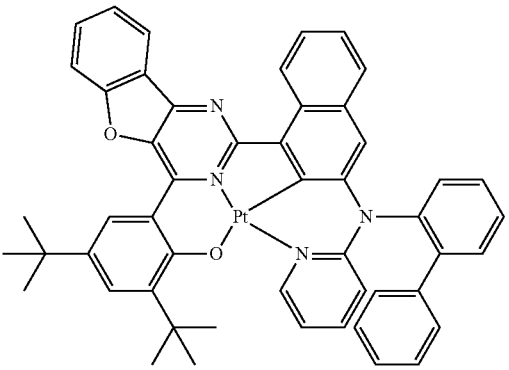
205 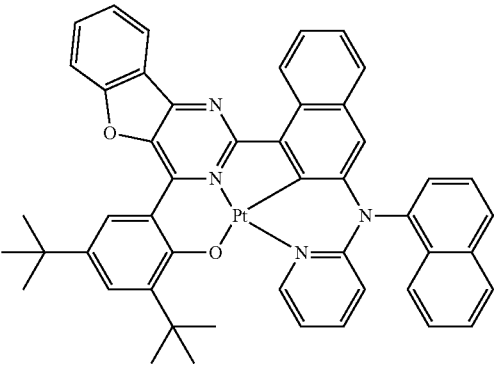
206 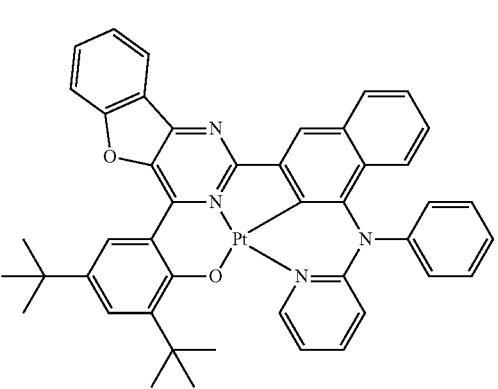
207 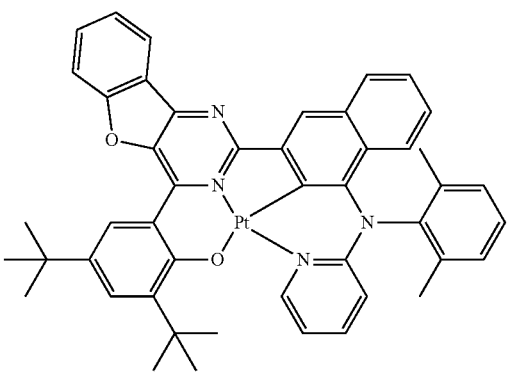
208 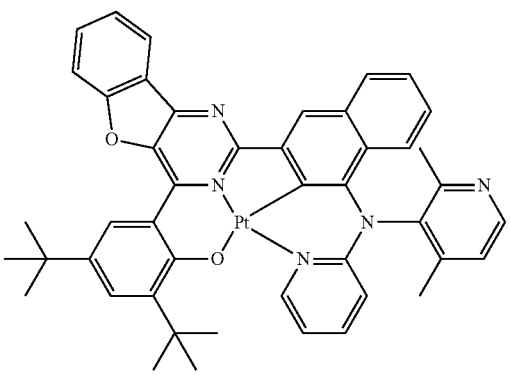

251
-continued
209
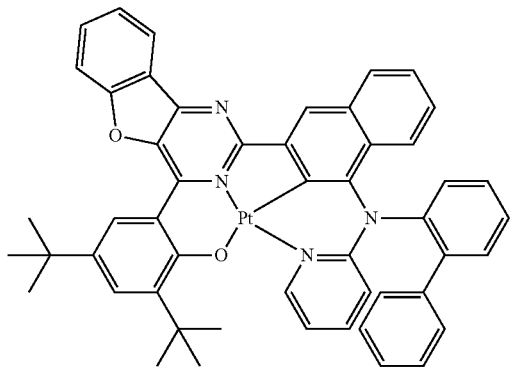
210
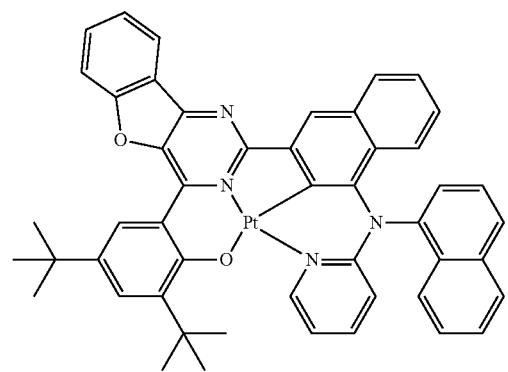
211
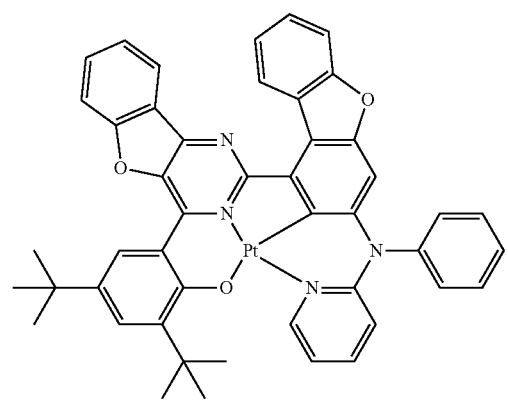
212
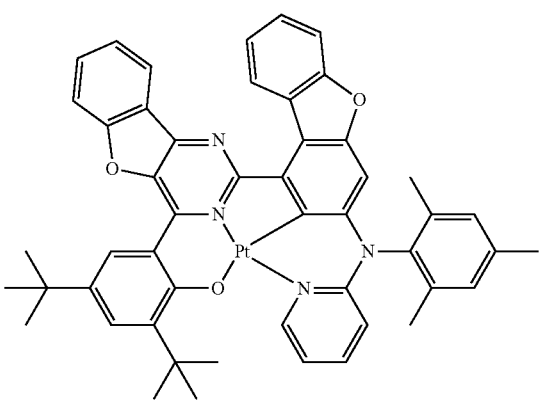
252
-continued
213
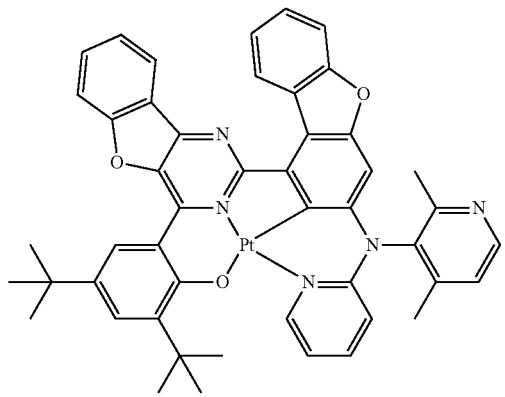
214
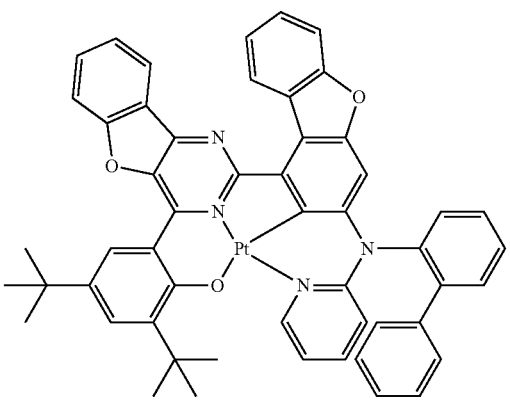
215
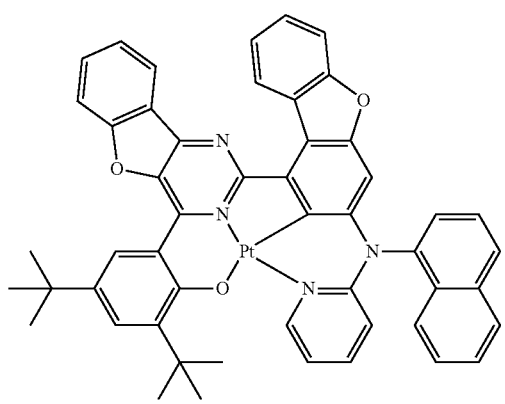
216
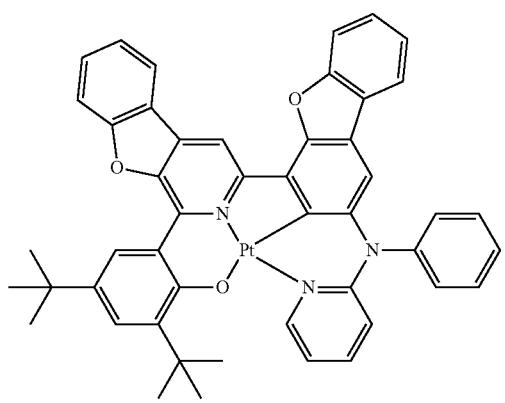

217
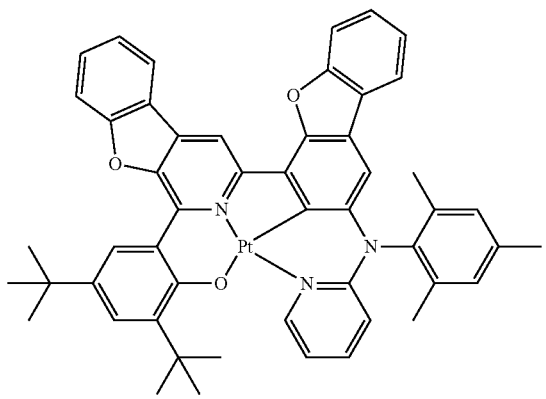
218
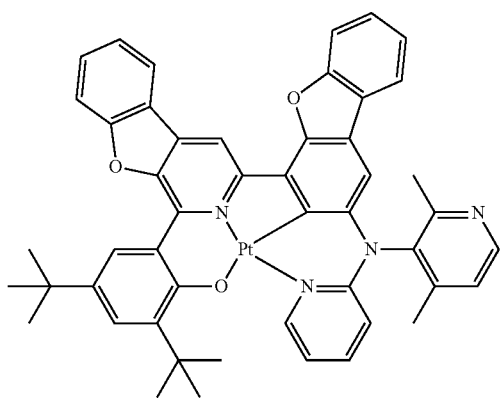
219
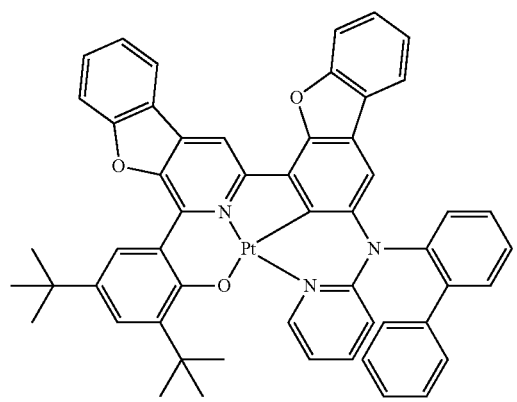
220
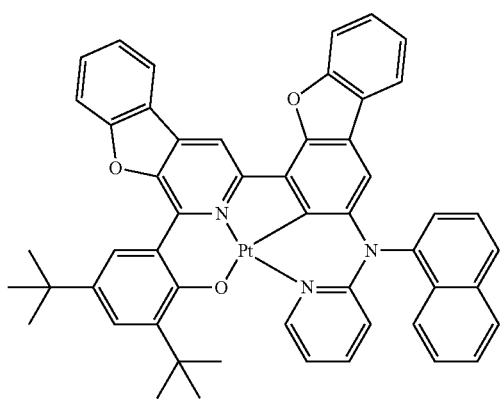
221
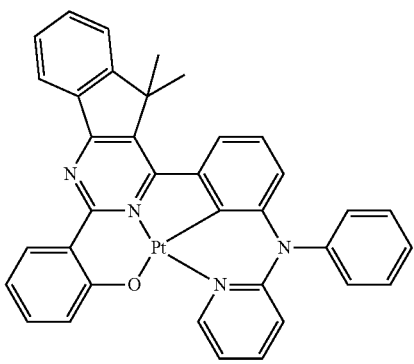
222
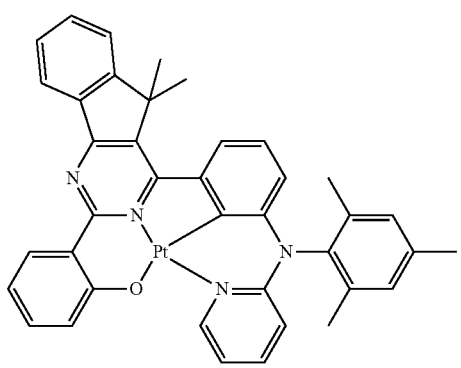
223
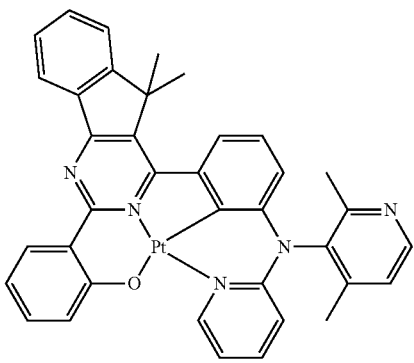
224
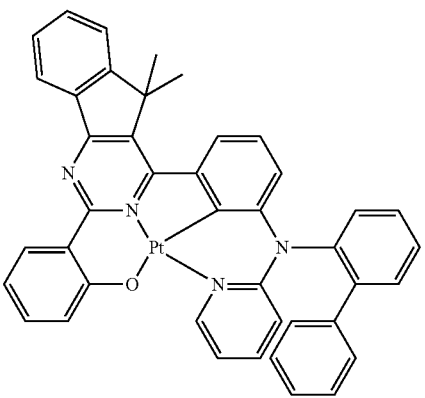

255
-continued
225
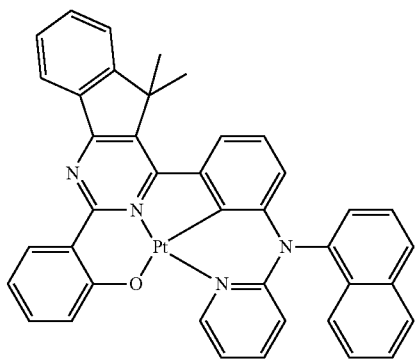
226
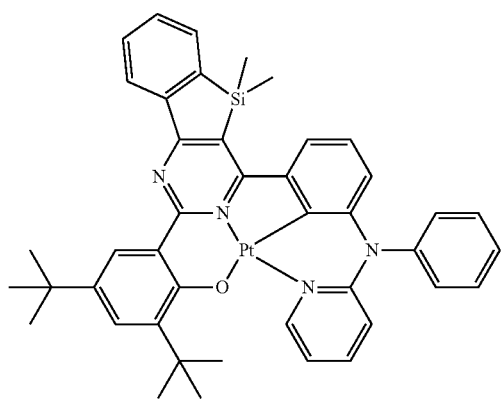
227
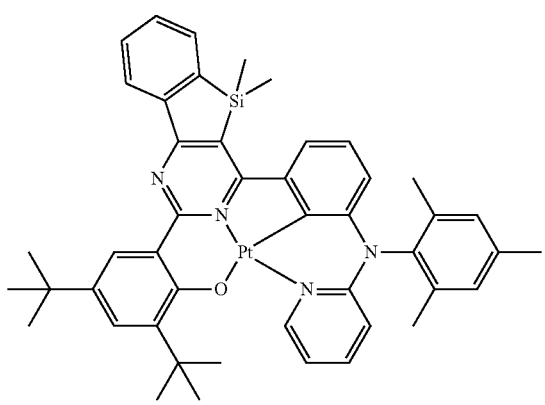
228
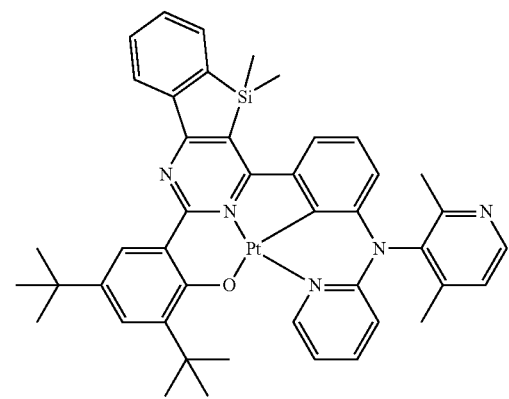
256
-continued
229
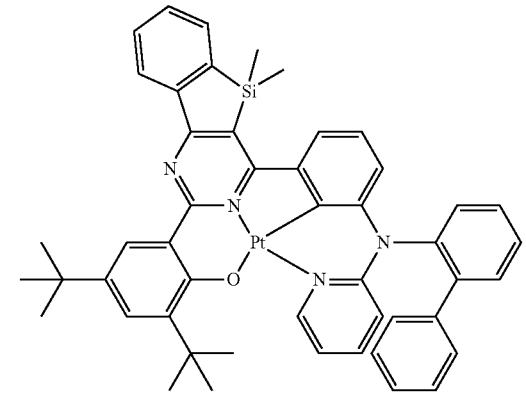
230
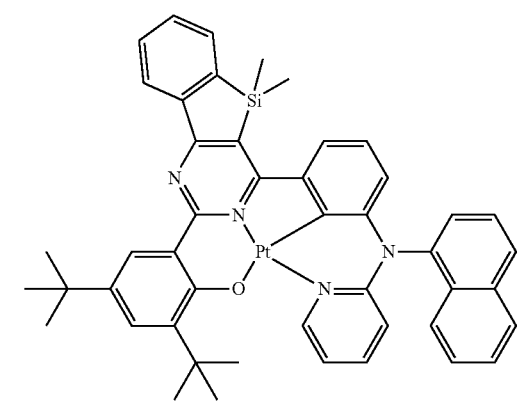
231
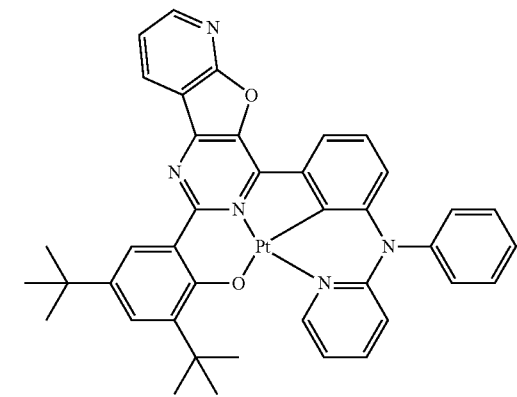
232
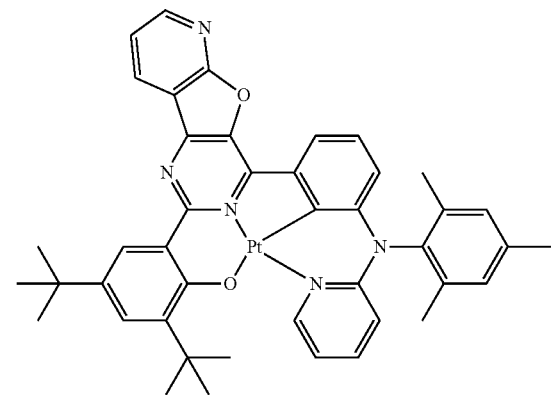

257
-continued
233
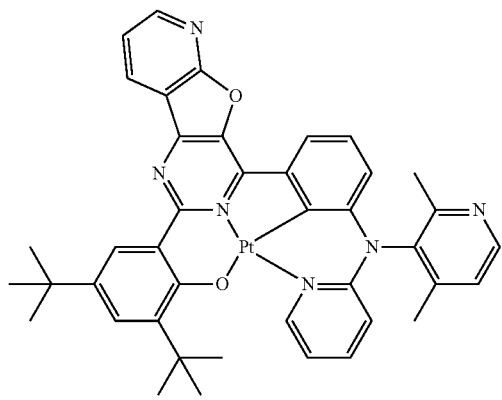
234
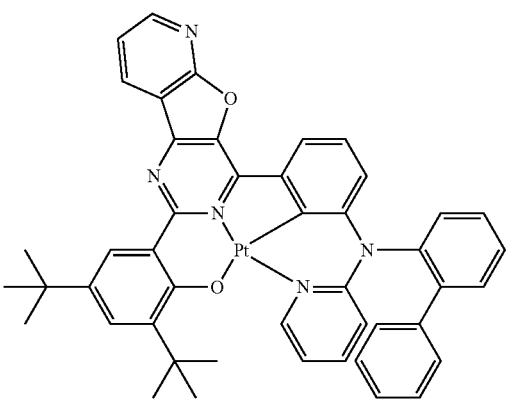
235
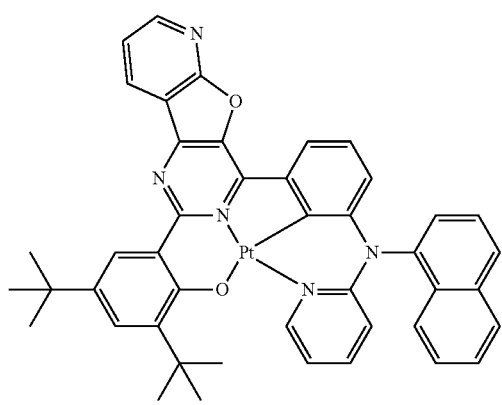
236
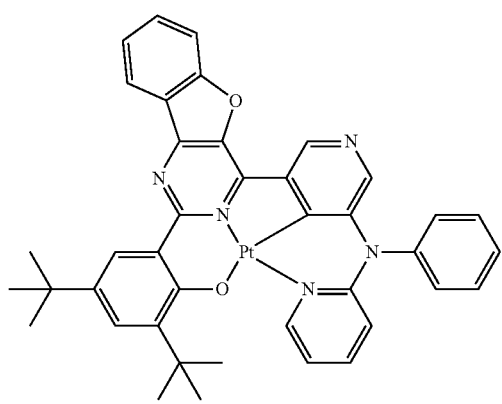
258
-continued
237
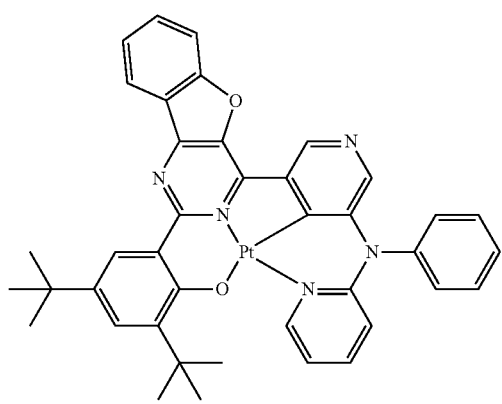
238
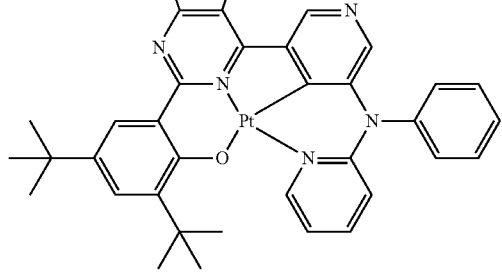
239
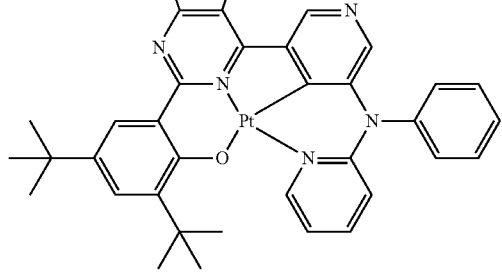

-continued

240

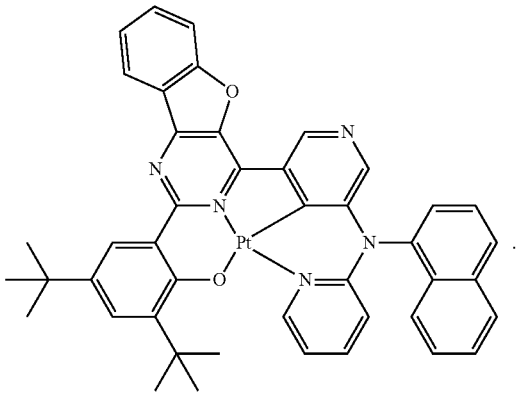

11. An organic light-emitting device comprising:
a first electrode;
a second electrode; and
an organic layer disposed between the first electrode and the second electrode, wherein the organic layer comprises an emission layer, and
wherein the organic layer comprises at least one organometallic compound of claim 1.

12. The organic light-emitting device of claim 11, wherein the first electrode is an anode,
the second electrode is a cathode, and
the organic layer comprises a hole transport region disposed between the first electrode and the emission layer, and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

13. The organic light-emitting device of claim 11, wherein the emission layer comprises the at least one organometallic compound.

14. The organic light-emitting device of claim 13, wherein the emission layer further comprises a host, wherein an amount of the host is greater than an amount of the at least one organometallic compound.

15. A diagnostic composition comprising at least one organometallic compound of claim 1.

* * * * *